US006664446B2

(12) United States Patent
Heard et al.

(10) Patent No.: US 6,664,446 B2
(45) Date of Patent: Dec. 16, 2003

(54) TRANSGENIC PLANTS COMPRISING POLYNUCLEOTIDES ENCODING TRANSCRIPTION FACTORS THAT CONFER DISEASE TOLERANCE

(75) Inventors: Jacqueline Heard, San Mateo, CA (US); Pierre Broun, San Mateo, CA (US); Jose Luis Riechmann, Oakland, CA (US); James Keddie, San Mateo, CA (US); Omaira Pineda, Castro Valley, CA (US); Luc Adam, Hayward, CA (US); Raymond Samaha, Capitola, CA (US); James Zhang, Palo Alto, CA (US); Guo-Liang Yu, Berkeley, CA (US); Oliver Ratcliffe, Oakland, CA (US); Marsha Pilgrim, Palo Alto, CA (US); Cai-Zhong Jiang, Fremont, CA (US); Lynne Reuber, San Mateo, CA (US)

(73) Assignee: Mendel Biotechnology, Inc., Hayward, CA (US)

( * ) Notice: Subject to any disclaimer, the term of this patent is extended or adjusted under 35 U.S.C. 154(b) by 0 days.

(21) Appl. No.: 09/533,029

(22) Filed: Mar. 22, 2000

(65) Prior Publication Data

US 2003/0046723 A1 Mar. 6, 2003

Related U.S. Application Data

(60) Provisional application No. 60/125,814, filed on Mar. 23, 1999.

(51) Int. Cl.$^7$ .......................... A01H 5/00; C12N 15/29; C12N 15/82
(52) U.S. Cl. ...................... 800/301; 435/419; 800/279; 800/287
(58) Field of Search .................... 435/468, 410, 435/419; 530/329; 536/23.1; 800/278, 279, 301, 287

(56) References Cited

U.S. PATENT DOCUMENTS 5,939,601 A * 8/1999 Klessig et al. .............. 800/279

FOREIGN PATENT DOCUMENTS

WO 97/471183 * 12/1997

OTHER PUBLICATIONS

Riechmann et al 1998, Biol. Chem. 379:633–646.*
Zhou et al 1997, The EMBO Journal 16(11):3207–3218.*
Ouattrocchio et al., Analysis of bHLH and MYB domain proteins: species–specific regulatory differences are caused by divergent evolution of target anthocyanin genes, 1998, The Plant Journal, vol. 13, No. 4, pp. 475–488.*
Riechmann and Meyerowitz (1998) Biol. Chem. 379:633–646.
Martin and Paz–Ares (1997) Trends Genet. 13:67–73.
Riechmann and Meyerowitz (1997) Biol. Chem. 378:1079–1101.
Ishiguro and Nakamura (1994) Mol. Gen. Genet. 244:563–571.
Zhang et al. (1992) Plant Cell 4:1575–1588.
Klug and Schwabe (1995) FA SEB J. 9: 597–604.
Buerglin in Duboule (ed.) (1994) Guidebook to the Homeobox Genes, Oxford University Press, Oxford, UK p p 27–71.
Forsburg and Guarente (1989) Genes Dev. 3:1166–1178.
Klein et al. (1996) Mol. Gen. Genet. 1996 250:7–16.
Souer et al. (1996) Cell 85:159–170.
Rouse et al. (1998) Science 279:1371–1373.
Littlewood et al. (1994) Prot. Profile 1:639–709.
Tucker et al. (1994) EMBO J. 13:2994–3002.
Foster et al. (1994) FASEB J. 8:192–200.
da Costa e Silva et al. (1993) Plant J. 4:125–135.
Bustin and Reeves (1996) Prog. Nucl. Acids Res. Mol. Biol. 54:35–100.
Di Laurenzio et al. (1996) Cell 86:423–433.
Wu et al (1997) Plant Physiol. 114:1421–1431.
Kennison (1995) Annu. Rev. Genet. 29:289–303.
Luo et al. (1996) Nature 383:794–799.
Giraudat et al. (1992) Plant Cell 4:1251–1261.
Dehesh et al. (1990) Science 250:1397–1399.
Chao et al. (1997) Cell 89 :1133–1144.
Reeves and Nissen (1990) J. Biol. Chem. 265: 8573–8582.
Zhou et al. (1995) Nucleic Acids Res, 23:1165–1169.
Lu and Ferl (1995) Plant Physiol. 109:721–723.
Bowman et al. (1999) Development 126:2387–2396.
Bohmert et al. (1998) EMBO J. 17:170–80.
Kim et al. (1997) Plant J. 11:1237–1251.
Hall et al. (1998) Plant Cell 10:925–936.
Giniger and Ptashne (1987) Nature 330:670–672.
Gill and Ptashne (1987) Cell 51:121–126.
Estruch et al. (1994) Nucl. Acids Res. 22:3983–3989.
Moore et al. (1998) Proc. Natl. Acad. Sci. 95:376–381.
Aoyama et al. (1995) Plant Cell 7:1773–1785.
Ma and Ptashne (1987) Cell 51:113–119.
Odell et al. (1985) Nature 313:810–812.
An et al. (1988) Plant Physiol. 88:547–552.
Fromm et al. (1989) Plant Cell 1: 977–984.
Bird et al. (1988) Plant Mol Biol 11:651–662.
Ringli and Keller (1998) Plant Mol Biol 37:977–988.
Kaiser et al, (1995) Plant Mol Biol 28:231–243.
Baerson et al. (1994) Plant Mol Biol 26:1947–1959.
Ohl et al. (1990) Plant Cell 2:837–848.

(List continued on next page.)

Primary Examiner—David T. Fox
Assistant Examiner—David H Kruse
(74) Attorney, Agent, or Firm—Jeffrey M. Libby; Matthew R. Kaser; Morrison & Foerster LLP

(57) ABSTRACT

Plants transformed with a plant APZ transcription factor encoding polynucleotide, isolated from Arabidopsis, that enhances tolerance to fungal diseases, especially fungal diseases caused by Fusarium, Erysiphe, Sclerotinia and Botrytis.

18 Claims, 5 Drawing Sheets

OTHER PUBLICATIONS

Baerson et al. (1993) Plant Mol Biol 22:255–267.
van der Kop et al. (1999) Plant Mol Biol 39: 979–990.
Baumann et al. (1999) Plant Cell 11:323–334.
Guevara–Garcia (1998) Plant Mol Biol 38:743–753.
Shi et al. (1998) Plant Mol Biol 38:1053–1060.
Willmott et al. (1998) 38: 817–825.
Ainley et al. (1993) Plant Mol Biol 22:13–23.
Kuhlemeier et al. (1989) Plant Cell 1:471–478.
Schaffner and Sheen (1991) Plant Cell 3:997–1021.
Siebertz et al. (1989) Plant Cell 1:961–968.
Gatz et al. (1997) Annu. Rev. Plant Physiol. Plant Mol Biol 48:89–108.
Odell et al. (1994) Plant Physiol 106:447–458.

* cited by examiner

Figure 1a

| SEQ ID No | GID No. | Family | Fragments | DNA or protein | coding sequence | conserved domain |
|---|---|---|---|---|---|---|
| 1 | G1043 | WRKY | 1-100, 30-48, 75-125, 150-200, 200-300, 350-400 | DNA | 43-927 | |
| 2 | G1043 | WRKY | 1-50, 50-75, 76-81, 82-100, 100-150, 150-200 | protein | | 120-179 |
| 3 | G759 | NAM | 1-100, 30-48, 75-125, 150-200, 200-300, 350-400 | DNA | 8-961 | |
| 4 | G759 | NAM | 1-50, 50-75, 76-81, 82-100, 100-150, 150-200 | protein | | 17-159 |
| 5 | G185 | WRKY | 1-100, 30-48, 75-125, 150-200, 200-300, 350-400 | DNA | 77-988 | |
| 6 | G185 | WRKY | 1-50, 50-75, 76-81, 82-100, 100-150, 150-200 | protein | | 113-172 |
| 7 | G629 | bZIP | 1-100, 30-48, 75-125, 150-200, 200-300, 350-400 | DNA | 169-1275 | |
| 8 | G629 | bZIP | 1-50, 50-75, 76-81, 82-100, 100-150, 150-200 | protein | | 92-152 |
| 9 | G435 | HB | 1-100, 30-48, 75-125, 150-200, 200-300, 350-400 | DNA | 32-502 | |
| 10 | G435 | HB | 1-50, 50-75, 76-81, 82-100, 100-150, 150-200 | protein | | 4-67 |
| 11 | G4 | AP2 | 1-100, 30-48, 75-125, 150-200, 200-300, 350-400 | DNA | 90-1217 | |
| 12 | G4 | AP2 | 1-50, 50-75, 76-81, 82-100, 100-150, 150-200 | protein | | 121-188 |
| 13 | G1035 | bZIP | 1-100, 30-48, 75-125, 150-200, 200-300, 350-400 | DNA | 103-624 | |
| 14 | G1035 | bZIP | 1-50, 50-75, 76-81, 82-100, 100-150, 150-200 | protein | | 39-91 |
| 15 | G179 | WRKY | 1-100, 30-48, 75-125, 150-200, 200-300, 350-400 | DNA | 68-511 | |
| 16 | G179 | WRKY | 1-50, 50-75, 76-81, 82-100, 100-150, 150-200 | protein | | 65-121 |
| 17 | G28 | AP2 | 1-100, 30-48, 75-125, 150-200, 200-300, 350-400 | DNA | 63-869 | |
| 18 | G28 | AP2 | 1-50, 50-75, 76-81, 82-100, 100-150, 150-200 | protein | | 145-213 |
| 19 | G1241 | MISC | 1-100, 30-48, 75-125, 150-200, 200-300, 350-400 | DNA | 108-605 | |
| 20 | G1241 | MISC | 1-50, 50-75, 76-81, 82-100, 100-150, 150-200 | protein | | |
| 21 | G19 | AP2 | 1-100, 30-48, 75-125, 150-200, 200-300, 350-400 | DNA | 70-816 | |
| 22 | G19 | AP2 | 1-50, 50-75, 76-81, 82-100, 100-150, 150-200 | protein | | 76-145 |
| 23 | G503 | NAM | 1-100, 30-48, 75-125, 150-200, 200-300, 350-400 | DNA | 80-886 | |
| 24 | G503 | NAM | 1-50, 50-75, 76-81, 82-100, 100-150, 150-200 | protein | | 12-158 |
| 25 | G263 | HS | 1-100, 30-48, 75-125, 150-200, 200-300, 350-400 | DNA | 48-902 | |
| 26 | G263 | HS | 1-50, 50-75, 76-81, 82-100, 100-150, 150-200 | protein | | 15-105 |
| 27 | G921 | WRKY | 1-100, 30-48, 75-125, 150-200, 200-300, 350-400 | DNA | 116-1024 | |
| 28 | G921 | WRKY | 1-50, 50-75, 76-81, 82-100, 100-150, 150-200 | protein | | 146-203 |
| 29 | G1275 | WRKY | 1-100, 30-48, 75-125, 150-200, 200-300, 350-400 | DNA | 58-579 | |
| 30 | G1275 | WRKY | 1-50, 50-75, 76-81, 82-100, 100-150, 150-200 | protein | | 113-169 |

Figure 1b

| SEQ ID No | GID No. | Family | Fragments | DNA or protein | coding sequence | conserved domain |
|---|---|---|---|---|---|---|
| 31 | G242 | MYB | 1-100, 30-48, 75-125, 150-200, 200-300, 350-400 | DNA | 66-983 | |
| 32 | G242 | MYB | 1-50, 50-75, 76-81, 82-100, 100-150, 150-200 | protein | | 6-105 |
| 33 | G1006 | AP2 | 1-100, 30-48, 75-125, 150-200, 200-300, 350-400 | DNA | 52-783 | |
| 34 | G1006 | AP2 | 1-50, 50-75, 76-81, 82-100, 100-150, 150-200 | protein | | 114-182 |
| 35 | G1049 | bZIP | 1-100, 30-48, 75-125, 150-200, 200-300, 350-400 | DNA | 29-550 | |
| 36 | G1049 | bZIP | 1-50, 50-75, 76-81, 82-100, 100-150, 150-200 | protein | | 77-132 |
| 37 | G502 | NAM | 1-100, 30-48, 75-125, 150-200, 200-300, 350-400 | DNA | 224-1186 | |
| 38 | G502 | NAM | 1-50, 50-75, 76-81, 82-100, 100-150, 150-200 | protein | | 10-155 |
| 39 | G239 | MYB | 1-100, 30-48, 75-125, 150-200, 200-300, 350-400 | DNA | 1-822 | |
| 40 | G239 | MYB | 1-50, 50-75, 76-81, 82-100, 100-150, 150-200 | protein | | 21-125 |
| 41 | G555 | bZIP | 1-100, 30-48, 75-125, 150-200, 200-300, 350-400 | DNA | 250-1242 | |
| 42 | G555 | bZIP | 1-50, 50-75, 76-81, 82-100, 100-150, 150-200 | protein | | 38-110 |
| 43 | G352 | Z | 1-100, 30-48, 75-125, 150-200, 200-300, 350-400 | DNA | 80-817 | |
| 44 | G352 | Z | 1-50, 50-75, 76-81, 82-100, 100-150, 150-200 | protein | | 99-119,166-186 |
| 45 | G1352 | Z | 1-100, 30-48, 75-125, 150-200, 200-300, 350-400 | DNA | 79-900 | |
| 46 | G1352 | Z | 1-50, 50-75, 76-81, 82-100, 100-150, 150-200 | protein | | 108-129,167-188 |
| 47 | G1089 | bZIPt2 | 1-100, 30-48, 75-125, 150-200, 200-300, 350-400 | DNA | 31-2427 | |
| 48 | G1089 | bZIPt2 | 1-50, 50-75, 76-81, 82-100, 100-150, 150-200 | protein | | 425-500 |
| 49 | G553 | bZIP | 1-100, 30-48, 75-125, 150-200, 200-300, 350-400 | DNA | 82-1236 | |
| 50 | G553 | bZIP | 1-50, 50-75, 76-81, 82-100, 100-150, 150-200 | protein | | 94-160 |
| 51 | G1221 | MISC | 1-100, 30-48, 75-125, 150-200, 200-300, 350-400 | DNA | 287-2314 | |
| 52 | G1221 | MISC | 1-50, 50-75, 76-81, 82-100, 100-150, 150-200 | protein | | 490-515 |
| 53 | G580 | bZIP | 1-100, 30-48, 75-125, 150-200, 200-300, 350-400 | DNA | 43-747 | |
| 54 | G580 | bZIP | 1-50, 50-75, 76-81, 82-100, 100-150, 150-200 | protein | | 162-218 |
| 55 | G270 | AKR | 1-100, 30-48, 75-125, 150-200, 200-300, 350-400 | DNA | 43-1350 | |
| 56 | G270 | AKR | 1-50, 50-75, 76-81, 82-100, 100-150, 150-200 | protein | | |
| 57 | G201 | MYB | 1-100, 30-48, 75-125, 150-200, 200-300, 350-400 | DNA | 1-1011 | |
| 58 | G201 | MYB | 1-50, 50-75, 76-81, 82-100, 100-150, 150-200 | protein | | 14-114 |
| 59 | G1417 | WRKY | 1-100, 30-48, 75-125, 150-200, 200-300, 350-400 | DNA | 32-1501 | |
| 60 | G1417 | WRKY | 1-50, 50-75, 76-81, 82-100, 100-150, 150-200 | protein | | 239-296 |

Figure 1c

| SEQ ID No | GID No. | Family | Fragments | DNA or protein | coding sequence | conserved domain |
|---|---|---|---|---|---|---|
| 61 | G233 | MYB | 1-100, 30-48, 75-125, 150-200, 200-300, 350-400 | DNA | 46-867 | |
| 62 | G233 | MYB | 1-50, 50-75, 76-81, 82-100, 100-150, 150-200 | protein | | 14-114 |
| 63 | G920 | WRKY | 1-100, 30-48, 75-125, 150-200, 200-300, 350-400 | DNA | 114-1154 | |
| 64 | G920 | WRKY | 1-50, 50-75, 76-81, 82-100, 100-150, 150-200 | protein | | 152-211 |
| 65 | G867 | AP2 | 1-100, 30-48, 75-125, 150-200, 200-300, 350-400 | DNA | 64-1098 | |
| 66 | G867 | AP2 | 1-50, 50-75, 76-81, 82-100, 100-150, 150-200 | protein | | 59-124 |
| 67 | G659 | MYB | 1-100, 30-48, 75-125, 150-200, 200-300, 350-400 | DNA | 1-984 | |
| 68 | G659 | MYB | 1-50, 50-75, 76-81, 82-100, 100-150, 150-200 | protein | | 16-116 |
| 69 | G620 | CAAT | 1-100, 30-48, 75-125, 150-200, 200-300, 350-400 | DNA | 40-666 | |
| 70 | G620 | CAAT | 1-50, 50-75, 76-81, 82-100, 100-150, 150-200 | protein | | 20-118 |
| 71 | G596 | AT-Hook | 1-100, 30-48, 75-125, 150-200, 200-300, 350-400 | DNA | 168-1121 | |
| 72 | G596 | AT-Hook | 1-50, 50-75, 76-81, 82-100, 100-150, 150-200 | protein | | 89-96 |
| 73 | G511 | NAM | 1-100, 30-48, 75-125, 150-200, 200-300, 350-400 | DNA | 31-738 | |
| 74 | G511 | NAM | 1-50, 50-75, 76-81, 82-100, 100-150, 150-200 | protein | | 8-159 |
| 75 | G471 | IAA/ARF | 1-100, 30-48, 75-125, 150-200, 200-300, 350-400 | DNA | 115-2112 | |
| 76 | G471 | IAA/ARF | 1-50, 50-75, 76-81, 82-100, 100-150, 150-200 | protein | | 22-354 |
| 77 | G385 | HB | 1-100, 30-48, 75-125, 150-200, 200-300, 350-400 | DNA | 37-2202 | |
| 78 | G385 | HB | 1-50, 50-75, 76-81, 82-100, 100-150, 150-200 | protein | | 60-123 |
| 79 | G261 | HS | 1-100, 30-48, 75-125, 150-200, 200-300, 350-400 | DNA | 458-1663 | |
| 80 | G261 | HS | 1-50, 50-75, 76-81, 82-100, 100-150, 150-200 | protein | | 16-104 |
| 81 | G25 | AP2 | 1-100, 30-48, 75-125, 150-200, 200-300, 350-400 | DNA | 80-595 | |
| 82 | G25 | AP2 | 1-50, 50-75, 76-81, 82-100, 100-150, 150-200 | protein | | 47-114 |
| 83 | G610 | BPF-1 | 1-100, 30-48, 75-125, 150-200, 200-300, 350-400 | DNA | 137-2059 | |
| 84 | G610 | BPF-1 | 1-50, 50-75, 76-81, 82-100, 100-150, 150-200 | protein | | 577-609 |
| 85 | G229 | MYB | 1-100, 30-48, 75-125, 150-200, 200-300, 350-400 | DNA | 41-1156 | |
| 86 | G229 | MYB | 1-50, 50-75, 76-81, 82-100, 100-150, 150-200 | protein | | 14-120 |
| 87 | G221 | MYB | 1-100, 30-48, 75-125, 150-200, 200-300, 350-400 | DNA | 115-795 | |
| 88 | G221 | MYB | 1-50, 50-75, 76-81, 82-100, 100-150, 150-200 | protein | | 21-125 |
| 89 | G186 | WRKY | 1-100, 30-48, 75-125, 150-200, 200-300, 350-400 | DNA | 100-1761 | |
| 90 | G186 | WRKY | 1-50, 50-75, 76-81, 82-100, 100-150, 150-200 | protein | | 312-369 |

Figure 1d

| SEQ ID No | GID No. | Family | Fragments | DNA or protein | coding sequence | conserved domain |
|---|---|---|---|---|---|---|
| 91 | G562 | bZIP | 1-100, 30-48, 75-125, 150-200, 200-300, 350-400 | DNA | 137-1285 | 253-315 |
| 92 | G562 | bZIP | 1-50, 50-75, 76-81, 82-100, 100-150, 150-200 | protein | | 253-315 |
| 93 | G255 | MYB | 1-100, 30-48, 75-125, 150-200, 200-300, 350-400 | DNA | 30-839 | |
| 94 | G255 | MYB | 1-50, 50-75, 76-81, 82-100, 100-150, 150-200 | protein | | 14-115 |
| 95 | G3 | AP2 | 1-100, 30-48, 75-125, 150-200, 200-300, 350-400 | DNA | 16-477 | |
| 96 | G3 | AP2 | 1-50, 50-75, 76-81, 82-100, 100-150, 150-200 | protein | | 11-95 |
| 97 | G713 | HB | 1-100, 30-48, 75-125, 150-200, 200-300, 350-400 | DNA | 58-765 | |
| 98 | G713 | HB | 1-50, 50-75, 76-81, 82-100, 100-150, 150-200 | protein | | 23-86 |
| 99 | G515 | NAM | 1-100, 30-48, 75-125, 150-200, 200-300, 350-400 | DNA | 154-1170 | |
| 100 | G515 | NAM | 1-50, 50-75, 76-81, 82-100, 100-150, 150-200 | protein | | 6-144 |
| 101 | G390 | HB | 1-100, 30-48, 75-125, 150-200, 200-300, 350-400 | DNA | 1-2526 | |
| 102 | G390 | HB | 1-50, 50-75, 76-81, 82-100, 100-150, 150-200 | protein | | 18-81 |
| 103 | G1034 | bZIP | 1-100, 30-48, 75-125, 150-200, 200-300, 350-400 | DNA | 214-1443 | |
| 104 | G1034 | bZIP | 1-50, 50-75, 76-81, 82-100, 100-150, 150-200 | protein | | 97-160 |
| 105 | G1149 | PAZ | 1-100, 30-48, 75-125, 150-200, 200-300, 350-400 | DNA | 1-2910 | |
| 106 | G1149 | PAZ | 1-50, 50-75, 76-81, 82-100, 100-150, 150-200 | protein | | 870-880 |
| 107 | G1334 | CAAT | 1-100, 30-48, 75-125, 150-200, 200-300, 350-400 | DNA | 76-885 | |
| 108 | G1334 | CAAT | 1-50, 50-75, 76-81, 82-100, 100-150, 150-200 | protein | | 18-190 |
| 109 | G1650 | HLH/MYC | 1-100, 30-48, 75-125, 150-200, 200-300, 350-400 | DNA | 84-1199 | |
| 110 | G1650 | HLH/MYC | 1-50, 50-75, 76-81, 82-100, 100-150, 150-200 | protein | | 284-334 |
| 111 | G241 | MYB | 1-100, 30-48, 75-125, 150-200, 200-300, 350-400 | DNA | | |
| 112 | G241 | MYB | 1-50, 50-75, 76-81, 82-100, 100-150, 150-200 | protein | | 14-116 |
| 113 | G348 | GATA Zn | 1-100, 30-48, 75-125, 150-200, 200-300, 350-400 | DNA | | |
| 114 | G171 | MADS | 1-100, 30-48, 75-125, 150-200, 200-300, 350-400 | DNA | | |
| 115 | G521 | NAM | 1-100, 30-48, 75-125, 150-200, 200-300, 350-400 | DNA | | |
| 116 | G1274 | WRKY | 1-100, 30-48, 75-125, 150-200, 200-300, 350-400 | DNA | | |
| 117 | G182 | WRKY | 1-100, 30-48, 75-125, 150-200, 200-300, 350-400 | DNA | | |
| 118 | G1290 | AKR | 1-100, 30-48, 75-125, 150-200, 200-300, 350-400 | DNA | | |
| 119 | G374 | Z | 1-100, 30-48, 75-125, 150-200, 200-300, 350-400 | DNA | | |
| 120 | G682 | MYB | 1-100, 30-48, 75-125, 150-200, 200-300, 350-400 | DNA | | |

Figure 1e

| SEQ ID No | GID No. | Family | Fragments | DNA or protein | coding sequence | conserved domain |
|---|---|---|---|---|---|---|
| 121 | G501 | NAM | 1-100, 30-48, 75-125, 150-200, 200-300, 350-400 | DNA | | |

SEQUENCE LISTING

<160> NUMBER OF SEQ ID NOS: 121

<210> SEQ ID NO 1
<211> LENGTH: 1099
<212> TYPE: DNA
<213> ORGANISM: Arabidopsis thaliana
<220> FEATURE:
<223> OTHER INFORMATION: G1043

<400> SEQUENCE: 1

```
aaataagata ccactcacca aaaacttcct caaaactaac aaatggatac taataaagca      60
aaaaagctta aagttatgaa ccaactcgtt gaaggccatg acttaacaac tcagcttcag     120
caactcctct ctcaacccgg gtccggtcta gaggatctag tggctaaaat cttagtgtgt     180
```

```
ttcaataaca ccatctccgt tcttgatacc ttcgaaccca tctcctcctc ctcatccctc    240
gccgccgttg agggatctca aaatgcttca tgtgataacg acggcaagtt tgaagattcc    300
ggcgatagtc ggaaaagatt gggacccgtt aagggtaaaa gaggatgcta caaaagaaaa    360
aagagatcgg agacgtgtac tatagagtcg actatacttg aggacgcatt ttcttggagg    420
aaatatggac aaaaggagat tcttaatgcc aaattcccaa gaagttactt tagatgcaca    480
cacaagtata cccaagggtg caaggcaaca aagcaagtcc agaaggttga gctcgaaccc    540
aagatgttca gtatcacata cataggaaac cacacgtgta acaccaacgc agaaactccc    600
aagagcaaga cttgtgacca tcatgatgag atcttcatgg attccgaaga tcacaagagt    660
cctagtttat ctacctcaat gaaggaagaa gacaatcctc atcgtcatca tggttcgtcc    720
acggagaatg acttgtcatt ggtgtggcca gaaatggttt tcgaagaaga ttatcatcat    780
caggccagtt acgtcaatgg gaaaacgagt acatctatcg atgttttggg ttctcaggat    840
ctcatggtgt ttggaggtgg cggcgatttc gagtttagcg aaaatgagca cttctctatc    900
ttcagttcat gttcgaatct atcttgagtt taccactact ataggactaa gaccatgagt    960
tttaatcatt aattaggcca tgtagagtgg aaaacatata atacatattt tgccctttc    1020 tctaatgagt gtatgtactg tacatatagt actataaata aaactcttgc tggattaaaa    1080
caaaaaaaaa aaaaaaaa                                                  1099
```

<210> SEQ ID NO 2
<211> LENGTH: 294
<212> TYPE: PRT
<213> ORGANISM: Arabidopsis thaliana
<220> FEATURE:
<223> OTHER INFORMATION: G1043

<400> SEQUENCE: 2

```
Met Asp Thr Asn Lys Ala Lys Lys Leu Lys Val Met Asn Gln Leu Val
  1               5                  10                  15

Glu Gly His Asp Leu Thr Thr Gln Leu Gln Gln Leu Leu Ser Gln Pro
             20                  25                  30

Gly Ser Gly Leu Glu Asp Leu Val Ala Lys Ile Leu Val Cys Phe Asn
         35                  40                  45

Asn Thr Ile Ser Val Leu Asp Thr Phe Glu Pro Ile Ser Ser Ser Ser
     50                  55                  60

Ser Leu Ala Ala Val Glu Gly Ser Gln Asn Ala Ser Cys Asp Asn Asp
 65                  70                  75                  80

Gly Lys Phe Glu Asp Ser Gly Asp Ser Arg Lys Arg Leu Gly Pro Val
                 85                  90                  95

Lys Gly Lys Arg Gly Cys Tyr Lys Arg Lys Lys Arg Ser Glu Thr Cys
            100                 105                 110

Thr Ile Glu Ser Thr Ile Leu Glu Asp Ala Phe Ser Trp Arg Lys Tyr
        115                 120                 125

Gly Gln Lys Glu Ile Leu Asn Ala Lys Phe Pro Arg Ser Tyr Phe Arg
    130                 135                 140

Cys Thr His Lys Tyr Thr Gln Gly Cys Lys Ala Thr Lys Gln Val Gln
145                 150                 155                 160

Lys Val Glu Leu Glu Pro Lys Met Phe Ser Ile Thr Tyr Ile Gly Asn
                165                 170                 175

His Thr Cys Asn Thr Asn Ala Gly Thr Pro Lys Ser Lys Thr Cys Asp
            180                 185                 190
```

```
His His Asp Glu Ile Phe Met Asp Ser Glu Asp His Lys Ser Pro Ser
            195                 200                 205

Leu Ser Thr Ser Met Lys Glu Glu Asp Asn Pro His Arg His Gly
            210                 215                 220

Ser Ser Thr Glu Asn Asp Leu Ser Leu Val Trp Pro Glu Met Val Phe
225                 230                 235                 240

Glu Glu Asp Tyr His His Gln Ala Ser Tyr Val Asn Gly Lys Thr Ser
                245                 250                 255

Thr Ser Ile Asp Val Leu Gly Ser Gln Asp Leu Met Val Phe Gly Gly
            260                 265                 270

Gly Gly Asp Phe Glu Phe Ser Glu Asn Glu His Phe Ser Ile Phe Ser
            275                 280                 285

Ser Cys Ser Asn Leu Ser
        290

<210> SEQ ID NO 3
<211> LENGTH: 1212
<212> TYPE: DNA
<213> ORGANISM: Arabidopsis thaliana
<220> FEATURE:
<223> OTHER INFORMATION: G759

<400> SEQUENCE: 3
aaaaaatatg gtatccaag aaactgaccc gttaacgcaa ttgagtttac caccgggttt       60
ccgattttac ccgaccgatg aagagcttat ggttcaatat ctctgtagaa aagcagctgg     120
ttacgatttc tctcttcagc tcatcgccga aatagatctt tacaaattcg atccatgggt    180
tttaccaaat aaagcattat ttggagaaaa agaatggtat ttttttagtc ctagggatag    240
aaaatatcca aacgggtcaa gacctaaccg ggttgccgga tcgggttatt ggaaagctac    300
gggtacggat aaataatct cgacggaagg acaaagagtt ggtattaaaa aagctttggt     360
gttttacatc ggaaaagctc taaaggtac taaaaccaat tggatcatgc atgagtatcg      420
tctcattgaa ccttctcgta gaacggaag cactaagttg gatgattggg ttctatgtcg      480
aatatacaag aagcaatcaa gtgcacaaaa acaagtttac gataatggaa tcgcgaatgc    540
tagagaattc agcaacaacg gtacttcgtc cacgacgtcg tcttcttctc actttgaaga    600
cgttcttgat tcgtttcatc aagagatcga caacagaaat ttccagtttt ctaacccaaa    660
ccgcatctcg tcgctcagac cggacttaac cgaacagaaa accgggttcc acggtcttgc    720
ggatacttct aacttcgatt gggctagttt tgccggtaat gttgagcata taactcggt    780 accggaactc ggaatgagtc atgttgttcc taatctcgag tacaactgtg ctacctgaa     840 gacggaggag gaagtcgaga gcagtcacgg gtttaataac tcgggcgagt tagctcaaaa    900
gggttatggt gttgactcgt ttgggtattc ggggcaagtt ggtgggtttg ggtttatgtg    960
atgatgaaat gctgacgcaa taaaataag tcgttaattt ttgtcccgtg gcaaatctta    1020
tatgtatttg aatttcaatt cttttgggtt aagagggaga ctcatagatt tagatgtaga   1080
tttgtaatct ttcatgcata gaaatttga cgaatagatt tcgtaacttt attttgttgc    1140
tgtttggtta tctttgtatt ggtataaatt tagtggattg aaattgcata ttgaaaaaaa   1200
aaaaaaaaaa aa                                                       1212

<210> SEQ ID NO 4
<211> LENGTH: 317
<212> TYPE: PRT
<213> ORGANISM: Arabidopsis thaliana
<220> FEATURE:
```

<223> OTHER INFORMATION: G759

<400> SEQUENCE: 4

```
Met Gly Ile Gln Glu Thr Asp Pro Leu Thr Gln Leu Ser Leu Pro Pro
 1               5                  10                  15

Gly Phe Arg Phe Tyr Pro Thr Asp Glu Glu Leu Met Val Gln Tyr Leu
             20                  25                  30

Cys Arg Lys Ala Ala Gly Tyr Asp Phe Ser Leu Gln Leu Ile Ala Glu
         35                  40                  45

Ile Asp Leu Tyr Lys Phe Asp Pro Trp Val Leu Pro Asn Lys Ala Leu
 50                  55                  60

Phe Gly Glu Lys Glu Trp Tyr Phe Phe Ser Pro Arg Asp Arg Lys Tyr
 65                  70                  75                  80

Pro Asn Gly Ser Arg Pro Asn Arg Val Ala Gly Ser Gly Tyr Trp Lys
                 85                  90                  95

Ala Thr Gly Thr Asp Lys Ile Ile Ser Thr Glu Gly Gln Arg Val Gly
            100                 105                 110

Ile Lys Lys Ala Leu Val Phe Tyr Ile Gly Lys Ala Pro Lys Gly Thr
        115                 120                 125

Lys Thr Asn Trp Ile Met His Glu Tyr Arg Leu Ile Glu Pro Ser Arg
130                 135                 140

Arg Asn Gly Ser Thr Lys Leu Asp Asp Trp Val Leu Cys Arg Ile Tyr
145                 150                 155                 160

Lys Lys Gln Ser Ser Ala Gln Lys Gln Val Tyr Asp Asn Gly Ile Ala
                165                 170                 175

Asn Ala Arg Glu Phe Ser Asn Asn Gly Thr Ser Ser Thr Thr Ser Ser
            180                 185                 190

Ser Ser His Phe Glu Asp Val Leu Asp Ser Phe His Gln Glu Ile Asp
        195                 200                 205

Asn Arg Asn Phe Gln Phe Ser Asn Pro Asn Arg Ile Ser Ser Leu Arg
210                 215                 220

Pro Asp Leu Thr Glu Gln Lys Thr Gly Phe His Gly Leu Ala Asp Thr
225                 230                 235                 240

Ser Asn Phe Asp Trp Ala Ser Phe Ala Gly Asn Val Glu His Asn Asn
                245                 250                 255

Ser Val Pro Glu Leu Gly Met Ser His Val Val Pro Asn Leu Glu Tyr
            260                 265                 270

Asn Cys Gly Tyr Leu Lys Thr Glu Glu Val Glu Ser Ser His Gly
        275                 280                 285

Phe Asn Asn Ser Gly Glu Leu Ala Gln Lys Gly Tyr Gly Val Asp Ser
290                 295                 300

Phe Gly Tyr Ser Gly Gln Val Gly Gly Phe Gly Phe Met
305                 310                 315
```

<210> SEQ ID NO 5
<211> LENGTH: 1205
<212> TYPE: DNA
<213> ORGANISM: Arabidopsis thaliana
<220> FEATURE:
<223> OTHER INFORMATION: G185

<400> SEQUENCE: 5

| atgcaaaaat aaacatagta acaatacttt aaactattta caccacttta atcttattct | 60 |
|---|---|
| ccactctttg aacgtaatgg agaagaacca tagtagtgga gagtgggaga agatgaagaa | 120 |
| cgagatcaac gagctaatga tagaaggaag agactatgca caccagtttg gatcagcttc | 180 |

```
atctcaagaa acacgtgaac atttagccaa aagattctt caatcttacc acaagtctct      240
caccatcatg aactactccg gcgaacttga ccaagtttct cagggtggag aagccccaa      300
gagcgatgat tccgatcaag aaccacttgt catcaagagt cgaagaagt caatgccaag     360
gtggagttca aaagtcagaa ttgcccctgg agctggtgtt gatagaacgc tggacgatgg     420
attcagttgg agaaagtacg gccagaagga tattctcgga gccaaatttc caagaggata     480
ctatagatgc acgtatagaa agtctcaagg atgtgaagcc actaaacaag tccaaagatc     540
tgatgaaaat cagatgctcc ttgagatcag ttaccgagga atacattctt gctctcaagc     600
tgcaaatgtc ggtacaacaa tgccgataca aaacctcgaa ccgaaccaga cccaagaaca     660
cggaaatctt gacatggtaa aggaaagtgt agacaactac aatcaccaag cacatttgca     720
tcacaacctt cactatccat tgtcatctac cccaaatcta gagaataaca atgcctatat     780
gcttcaaatg cgagatcaaa acatcgaata ttttggatct acgagcttct ctagtgatct     840
aggaactagt atcaactaca attttccagc atctggctcg gcttctcact cagcatcaaa     900
ctctccgtcc accgtccctt tggaatcccc gtttgaaagc tatgatccaa atcatccata     960
tggaggattt ggtgggttct attcttagtt atctacttaa gggagggacg gaacttttta   1020
catgacctct tgattaaaga gagagttttc ataatagcta atcaatttcc tattcaaata   1080
tccgagtttt ttttctaatc atgtttatca attgtcttat tacagaaggc ttattttcag   1140
gtctatgttg aaataaatgg atttgtactc gtaggtatga tccttgttat ctaaaaaaaa   1200
aaaaa                                                                1205

<210> SEQ ID NO 6
<211> LENGTH: 303
<212> TYPE: PRT
<213> ORGANISM: Arabidopsis thaliana
<220> FEATURE:
<223> OTHER INFORMATION: G185

<400> SEQUENCE: 6

Met Glu Lys Asn His Ser Ser Gly Glu Trp Glu Lys Met Lys Asn Glu
 1               5                  10                  15

Ile Asn Glu Leu Met Ile Glu Gly Arg Asp Tyr Ala His Gln Phe Gly
                20                  25                  30

Ser Ala Ser Gln Glu Thr Arg Glu His Leu Ala Lys Lys Ile Leu
        35                  40                  45

Gln Ser Tyr His Lys Ser Leu Thr Ile Met Asn Tyr Ser Gly Glu Leu
    50                  55                  60

Asp Gln Val Ser Gln Gly Gly Ser Pro Lys Ser Asp Asp Ser Asp
65                  70                  75                  80

Gln Glu Pro Leu Val Ile Lys Ser Ser Lys Ser Met Pro Arg Trp
                85                  90                  95

Ser Ser Lys Val Arg Ile Ala Pro Gly Ala Gly Val Asp Arg Thr Leu
                100                 105                 110

Asp Asp Gly Phe Ser Trp Arg Lys Tyr Gly Gln Lys Asp Ile Leu Gly
            115                 120                 125

Ala Lys Phe Pro Arg Gly Tyr Tyr Arg Cys Thr Tyr Arg Lys Ser Gln
        130                 135                 140

Gly Cys Glu Ala Thr Lys Gln Val Gln Arg Ser Asp Glu Asn Gln Met
145                 150                 155                 160

Leu Leu Glu Ile Ser Tyr Arg Gly Ile His Ser Cys Ser Gln Ala Ala
                165                 170                 175
```

Asn Val Gly Thr Thr Met Pro Ile Gln Asn Leu Glu Pro Asn Gln Thr
            180                 185                 190

Gln Glu His Gly Asn Leu Asp Met Val Lys Glu Ser Val Asp Asn Tyr
        195                 200                 205

Asn His Gln Ala His Leu His His Asn Leu His Tyr Pro Leu Ser Ser
    210                 215                 220

Thr Pro Asn Leu Glu Asn Asn Ala Tyr Met Leu Gln Met Arg Asp
225                 230                 235                 240

Gln Asn Ile Glu Tyr Phe Gly Ser Thr Ser Phe Ser Ser Asp Leu Gly
                245                 250                 255

Thr Ser Ile Asn Tyr Asn Phe Pro Ala Ser Gly Ser Ala Ser His Ser
            260                 265                 270

Ala Ser Asn Ser Pro Ser Thr Val Pro Leu Glu Ser Pro Phe Glu Ser
        275                 280                 285

Tyr Asp Pro Asn His Pro Tyr Gly Gly Phe Gly Gly Phe Tyr Ser
    290                 295                 300

```
<210> SEQ ID NO 7
<211> LENGTH: 1557
<212> TYPE: DNA
<213> ORGANISM: Arabidopsis thaliana
<220> FEATURE:
<223> OTHER INFORMATION: G629

<400> SEQUENCE: 7
cgaaatgaaa aaattctctg tattaccaga aacgtgtttc ataagcatct ttaactcttc      60
agctctcaaa ttcttcatga atatctctgc ttatcggatc aagtgagagc aaatgcaatt     120
tttaagagcc agctattgga tctataactg aagaggatat atatagagat gatgagttct     180
tcttctccaa cacaacttgc atctttaaga gacatgggaa tctatgagcc atttcaacaa     240
attgtcggtt ggggaaatgt tttcaaatct gatatcaatg atcatagtcc caatactgct     300
acttcctcta ttattcaggt tgatcctaga attgatgatc acaacaacaa catcaagata     360
aattatgatt cttctcataa ccagatcgaa gcagaacaac cttctagtaa tgataatcaa     420
gatgatgatg caggattca tgataagatg aaacggcgtt tagcgcagaa ccgagaagcg      480
gctcgcaaaa gtcgtttgag aaagaaggct tatgttcagc agttagagga aagccggtta     540
aagttatcgc agttagagca agaactcgaa aaggttaagc agcagggcca tttaggacca     600
tctgggagta ttaacacagg gattgcatca tttgagatgg aatattcaca ctggctacaa     660
gaacaaagca agaagttag cgaactacga acagcgcttc aatctcatat aagcgacata      720
gaactcaaga tgctagtaga gagttgcttg aaccattacg ctaatctttt ccgaatgaaa     780
tccgatgcag caaaagccga tgttttctac ttgatatcgg aatgtggcg aacttcaacc      840 gaaagattct tccaatggat tggagggttt cgtccatccg aacttttaaa cgttgtgatg     900
ccttatcttc aaccattaac ggatcaacaa atcttggaag tgagaaacct ccaacaatca     960
tcacaacaag cagaggatgc tctgtctcaa gggattgata aacttcaaca gagtttagct    1020
gaaagcattg tgattgatgc ggttatcgag tccacgcatt atcccactca catggctgca    1080
gctatagaga atcttcaagc attagaagga tttgtgaatc aagcagatca tctgaggcaa    1140
caaactttgc aacaaatggc gaagatctta acgacaagac aatcggctcg aggtttacta    1200
gctttaggag agtatcttca tagacttcgt gctcttagtt ctctttgggc agctcgtcca    1260
caagaaccaa cttaaaagag gaacttatta aaactttaaa aacaagaaac agcagaatca    1320
```

-continued

```
aaagtcttga agaagcatac tcatcacaaa gcttggaagg atgttttaaa aaagatcttt    1380
gttaattaag tagagtgaga ttctcttgat tagaacttta tggttttttgc tttatgaagt   1440 atctctccag agaagattgt aaatttgggt tgaaactttg taatatatta agatccacca   1500
aataagtttg aaatctgagc aatttgataa taaaaaaaaa aaaaaaaaaa aaaaaaa      1557

<210> SEQ ID NO 8
<211> LENGTH: 368
<212> TYPE: PRT
<213> ORGANISM: Arabidopsis thaliana
<220> FEATURE:
<223> OTHER INFORMATION: G629

<400> SEQUENCE: 8

Met Met Ser Ser Ser Pro Thr Gln Leu Ala Ser Leu Arg Asp Met
  1               5                  10                  15

Gly Ile Tyr Glu Pro Phe Gln Gln Ile Val Gly Trp Gly Asn Val Phe
                 20                  25                  30

Lys Ser Asp Ile Asn Asp His Ser Pro Asn Thr Ala Thr Ser Ser Ile
             35                  40                  45

Ile Gln Val Asp Pro Arg Ile Asp Asp His Asn Asn Asn Ile Lys Ile
         50                  55                  60

Asn Tyr Asp Ser Ser His Asn Gln Ile Glu Ala Glu Gln Pro Ser Ser
 65                  70                  75                  80

Asn Asp Asn Gln Asp Asp Asp Gly Arg Ile His Asp Lys Met Lys Arg
                 85                  90                  95

Arg Leu Ala Gln Asn Arg Glu Ala Ala Arg Lys Ser Arg Leu Arg Lys
            100                 105                 110

Lys Ala Tyr Val Gln Gln Leu Glu Glu Ser Arg Leu Lys Leu Ser Gln
        115                 120                 125

Leu Glu Gln Glu Leu Glu Lys Val Lys Gln Gln Gly His Leu Gly Pro
    130                 135                 140

Ser Gly Ser Ile Asn Thr Gly Ile Ala Ser Phe Glu Met Glu Tyr Ser
145                 150                 155                 160

His Trp Leu Gln Glu Gln Ser Arg Arg Val Ser Glu Leu Arg Thr Ala
                165                 170                 175

Leu Gln Ser His Ile Ser Asp Ile Glu Leu Lys Met Leu Val Glu Ser
            180                 185                 190

Cys Leu Asn His Tyr Ala Asn Leu Phe Arg Met Lys Ser Asp Ala Ala
        195                 200                 205

Lys Ala Asp Val Phe Tyr Leu Ile Ser Gly Met Trp Arg Thr Ser Thr
    210                 215                 220

Glu Arg Phe Phe Gln Trp Ile Gly Gly Phe Arg Pro Ser Glu Leu Leu
225                 230                 235                 240

Asn Val Val Met Pro Tyr Leu Gln Pro Leu Thr Asp Gln Gln Ile Leu
                245                 250                 255

Glu Val Arg Asn Leu Gln Gln Ser Ser Gln Gln Ala Glu Asp Ala Leu
            260                 265                 270

Ser Gln Gly Ile Asp Lys Leu Gln Gln Ser Leu Ala Glu Ser Ile Val
        275                 280                 285

Ile Asp Ala Val Ile Glu Ser Thr His Tyr Pro Thr His Met Ala Ala
    290                 295                 300

Ala Ile Glu Asn Leu Gln Ala Leu Glu Gly Phe Val Asn Gln Ala Asp
305                 310                 315                 320

His Leu Arg Gln Gln Thr Leu Gln Gln Met Ala Lys Ile Leu Thr Thr
```

```
                      325                 330                 335
Arg Gln Ser Ala Arg Gly Leu Leu Ala Leu Gly Glu Tyr Leu His Arg
                340                 345                 350

Leu Arg Ala Leu Ser Ser Leu Trp Ala Ala Arg Pro Gln Glu Pro Thr
            355                 360                 365

<210> SEQ ID NO 9
<211> LENGTH: 627
<212> TYPE: DNA
<213> ORGANISM: Arabidopsis thaliana
<220> FEATURE:
<223> OTHER INFORMATION: G435

<400> SEQUENCE: 9
aacaaaagaa aaacaaaaa agaagagaaa aatggagaat tctcagagtc agggtaaaaa      60
caagaagaag aggctaacac aagatcaagt tagacaactg gagaagtgct tcactatgaa     120
caagaagctt gagccagatc tgaaacttca actgtcgaac cagcttggtc tacctcaaag    180
acaagtcgct gtctggttcc aaaacaagcg agccaggttc aagactcagt ctcttgaggt    240
ccaacactgc actcttcagt ccaagcacga agcagctctc tccgacaagg caaagttaga    300
gcatcaagtg cagtttctcc aagatgagct gaagagagca aggaatcagc ttgctctgtt    360
cacaaatcaa gattctcctg ttgataattc taatcttggt tcttgtgatg aagatcatga    420
tgatcaagtg gtggtattcg acgagcttta cgcttgcttt gttagcaatg gacatggatc    480
ttcatcaacc tcatgggtct gattctgttt cgacgcagac aagattccaa tatatatagt    540
cttgtctctg ttttgtttcg tttgatctgt ttctctttgt ctgaatagat ttaaaatttg    600
taattaaagt cattcagaca ttcacta                                         627

<210> SEQ ID NO 10
<211> LENGTH: 156
<212> TYPE: PRT
<213> ORGANISM: Arabidopsis thaliana
<220> FEATURE:
<223> OTHER INFORMATION: G435

<400> SEQUENCE: 10

Met Glu Asn Ser Gln Ser Gln Gly Lys Asn Lys Lys Arg Leu Thr
 1               5                  10                  15

Gln Asp Gln Val Arg Gln Leu Glu Lys Cys Phe Thr Met Asn Lys Lys
            20                  25                  30

Leu Glu Pro Asp Leu Lys Leu Gln Leu Ser Asn Gln Leu Gly Leu Pro
        35                  40                  45

Gln Arg Gln Val Ala Val Trp Phe Gln Asn Lys Arg Ala Arg Phe Lys
    50                  55                  60

Thr Gln Ser Leu Glu Val Gln His Cys Thr Leu Gln Ser Lys His Glu
65                  70                  75                  80

Ala Ala Leu Ser Asp Lys Ala Lys Leu Glu His Gln Val Gln Phe Leu
                85                  90                  95

Gln Asp Glu Leu Lys Arg Ala Arg Asn Gln Leu Ala Leu Phe Thr Asn
            100                 105                 110

Gln Asp Ser Pro Val Asp Asn Ser Asn Leu Gly Ser Cys Asp Glu Asp
        115                 120                 125

His Asp Asp Gln Val Val Val Phe Asp Glu Leu Tyr Ala Cys Phe Val
    130                 135                 140

Ser Asn Gly His Gly Ser Ser Thr Ser Trp Val
145                 150                 155
```

<210> SEQ ID NO 11
<211> LENGTH: 1577
<212> TYPE: DNA
<213> ORGANISM: Arabidopsis thaliana
<220> FEATURE:
<223> OTHER INFORMATION: G4

<400> SEQUENCE: 11

```
aaagaatcga atatttatta tttcgccccg aagattctat ttctgatcat ttacacccct      60
aaaagagta gagctttcgt gaagccacca tgtgtggagg agctataatc tccgatttca     120
tacctccgcc gaggtccctc cgcgtcacta acgagtttat ctggccggat ctgaaaaaca     180
aagtgaaagc ttcaaagaag agatcgaata agcgatccga tttcttcgat cttgacgatg     240
atttcgaagc tgatttccaa gggtttaagg atgactcggc ttttgactgc gaagacgatg     300
atgatgtctt cgtcaatgtt aagccttccg tcttcaccgc aactactaag cccgtagctt     360
ccgctttcgt ctccactgta ggttcagcat gccaagaa actgtagag tccgctgagc       420
aagctgagaa atcttctaag aggaagagga agaatcaata ccgagggatt aggcagcgtc     480
cttggggaaa atgggctgcg gagatccgtg atccgagaaa aggctcccga aatggcttg     540
gaacattcga cactgctgag gaagcagcaa gagcttatga tgctgcagca cgcagaatcc     600
gtggcacgaa agctaaggtg aattttcccg aggagaagaa ccctagcgtc gtatcccaga     660
aacgtcctag tgctaagact aataatcttc agaaatcagt ggctaaacca acaaaagcg     720
taactttggt tcagcagcca acacatctga gtcagcagta ctgcaacaac tcctttgaca     780
actcttttgg tgatatgagt ttcatggaag agaagcctca gatgtacaac aatcagtttg     840
ggttaacaaa ctcgttcgat gctggaggta acaatggata ccagtatttc agttccgatc     900
agggcagtaa ctccttcgac tgttctgagt tcgggtggag tgatcacggc cctaaaacac     960
ccgagatctc ttcaatgctt gtcaataaca acgaagcatc atttgttgaa gaaaccaatg    1020
cagccaagaa gctcaaacca aactctgatg agtcagacga tctgatggca taccttgaca    1080
acgccttgtg ggacacccca ctagaagtgg aagccatgct tggcgcagat gctggtgctg    1140
tgactcagga gaggaaaac ccagtggagc tatggagctt agatgagatc aatttcatgc    1200
tggaaggaga cttttgaagt gatcgatggt tccttagttt gtaaataaag ctgtgttgga    1260
ttttgctgtt ggggatggt acaagtcaca cctcaagctc tatgcattgg tatctcatga    1320
gccttctctt ccatagagag tttctctttt aattttgtcg aaataaaaaa ggtgtgatga    1380
agtaaataga ggtataataa tatctatcta ttaagtcttg ttttgttctt tcattttgt    1440
atttcttttc tatttaaaag acagtttatt agtcttctga gctctctttt tgatctttgt    1500
tatagcgtat catcaccctc gaaagtgtaa tgttttgtac ccccaaactt gtttagcatt    1560
ataataaagt ctctttg                                                  1577
```

<210> SEQ ID NO 12
<211> LENGTH: 375
<212> TYPE: PRT
<213> ORGANISM: Arabidopsis thaliana
<220> FEATURE:
<223> OTHER INFORMATION: G4

<400> SEQUENCE: 12

```
Met Cys Gly Gly Ala Ile Ile Ser Asp Phe Ile Pro Pro Arg Ser
 1               5                  10                  15

Leu Arg Val Thr Asn Glu Phe Ile Trp Pro Asp Leu Lys Asn Lys Val
```

|  | 20 |  |  |  | 25 |  |  |  | 30 |  |  |
|---|---|---|---|---|---|---|---|---|---|---|---|

Lys Ala Ser Lys Lys Arg Ser Asn Lys Arg Ser Asp Phe Phe Asp Leu
             35                  40                  45

Asp Asp Asp Phe Glu Ala Asp Phe Gln Gly Phe Lys Asp Asp Ser Ala
 50                  55                  60

Phe Asp Cys Glu Asp Asp Asp Val Phe Val Asn Val Lys Pro Phe
 65                  70                  75                  80

Val Phe Thr Ala Thr Thr Lys Pro Val Ala Ser Ala Phe Val Ser Thr
                 85                  90                  95

Val Gly Ser Ala Tyr Ala Lys Lys Thr Val Glu Ser Ala Glu Gln Ala
                100                 105                 110

Glu Lys Ser Ser Lys Arg Lys Arg Lys Asn Gln Tyr Arg Gly Ile Arg
            115                 120                 125

Gln Arg Pro Trp Gly Lys Trp Ala Ala Glu Ile Arg Asp Pro Arg Lys
130                 135                 140

Gly Ser Arg Glu Trp Leu Gly Thr Phe Asp Thr Ala Glu Glu Ala Ala
145                 150                 155                 160

Arg Ala Tyr Asp Ala Ala Ala Arg Arg Ile Arg Gly Thr Lys Ala Lys
                165                 170                 175

Val Asn Phe Pro Glu Glu Lys Asn Pro Ser Val Val Ser Gln Lys Arg
            180                 185                 190

Pro Ser Ala Lys Thr Asn Asn Leu Gln Lys Ser Val Ala Lys Pro Asn
        195                 200                 205

Lys Ser Val Thr Leu Val Gln Gln Pro Thr His Leu Ser Gln Gln Tyr
    210                 215                 220

Cys Asn Asn Ser Phe Asp Asn Ser Phe Gly Asp Met Ser Phe Met Glu
225                 230                 235                 240

Glu Lys Pro Gln Met Tyr Asn Asn Gln Phe Gly Leu Thr Asn Ser Phe
                245                 250                 255

Asp Ala Gly Gly Asn Asn Gly Tyr Gln Tyr Phe Ser Ser Asp Gln Gly
            260                 265                 270

Ser Asn Ser Phe Asp Cys Ser Glu Phe Gly Trp Ser Asp His Gly Pro
        275                 280                 285

Lys Thr Pro Glu Ile Ser Ser Met Leu Val Asn Asn Asn Glu Ala Ser
    290                 295                 300

Phe Val Glu Glu Thr Asn Ala Ala Lys Lys Leu Lys Pro Asn Ser Asp
305                 310                 315                 320

Glu Ser Asp Asp Leu Met Ala Tyr Leu Asp Asn Ala Leu Trp Asp Thr
                325                 330                 335

Pro Leu Glu Val Glu Ala Met Leu Gly Ala Asp Ala Gly Ala Val Thr
            340                 345                 350

Gln Glu Glu Glu Asn Pro Val Glu Leu Trp Ser Leu Asp Glu Ile Asn
        355                 360                 365

Phe Met Leu Glu Gly Asp Phe
    370                 375

<210> SEQ ID NO 13
<211> LENGTH: 903
<212> TYPE: DNA
<213> ORGANISM: Arabidopsis thaliana
<220> FEATURE:
<223> OTHER INFORMATION: G1035

<400> SEQUENCE: 13
ccataataat atattaaaac tatatactat aatcttttta cataataaac tttgggtcct    60

```
gcgtcttaat catagtactt aattttctct gtgtgtttta atatgaataa taaaactgaa      120
atgggatctt ccacaagtgg aaattgctcg tcggtttcaa ccactggttt agctaactcc      180
ggttcagaat ctgatctccg caacgtgat ctaatcgacg agcggaagag aaagaggaaa       240
cagtcgaaca gagaatctgc gaggaggtcg aggatgagga agcagaagca tttggatgat     300
ctcactgctc aggtgactca tctacgtaaa gaaaacgctc agatcgtcgc cggaatcgcc     360
gtcacgacgc agcactacgt cactatcgag gcggagaacg acattctcag agctcaggtt    420
cttgaactta accaccgtct ccaatctctt aacgagatcg ttgatttcgt cgaatcttct     480
tcttcaggat tcggtatgga gaccggtcag ggattattcg acggtggatt attcgacggc     540
gtgatgaatc ctatgaatct agggttttat aatcaaccaa tcatggcttc tgcttctact     600
gctggtgatg tttttcaactg ttagaaaact tcacatcatt atcatcgtga gtgagactaa    660
tcatcgcagc aggggtaaaa ctgtaatttt tcttataaat tatgtgatga tgctttgttt      720
ctttatttta taagatggtt aattagtgtt taaaactgat tgtaatgata gacagtgtaa      780
gaaatgtgtg atatcatgga gatggtgatg tgagtttggt acaaatattt taagatcttt     840
tctttctata tattaaaagt gaagaaataa tatttttgtca ttttcttaaa aaaaaaaaa      900 aaa                                                                    903
```

<210> SEQ ID NO 14
<211> LENGTH: 173
<212> TYPE: PRT
<213> ORGANISM: Arabidopsis thaliana
<220> FEATURE:
<223> OTHER INFORMATION: G1035

<400> SEQUENCE: 14

Met Asn Asn Lys Thr Glu Met Gly Ser Ser Thr Ser Gly Asn Cys Ser
 1               5                  10                  15

Ser Val Ser Thr Thr Gly Leu Ala Asn Ser Gly Ser Glu Ser Asp Leu
            20                  25                  30

Arg Gln Arg Asp Leu Ile Asp Glu Arg Lys Arg Lys Arg Lys Gln Ser
        35                  40                  45

Asn Arg Glu Ser Ala Arg Arg Ser Arg Met Arg Lys Gln Lys His Leu
    50                  55                  60

Asp Asp Leu Thr Ala Gln Val Thr His Leu Arg Lys Glu Asn Ala Gln
65                  70                  75                  80

Ile Val Ala Gly Ile Ala Val Thr Thr Gln His Tyr Val Thr Ile Glu
                85                  90                  95

Ala Glu Asn Asp Ile Leu Arg Ala Gln Val Leu Glu Leu Asn His Arg
            100                 105                 110

Leu Gln Ser Leu Asn Glu Ile Val Asp Phe Val Glu Ser Ser Ser Ser
        115                 120                 125

Gly Phe Gly Met Glu Thr Gly Gln Gly Leu Phe Asp Gly Gly Leu Phe
    130                 135                 140

Asp Gly Val Met Asn Pro Met Asn Leu Gly Phe Tyr Asn Gln Pro Ile
145                 150                 155                 160

Met Ala Ser Ala Ser Thr Ala Gly Asp Val Phe Asn Cys
                165                 170

<210> SEQ ID NO 15
<211> LENGTH: 724
<212> TYPE: DNA
<213> ORGANISM: Arabidopsis thaliana

<220> FEATURE:
<223> OTHER INFORMATION: G179

<400> SEQUENCE: 15

| gtctttctct | ccctcccctc | cttggctttt | ttcaagttcc | caccataaac | gcagagggag | 60 |
| ttaagaaatg | gaggatagga | ggtgtgatgt | gttgtttcca | tgttcatcat | cggttgatcc | 120 |
| tcgcttgaca | gagtttcatg | gggtcgacaa | ctctgctcag | ccgacaacat | catccgaaga | 180 |
| gaagccaagg | agtaagaaga | agaagaaaga | gagagaagcg | aggtacgcgt | tccagacaag | 240 |
| aagccaggtt | gatatactgg | atgatggata | caggtggagg | aagtacggcc | aaaaagcagt | 300 |
| caagaacaat | ccattcccca | ggagctatta | taagtgcaca | gaagaaggat | gcagagtgaa | 360 |
| gaagcaagtg | cagaggcaat | ggggagacga | aggagtggtg | gtgacgacat | accaaggtgt | 420 |
| tcatacacat | gccgttgata | aaccctctga | taatttccac | cacatcttga | cacaaatgca | 480 |
| catcttccct | cccttttgct | tgaaggaatg | attagaggaa | ttggattgta | atatttactt | 540 |
| tcccaaaaac | gttgggctca | caccatcaga | cctttacttt | taaactagca | gcaactcaca | 600 |
| tatctcaaaa | atactaatcc | ttatctttgt | ctttatggga | cctttgaatc | catctgcttt | 660 |
| ggtgtcttag | tctcggctgc | cctgtaatcg | aaagtatatt | catcatcaaa | ttaccaaaca | 720 |
| taaa | | | | | | 724 |

<210> SEQ ID NO 16
<211> LENGTH: 147
<212> TYPE: PRT
<213> ORGANISM: Arabidopsis thaliana
<220> FEATURE:
<223> OTHER INFORMATION: G179

<400> SEQUENCE: 16

Met Glu Asp Arg Arg Cys Asp Val Leu Phe Pro Cys Ser Ser Val
1               5                   10                  15
Asp Pro Arg Leu Thr Glu Phe His Gly Val Asp Asn Ser Ala Gln Pro
            20                  25                  30
Thr Thr Ser Ser Glu Glu Lys Pro Arg Ser Lys Lys Lys Lys Glu
        35                  40                  45
Arg Glu Ala Arg Tyr Ala Phe Gln Thr Arg Ser Gln Val Asp Ile Leu
    50                  55                  60
Asp Asp Gly Tyr Arg Trp Arg Lys Tyr Gly Gln Lys Ala Val Lys Asn
65                  70                  75                  80
Asn Pro Phe Pro Arg Ser Tyr Tyr Lys Cys Thr Glu Gly Cys Arg
                85                  90                  95
Val Lys Lys Gln Val Gln Arg Gln Trp Gly Asp Glu Gly Val Val Val
            100                 105                 110
Thr Thr Tyr Gln Gly Val His Thr His Ala Val Asp Lys Pro Ser Asp
        115                 120                 125
Asn Phe His His Ile Leu Thr Gln Met His Ile Phe Pro Pro Phe Cys
    130                 135                 140
Leu Lys Glu
145

<210> SEQ ID NO 17
<211> LENGTH: 964
<212> TYPE: DNA
<213> ORGANISM: Arabidopsis thaliana
<220> FEATURE:
<223> OTHER INFORMATION: G28

-continued

```
<400> SEQUENCE: 17
gaaatctcaa caagaaccaa accaaacaac aaaaaaacat tcttaataat tatctttctg      60
ttatgtcgat gacggcggat tctcaatctg attatgcttt tcttgagtcc atacgacgac     120
acttactagg agaatcggag ccgatactca gtgagtcgac agcgagttcg gttactcaat     180
cttgtgtaac cggtcagagc attaaaccgg tgtacgacg aaaccctagc tttagcaaac      240
tgtatccttg cttcaccgag agctggggag atttgccgtt gaaagaaaac gattctgagg     300
atatgttagt ttacggtatc ctcaacgacg cctttcacgg cggttgggag ccgtcttctt     360
cgtcttccga cgaagatcgt agctctttcc cgagtgttaa gatcgagact ccggagagtt     420
tcgcggcggt ggattctgtt ccggtcaaga aggagaagac gagtcctgtt tcggcggcgg     480
tgacggcggc gaagggaaag cattatagag gagtgagaca aaggccgtgg gggaaatttg     540
cggcggagat tagagatccg gcgaagaacg gagctagggt ttggttagga acgtttgaga     600
cggcggagga cgcggcgttg gcttacgaca gagctgcttt caggatgcgt ggttcccgcg     660
ctttgttgaa ttttccgttg agagttaatt caggagaacc cgacccggtt cgaatcaagt     720
ccaagagatc ttcttttttct tcttctaacg agaacggagc tccgaagaag aggagaacgg     780
tggccgccgg tggtggaatg gataagggat tgacggtgaa gtgcgaggtt gttgaagtgg     840
cacgtggcga tcgtttattg gttttataat tttgattttt ctttgttgga tgattatatg     900
attcttcaaa aagaagaac gttaataaaa aaattcgttt attattaaaa aaaaaaaaa       960
aaaa                                                                  964

<210> SEQ ID NO 18
<211> LENGTH: 268
<212> TYPE: PRT
<213> ORGANISM: Arabidopsis thaliana
<220> FEATURE:
<223> OTHER INFORMATION: G28

<400> SEQUENCE: 18

Met Ser Met Thr Ala Asp Ser Gln Ser Asp Tyr Ala Phe Leu Glu Ser
  1               5                  10                  15

Ile Arg Arg His Leu Leu Gly Glu Ser Glu Pro Ile Leu Ser Glu Ser
             20                  25                  30

Thr Ala Ser Ser Val Thr Gln Ser Cys Val Thr Gly Gln Ser Ile Lys
         35                  40                  45

Pro Val Tyr Gly Arg Asn Pro Ser Phe Ser Lys Leu Tyr Pro Cys Phe
     50                  55                  60

Thr Glu Ser Trp Gly Asp Leu Pro Leu Lys Glu Asn Asp Ser Glu Asp
 65                  70                  75                  80

Met Leu Val Tyr Gly Ile Leu Asn Asp Ala Phe His Gly Gly Trp Glu
                 85                  90                  95

Pro Ser Ser Ser Ser Asp Glu Asp Arg Ser Ser Phe Pro Ser Val
            100                 105                 110

Lys Ile Glu Thr Pro Glu Ser Phe Ala Ala Val Asp Ser Val Pro Val
        115                 120                 125

Lys Lys Glu Lys Thr Ser Pro Val Ser Ala Ala Val Thr Ala Ala Lys
    130                 135                 140

Gly Lys His Tyr Arg Gly Val Arg Gln Arg Pro Trp Gly Lys Phe Ala
145                 150                 155                 160

Ala Glu Ile Arg Asp Pro Ala Lys Asn Gly Ala Arg Val Trp Leu Gly
                165                 170                 175
```

```
Thr Phe Glu Thr Ala Glu Asp Ala Ala Leu Ala Tyr Asp Arg Ala Ala
            180                 185                 190

Phe Arg Met Arg Gly Ser Arg Ala Leu Leu Asn Phe Pro Leu Arg Val
        195                 200                 205

Asn Ser Gly Glu Pro Asp Pro Val Arg Ile Lys Ser Lys Arg Ser Ser
210                 215                 220

Phe Ser Ser Asn Glu Asn Gly Ala Pro Lys Lys Arg Arg Thr Val
225                 230                 235                 240

Ala Ala Gly Gly Gly Met Asp Lys Gly Leu Thr Val Lys Cys Glu Val
                245                 250                 255

Val Glu Val Ala Arg Gly Asp Arg Leu Leu Val Leu
            260                 265

<210> SEQ ID NO 19
<211> LENGTH: 822
<212> TYPE: DNA
<213> ORGANISM: Arabidopsis thaliana
<220> FEATURE:
<223> OTHER INFORMATION: G1241

<400> SEQUENCE: 19
aagctgactc tagcagatct ggtaccgtcg acccacgcgt ccgctcttcc cttatcttct    60
tcttataccc ttcgaccaac gaagaaccct agaaatcgat taacaagatg aatagggaaa   120
agttgatgaa gatggctaac actgtccgca ctggcggaaa ggggacagta agaagaaaga   180
agaaggctgt tcacaagacc actacaaccg atgacaagag gctccagagc actcttaaga   240
gagttggagt caattccatt cccgccattg aagaagttaa cattttaag gatgatgtag    300
tcattcagtt cattaaccct aaagttcaag cttcaattgc tgctaacaca tgggttgtga   360
gtggtacacc acagacgaaa aaattgcaag acattcttcc tcagattatc agccaacttg   420
gaccagataa cttggacaac ctgaggaagc tagcagagca attccagaaa caagctccag   480
gtgcaggtga tgtcccagca acaatccaag aagaggacga tgatgatgat gtcccagatc   540
ttgtagtggg agagactttc gagacccctg ctactgaaga ggctcccaaa gctgctgctt   600
cttagaggag gaggaagaag aaggagaaga gctcacctgc aaaacccatc ataaaaatgt   660
tgtcgctcg acctcttctg agcactgtca gattcttgtt ttctctaatg cttgcgaaca    720
gaaagacttg gttttattat cacttgatgc ttttggtcc gaacagcaat tttccttta    780
ttaaggttag atcgcttttt gtttaaaaaa aaaaaaaaa aa                       822

<210> SEQ ID NO 20
<211> LENGTH: 165
<212> TYPE: PRT
<213> ORGANISM: Arabidopsis thaliana
<220> FEATURE:
<223> OTHER INFORMATION: G1241

<400> SEQUENCE: 20

Met Asn Arg Glu Lys Leu Met Lys Met Ala Asn Thr Val Arg Thr Gly
1               5                   10                  15

Gly Lys Gly Thr Val Arg Arg Lys Lys Ala Val His Lys Thr Thr
            20                  25                  30

Thr Thr Asp Asp Lys Arg Leu Gln Ser Thr Leu Lys Arg Val Gly Val
        35                  40                  45

Asn Ser Ile Pro Ala Ile Glu Glu Val Asn Ile Phe Lys Asp Asp Val
    50                  55                  60

Val Ile Gln Phe Ile Asn Pro Lys Val Gln Ala Ser Ile Ala Ala Asn
```

| | 65 | | | 70 | | | 75 | | | 80 | |
|---|---|---|---|---|---|---|---|---|---|---|---|

Thr Trp Val Val Ser Gly Thr Pro Gln Thr Lys Lys Leu Gln Asp Ile
                            85                            90                            95

Leu Pro Gln Ile Ile Ser Gln Leu Gly Pro Asp Asn Leu Asp Asn Leu
                   100                           105                      110

Arg Lys Leu Ala Glu Gln Phe Gln Lys Gln Ala Pro Gly Ala Gly Asp
        115                       120                           125

Val Pro Ala Thr Ile Gln Glu Glu Asp Asp Asp Asp Val Pro Asp
    130                       135                       140

Leu Val Val Gly Glu Thr Phe Glu Thr Pro Ala Thr Glu Glu Ala Pro
145                  150                       155                       160

Lys Ala Ala Ala Ser
            165

<210> SEQ ID NO 21
<211> LENGTH: 1055
<212> TYPE: DNA
<213> ORGANISM: Arabidopsis thaliana
<220> FEATURE:
<223> OTHER INFORMATION: G19

<400> SEQUENCE: 21

```
ataaaggcat tcagctcca ccgtaggaaa ctttctcttg aaagaaaccc acagcaacaa      60
acagagaaaa tgtgtggcgg tgctattatt ccgattatg cccctctcgt caccaaggcc     120
aagggccgta aactcacggc tgaggaactc tggtcagagc tcgatgcttc cgccgccgac    180
gacttctggg gtttctattc cacctccaaa ctccatccca ccaaccaagt taacgtgaaa    240
gaggaggcag tgaagaagga gcaggcaaca gagccgggga acggaggaa gaggaagaat     300
gtttatagag ggatacgtaa gcgtccatgg ggaaatggg cggctgagat tcgagatcca    360
cgaaaaggtg ttagagtttg gcttggtacg ttcaacacgg cggaggaagc tgccatggct    420
tatgatgttg cggccaagca gatccgtggt gataaagcca agctcaactt cccagatctg    480
caccatcctc ctcctcctaa ttatactcct ccgccgtcat cgccacgatc aaccgatcag    540
cctccggcga agaaggtctg cgttgtctct cagagtgaga gcgagttaag tcagccgagt    600
ttcccggtgg agtgtatagg atttggaaat ggggacgagt tcagaaacct gagttacgga    660
tttgagccgg attatgatct gaaacagcag atatcgagct ggaatcgtt ccttgagctg     720
gacggtaaca cggcggagca accgagtcag cttgatgagt ccgtttccga ggtggatatg    780
tggatgcttg atgatgtcat tgcgtcgtat gagtaaaaga aaaaaaataa gtttaaaaaa    840
agttaaataa agtctgtaat atatatgtaa ccgccgttac tttaaaagg tttttaccgt     900
cgcattggac tgctgatgat gtctgttgtg taatgtgtag aatgtgacca aatggacgtt    960
atattacggt ttgtggtatt attagtttct tagatggaaa aacttacatg tgtaaataag   1020
atttgtaatg taagacgaag tacttataac ttctt                             1055
```

<210> SEQ ID NO 22
<211> LENGTH: 248
<212> TYPE: PRT
<213> ORGANISM: Arabidopsis thaliana
<220> FEATURE:
<223> OTHER INFORMATION: G19

<400> SEQUENCE: 22

Met Cys Gly Gly Ala Ile Ile Ser Asp Tyr Ala Pro Leu Val Thr Lys
 1             5                    10                   15

| | | | | | | | | | | | |
|---|---|---|---|---|---|---|---|---|---|---|---|
|Ala|Lys|Gly|Arg|Lys|Leu|Thr|Ala|Glu|Glu|Leu|Trp|Ser|Glu|Leu|Asp|
| | | |20| | | | |25| | | | |30| | |

Ala Lys Gly Arg Lys Leu Thr Ala Glu Glu Leu Trp Ser Glu Leu Asp
             20                  25                  30

Ala Ser Ala Ala Asp Asp Phe Trp Gly Phe Tyr Ser Thr Ser Lys Leu
         35                  40                  45

His Pro Thr Asn Gln Val Asn Val Lys Glu Glu Ala Val Lys Lys Glu
     50                  55                  60

Gln Ala Thr Glu Pro Gly Lys Arg Arg Lys Arg Lys Asn Val Tyr Arg
 65              70                  75                  80

Gly Ile Arg Lys Arg Pro Trp Gly Lys Trp Ala Ala Glu Ile Arg Asp
                 85                  90                  95

Pro Arg Lys Gly Val Arg Val Trp Leu Gly Thr Phe Asn Thr Ala Glu
             100                 105                 110

Glu Ala Ala Met Ala Tyr Asp Val Ala Ala Lys Gln Ile Arg Gly Asp
         115                 120                 125

Lys Ala Lys Leu Asn Phe Pro Asp Leu His His Pro Pro Pro Asn
130                 135                 140

Tyr Thr Pro Pro Ser Ser Pro Arg Ser Thr Asp Gln Pro Pro Ala
145                 150                 155                 160

Lys Lys Val Cys Val Val Ser Gln Ser Glu Ser Leu Ser Gln Pro
                165                 170                 175

Ser Phe Pro Val Glu Cys Ile Gly Phe Gly Asn Gly Asp Glu Phe Gln
             180                 185                 190

Asn Leu Ser Tyr Gly Phe Glu Pro Asp Tyr Asp Leu Lys Gln Gln Ile
             195                 200                 205

Ser Ser Leu Glu Ser Phe Leu Glu Leu Asp Gly Asn Thr Ala Glu Gln
    210                 215                 220

Pro Ser Gln Leu Asp Glu Ser Val Ser Glu Val Asp Met Trp Met Leu
225                 230                 235                 240

Asp Asp Val Ile Ala Ser Tyr Glu
                245

<210> SEQ ID NO 23
<211> LENGTH: 914
<212> TYPE: DNA
<213> ORGANISM: Arabidopsis thaliana
<220> FEATURE:
<223> OTHER INFORMATION: G503

<400> SEQUENCE: 23

```
gaacatcaaa aactaacaca cagaaagaaa aaaacagtt cctgttccat tagattcttt    60
tctaaattgt ctgaaaatca tggaagtaac ttcccaatct accctccctc cagggttccg   120
atttcatcct accgacgaag aactcatcgt ttactatctc cgaaaccaga ccatgtctaa   180
accatgccct gtctccatca tcccagaagt tgatatctac aaattcgacc catggcaatt   240
acccgagaaa acagagtttg gagaaaatga gtggtatttc ttcagcccta gagaaagaaa   300
atatccaaac ggagtcagac caaaccgggc agctgtttcc ggttattgga agcaaccgg   360
tacagacaaa gccattcaca gcggttcgag taacgtaggt gtcaagaaag ctctcgtctt   420
ctacaaaggt agacctccta aaggaatcaa aactgactgg atcatgcatg agtatcgtct   480
ccatgattca cgtaaagcat caacgaaacg tagcggatct atgaggttag atgaatgggt   540
actatgtagg atatacaaga agagaggagc aagtaagctt ctgaatgagc aagagggttt   600
catggacgaa gtactaatgg aggatgagac caaagttgtt attaacgaag cagagagaag   660
aaatgatgaa gagataatga tgatgacgtc gatgaaactt ccaaggacgt gttcgctggc   720
```

```
tcatttgttg gaaatggatt acatgggacc cgtctctcac attgataatt ttagtcagtt      780
cgatcatctt catcaacctg attcggagtc tagttggttc ggggatctac agtttaacca      840
agacgagatc ttaaaccatc atcgtcaagc tatgtttaag ttttagtgat ggggtcagta      900
aaaaaaaaaa aaaa                                                        914
```

<210> SEQ ID NO 24
<211> LENGTH: 268
<212> TYPE: PRT
<213> ORGANISM: Arabidopsis thaliana
<220> FEATURE:
<223> OTHER INFORMATION: G503

<400> SEQUENCE: 24

```
Met Glu Val Thr Ser Gln Ser Thr Leu Pro Pro Gly Phe Arg Phe His
  1               5                  10                  15

Pro Thr Asp Glu Glu Leu Ile Val Tyr Tyr Leu Arg Asn Gln Thr Met
             20                  25                  30

Ser Lys Pro Cys Pro Val Ser Ile Ile Pro Glu Val Asp Ile Tyr Lys
         35                  40                  45

Phe Asp Pro Trp Gln Leu Pro Glu Lys Thr Glu Phe Gly Glu Asn Glu
     50                  55                  60

Trp Tyr Phe Phe Ser Pro Arg Glu Arg Lys Tyr Pro Asn Gly Val Arg
 65                  70                  75                  80

Pro Asn Arg Ala Ala Val Ser Gly Tyr Trp Lys Ala Thr Gly Thr Asp
                 85                  90                  95

Lys Ala Ile His Ser Gly Ser Ser Asn Val Gly Val Lys Lys Ala Leu
            100                 105                 110

Val Phe Tyr Lys Gly Arg Pro Pro Lys Gly Ile Lys Thr Asp Trp Ile
        115                 120                 125

Met His Glu Tyr Arg Leu His Asp Ser Arg Lys Ala Ser Thr Lys Arg
    130                 135                 140

Ser Gly Ser Met Arg Leu Asp Glu Trp Val Leu Cys Arg Ile Tyr Lys
145                 150                 155                 160

Lys Arg Gly Ala Ser Lys Leu Leu Asn Glu Gln Gly Phe Met Asp
                165                 170                 175

Glu Val Leu Met Glu Asp Glu Thr Lys Val Val Ile Asn Glu Ala Glu
            180                 185                 190

Arg Arg Asn Asp Glu Glu Ile Met Met Met Thr Ser Met Lys Leu Pro
        195                 200                 205

Arg Thr Cys Ser Leu Ala His Leu Leu Glu Met Asp Tyr Met Gly Pro
    210                 215                 220

Val Ser His Ile Asp Asn Phe Ser Gln Phe Asp His Leu His Gln Pro
225                 230                 235                 240

Asp Ser Glu Ser Ser Trp Phe Gly Asp Leu Gln Phe Asn Gln Asp Glu
                245                 250                 255

Ile Leu Asn His His Arg Gln Ala Met Phe Lys Phe
            260                 265
```

<210> SEQ ID NO 25
<211> LENGTH: 1121
<212> TYPE: DNA
<213> ORGANISM: Arabidopsis thaliana
<220> FEATURE:
<223> OTHER INFORMATION: G263

<400> SEQUENCE: 25

-continued

```
tttttagttt tattttttctg tggtaaaata aaaaaagttc gccggagatg acggctgtga      60
cggcggcgca aagatcagtt ccggcgccgt ttttaagcaa aacgtatcag ctagttgatg     120
atcatagcac agacgacgtc gtttcatgga acgaagaagg aacagctttt gtcgtgtgga     180
aaacagcaga gtttgctaaa gatcttcttc ctcaatactt caagcataat aatttctcaa     240
gcttcattcg tcagctcaac acttacggat ttcgtaaaac tgtaccggat aaatgggaat     300
ttgcaaacga ttatttccgg agaggcgggg aggatctgtt gacggacata cgacggcgta     360
aatcggtgat tgcttcaacg gcggggaaat gtgttgttgt tggttcgcct tctgagtcta     420
attctggtgg tggtgatgat cacggttcaa gctccacgtc atcacccggt tcgtcgaaga     480
atcctggttc ggtggagaac atggttgctg atttatcagg agagaacgag aagcttaaac     540
gtgaaaacaa taacttgagc tcggagctcg cggcggcgaa gaagcagcgc gatgagctag     600
tgacgttctt gacgggtcat ctgaaagtaa gaccggaaca aatcgataaa atgatcaaag     660
gagggaaatt taaaccggtg gagtctgacg aagagagtga gtgcgaaggt tgcgacggcg     720
gcggaggagc agaggagggg gtaggtgaag gattgaaatt gtttggggtg tggttgaaag     780
gagagagaaa aaagagggac cgggatgaaa agaattatgt ggtgagtggg tcccgtatga     840
cggaaataaa gaacgtggac tttcacgcgc cgttgtggaa aagcagcaaa gtctgcaact     900
aaaaaaagag tagaagactg ttcaaaccag cgtgtgacac gtcatcgacg acgacgaaaa     960
aaatgattta aaaactattt ttttccgtaa aggaagaaaa gttatttttta tgttttaaaa    1020
aggtgaagaa ggtccagaag gatcaacgca aatatataaa tggattttca tgtattatat    1080
aatttaatta gtgtattaag aaaataaaac aaaaaaaaaa a                         1121
```

<210> SEQ ID NO 26
<211> LENGTH: 284
<212> TYPE: PRT
<213> ORGANISM: Arabidopsis thaliana
<220> FEATURE:
<223> OTHER INFORMATION: G263

<400> SEQUENCE: 26

```
Met Thr Ala Val Thr Ala Ala Gln Arg Ser Val Pro Ala Pro Phe Leu
  1               5                  10                  15

Ser Lys Thr Tyr Gln Leu Val Asp Asp His Ser Thr Asp Asp Val Val
             20                  25                  30

Ser Trp Asn Glu Glu Gly Thr Ala Phe Val Val Trp Lys Thr Ala Glu
         35                  40                  45

Phe Ala Lys Asp Leu Leu Pro Gln Tyr Phe Lys His Asn Asn Phe Ser
     50                  55                  60

Ser Phe Ile Arg Gln Leu Asn Thr Tyr Gly Phe Arg Lys Thr Val Pro
 65                  70                  75                  80

Asp Lys Trp Glu Phe Ala Asn Asp Tyr Phe Arg Arg Gly Gly Glu Asp
                 85                  90                  95

Leu Leu Thr Asp Ile Arg Arg Lys Ser Val Ile Ala Ser Thr Ala
            100                 105                 110

Gly Lys Cys Val Val Val Gly Ser Pro Ser Glu Ser Asn Ser Gly Gly
        115                 120                 125

Gly Asp Asp His Gly Ser Ser Thr Ser Ser Pro Gly Ser Ser Lys
    130                 135                 140

Asn Pro Gly Ser Val Glu Asn Met Val Ala Asp Leu Ser Gly Glu Asn
145                 150                 155                 160

Glu Lys Leu Lys Arg Glu Asn Asn Asn Leu Ser Ser Glu Leu Ala Ala
```

```
                    165                 170                 175
Ala Lys Lys Gln Arg Asp Glu Leu Val Thr Phe Leu Thr Gly His Leu
                180                 185                 190

Lys Val Arg Pro Glu Gln Ile Asp Lys Met Ile Lys Gly Gly Lys Phe
            195                 200                 205

Lys Pro Val Glu Ser Asp Glu Ser Glu Cys Glu Gly Cys Asp Gly
        210                 215                 220

Gly Gly Gly Ala Glu Glu Gly Val Gly Glu Gly Leu Lys Leu Phe Gly
225                 230                 235                 240

Val Trp Leu Lys Gly Glu Arg Lys Lys Arg Asp Arg Asp Glu Lys Asn
                245                 250                 255

Tyr Val Val Ser Gly Ser Arg Met Thr Glu Ile Lys Asn Val Asp Phe
            260                 265                 270

His Ala Pro Leu Trp Lys Ser Ser Lys Val Cys Asn
        275                 280

<210> SEQ ID NO 27
<211> LENGTH: 1130
<212> TYPE: DNA
<213> ORGANISM: Arabidopsis thaliana
<220> FEATURE:
<223> OTHER INFORMATION: G291
<220> FEATURE:
<223> OTHER INFORMATION: "n" bases at various positions throughout the
      sequence may be A, T, C, G, other or unknown

<400> SEQUENCE: 27
ccaagatcga ctcttacttc gaatctctct caactttctt cctcagctta cgggaacttc      60
cacacatata catccacaag aacccatatc gaagattcat cctacatata tttacatgga    120
tcagtactca tcctctttgg tcgatacttc attagatctc actattggcg ttactcgtat    180
gcgagttgaa gaagatccac cgacaagtgc tttggtggaa gaattaaacc gagttagtgc    240
tgagaacaag aagctctcgg agatgctaac tttgatgtgt gacaactaca acgtcttgag    300
gaagcaactt atggaatatg ttaacaagag caacataacc gagagggatc aaatcagccc    360
tcccaagaaa cgcaaatccc ggcgagaga ggacgcattc agctgcgcgg ttattggcgg    420
agtgtcggag agtagctcaa cggatcaaga tgagtatttg tgtaagaagc agagagaaga    480
gactgtcgtg aaggagaaag tctcaagggt ctattacaag accgaagctt ctgacactac    540
cctcgttgtg aaagatgggt atcaatggag gaaatatgga cagaaagtga ctagagacaa    600
tccatctcca agagcttact tcaaatgtgc ttgtgctcca agctgttctg tcaaaaagaa    660
ggttcagaga agtgtggagg atcagtccgt gttagttgca acttatgagg gtgaacacaa    720
ccatccaatg ccatcgcaga tcgattcaaa caatggctta aaccgccaca tctctcatgg    780
tggttcagct tcaacacccg ttgcagcaaa cagaagaagt agcttgactg tgccggtgac    840
taccgtagat atgattgaat cgaagaaagt gacgagccca acgtcaagaa tcgattttcc    900
ccaagttcag aaactttggg tggagcaaat ggcttcttcc ttaaccaaag atcctaactt    960
tacagcagct ttagcagcag ctgttaccgg aaaattgtat caacagaatc ataccgagaa   1020
atagtttagc ttcaaattcc gttagagttt ttagatttga atttgtcatg agtaagagaa   1080
agagagtaga ttataatccn ttgtgatact gaaaaaaaaa aaaaaaaaaa              1130

<210> SEQ ID NO 28
<211> LENGTH: 302
<212> TYPE: PRT
<213> ORGANISM: Arabidopsis thaliana
```

<220> FEATURE:
<223> OTHER INFORMATION: G291

<400> SEQUENCE: 28

```
Met Asp Gln Tyr Ser Ser Ser Leu Val Asp Thr Ser Leu Asp Leu Thr
 1               5                  10                  15
Ile Gly Val Thr Arg Met Arg Val Glu Glu Asp Pro Pro Thr Ser Ala
             20                  25                  30
Leu Val Glu Glu Leu Asn Arg Val Ser Ala Glu Asn Lys Lys Leu Ser
         35                  40                  45
Glu Met Leu Thr Leu Met Cys Asp Asn Tyr Asn Val Leu Arg Lys Gln
     50                  55                  60
Leu Met Glu Tyr Val Asn Lys Ser Asn Ile Thr Glu Arg Asp Gln Ile
 65                  70                  75                  80
Ser Pro Pro Lys Lys Arg Lys Ser Pro Ala Arg Glu Asp Ala Phe Ser
                 85                  90                  95
Cys Ala Val Ile Gly Gly Val Ser Glu Ser Ser Ser Thr Asp Gln Asp
            100                 105                 110
Glu Tyr Leu Cys Lys Lys Gln Arg Glu Glu Thr Val Val Lys Glu Lys
        115                 120                 125
Val Ser Arg Val Tyr Tyr Lys Thr Glu Ala Ser Asp Thr Thr Leu Val
    130                 135                 140
Val Lys Asp Gly Tyr Gln Trp Arg Lys Tyr Gly Gln Lys Val Thr Arg
145                 150                 155                 160
Asp Asn Pro Ser Pro Arg Ala Tyr Phe Lys Cys Ala Cys Ala Pro Ser
                165                 170                 175
Cys Ser Val Lys Lys Lys Val Gln Arg Ser Val Glu Asp Gln Ser Val
            180                 185                 190
Leu Val Ala Thr Tyr Glu Gly Glu His Asn His Pro Met Pro Ser Gln
        195                 200                 205
Ile Asp Ser Asn Asn Gly Leu Asn Arg His Ile Ser His Gly Gly Ser
    210                 215                 220
Ala Ser Thr Pro Val Ala Asn Arg Arg Ser Ser Leu Thr Val Pro
225                 230                 235                 240
Val Thr Thr Val Asp Met Ile Glu Ser Lys Lys Val Thr Ser Pro Thr
                245                 250                 255
Ser Arg Ile Asp Phe Pro Gln Val Gln Lys Leu Leu Val Glu Gln Met
            260                 265                 270
Ala Ser Ser Leu Thr Lys Asp Pro Asn Phe Thr Ala Ala Leu Ala Ala
        275                 280                 285
Ala Val Thr Gly Lys Leu Tyr Gln Gln Asn His Thr Glu Lys
    290                 295                 300
```

<210> SEQ ID NO 29
<211> LENGTH: 748
<212> TYPE: DNA
<213> ORGANISM: Arabidopsis thaliana
<220> FEATURE:
<223> OTHER INFORMATION: G1275

<400> SEQUENCE: 29

```
ccaagaaaag ggaagatcac gcattcttat aggcgtaatt cgtaaatagt ggtgagtatg      60
aatgatgcag acacaaactt ggggagtagt ttcagcgatg atactcactc tgtgttcgag     120
tttccggagc tagacttgtc agatgaatgg atggatgatg atcttgtgtc tgcggtttcc     180
gggatgaatc agtcttatgg ttatcagact agtgatgttg ctggtgcttt attctcaggt     240
```

```
tcttctagct gtttcagtca tcctgaatct ccaagtacca aaacttatgt tgctgctaca      300
gccactgctt ctgccgacaa ccaaaacaag aaagaaaaga aaaaaattaa agggagagtt      360
gcgttcaaga cacggtccga ggtggaagtg cttgacgacg ggttcaagtg gagaaagtat      420
gggaagaaga tggtgaagaa cagcccacat ccaagaaact actacaaatg ttcagttgat      480
ggctgtcccg tgaagaaaag ggttgaacga gacagagatg atccgagctt tgtgataaca      540
acttacgagg gttcccacaa tcactcaagc atgaactaag actcgaacta aggctcaagg      600
cgaccatgct atattcagca catcttattt tctatggtta cgaacgatac ttaaaactgc      660
ttctagttct ttatatccat tgtaaactgg ttgcaggttc acaaattttg agaggtttat      720
gacattctaa atctgtagta cttatata                                         748
```

<210> SEQ ID NO 30
<211> LENGTH: 173
<212> TYPE: PRT
<213> ORGANISM: Arabidopsis thaliana
<220> FEATURE:
<223> OTHER INFORMATION: G1275

<400> SEQUENCE: 30

```
Met Asn Asp Ala Asp Thr Asn Leu Gly Ser Ser Phe Ser Asp Asp Thr
 1               5                  10                  15

His Ser Val Phe Glu Phe Pro Glu Leu Asp Leu Ser Asp Glu Trp Met
                20                  25                  30

Asp Asp Leu Val Ser Ala Val Ser Gly Met Asn Gln Ser Tyr Gly
            35                  40                  45

Tyr Gln Thr Ser Asp Val Ala Gly Ala Leu Phe Ser Gly Ser Ser Ser
     50                  55                  60

Cys Phe Ser His Pro Glu Ser Pro Ser Thr Lys Thr Tyr Val Ala Ala
 65                  70                  75                  80

Thr Ala Thr Ala Ser Ala Asp Asn Gln Asn Lys Lys Glu Lys Lys Lys
                 85                  90                  95

Ile Lys Gly Arg Val Ala Phe Lys Thr Arg Ser Glu Val Glu Val Leu
            100                 105                 110

Asp Asp Gly Phe Lys Trp Arg Lys Tyr Gly Lys Lys Met Val Lys Asn
        115                 120                 125

Ser Pro His Pro Arg Asn Tyr Tyr Lys Cys Ser Val Asp Gly Cys Pro
    130                 135                 140

Val Lys Lys Arg Val Glu Arg Asp Arg Asp Asp Pro Ser Phe Val Ile
145                 150                 155                 160

Thr Thr Tyr Glu Gly Ser His Asn His Ser Ser Met Asn
                165                 170
```

<210> SEQ ID NO 31
<211> LENGTH: 1195
<212> TYPE: DNA
<213> ORGANISM: Arabidopsis thaliana
<220> FEATURE:
<223> OTHER INFORMATION: G242

<400> SEQUENCE: 31

```
ctctcaaaac caaaatcact aaagaggaga agattgctaa agtttgataa acattccaa       60 aatcaatggc tgataggatc aaaggtccat ggagtcctga agaagacgag cagcttcgta     120
ggcttgttgt taaatacggt ccaagaaact ggacagtgat tagcaaatct attcccggta     180
gatcggggaa atcgtgtcgt ttacggtggt gcaaccagct ttcgccgcaa gttgagcatc     240
```

-continued

```
ggccgttttc ggctgaggaa gacgagacga tcgcacgtgc tcacgctcag ttcgggaata    300
aatgggcgac gattgctcgt cttctcaacg gtcgtacgga caacgccgtg aagaatcact    360
ggaactcgac gctcaagagg aaatgcggcg gttacgacca tcggggttac gatggttcgg    420
aggatcatcg gccggttaag agatcggtga gtgcgggatc tccacctgtt gttactgggc    480
tttacatgag cccaggaagc ccaactggat ctgatgtcag tgattcaagt actatcccga    540
tattccttc cgttgagctt tcaagcctg tgcctagacc tggtgctgtt gtgctaccgc    600
ttcctatcga aacgtcgtct ttttccgatg atccaccgac ttcgttaagc ttgtcacttc    660
ctggtgccga cgtaagcgag gagtcaaacc gtagccacga gtcaacgaat atcaacaaca    720
ccacttcgag ccgccacaac cacaacaata cggtgtcgtt tatgccgttt agtggtgggt    780
ttagaggtgc gattgaggaa atggggaagt cttttcccgg taacggaggc gagtttatgg    840
cggtggtgca agagatgatt aaggcggaag tgaggagtta catgacgag atgcaacgga    900
acaatggtgg cggattcgtc ggaggattca ttgataatgg catgattccg atgagtcaaa    960
ttggagttgg gagaatcgag tagacaaagt gagattatta ggaaactgtt taaattggag   1020
aagaagaaaa atgctctgtt tttttctcct ttggattagg cttaagaatt tgggttttta   1080
aggaaatgta tagaggaaat cgagtgaaca aagctcgaga gctggggacg tagtgacgaa   1140
gacgaagatc aaatttctct taagctattc aggaaaataa aataaatttt tattt         1195
```

<210> SEQ ID NO 32
<211> LENGTH: 305
<212> TYPE: PRT
<213> ORGANISM: Arabidopsis thaliana
<220> FEATURE:
<223> OTHER INFORMATION: G242

<400> SEQUENCE: 32

Met Ala Asp Arg Ile Lys Gly Pro Trp Ser Pro Glu Glu Asp Glu Gln
1               5                   10                  15

Leu Arg Arg Leu Val Val Lys Tyr Gly Pro Arg Asn Trp Thr Val Ile
            20                  25                  30

Ser Lys Ser Ile Pro Gly Arg Ser Gly Lys Ser Cys Arg Leu Arg Trp
        35                  40                  45

Cys Asn Gln Leu Ser Pro Gln Val Glu His Arg Pro Phe Ser Ala Glu
    50                  55                  60

Glu Asp Glu Thr Ile Ala Arg Ala His Ala Gln Phe Gly Asn Lys Trp
65                  70                  75                  80

Ala Thr Ile Ala Arg Leu Leu Asn Gly Arg Thr Asp Asn Ala Val Lys
                85                  90                  95

Asn His Trp Asn Ser Thr Leu Lys Arg Lys Cys Gly Gly Tyr Asp His
            100                 105                 110

Arg Gly Tyr Asp Gly Ser Glu Asp His Arg Pro Val Lys Arg Ser Val
        115                 120                 125

Ser Ala Gly Ser Pro Val Val Thr Gly Leu Tyr Met Ser Pro Gly
    130                 135                 140

Ser Pro Thr Gly Ser Asp Val Ser Asp Ser Ser Thr Ile Pro Ile Leu
145                 150                 155                 160

Pro Ser Val Glu Leu Phe Lys Pro Val Pro Arg Pro Gly Ala Val Val
                165                 170                 175

Leu Pro Leu Pro Ile Glu Thr Ser Ser Phe Ser Asp Asp Pro Pro Thr
            180                 185                 190

Ser Leu Ser Leu Ser Leu Pro Gly Ala Asp Val Ser Glu Glu Ser Asn
            195                 200                 205

Arg Ser His Glu Ser Thr Asn Ile Asn Asn Thr Thr Ser Ser Arg His
    210                 215                 220

Asn His Asn Asn Thr Val Ser Phe Met Pro Phe Ser Gly Gly Phe Arg
225                 230                 235                 240

Gly Ala Ile Glu Glu Met Gly Lys Ser Phe Pro Gly Asn Gly Gly Glu
                245                 250                 255

Phe Met Ala Val Val Gln Glu Met Ile Lys Ala Glu Val Arg Ser Tyr
            260                 265                 270

Met Thr Glu Met Gln Arg Asn Asn Gly Gly Phe Val Gly Gly Phe
        275                 280                 285

Ile Asp Asn Gly Met Ile Pro Met Ser Gln Ile Gly Val Gly Arg Ile
    290                 295                 300

Glu
305

<210> SEQ ID NO 33
<211> LENGTH: 913
<212> TYPE: DNA
<213> ORGANISM: Arabidopsis thaliana
<220> FEATURE:
<223> OTHER INFORMATION: G1006

<400> SEQUENCE: 33

| | | | | | |
|---|---|---|---|---|---|
| gataaatcaa | tcaacaaaac | aaaaaaaact | ctatagttag | tttctctgaa | aatgtacgga | 60 |
| cagtgcaata | tagaatccga | ctacgctttg | ttggagtcga | taacacgtca | cttgctagga | 120 |
| ggaggaggag | agaacgagct | gcgactcaat | gagtcaacac | cgagttcgtg | tttcacagag | 180 |
| agttggggag | gtttgccatt | gaaagagaat | gattcagagg | acatgttggt | gtacggactc | 240 |
| ctcaaagatg | ccttccattt | tgacacgtca | tcatcggact | gagctgtctt | ttttgatttt | 300 |
| ccggcggtta | aagtcgagcc | aactgagaac | tttacggcga | tggaggagaa | accaaagaaa | 360 |
| gcgataccgg | ttacggagac | ggcagtgaag | gcgaagcatt | acagaggagt | gaggcagaga | 420 |
| ccgtggggga | aattcgcggc | ggagatacgt | gatccggcga | agaatggagc | tagggtttgg | 480 |
| ttagggacgt | tgagacggc | ggaagatgcg | gctttagctt | acgatatagc | tgcttttagg | 540 |
| atgcgtggtt | cccgcgcttt | attgaatttt | ccgttgaggg | ttaattccgg | tgaacctgac | 600 |
| ccggttcgga | tcacgtctaa | gagatcttct | tcgtcgtcgt | cgtcgtcgtc | ctcttctacg | 660 |
| tcgtcgtctg | aaaacgggaa | gttgaaacga | aggagaaaag | cagagaatct | gacgtcggag | 720 |
| gtggtgcagg | tgaagtgtga | ggttggtgat | gagacacgtg | ttgatgagtt | attggtttca | 780 |
| taagtttgat | cttgtgtgtt | ttgtagttga | atagttttgc | tataaatgtt | gaggcaccaa | 840 |
| gtaaagtgt | tcccgtgatg | taaattagtt | actaaacaga | gccatatatc | ttcaatcaaa | 900 |
| aaaaaaaaaa | aaa | | | | | 913 |

<210> SEQ ID NO 34
<211> LENGTH: 243
<212> TYPE: PRT
<213> ORGANISM: Arabidopsis thaliana
<220> FEATURE:
<223> OTHER INFORMATION: G1006

<400> SEQUENCE: 34

Met Tyr Gly Gln Cys Asn Ile Glu Ser Asp Tyr Ala Leu Leu Glu Ser
1               5                   10                  15

| | | | | | | | | | | | |
|---|---|---|---|---|---|---|---|---|---|---|---|
|Ile|Thr|Arg|His|Leu|Gly|Gly|Gly|Glu|Asn|Glu|Leu|Arg|Leu|
| | |20| | | |25| | | |30| | | |

Ile Thr Arg His Leu Gly Gly Gly Glu Asn Glu Leu Arg Leu
            20                  25              30

Asn Glu Ser Thr Pro Ser Ser Cys Phe Thr Glu Ser Trp Gly Gly Leu
        35                  40                  45

Pro Leu Lys Glu Asn Asp Ser Glu Asp Met Leu Val Tyr Gly Leu Leu
        50                  55                  60

Lys Asp Ala Phe His Phe Asp Thr Ser Ser Asp Leu Ser Cys Leu
65                  70                  75                  80

Phe Asp Phe Pro Ala Val Lys Val Glu Pro Thr Glu Asn Phe Thr Ala
                85                  90                  95

Met Glu Glu Lys Pro Lys Lys Ala Ile Pro Val Thr Glu Thr Ala Val
            100                 105                 110

Lys Ala Lys His Tyr Arg Gly Val Arg Gln Arg Pro Trp Gly Lys Phe
            115                 120                 125

Ala Ala Glu Ile Arg Asp Pro Ala Lys Asn Gly Ala Arg Val Trp Leu
        130                 135                 140

Gly Thr Phe Glu Thr Ala Glu Asp Ala Ala Leu Ala Tyr Asp Ile Ala
145                 150                 155                 160

Ala Phe Arg Met Arg Gly Ser Arg Ala Leu Leu Asn Phe Pro Leu Arg
                165                 170                 175

Val Asn Ser Gly Glu Pro Asp Pro Val Arg Ile Thr Ser Lys Arg Ser
            180                 185                 190

Ser Ser Ser Ser Ser Ser Ser Ser Ser Thr Ser Ser Ser Glu Asn
        195                 200                 205

Gly Lys Leu Lys Arg Arg Arg Lys Ala Glu Asn Leu Thr Ser Glu Val
        210                 215                 220

Val Gln Val Lys Cys Glu Val Gly Asp Glu Thr Arg Val Asp Glu Leu
225                 230                 235                 240

Leu Val Ser

<210> SEQ ID NO 35
<211> LENGTH: 725
<212> TYPE: DNA
<213> ORGANISM: Arabidopsis thaliana
<220> FEATURE:
<223> OTHER INFORMATION: G1049

<400> SEQUENCE: 35

```
ctaactttct tcccaagtaa acttcaaaat gcagccgcaa acagacgttt tcagcctcca     60
taactaccta aactcatcga tactgcagtc tccgtatcct tctaatttcc cgatatctac    120
gccatttcca accaacggtc aaaacccgta cctcctctac ggattccaaa gcccctacaaa   180
caatccacaa tccatgagcc taagcagcaa caactcaaca tcagatgaag cagaagagca    240
gcagacgaac aacaatataa tcaacgagcg gaagcagaga aggatgattt caaaccgaga    300
atccgcaagg agatcgcgta tgaggaagca aagacacctt gacgagcttt ggtcacaagt    360
gatgtggtta aggatcgaga atcatcagtt gcttgataag cttaacaatc tctctgagtc    420
tcacgacaag gttcttcaag agaatgctca gcttaaagaa gaaacatttg agcttaagca    480
agtgatcagc gatatgcaaa ttcaaagccc tttctcttgc tttagagacg atataatccc    540
cattgaataa agcatttttc cccgattcat atttatgaaa attttcttca agagtatgtt    600
tctttgtatg tatatgtgga gatgtatttc agggttttga taatatgacc ctttacgacg    660
acgttttag attgtagtaa atttataaac taaagaagat tagtgttaat gaagaacaaa    720
tataa                                                                725
```

<210> SEQ ID NO 36
<211> LENGTH: 173
<212> TYPE: PRT
<213> ORGANISM: Arabidopsis thaliana
<220> FEATURE:
<223> OTHER INFORMATION: G1049

<400> SEQUENCE: 36

```
Met Gln Pro Gln Thr Asp Val Phe Ser Leu His Asn Tyr Leu Asn Ser
 1               5                  10                  15

Ser Ile Leu Gln Ser Pro Tyr Pro Ser Asn Phe Pro Ile Ser Thr Pro
            20                  25                  30

Phe Pro Thr Asn Gly Gln Asn Pro Tyr Leu Leu Tyr Gly Phe Gln Ser
        35                  40                  45

Pro Thr Asn Asn Pro Gln Ser Met Ser Leu Ser Ser Asn Asn Ser Thr
    50                  55                  60

Ser Asp Glu Ala Glu Glu Gln Thr Asn Asn Ile Ile Asn Glu
 65                 70                  75                  80

Arg Lys Gln Arg Arg Met Ile Ser Asn Arg Glu Ser Ala Arg Arg Ser
                85                  90                  95

Arg Met Arg Lys Gln Arg His Leu Asp Glu Leu Trp Ser Gln Val Met
            100                 105                 110

Trp Leu Arg Ile Glu Asn His Gln Leu Leu Asp Lys Leu Asn Asn Leu
        115                 120                 125

Ser Glu Ser His Asp Lys Val Leu Gln Glu Asn Ala Gln Leu Lys Glu
    130                 135                 140

Glu Thr Phe Glu Leu Lys Gln Val Ile Ser Asp Met Gln Ile Gln Ser
145                 150                 155                 160

Pro Phe Ser Cys Phe Arg Asp Asp Ile Ile Pro Ile Glu
                165                 170
```

<210> SEQ ID NO 37
<211> LENGTH: 1409
<212> TYPE: DNA
<213> ORGANISM: Arabidopsis thaliana
<220> FEATURE:
<223> OTHER INFORMATION: G502

<400> SEQUENCE: 37

```
ttgatgccgc tcaatcccac tatccttcgc aaggacccct cctctatata aggaagttca      60
tttcatttgg agaggacacg ctgacaagct gactctagca gatctgggac cgtcgaccca     120
cgcgtccgaa ttgattagga taggatcagg atcatcctca acaacctcct cctaattcct     180
cctccattca tagtaacaat aatattaaga aagagggtaa actatgtcag aattattaca     240
gttgcctcca ggtttccgat ttcaccctac cgatgaagag cttgtcatgc actatctctg     300
ccgcaaatgt gcctctcagt ccatcgccgt tccgatcatc gctgagatcg atctctacaa     360
atacgatcca tgggagcttc ctggtttagc cttgtatggt gagaaggaat ggtacttctt     420
ctctcccagg gacagaaaat atcccaacgg ttcgcgtcct aaccggtccg ctggttctgg     480
ttactggaaa gctaccggag ctgataaacc gatcggacta cctaaaccgg tcggaattaa     540
gaaagctctt gttttctacg ccggcaaagc tccaagggga gagaaaacca attggatcat     600
gcacgagtac cgtctcgccg acgttgaccg gtccgttcgc aagaagaaga atagtctcag     660
gctggatgat tgggttctct gccggattta caacaaaaaa ggagctaccg agaggcgggg     720
accaccgcct ccggttgttt acggcgacga aatcatggag gagaagccga aggtgacgga     780
```

-continued

```
gatggttatg cctccgccgc cgcaacagac aagtgagttc gcgtatttcg acacgtcgga    840
ttcggtgccg aagctgcata ctacggattc gagttgctcg gagcaggtgg tgtcgccgga    900
gttcacgagc gaggttcaga gcgagcccaa gtggaaagat tggtcggccg taagtaatga    960
caataacaat accttgatt ttgggtttaa ttacattgat gccaccgtgg ataacgcgtt    1020
tggaggagga gggagtagta atcagatgtt tccgctacag gatatgttca tgtacatgca    1080
gaagccttac tagaagggaa ttcctttcct gccgccgaaa cgcaacgcaa aacgaccctc    1140 gttttttgcgt ttatggcaac acgagaccgt tttatatggt caatgagtgt gccgattcgg    1200
ccattagatt tctgttcagt cttcgtttat tctatagacc gtccgatttc agatcatccc    1260
taatcggacg tggtcgttg gatgtatcag tagtgtatta ctgtgttagg tagaagaaaa    1320
tccacttgtt cttaaattgg cataaaagtc agaagctaat atttatatgt gccgcaatca    1380
atttaatatt ttctgtctaa aaaaaaaaa                                      1409
```

<210> SEQ ID NO 38
<211> LENGTH: 319
<212> TYPE: PRT
<213> ORGANISM: Arabidopsis thaliana
<220> FEATURE:
<223> OTHER INFORMATION: G502

<400> SEQUENCE: 38

```
Met Ser Glu Leu Leu Gln Leu Pro Pro Gly Phe Arg Phe His Pro Thr
 1               5                  10                  15

Asp Glu Glu Leu Val Met His Tyr Leu Cys Arg Lys Cys Ala Ser Gln
                20                  25                  30

Ser Ile Ala Val Pro Ile Ile Ala Glu Ile Asp Leu Tyr Lys Tyr Asp
            35                  40                  45

Pro Trp Glu Leu Pro Gly Leu Ala Leu Tyr Gly Glu Lys Glu Trp Tyr
        50                  55                  60

Phe Phe Ser Pro Arg Asp Arg Lys Tyr Pro Asn Gly Ser Arg Pro Asn
 65                  70                  75                  80

Arg Ser Ala Gly Ser Gly Tyr Trp Lys Ala Thr Gly Ala Asp Lys Pro
                85                  90                  95

Ile Gly Leu Pro Lys Pro Val Gly Ile Lys Lys Ala Leu Val Phe Tyr
            100                 105                 110

Ala Gly Lys Ala Pro Lys Gly Glu Lys Thr Asn Trp Ile Met His Glu
        115                 120                 125

Tyr Arg Leu Ala Asp Val Asp Arg Ser Val Arg Lys Lys Asn Ser
    130                 135                 140

Leu Arg Leu Asp Asp Trp Val Leu Cys Arg Ile Tyr Asn Lys Lys Gly
145                 150                 155                 160

Ala Thr Glu Arg Arg Gly Pro Pro Pro Val Val Tyr Gly Asp Glu
                165                 170                 175

Ile Met Glu Glu Lys Pro Lys Val Thr Glu Met Val Met Pro Pro
            180                 185                 190

Pro Gln Gln Thr Ser Glu Phe Ala Tyr Phe Asp Thr Ser Asp Ser Val
        195                 200                 205

Pro Lys Leu His Thr Thr Asp Ser Ser Cys Ser Glu Gln Val Val Ser
    210                 215                 220

Pro Glu Phe Thr Ser Glu Val Gln Ser Glu Pro Lys Trp Lys Asp Trp
225                 230                 235                 240

Ser Ala Val Ser Asn Asp Asn Asn Asn Thr Leu Asp Phe Gly Phe Asn
```

| | | | | | | | | | | | |
|---|---|---|---|---|---|---|---|---|---|---|---|
| | | | 245 | | | | 250 | | | 255 | |
| Tyr | Ile | Asp | Ala | Thr | Val | Asp | Asn | Ala | Phe | Gly | Gly Gly Ser Ser |
| | | | 260 | | | | 265 | | | | 270 |

Asn Gln Met Phe Pro Leu Gln Asp Met Phe Met Tyr Met Gln Lys Pro
         275                 280                 285

Tyr Lys Gly Ile Pro Phe Leu Pro Pro Lys Arg Asn Ala Lys Arg Pro
     290                 295                 300

Ser Phe Leu Arg Leu Trp Gln His Glu Thr Val Leu Tyr Gly Gln
305                 310                 315

<210> SEQ ID NO 39
<211> LENGTH: 1347
<212> TYPE: DNA
<213> ORGANISM: Arabidopsis thaliana
<220> FEATURE:
<223> OTHER INFORMATION: G239

<400> SEQUENCE: 39

| | | |
|---|---|---|
| atggaagatt acgagcgaat aaactcaaac tctccaacac atgaagaaga ttctgatgta | 60 |
| cggaaaggtc catggaccga ggaagaagat gcaatcctag tcaacttcgt ctctattcat | 120 |
| ggcgatgctc gttggaacca catcgctcgt tcctctgggc taaagcgaac tggtaagagt | 180 |
| tgtagattaa gatggcttaa ttacttacgt ccagatgtta agagggcaa catcactctc | 240 |
| gaagaacaat ttatgatcct caaactccat tctcttttggg gcaataggtg gtcgaagatt | 300 |
| gcgcaatatc taccgggaag aacagataat gaaataaaga attattggag aactcgagtc | 360 |
| caaaagcaag ccaaacacct aagatgcgat gttaacagta atcttttcaa ggagactatg | 420 |
| agaaatgttt ggatgccgag attagtggaa cgaatcaacg cccaatcatt acccaccacg | 480 |
| tgtgaacaag tggagtcaat gatcaccgac ccaagtcaac cagttaacga accgagtccg | 540 |
| gtcgagccgg gtttcgttca attcagccag aatcatcatc agcaattcgt accggctacg | 600 |
| gaattgtcag caacgtcttc gaattctccg gctgagacgt tttcggacgt tcgaggtggg | 660 |
| gtggtgaacg ggtcaggtta tgatccgtcg ggtcaaacgg gtttcggaga gttcaacgat | 720 |
| tggggctgtg ttggtgggga caacatgtgg actgacgagg agagttttttg gttcttgcag | 780 |
| gaccagttct gccccgatac gacatcgtat tcgtataatt aaggaaatat acgattacta | 840 |
| tacgtaacga ggaattcaat tgcgtcacgt ttggtgtaat attcattcgt gcgtgatgcc | 900 |
| aattttagat acggccttgg tatacgaatc tttgacttaa ttattatctt ttcttttcct | 960 |
| ctcttgtttt aaaccccctga ttaaattaag atttgatcat cagacgagga tatttgtgat | 1020 |
| tcactgatttt gtgatattga tatatgtgaa ttatttgata taacgttttta aaaaccaaca | 1080 |
| aaaaaaaaaa atcattccaa ggaaaagttc ttaattttga tactcgaaaa gagcgtagac | 1140 |
| tgactcgaat cagttcatat tttctttggt tcgtttttatt tacgacaaaa ttcactaaca | 1200 |
| aaaattaaaa aacgacaaaa cgaaaatatg actaaattta ttttttttgtc agttaaccac | 1260 |
| tgattatagg ttgaaattgt cacaacacat gatttatctt gatagaaatt tagtagtcca | 1320 |
| gaatgctgca tggttgatcc taagaaa | 1347 |

<210> SEQ ID NO 40
<211> LENGTH: 273
<212> TYPE: PRT
<213> ORGANISM: Arabidopsis thaliana
<220> FEATURE:
<223> OTHER INFORMATION: G239

<400> SEQUENCE: 40

```
Met Glu Asp Tyr Glu Arg Ile Asn Ser Asn Ser Pro Thr His Glu Glu
  1               5                  10                  15
Asp Ser Asp Val Arg Lys Gly Pro Trp Thr Glu Glu Asp Ala Ile
             20                  25                  30
Leu Val Asn Phe Val Ser Ile His Gly Asp Ala Arg Trp Asn His Ile
             35                  40                  45
Ala Arg Ser Ser Gly Leu Lys Arg Thr Gly Lys Ser Cys Arg Leu Arg
         50                  55                  60
Trp Leu Asn Tyr Leu Arg Pro Asp Val Arg Arg Gly Asn Ile Thr Leu
 65              70                  75                  80
Glu Glu Gln Phe Met Ile Leu Lys Leu His Ser Leu Trp Gly Asn Arg
                 85                  90                  95
Trp Ser Lys Ile Ala Gln Tyr Leu Pro Gly Arg Thr Asp Asn Glu Ile
                100                 105                 110
Lys Asn Tyr Trp Arg Thr Arg Val Gln Lys Gln Ala Lys His Leu Arg
            115                 120                 125
Cys Asp Val Asn Ser Asn Leu Phe Lys Glu Thr Met Arg Asn Val Trp
        130                 135                 140
Met Pro Arg Leu Val Glu Arg Ile Asn Ala Gln Ser Leu Pro Thr Thr
145                 150                 155                 160
Cys Glu Gln Val Glu Ser Met Ile Thr Asp Pro Ser Gln Pro Val Asn
                165                 170                 175
Glu Pro Ser Pro Val Glu Pro Gly Phe Val Gln Phe Ser Gln Asn His
                180                 185                 190
His Gln Gln Phe Val Pro Ala Thr Glu Leu Ser Ala Thr Ser Ser Asn
            195                 200                 205
Ser Pro Ala Glu Thr Phe Ser Asp Val Arg Gly Gly Val Val Asn Gly
        210                 215                 220
Ser Gly Tyr Asp Pro Ser Gly Gln Thr Gly Phe Gly Glu Phe Asn Asp
225                 230                 235                 240
Trp Gly Cys Val Gly Gly Asp Asn Met Trp Thr Asp Glu Glu Ser Phe
                245                 250                 255
Trp Phe Leu Gln Asp Gln Phe Cys Pro Asp Thr Thr Ser Tyr Ser Tyr
                260                 265                 270
Asn
```

```
<210> SEQ ID NO 41
<211> LENGTH: 1360
<212> TYPE: DNA
<213> ORGANISM: Arabidopsis thaliana
<220> FEATURE:
<223> OTHER INFORMATION: G555

<400> SEQUENCE: 41
caaaagtagt aacctttgtt ggtgattgat actatatctg ttgtgggttt tagacaaaga    60
ccacgtcttt gcagttgtag attggaattt tccggatctt tctctaaatc gcttttctc   120
cgagcaactt tgtttgggg ttaagctcaa agaatccgtt cttttcagtc tttactccat   180
ctagggtacc acgattggat cggttttat ctgatgattt agtaacagag attttgaaga   240
aaagaaaaa tgggagatac tagtccaaga acatcagtct caacagatgg agacactgat   300
cataataacc taatgttcga tgaagggcat ttgggtatcg gtgcttctga ttctagtgac   360
cgttcaaaga gtaaaatgga tcaaaagacg cttcgtaggc tcgctcaaaa ccgtgaggct   420
gcaaggaaaa gcagattgag gaagaaagca tatgttcagc agctagagaa cagtcgattg   480
```

-continued

```
aagctaacac aacttgagca ggagctacaa agagcacggc aacagggtgt ctttatctca    540
agctctggag accaagccca ttctaccgct ggagatgggg caatggcatt tgatgtagaa    600
tacagacgat ggcaggaaga taaaaacaga cagatgaagg agctgagttc tgctatagat    660
tctcacgcga ctgattctga gcttcggata attgtagatg gagtaatagc tcactatgag    720
gagctttaca ggataaaagg caacgcagct aagagtgatg tcttccattt attatcaggg    780
atgtggaaaa ccccagctga gagatgtttc ttgtggctcg gcggtttccg ttcatcagaa    840
cttctcaagc ttatagcgtg tcagttggag cccttgacag aacaacaatc gctagacata    900
aataacttgc aacagtcaac tcagcaagca gaagatgctt tgtctcaagg gatggacaac    960
ttacagcaat cactcgctga tactttatcg agtgggactc tcggttcaag ttcatcaggg   1020
aatgtagcta gctacatggg tcagatggcc atggcgatgg ggaagttagg taccccttgaa  1080 ggatttatcc gccaggctga taacttaagg ctacaaacat atcaacagat ggtgagacta   1140
ttaacaaccc gacaatcggc tcgtgctctc cttgcagtac acaattatac attgcggtta   1200
cgtgctctta gctctctatg gcttgccaga ccaagagagt gaaccatgac tctattatac   1260
ttcaacgaag gtccagaaaa tttgagattc ttagcataag atttgacgac tttagacacg   1320
tagctcgtat acaagattat gattatactg ttttgtgttg                         1360
```

<210> SEQ ID NO 42
<211> LENGTH: 330
<212> TYPE: PRT
<213> ORGANISM: Arabidopsis thaliana
<220> FEATURE:
<223> OTHER INFORMATION: G555

<400> SEQUENCE: 42

```
Met Gly Asp Thr Ser Pro Arg Thr Ser Val Ser Thr Asp Gly Asp Thr
  1               5                  10                  15

Asp His Asn Asn Leu Met Phe Asp Glu Gly His Leu Gly Ile Gly Ala
                 20                  25                  30

Ser Asp Ser Ser Asp Arg Ser Lys Ser Lys Met Asp Gln Lys Thr Leu
             35                  40                  45

Arg Arg Leu Ala Gln Asn Arg Glu Ala Ala Arg Lys Ser Arg Leu Arg
         50                  55                  60

Lys Lys Ala Tyr Val Gln Gln Leu Glu Asn Ser Arg Leu Lys Leu Thr
 65                  70                  75                  80

Gln Leu Glu Gln Glu Leu Gln Arg Ala Arg Gln Gln Gly Val Phe Ile
                 85                  90                  95

Ser Ser Ser Gly Asp Gln Ala His Ser Thr Ala Gly Asp Gly Ala Met
            100                 105                 110

Ala Phe Asp Val Glu Tyr Arg Arg Trp Gln Glu Asp Lys Asn Arg Gln
        115                 120                 125

Met Lys Glu Leu Ser Ser Ala Ile Asp Ser His Ala Thr Asp Ser Glu
    130                 135                 140

Leu Arg Ile Ile Val Asp Gly Val Ile Ala His Tyr Glu Glu Leu Tyr
145                 150                 155                 160

Arg Ile Lys Gly Asn Ala Ala Lys Ser Asp Val Phe His Leu Leu Ser
                165                 170                 175

Gly Met Trp Lys Thr Pro Ala Glu Arg Cys Phe Leu Trp Leu Gly Gly
            180                 185                 190

Phe Arg Ser Ser Glu Leu Leu Lys Leu Ile Ala Cys Gln Leu Glu Pro
        195                 200                 205
```

Leu Thr Glu Gln Gln Ser Leu Asp Ile Asn Asn Leu Gln Gln Ser Thr
                210                 215                 220

Gln Gln Ala Glu Asp Ala Leu Ser Gln Gly Met Asp Asn Leu Gln Gln
225                 230                 235                 240

Ser Leu Ala Asp Thr Leu Ser Ser Gly Thr Leu Gly Ser Ser Ser Ser
                245                 250                 255

Gly Asn Val Ala Ser Tyr Met Gly Gln Met Ala Met Ala Met Gly Lys
                260                 265                 270

Leu Gly Thr Leu Glu Gly Phe Ile Arg Gln Ala Asp Asn Leu Arg Leu
            275                 280                 285

Gln Thr Tyr Gln Gln Met Val Arg Leu Leu Thr Thr Arg Gln Ser Ala
290                 295                 300

Arg Ala Leu Leu Ala Val His Asn Tyr Thr Leu Arg Leu Arg Ala Leu
305                 310                 315                 320

Ser Ser Leu Trp Leu Ala Arg Pro Arg Glu
                325                 330

<210> SEQ ID NO 43
<211> LENGTH: 817
<212> TYPE: DNA
<213> ORGANISM: Arabidopsis thaliana
<220> FEATURE:
<223> OTHER INFORMATION: G352

<400> SEQUENCE: 43 aataccaccac acacttcact ctttcttcat cttcttcttc ttaaatagct cgaaatcaca      60
tctcacagaa ttaaatctta tggctctcga gactctcaat tctccaacag ctaccaccac     120
cgctcggcct cttctccggt atcgtgaaga aatggagcct gagaatctcg agcaatgggc     180
taaaagaaaa cgaacaaaac gtcaacgttt tgatcacggt catcagaatc aagaaacgaa     240
caagaacctt ccttctgaag aagagtatct cgctctttgt ctcctcatgc tcgctcgtgg     300
ctccgccgta caatctcctc ctcttcctcc tctaccgtca cgtgcgtcac cgtccgatca     360
ccgagattac aagtgtacgg tctgtgggaa gtccttttcg tcataccaag ccttaggtgg     420
acacaagacg agtcaccgga aaccgacgaa cactagtatc acttccggta accaagaact     480
gtctaataac agtcacagta acagcggttc cgttgttatt aacgttaccg tgaacactgg     540
taacggtgtt agtcaaagcg gaaagattca cacttgctca atctgtttca gtcgtttgc      600 gtctggtcaa gccttaggtg gacacaaacg gtgtcactat gacggtggca acaacggtaa     660
cggtaacgga agtagcagca acagcgtaga actcgtcgct ggtagtgacg tcagcgatgt     720
tgataatgag agatggtccg aagaaagtgc gatcggtggc caccgtggat ttgacctaaa     780
cttaccggct gatcaagtct cagtgacgac ttcttaa                              817

<210> SEQ ID NO 44
<211> LENGTH: 245
<212> TYPE: PRT
<213> ORGANISM: Arabidopsis thaliana
<220> FEATURE:
<223> OTHER INFORMATION: G352

<400> SEQUENCE: 44

Met Ala Leu Glu Thr Leu Asn Ser Pro Thr Ala Thr Thr Thr Ala Arg
  1               5                  10                  15

Pro Leu Leu Arg Tyr Arg Glu Glu Met Glu Pro Glu Asn Leu Glu Gln
                20                  25                  30

```
Trp Ala Lys Arg Lys Arg Thr Lys Arg Gln Arg Phe Asp His Gly His
         35                  40                  45

Gln Asn Gln Glu Thr Asn Lys Asn Leu Pro Ser Glu Glu Tyr Leu
 50                  55                  60

Ala Leu Cys Leu Leu Met Leu Ala Arg Gly Ser Ala Val Gln Ser Pro
 65                  70                  75                  80

Pro Leu Pro Pro Leu Pro Ser Arg Ala Ser Pro Ser Asp His Arg Asp
                 85                  90                  95

Tyr Lys Cys Thr Val Cys Gly Lys Ser Phe Ser Ser Tyr Gln Ala Leu
                100                 105                 110

Gly Gly His Lys Thr Ser His Arg Lys Pro Thr Asn Thr Ser Ile Thr
            115                 120                 125

Ser Gly Asn Gln Glu Leu Ser Asn Asn Ser His Ser Asn Ser Gly Ser
130                 135                 140

Val Val Ile Asn Val Thr Val Asn Thr Gly Asn Gly Val Ser Gln Ser
145                 150                 155                 160

Gly Lys Ile His Thr Cys Ser Ile Cys Phe Lys Ser Phe Ala Ser Gly
                165                 170                 175

Gln Ala Leu Gly Gly His Lys Arg Cys His Tyr Asp Gly Gly Asn Asn
                180                 185                 190

Gly Asn Gly Asn Gly Ser Ser Asn Ser Val Glu Leu Val Ala Gly
            195                 200                 205

Ser Asp Val Ser Asp Val Asp Asn Glu Arg Trp Ser Glu Glu Ser Ala
210                 215                 220

Ile Gly Gly His Arg Gly Phe Asp Leu Asn Leu Pro Ala Asp Gln Val
225                 230                 235                 240

Ser Val Thr Thr Ser
            245

<210> SEQ ID NO 45
<211> LENGTH: 1001
<212> TYPE: DNA
<213> ORGANISM: Arabidopsis thaliana
<220> FEATURE:
<223> OTHER INFORMATION: G1352

<400> SEQUENCE: 45
gcgcgattaa aaactctcaa cttttctctc aaatttctga tcctttgatc caacagttag      60
aagaagattc atctgatcat ggccctcgaa gcgatgaaca ctccaacttc ttctttcacc     120
agaatcgaaa cgaaagaaga tttgatgaac gacgccgttt tcattgagcc gtggcttaaa     180
cgcaaacgct ccaaacgtca gcgttctcac agcccttctt cgtcttcttc ctcaccgcct     240
cgatctcgac ccaaatccca gaatcaagat cttacggaag aagagtatct cgctctttgt     300
ctcctcatgc tcgctaaaga tcaaccgtcg caaacgcgat tcatcaaca gtcgcaatcg      360 ttaacgccgc cgccagaatc aaagaacctt ccgtacaagt gtaacgtctg tgaaaaagcg     420
tttccttcct atcaggcttt aggcggtcac aaagcaagtc accgaatcaa accaccaacc     480
gtaatctcaa caaccgccga tgattcaaca gctccgacca tctccatcgt cgccggagaa     540
aaacatccga ttgctgcctc cggaaagatc acgagtgtt caatctgtca taaagtgttt      600
ccgacgggtc aagctttagg cggtcacaaa cgttgtcact acgaaggcaa cctcggcggc     660
ggaggaggag gaggaagcaa atcaatcagt cacagtggaa gcgtgtcgag cacggtatcg     720
gaagaaagga gccaccgtgg attcatcgat ctaaacctac cggcgttacc tgaactcagc     780
cttcatcaca atccaatcgt cgacgaagag atcttgagtc cgttgaccgg taaaaaaccg     840
```

```
cttttgttga ccgatcacga ccaagtcatc aagaaagaag atttatcttt aaaaatctaa      900
tactcgacta ttaattcttg tgtgattttt ttcgttacaa ccatagtttc attttcattt      960
ttttagttac aaatttttaa ttgttctgat ttggattgaa a                         1001
```

<210> SEQ ID NO 46
<211> LENGTH: 273
<212> TYPE: PRT
<213> ORGANISM: Arabidopsis thaliana
<220> FEATURE:
<223> OTHER INFORMATION: G1352

<400> SEQUENCE: 46

```
Met Ala Leu Glu Ala Met Asn Thr Pro Thr Ser Ser Phe Thr Arg Ile
 1               5                  10                  15

Glu Thr Lys Glu Asp Leu Met Asn Asp Ala Val Phe Ile Glu Pro Trp
            20                  25                  30

Leu Lys Arg Lys Arg Ser Lys Arg Gln Arg Ser His Ser Pro Ser Ser
        35                  40                  45

Ser Ser Ser Ser Pro Pro Arg Ser Arg Pro Lys Ser Gln Asn Gln Asp
    50                  55                  60

Leu Thr Glu Glu Tyr Leu Ala Leu Cys Leu Leu Met Leu Ala Lys
65                  70                  75                  80

Asp Gln Pro Ser Gln Thr Arg Phe His Gln Gln Ser Gln Ser Leu Thr
                85                  90                  95

Pro Pro Pro Glu Ser Lys Asn Leu Pro Tyr Lys Cys Asn Val Cys Glu
            100                 105                 110

Lys Ala Phe Pro Ser Tyr Gln Ala Leu Gly Gly His Lys Ala Ser His
        115                 120                 125

Arg Ile Lys Pro Pro Thr Val Ile Ser Thr Thr Ala Asp Asp Ser Thr
    130                 135                 140

Ala Pro Thr Ile Ser Ile Val Ala Gly Glu Lys His Pro Ile Ala Ala
145                 150                 155                 160

Ser Gly Lys Ile His Glu Cys Ser Ile Cys His Lys Val Phe Pro Thr
                165                 170                 175

Gly Gln Ala Leu Gly Gly His Lys Arg Cys His Tyr Glu Gly Asn Leu
            180                 185                 190

Gly Gly Gly Gly Gly Gly Ser Lys Ser Ile Ser His Ser Gly Ser
        195                 200                 205

Val Ser Ser Thr Val Ser Glu Glu Arg Ser His Arg Gly Phe Ile Asp
    210                 215                 220

Leu Asn Leu Pro Ala Leu Pro Glu Leu Ser Leu His His Asn Pro Ile
225                 230                 235                 240

Val Asp Glu Glu Ile Leu Ser Pro Leu Thr Gly Lys Lys Pro Leu Leu
                245                 250                 255

Leu Thr Asp His Asp Gln Val Ile Lys Lys Glu Asp Leu Ser Leu Lys
            260                 265                 270

Ile
```

<210> SEQ ID NO 47
<211> LENGTH: 2663
<212> TYPE: DNA
<213> ORGANISM: Arabidopsis thaliana
<220> FEATURE:
<223> OTHER INFORMATION: G1089

<400> SEQUENCE: 47

-continued

```
aagtaagaga gcttcttaag gaagaagaag atgggttgtg ctcaatcaaa gatcgagaac    60
gaagaagcag ttactcgttg caaagaacga aaacaattga tgaaagacgc cgtcactgct   120
cgtaacgctt tcgccgccgc tcactcagct tacgctatgg ctcttaaaaa caccggagct   180
gctctttccg attactctca cggcgagttt ttagtctcta atcactcgtc ttcctccgca   240
gctgcagcaa tcgcttctac ttcttctctt cccactgcta tatctcctcc tcttccttct   300
tccaccgctc cggtttctaa ttcaaccgct tcttcttcct ccgctgcggt tcctcagccg   360
attcctgata ctcttcctcc tcctcctcct ccaccaccgc ttcctcttca acgtgctgct   420
actatgccgg agatgaacgg tagatccggt ggtggtcatg ctggtagtgg actcaacgga   480
attgaagaag atggagccct agataacgat gatgatgacg atgatgatga tgatgactct   540
gaaatggaga atcgtgatcg tttgattagg aaatcgagaa gccgtggagg tagtactaga   600
ggaaatagga cgacgattga agatcatcat cttcaggagg agaaagctcc gccacctccc   660
cctttggcga attcgcggcc aattccgccg ccacgtcagc atcagcatca acatcagcaa   720
cagcaacaac aaccttttcta cgattacttc ttccctaatg ttgagaatat gcctggaact   780
actttagaag atactcctcc acaaccacaa ccacaaccaa caaggcctgt gcctcctcaa   840
ccacattcac cagtcgttac tgaggatgac gaagatgagg aggaggaaga ggaggaagag   900
gaggaggaag aggagacggt gattgaacgg aaaccactgg tggaggaaag accgaagaga   960
gtagaggaag tgacgattga attggaaaaa gttactaatt tgagagggat gaagaagagt  1020
aaagggatag ggattcccgg agagaggaga ggaatgcgaa tgccggtgac tgcgacgcat  1080
ttggcgaatg tattcattga gcttgatgat aatttcttga aagcttctga agtgctcat  1140
gatgtttcta agatgcttga agctactagg ctccattacc attctaattt tgcagataac  1200
cgaggacata ttgatcactc tgctagagtg atgcgtgtaa ttacatggaa tagatcatt  1260
agaggaatac caaatgctga tgatgggaaa gatgatgttg atttggaaga gaatgaaact  1320
catgctactg ttcttgacaa attgctagca tgggaaaaga agctctatga cgaagtcaag  1380
gctggcgaac tcatgaaaat cgagtaccag aaaaaggttg ctcatttaaa tcgggtgaag  1440
aaacgaggtg gccactcgga ttcattagag agagctaaag cagcagtaag tcatttgcat  1500
acaagatata tagttgatat gcaatccatg gactccacag tttcagaaat caatcgtctt  1560
agggatgaac aactatacct aaagctcgtt caccttgttg aggcgatggg aagatgtgg  1620
gaaatgatgc aaatacatca tcaaagacaa gctgagatct caaaggtgtt gagatctcta  1680
gatgtttcac aagcggtgaa agaaacaaat gatcatcatc acgaacgcac catccagctc  1740
ttggcagtgg ttcaagaatg gcacacgcag ttttgcagga tgatagatca tcagaaagaa  1800
tacataaaag cacttggcgg atggctaaag ctaaatctca tccctatcga agcacactc  1860
aaggagaaag tatcttcgcc tcctcgagtt cccaatcccg caatccaaaa actcctccac  1920
gcttggtatg accgtttaga caaaatcccc gacgaaatgg ctaaaagtgc cataatcaat  1980
ttcgcagcgg ttgtaagcac gataatgcag cagcaagaag acgagataag tctcagaaac  2040
aaatgcgaag agacaagaaa agaattggga agaaaaatta gacagtttga ggattggtac  2100
cacaaataca tccagaagag aggaccggag gggatgaatc cggatgaagc ggataacgat  2160
cataatgatg aggtcgctgt gaggcaattc aatgtagaac aaattaagaa gaggttggaa  2220
gaagaagaag aagcttacca tagacaaagc catcaagtta gagagaagtc actggcagt  2280
cttcgaactc gcctccccga gctttttcag gcaatgtccg aggttgcgta ttcatgttcg  2340
```

```
gatatgtata gagctataac gtatgcgagt aagcggcaaa gccaaagcga acggcatcag    2400
aaacctagcc agggacagag ttcgtaagaa ctaatgtaag atcagagtaa tgtcttcttc    2460
ttctttgatc ttgaatattt aagcacacac atacatacaa cgtatagcta aatctttatc    2520
attgctttct tatattaagg ttttggcttt tgtaagaagg tttcttacat atgagattca    2580
tatagtgttt gattcttaag gaactgttct gttgagtaat aagaaagttg tgtattgaaa    2640
tagagttgca tttgttaatt ttg                                           2663
```

<210> SEQ ID NO 48
<211> LENGTH: 798
<212> TYPE: PRT
<213> ORGANISM: Arabidopsis thaliana
<220> FEATURE:
<223> OTHER INFORMATION: G1089

<400> SEQUENCE: 48

```
Met Gly Cys Ala Gln Ser Lys Ile Glu Asn Glu Ala Val Thr Arg
 1               5                  10                  15

Cys Lys Glu Arg Lys Gln Leu Met Lys Asp Ala Val Thr Ala Arg Asn
            20                  25                  30

Ala Phe Ala Ala His Ser Ala Tyr Ala Met Ala Leu Lys Asn Thr
        35                  40                  45

Gly Ala Ala Leu Ser Asp Tyr Ser His Gly Glu Phe Leu Val Ser Asn
    50                  55                  60

His Ser Ser Ser Ala Ala Ala Ile Ala Ser Thr Ser Ser Leu
65                  70                  75                  80

Pro Thr Ala Ile Ser Pro Pro Leu Pro Ser Ser Thr Ala Pro Val Ser
                85                  90                  95

Asn Ser Thr Ala Ser Ser Ser Ala Ala Val Pro Gln Pro Ile Pro
            100                 105                 110

Asp Thr Leu Pro Pro Pro Pro Pro Pro Leu Pro Leu Gln Arg
        115                 120                 125

Ala Ala Thr Met Pro Glu Met Asn Gly Arg Ser Gly Gly His Ala
    130                 135                 140

Gly Ser Gly Leu Asn Gly Ile Glu Glu Asp Gly Ala Leu Asp Asn Asp
145                 150                 155                 160

Asp Asp Asp Asp Asp Asp Asp Ser Glu Met Glu Asn Arg Asp
                165                 170                 175

Arg Leu Ile Arg Lys Ser Arg Ser Arg Gly Gly Ser Thr Arg Gly Asn
            180                 185                 190

Arg Thr Thr Ile Glu Asp His His Leu Gln Glu Glu Lys Ala Pro Pro
        195                 200                 205

Pro Pro Pro Leu Ala Asn Ser Arg Pro Ile Pro Pro Arg Gln His
    210                 215                 220

Gln His Gln His Gln Gln Gln Gln Gln Pro Phe Tyr Asp Tyr Phe
225                 230                 235                 240

Phe Pro Asn Val Glu Asn Met Pro Gly Thr Thr Leu Glu Asp Thr Pro
                245                 250                 255

Pro Gln Pro Gln Pro Gln Pro Thr Arg Pro Val Pro Gln Pro His
            260                 265                 270

Ser Pro Val Val Thr Glu Asp Asp Glu Asp Glu Glu Glu Glu Glu
        275                 280                 285

Glu Glu Glu Glu Glu Glu Glu Thr Val Ile Glu Arg Lys Pro Leu Val
    290                 295                 300
```

-continued

```
Glu Glu Arg Pro Lys Arg Val Glu Val Thr Ile Glu Leu Glu Lys
305                 310                 315                 320

Val Thr Asn Leu Arg Gly Met Lys Lys Ser Lys Gly Ile Gly Ile Pro
            325                 330                 335

Gly Glu Arg Arg Gly Met Arg Met Pro Val Thr Ala Thr His Leu Ala
            340                 345                 350

Asn Val Phe Ile Glu Leu Asp Asp Asn Phe Leu Lys Ala Ser Glu Ser
            355                 360                 365

Ala His Asp Val Ser Lys Met Leu Glu Ala Thr Arg Leu His Tyr His
    370                 375                 380

Ser Asn Phe Ala Asp Asn Arg Gly His Ile Asp His Ser Ala Arg Val
385                 390                 395                 400

Met Arg Val Ile Thr Trp Asn Arg Ser Phe Arg Gly Ile Pro Asn Ala
            405                 410                 415

Asp Asp Gly Lys Asp Asp Val Asp Leu Glu Glu Asn Glu Thr His Ala
            420                 425                 430

Thr Val Leu Asp Lys Leu Leu Ala Trp Glu Lys Lys Leu Tyr Asp Glu
            435                 440                 445

Val Lys Ala Gly Glu Leu Met Lys Ile Glu Tyr Gln Lys Lys Val Ala
    450                 455                 460

His Leu Asn Arg Val Lys Lys Arg Gly His Ser Asp Ser Leu Glu
465                 470                 475                 480

Arg Ala Lys Ala Ala Val Ser His Leu His Thr Arg Tyr Ile Val Asp
            485                 490                 495

Met Gln Ser Met Asp Ser Thr Val Ser Glu Ile Asn Arg Leu Arg Asp
            500                 505                 510

Glu Gln Leu Tyr Leu Lys Leu Val His Leu Val Glu Ala Met Gly Lys
    515                 520                 525

Met Trp Glu Met Met Gln Ile His His Gln Arg Gln Ala Glu Ile Ser
    530                 535                 540

Lys Val Leu Arg Ser Leu Asp Val Ser Gln Ala Val Lys Glu Thr Asn
545                 550                 555                 560

Asp His His His Glu Arg Thr Ile Gln Leu Leu Ala Val Val Gln Glu
            565                 570                 575

Trp His Thr Gln Phe Cys Arg Met Ile Asp His Gln Lys Glu Tyr Ile
            580                 585                 590

Lys Ala Leu Gly Gly Trp Leu Lys Leu Asn Leu Ile Pro Ile Glu Ser
            595                 600                 605

Thr Leu Lys Glu Lys Val Ser Ser Pro Pro Arg Val Pro Asn Pro Ala
    610                 615                 620

Ile Gln Lys Leu Leu His Ala Trp Tyr Asp Arg Leu Asp Lys Ile Pro
625                 630                 635                 640

Asp Glu Met Ala Lys Ser Ala Ile Ile Asn Phe Ala Ala Val Val Ser
            645                 650                 655

Thr Ile Met Gln Gln Gln Glu Asp Glu Ile Ser Leu Arg Asn Lys Cys
            660                 665                 670

Glu Glu Thr Arg Lys Glu Leu Gly Arg Lys Ile Arg Gln Phe Glu Asp
            675                 680                 685

Trp Tyr His Lys Tyr Ile Gln Lys Arg Gly Pro Glu Gly Met Asn Pro
            690                 695                 700

Asp Glu Ala Asp Asn Asp His Asn Asp Glu Val Ala Val Arg Gln Phe
705                 710                 715                 720

Asn Val Glu Gln Ile Lys Lys Arg Leu Glu Glu Glu Glu Ala Tyr
```

```
                  725                 730                 735
His Arg Gln Ser His Gln Val Arg Glu Lys Ser Leu Ala Ser Leu Arg
                740                 745                 750
Thr Arg Leu Pro Glu Leu Phe Gln Ala Met Ser Glu Val Ala Tyr Ser
                755                 760                 765
Cys Ser Asp Met Tyr Arg Ala Ile Thr Tyr Ala Ser Lys Arg Gln Ser
            770                 775                 780
Gln Ser Glu Arg His Gln Lys Pro Ser Gln Gly Gln Ser Ser
785                 790                 795
```

<210> SEQ ID NO 49
<211> LENGTH: 1529
<212> TYPE: DNA
<213> ORGANISM: Arabidopsis thaliana
<220> FEATURE:
<223> OTHER INFORMATION: G553

<400> SEQUENCE: 49

```
ttgatcggaa tattccttt agaatgccaa gattcattct tcatctctcg agctcctcat      60
gaatttcttc tctgcttatc aatggagatg atgagctctt cttcttctac tactcaagtt    120
gtatcattca gagacatggg gatgtatgaa ccatttcaac agttatctgg ttgggagagt    180
cctttcaaat cagatatcaa caatattact agtaatcaga ataacaatca gagttcttca    240
acaacacttg aggttgatgc tagaccagaa gcagatgata acaatagagt gaattatact    300
tctgtgtata taactctct tgaagcagaa ccgtcgagta ataatgatca ggacgaagac      360
cggatcaatg ataagatgaa acggcgtttg gctcagaacc gagaagctgc tcgcaaaagt    420
cgtttgagaa agaaggccca tgttcaacag ttagaagaaa gccggttgaa gttgtcacag    480
ctcgagcagg aacttgtaag agctaggcag cagggattat gcgtacgcaa ttcttcagat    540
actagttatc taggaccagc tgggaatatg aactcaggta ttgctgcatt tgagatggaa    600
tacacacact ggctagaaga gcaaaacagg agagttagtg agattcgaac agcgctccaa    660
gctcatatag gtgacattga gctcaaaatg ttggtagata gttgcttgaa ccactacgca    720
aatctcttcc gcatgaaagc tgatgctgca aaggctgatg tgttcttctt gatgtcggga    780
atgtggcgaa cttcaactga acgcttcttc caatggattg gaggtttccg cccatccgag    840
cttttaaatg ttgtgatgcc atacgttgag cccttaaccg atcagcaact gttggaggtg    900
cgtaacctgc aacagtcgtc tcagcaagca gaggaggctc tctctcaagg cttagataaa    960
cttcagcagg gtttggtcga agcatagca attcagataa aagttgttga gtctgtgaat    1020
cacgggctc caatggcttc agccatggag aatcttcaag cattggagag ttttgtgaac    1080
caggcggatc atctgagaca acagaccctg cagcaaatga gtaagatatt gacgacaaga   1140
caggctgctc gagggttgct cgctctagga gaatacttcc acaggctgcg tgctcttagt   1200
tctctctggg cagctcgtcc acgagaacac acttgacaag ttaggaggca aacaaaacaa   1260
agagaaagaa gcacaaggca gatgatgtta gctatagga cttgctttat ctctcagaaa    1320
gtgttggctg atattttctc cattagagag catcatcttc ctcattgatg attttgttta   1380
cttgaaagga ataagagatg tgtaaatttg ggtggaaaac atgtaatgtc tttgatgcat   1440
taggctcttt atttgtaaaa tatataggt ttgttgtcac tcatctcctc gtatatgaaa    1500
atttgagccc acaatcaaat tttttgtct                                    1529
```

<210> SEQ ID NO 50
<211> LENGTH: 384

-continued

```
<212> TYPE: PRT
<213> ORGANISM: Arabidopsis thaliana
<220> FEATURE:
<223> OTHER INFORMATION: G553

<400> SEQUENCE: 50

Met Glu Met Met Ser Ser Ser Ser Thr Thr Gln Val Val Ser Phe
 1               5                  10                  15

Arg Asp Met Gly Met Tyr Glu Pro Phe Gln Gln Leu Ser Gly Trp Glu
            20                  25                  30

Ser Pro Phe Lys Ser Asp Ile Asn Asn Ile Thr Ser Asn Gln Asn Asn
        35                  40                  45

Asn Gln Ser Ser Ser Thr Thr Leu Glu Val Asp Ala Arg Pro Glu Ala
 50                  55                  60

Asp Asp Asn Asn Arg Val Asn Tyr Thr Ser Val Tyr Asn Asn Ser Leu
 65                  70                  75                  80

Glu Ala Glu Pro Ser Ser Asn Asn Asp Gln Asp Glu Asp Arg Ile Asn
                85                  90                  95

Asp Lys Met Lys Arg Arg Leu Ala Gln Asn Arg Glu Ala Ala Arg Lys
            100                 105                 110

Ser Arg Leu Arg Lys Lys Ala His Val Gln Gln Leu Glu Glu Ser Arg
        115                 120                 125

Leu Lys Leu Ser Gln Leu Glu Gln Glu Leu Val Arg Ala Arg Gln Gln
130                 135                 140

Gly Leu Cys Val Arg Asn Ser Asp Thr Ser Tyr Leu Gly Pro Ala
145                 150                 155                 160

Gly Asn Met Asn Ser Gly Ile Ala Ala Phe Glu Met Glu Tyr Thr His
                165                 170                 175

Trp Leu Glu Glu Gln Asn Arg Arg Val Ser Glu Ile Arg Thr Ala Leu
            180                 185                 190

Gln Ala His Ile Gly Asp Ile Glu Leu Lys Met Leu Val Asp Ser Cys
        195                 200                 205

Leu Asn His Tyr Ala Asn Leu Phe Arg Met Lys Ala Asp Ala Ala Lys
210                 215                 220

Ala Asp Val Phe Phe Leu Met Ser Gly Met Trp Arg Thr Ser Thr Glu
225                 230                 235                 240

Arg Phe Phe Gln Trp Ile Gly Gly Phe Arg Pro Ser Glu Leu Leu Asn
                245                 250                 255

Val Val Met Pro Tyr Val Glu Pro Leu Thr Asp Gln Gln Leu Leu Glu
            260                 265                 270

Val Arg Asn Leu Gln Gln Ser Ser Gln Gln Ala Glu Glu Ala Leu Ser
        275                 280                 285

Gln Gly Leu Asp Lys Leu Gln Gln Gly Leu Val Glu Ser Ile Ala Ile
290                 295                 300

Gln Ile Lys Val Val Glu Ser Val Asn His Gly Ala Pro Met Ala Ser
305                 310                 315                 320

Ala Met Glu Asn Leu Gln Ala Leu Glu Ser Phe Val Asn Gln Ala Asp
                325                 330                 335

His Leu Arg Gln Gln Thr Leu Gln Gln Met Ser Lys Ile Leu Thr Thr
            340                 345                 350

Arg Gln Ala Ala Arg Gly Leu Leu Ala Leu Gly Glu Tyr Phe His Arg
        355                 360                 365

Leu Arg Ala Leu Ser Ser Leu Trp Ala Ala Arg Pro Arg Glu His Thr
370                 375                 380
```

<210> SEQ ID NO 51
<211> LENGTH: 2491
<212> TYPE: DNA
<213> ORGANISM: Arabidopsis thaliana
<220> FEATURE:
<223> OTHER INFORMATION: G1221

<400> SEQUENCE: 51

| | | | | | |
|---|---|---|---|---|---|
| gtccattttt | aaaaaatcaa | ctataccatt | tttagctatt | ctttggtctt | cgtttcgtgt | 60 |
| aagcatgtca | atgttttttt | tcttttatct | ctttgggaaa | cgggagtgtg | gtcttcgtgt | 120 |
| gtgtgtccct | gtttcattaa | ccaataatta | tgcttgggag | tggaaagcaa | gaaaaattct | 180 |
| aaactttata | taaaattccc | agaatcaatt | gatccaaaaa | gagtattgtc | aaaaaagata | 240 |
| atcaagaaga | agaaactctg | ttttttttgtt | ctgttcttgg | aaaaaaatga | ggagtatgat | 300 |
| gatggagaga | gagggaagga | atgagataga | aagagaagta | atagatgact | tggaagagac | 360 |
| gcaaaacgaa | ggagatgatt | tcaagtcaat | acctccatgg | aaggaacaaa | tcactttcag | 420 |
| aggaattgtt | gcaagtttaa | tcattggtat | aatctacagt | gtgatcgtga | tgaaactaaa | 480 |
| cctaacaaca | ggtttggtcc | caaacctaaa | tgtctctgca | gcacttttag | cctttgtctt | 540 |
| ccttagaagc | tggaccaagc | tgttgaccaa | agccgggatt | gtgactaaac | cgttcactaa | 600 |
| acaagagaac | actgttgtcc | aaacatgtgc | tgttgcttgt | tacagcattg | cagttggagg | 660 |
| tgggtttggt | tcataccttc | ttggttttgaa | cagaattact | tatgaacagt | caggaggaac | 720 |
| tcacactgat | gggaattatc | cggaaggcac | gaaagagcct | ggaatcggtt | ggatgaccgc | 780 |
| tttcttgttc | tttacttgct | ttgttggtct | tttagcattg | gttcctctaa | gaaagatcat | 840 |
| gatcatagac | tacaagctga | catatccaag | tggaacagct | accgcggttt | tgatcaacgg | 900 |
| tttccacact | cctaaaggca | ataaaatggc | caagaaacaa | gtgtttgggt | tgtgaagta | 960 |
| cttctcattt | agcttcattt | gggctttctt | ccaatggttc | ttctctggtg | gtacagagtg | 1020 |
| cggtttcatt | cagtttccaa | ctttcggggtt | agaagctttg | aagaacacat | tctacttcga | 1080 |
| ctttagcatg | acatacgttg | gagcaggaat | gatctgtccc | catattgtca | atatatcttt | 1140 |
| gcttttttggc | gcggttctgt | cttggggaat | catgtggcca | ctcattaaag | gtcttaaagg | 1200 |
| agattggttc | ccatcaactc | ttcctgaaaa | cagcatgaag | agtctcaatg | gttacaaggt | 1260 |
| gtttatatca | atctcattga | tcctcggaga | cgggctttac | caattcatca | agatactttt | 1320 |
| taagacagga | ataaacatgt | acgtcaagtt | aaacaatcgc | aactctggga | atctaattc | 1380 |
| ggagaaagat | aagcaatcta | ttgcagatct | taaaagagat | gagatctttg | taagagacag | 1440 |
| cattccatta | tgggttgcag | cagtaggaaa | cgcagcgttc | tctgttgtct | cgatcatcgc | 1500 |
| gatccctata | atgttccccg | agctgaaatg | gtacttcata | gtcgtagctt | acatgttagc | 1560 |
| tccatcgtta | ggtttcagta | acgcttatgg | agcagggcta | acagatatga | acatggctta | 1620 |
| taactatggt | aaagtcgctc | tgtttatctt | agccgctatg | gcagggaaac | aaaatggtgt | 1680 |
| agtcgcggga | cttgtcggat | gcgggttgat | aaaatcgatt | gtatcgattt | cttctgacct | 1740 |
| aatgcacgat | ttcaagacag | gacatttgac | tctgacttca | cctaggtcga | tgcttgtgag | 1800 |
| tcaagcgatc | ggtacagcga | tcggatgcgt | tgtggcgcct | ctaactttct | tcttgtttta | 1860 |
| taaagctttc | gatgtcggga | accaggaggg | agagtacaaa | gctccttacg | ctttggtata | 1920 |
| cagaaacatg | gcaattcttg | gagttgaagg | tttctctgct | ttgcctcaac | attgtttaca | 1980 |
| gctttgttac | gggttttttcg | cattcgcggt | ggcggcaaat | ctcgttaggg | ataggttacc | 2040 |
| ggataagata | gggaattggg | ttccattacc | gatggcaatg | gcggttccgt | ttcttgttgg | 2100 |

```
aggdtactttgctattgatatgtgtgtgggaagtttgattgtgtttgcttggaatatgag      2160 agatcgagttaaagccggtttaatggtaccggcggttgcttccggtttgatatgtggaga      2220 tggtctatggattttgccgtcgtcggttcttgctttggccggcgttagacctcctatatg      2280 tatgggcttcatgccgagtaaatattcgagttaaagatagcttttttacgagtttttactt      2340 ttttgtgtagcgacaaaaaaattagctaaagaattgtggaacaaaaaaaacagtttata      2400 taggaattgtactttgtaagtttgtatacacaataaagtaataaactagtctctcaattc      2460 tatttaaaaaaaaaaaaaaaaaaaaaaaaa                                   2491
```

<210> SEQ ID NO 52
<211> LENGTH: 675
<212> TYPE: PRT
<213> ORGANISM: Arabidopsis thaliana
<220> FEATURE:
<223> OTHER INFORMATION: G1221

<400> SEQUENCE: 52

```
Met Arg Ser Met Met Met Glu Arg Glu Gly Arg Asn Glu Ile Glu Arg
  1               5                  10                  15

Glu Val Ile Asp Asp Leu Glu Glu Thr Gln Asn Glu Gly Asp Asp Phe
             20                  25                  30

Lys Ser Ile Pro Pro Trp Lys Glu Gln Ile Thr Phe Arg Gly Ile Val
         35                  40                  45

Ala Ser Leu Ile Ile Gly Ile Ile Tyr Ser Val Ile Val Met Lys Leu
     50                  55                  60

Asn Leu Thr Thr Gly Leu Val Pro Asn Leu Asn Val Ser Ala Ala Leu
 65                  70                  75                  80

Leu Ala Phe Val Phe Leu Arg Ser Trp Thr Lys Leu Leu Thr Lys Ala
                 85                  90                  95

Gly Ile Val Thr Lys Pro Phe Thr Lys Gln Glu Asn Thr Val Val Gln
                100                 105                 110

Thr Cys Ala Val Ala Cys Tyr Ser Ile Ala Val Gly Gly Gly Phe Gly
            115                 120                 125

Ser Tyr Leu Leu Gly Leu Asn Arg Ile Thr Tyr Glu Gln Ser Gly Gly
        130                 135                 140

Thr His Thr Asp Gly Asn Tyr Pro Glu Gly Thr Lys Glu Pro Gly Ile
145                 150                 155                 160

Gly Trp Met Thr Ala Phe Leu Phe Phe Thr Cys Phe Val Gly Leu Leu
                165                 170                 175

Ala Leu Val Pro Leu Arg Lys Ile Met Ile Asp Tyr Lys Leu Thr
            180                 185                 190

Tyr Pro Ser Gly Thr Ala Thr Ala Val Leu Ile Asn Gly Phe His Thr
        195                 200                 205

Pro Lys Gly Asn Lys Met Ala Lys Lys Gln Val Phe Gly Phe Val Lys
    210                 215                 220

Tyr Phe Ser Phe Ser Phe Ile Trp Ala Phe Phe Gln Trp Phe Ser
225                 230                 235                 240

Gly Gly Thr Glu Cys Gly Phe Ile Gln Phe Pro Thr Phe Gly Leu Glu
                245                 250                 255

Ala Leu Lys Asn Thr Phe Tyr Phe Asp Phe Ser Met Thr Tyr Val Gly
            260                 265                 270

Ala Gly Met Ile Cys Pro His Ile Val Asn Ile Ser Leu Leu Phe Gly
        275                 280                 285
```

-continued

Ala Val Leu Ser Trp Gly Ile Met Trp Pro Leu Ile Lys Gly Leu Lys
        290                 295                 300

Gly Asp Trp Phe Pro Ser Thr Leu Pro Glu Asn Ser Met Lys Ser Leu
305                 310                 315                 320

Asn Gly Tyr Lys Val Phe Ile Ser Ile Ser Leu Ile Leu Gly Asp Gly
                325                 330                 335

Leu Tyr Gln Phe Ile Lys Ile Leu Phe Lys Thr Gly Ile Asn Met Tyr
            340                 345                 350

Val Lys Leu Asn Asn Arg Asn Ser Gly Lys Ser Asn Ser Glu Lys Asp
        355                 360                 365

Lys Gln Ser Ile Ala Asp Leu Lys Arg Asp Glu Ile Phe Val Arg Asp
    370                 375                 380

Ser Ile Pro Leu Trp Val Ala Val Gly Asn Ala Ala Phe Ser Val
385                 390                 395                 400

Val Ser Ile Ile Ala Ile Pro Ile Met Phe Pro Glu Leu Lys Trp Tyr
                405                 410                 415

Phe Ile Val Val Ala Tyr Met Leu Ala Pro Ser Leu Gly Phe Ser Asn
            420                 425                 430

Ala Tyr Gly Ala Gly Leu Thr Asp Met Asn Met Ala Tyr Asn Tyr Gly
        435                 440                 445

Lys Val Ala Leu Phe Ile Leu Ala Ala Met Ala Gly Lys Gln Asn Gly
    450                 455                 460

Val Val Ala Gly Leu Val Gly Cys Gly Leu Ile Lys Ser Ile Val Ser
465                 470                 475                 480

Ile Ser Ser Asp Leu Met His Asp Phe Lys Thr Gly His Leu Thr Leu
                485                 490                 495

Thr Ser Pro Arg Ser Met Leu Val Ser Gln Ala Ile Gly Thr Ala Ile
            500                 505                 510

Gly Cys Val Val Ala Pro Leu Thr Phe Phe Leu Phe Tyr Lys Ala Phe
        515                 520                 525

Asp Val Gly Asn Gln Glu Gly Glu Tyr Lys Ala Pro Tyr Ala Leu Val
    530                 535                 540

Tyr Arg Asn Met Ala Ile Leu Gly Val Glu Gly Phe Ser Ala Leu Pro
545                 550                 555                 560

Gln His Cys Leu Gln Leu Cys Tyr Gly Phe Phe Ala Phe Ala Val Ala
                565                 570                 575

Ala Asn Leu Val Arg Asp Arg Leu Pro Asp Lys Ile Gly Asn Trp Val
            580                 585                 590

Pro Leu Pro Met Ala Met Ala Val Pro Phe Leu Val Gly Gly Tyr Phe
        595                 600                 605

Ala Ile Asp Met Cys Val Gly Ser Leu Ile Val Phe Ala Trp Asn Met
    610                 615                 620

Arg Asp Arg Val Lys Ala Gly Leu Met Val Pro Ala Val Ala Ser Gly
625                 630                 635                 640

Leu Ile Cys Gly Asp Gly Leu Trp Ile Leu Pro Ser Ser Val Leu Ala
                645                 650                 655

Leu Ala Gly Val Arg Pro Pro Ile Cys Met Gly Phe Met Pro Ser Lys
            660                 665                 670

Tyr Ser Ser
        675

<210> SEQ ID NO 53
<211> LENGTH: 1054
<212> TYPE: DNA

-continued

```
<213> ORGANISM: Arabidopsis thaliana
<220> FEATURE:
<223> OTHER INFORMATION: G580

<400> SEQUENCE: 53
ccaaaaaaca aagcattcta tgctattctg ttctgttctc caatgttgtc atcagcaaag      60
cataataaga tcaacaacca tagtgccttt tcaatttcct cttcatcatc atcattatca    120
acatcatcct ccctaggcca taacaaatct caagtcacca tggaagaagt atggaaagaa    180
atcaaccttg gttcacttca ctaccatcgg caactaaaca ttggtcatga accaatgtta    240
aagaaccaaa accctaataa ctccatcttt caagatttcc tcaacatgcc tctgaatcaa    300
ccaccaccac caccaccacc accttcctct tccaccattg tcactgctct ctatggctct    360
ctgcctcttc cgcctcctgc cactgtcctc agcttaaact ccggtgttgg attcgagttt    420
cttgatacca cagaaaatct tcttgcttct aaccctcgct cctttgagga atctgcaaag    480
tttggttgtc ttggtaagaa aagaggccaa gattctgatg atactagagg agacagaagg    540
tataagcgta tgatcaagaa cagagaatct gctgctcgtt caagggctag gaagcaggca    600
tatacaaacg aacttgagct tgaaattgct cacttgcaga cagagaatgc aagactcaag    660
atacaacaag agcagctgaa aatagccgaa gcaactcaaa accaagtaaa gaaaacacta    720
caacggtctt ccacagctcc attttgagaa aaatctacta tttctttttg ggggagtttc    780
aagtgtttct tatgaagatg agaaaaacag aaaaagtttg tacattttag ctaagttaaa    840
tttgtggtgg taagtaatgt aaaagaaaag tgtgtgtaga agaaaagtgt ctagaaaaag    900
aaagcaacta actttcttct tcttctctgg tttcctatca actcttttga cttttgtact    960
ttttttcttc tctacttaac ctctattatt gtaatgccaa gtcaagtcct tatctagcta   1020
gtacatgagt ttctgttttc actggttaag ccat                               1054

<210> SEQ ID NO 54
<211> LENGTH: 234
<212> TYPE: PRT
<213> ORGANISM: Arabidopsis thaliana
<220> FEATURE:
<223> OTHER INFORMATION: G580

<400> SEQUENCE: 54
```

Met Leu Ser Ser Ala Lys His Asn Lys Ile Asn Asn His Ser Ala Phe
1               5                   10                  15

Ser Ile Ser Ser Ser Ser Ser Leu Ser Thr Ser Ser Ser Leu Gly
            20                  25                  30

His Asn Lys Ser Gln Val Thr Met Glu Glu Val Trp Lys Glu Ile Asn
        35                  40                  45

Leu Gly Ser Leu His Tyr His Arg Gln Leu Asn Ile Gly His Glu Pro
    50                  55                  60

Met Leu Lys Asn Gln Asn Pro Asn Asn Ser Ile Phe Gln Asp Phe Leu
65                  70                  75                  80

Asn Met Pro Leu Asn Gln Pro Pro Pro Pro Pro Pro Ser Ser
                85                  90                  95

Ser Thr Ile Val Thr Ala Leu Tyr Gly Ser Leu Pro Leu Pro Pro Pro
            100                 105                 110

Ala Thr Val Leu Ser Leu Asn Ser Gly Val Gly Phe Glu Phe Leu Asp
        115                 120                 125

Thr Thr Glu Asn Leu Leu Ala Ser Asn Pro Arg Ser Phe Glu Glu Ser
    130                 135                 140

| | | | | | | | | | | | |
|---|---|---|---|---|---|---|---|---|---|---|---|
|Ala|Lys|Phe|Gly|Cys|Leu|Gly|Lys|Lys|Arg|Gly|Gln|Asp|Ser|Asp|
|145| | | | |150| | | | |155| | | |160|

Thr Arg Gly Asp Arg Arg Tyr Lys Arg Met Ile Lys Asn Arg Glu Ser
              165                    170                    175

Ala Ala Arg Ser Arg Ala Arg Lys Gln Ala Tyr Thr Asn Glu Leu Glu
          180                    185                    190

Leu Glu Ile Ala His Leu Gln Thr Glu Asn Ala Arg Leu Lys Ile Gln
        195                    200                  205

Gln Glu Gln Leu Lys Ile Ala Glu Ala Thr Gln Asn Gln Val Lys Lys
    210                  215                  220

Thr Leu Gln Arg Ser Ser Thr Ala Pro Phe
225              230

<210> SEQ ID NO 55
<211> LENGTH: 1575
<212> TYPE: DNA
<213> ORGANISM: Arabidopsis thaliana
<220> FEATURE:
<223> OTHER INFORMATION: G270

<400> SEQUENCE: 55

```
aactcacaat agggcacgaa cggccgcccg ggcaggacga taatgcagtc actgtccacg      60
ccacacacca tctctcttct tctccccaga acctctccgt ctcgtctttc tccctctctt     120
cactcccttg ctttccccac tcgattacgg tctcttttcct attcttctca aacgtcgatc    180
ctccccgatg ccgcgatga tttcattgtc ggtgactgtc tcgtctacga ggacggcgtc     240
ttcgaagacc cttaccttga taaggaggtc actcaggttg cgaagcagga gcgcaagaag     300
aatcggcgtg gcggggctaa gagattagat gaatccgaga ttgagcccga gaacctcgtg     360
ccagaggaat ggagggatat tcaggcggag gtgaatctga cgaagaagga caagcgcaaa     420
atagcgcagg agatggagtt cggggttcgg gtggagaaga gaggcaagg gctaattccg      480
ctgaggaaag ttgacttgaa tgactttctc acgtacaagg aagccaagtt ggctcaattg     540
aggcctgtca ttctcgataa accgggaaat ttctccgacg acagtggagc gtcaagcgat     600
ggagagaccg ctgtatcatc tcccagcgag cgagtggctc ctaagaaccc tagatgggca     660
gtttacggaa agggattcga ccacgttgcc aagttcttca atagcgacaa gtacgatccc     720
agcgacaaga atccgacgg ccctcgaaag ctgctttcaa aagaagagaa gtttatgctc      780
aatagccgga atcctgacct agccgttgcc acatcaaaaa aatggcttcc tcttcacaca     840
ctggcagcat gtggagagtt ttatctggtt gattccttgc taaagcacaa tcttgatatc     900
aatgcaaccg atgtgggcgg cttgacagta cttcaccgag caatcattgg taagaagcag     960
gctattacta actacctgct gagggaatcg gcaaatccat tgttcttga tgacgaaggt     1020
gcgacctga tgcactatgc tgtgcaaaca gcatcagctc ccacaataaa acttctccta     1080
ctgtataacg ctgatataaa cgctcaggac agggacgggt ggactccact gcacgttgca     1140
gtacaggcca aagaagcga cattgtaaag cttcttttga taaaagggc ggacatagaa     1200
gtgaagaaca aggatgggtt aactccgctt gggcttgcc tctaccttgg aagagagata     1260
aggacgtatg aggtgatgaa gctgttgaaa gagtttccac ttagcagaca caagaagaga     1320
ttggtaacaa cagatgaaga tattgaatag tccttcaat ttcagcttga agtacactca      1380
cttatgagaa cctgagaaaa ggagatggag gtaaaggtga tgattaggc attggaacct     1440
cggagtcgga gtgggtccac tgtctcactt ccttaaattt ggtttgctgt tagtcttatc     1500
catcgatttt ggatatttat cacaacttga tccattctta agaaaatat ctgaaaataa     1560
```
aaaaaaaaaa aaaaa                                                   1575

<210> SEQ ID NO 56
<211> LENGTH: 435
<212> TYPE: PRT
<213> ORGANISM: Arabidopsis thaliana
<220> FEATURE:
<223> OTHER INFORMATION: G270

<400> SEQUENCE: 56

```
Met Gln Ser Leu Ser Thr Pro His Thr Ile Ser Leu Leu Pro Arg
 1               5                  10                  15

Thr Ser Pro Ser Arg Leu Ser Pro Ser Leu His Ser Leu Ala Phe Pro
                20                  25                  30

Thr Arg Leu Arg Ser Leu Ser Tyr Ser Ser Gln Thr Ser Ile Leu Pro
            35                  40                  45

Asp Ala Gly Asp Asp Phe Ile Val Gly Asp Cys Leu Val Tyr Glu Asp
        50                  55                  60

Gly Val Phe Glu Asp Pro Tyr Leu Asp Lys Glu Val Thr Gln Val Ala
 65                  70                  75                  80

Lys Gln Glu Arg Lys Lys Asn Arg Arg Gly Gly Ala Lys Arg Leu Asp
                85                  90                  95

Glu Ser Glu Ile Glu Pro Glu Asn Leu Val Pro Glu Glu Trp Arg Asp
            100                 105                 110

Ile Gln Ala Glu Val Asn Leu Thr Lys Lys Asp Lys Arg Lys Ile Ala
        115                 120                 125

Gln Glu Met Glu Phe Gly Val Arg Val Glu Lys Lys Arg Gln Gly Leu
    130                 135                 140

Ile Pro Leu Arg Lys Val Asp Leu Asn Asp Phe Leu Thr Tyr Lys Glu
145                 150                 155                 160

Ala Lys Leu Ala Gln Leu Arg Pro Val Ile Leu Asp Lys Pro Gly Asn
                165                 170                 175

Phe Ser Asp Asp Ser Gly Ala Ser Ser Asp Gly Glu Thr Ala Val Ser
            180                 185                 190

Ser Pro Ser Glu Arg Val Ala Pro Lys Asn Pro Arg Trp Ala Val Tyr
        195                 200                 205

Gly Lys Gly Phe Asp His Val Ala Lys Phe Phe Asn Ser Asp Lys Tyr
    210                 215                 220

Asp Pro Ser Asp Lys Ser Asp Gly Pro Arg Lys Leu Leu Ser Lys
225                 230                 235                 240

Glu Glu Lys Phe Met Leu Asn Ser Arg Asn Pro Asp Leu Ala Val Ala
                245                 250                 255

Thr Ser Lys Lys Trp Leu Pro Leu His Thr Leu Ala Ala Cys Gly Glu
            260                 265                 270

Phe Tyr Leu Val Asp Ser Leu Leu Lys His Asn Leu Asp Ile Asn Ala
        275                 280                 285

Thr Asp Val Gly Gly Leu Thr Val Leu His Arg Ala Ile Ile Gly Lys
    290                 295                 300

Lys Gln Ala Ile Thr Asn Tyr Leu Leu Arg Glu Ser Ala Asn Pro Phe
305                 310                 315                 320

Val Leu Asp Asp Glu Gly Ala Thr Leu Met His Tyr Ala Val Gln Thr
                325                 330                 335

Ala Ser Ala Pro Thr Ile Lys Leu Leu Leu Tyr Asn Ala Asp Ile
            340                 345                 350
```

```
Asn Ala Gln Asp Arg Asp Gly Trp Thr Pro Leu His Val Ala Val Gln
            355                 360                 365

Ala Arg Arg Ser Asp Ile Val Lys Leu Leu Ile Lys Gly Ala Asp
        370                 375                 380

Ile Glu Val Lys Asn Lys Asp Gly Leu Thr Pro Leu Gly Leu Cys Leu
385                 390                 395                 400

Tyr Leu Gly Arg Glu Ile Arg Thr Tyr Glu Val Met Lys Leu Leu Lys
                405                 410                 415

Glu Phe Pro Leu Ser Arg His Lys Lys Arg Leu Val Thr Thr Asp Glu
            420                 425                 430

Asp Ile Glu
        435

<210> SEQ ID NO 57
<211> LENGTH: 1292
<212> TYPE: DNA
<213> ORGANISM: Arabidopsis thaliana
<220> FEATURE:
<223> OTHER INFORMATION: G201

<400> SEQUENCE: 57
atgtcaagaa agccatgttg tgtgggagaa ggactgaaga aaggagcatg gactgccgaa      60
gaagacaaga aactcatctc ttacattcat gaacacggtg gaggaggctg gcgtgacatt     120
ccccaaaaag ctggactaaa cgatgtggaa aagagttgta gattgcgatg ggctaactat     180
ttgaaacctg acatcaagag aggagagttt agctatgagg aggaacagat tatcatcatg     240
ctacacgctt ctcgcggcaa caagtggtca gtcatagcga acatttgcc caaaagaaca      300 gataacgaga ttaagaacta ctggaacacg catctcaaaa agctcctgat cgataaggga     360
atcgatcccg tgacccacaa gccacttgcc tatgactcaa cccggatga gcaatcgcaa      420 tcgggttcca tctctccaaa gtctcttcct ccttcaagct ccaaaaatgt accggagata     480
accagcagtg acgagacacc gaaatatgat gcttccttga ctccaagaa acgttgtttt      540 aagagatcga gttctacatc aaaactgtta acaaagttg cagctagggc ttcttccatg      600
ggaactatac taggcgcctc catcgaagga accttgatca gctctacacc gttgtcttca     660
tgtctaaatg atgactttc tgaaacaagt caatttcaga tggaagaatt tgatccattc      720
tatcagtcat ctgaacacat aattgatcat atgaaagaag atatcagcat caacaattcc     780
gaatacaatt tctcgcagtt tctcgagcag tttagtaaca cgaaggga agaagctgac       840 aatactggag gaggatataa ccaagatctt cttatgtctg atgtctcatc aacaagcgtt     900
gatgaagacg agatgatgca aaacataact ggttggtcaa attatctcct tgaccattcc     960
gatttcaatt atgacacgag ccaagattat gacgacaaga acttcatatg atccgttgat    1020
tgcttaccgg actagagttg accggttaat gtcatatggt tctcttagat atttgtcaag    1080
ttatagtaaa ggtccactat agggtcacta tatattaata ttcagtaatg gattctctta    1140
gttagagaac cttgtgatgc cgtggatcaa ttagtatttg atttgcggga gacacgagtt    1200 tttttttcctt ctattgttgt ttgtggattt acgtactata aataataaat aaaacaccca    1260
tttgattgca aaaaaaaaaa aaaaaaaaaa aa                                   1292

<210> SEQ ID NO 58
<211> LENGTH: 336
<212> TYPE: PRT
<213> ORGANISM: Arabidopsis thaliana
<220> FEATURE:
<223> OTHER INFORMATION: G201
```

<400> SEQUENCE: 58

```
Met Ser Arg Lys Pro Cys Cys Val Gly Glu Gly Leu Lys Lys Gly Ala
  1               5                  10                  15

Trp Thr Ala Glu Glu Asp Lys Lys Leu Ile Ser Tyr Ile His Glu His
             20                  25                  30

Gly Gly Gly Gly Trp Arg Asp Ile Pro Gln Lys Ala Gly Leu Lys Arg
         35                  40                  45

Cys Gly Lys Ser Cys Arg Leu Arg Trp Ala Asn Tyr Leu Lys Pro Asp
     50                  55                  60

Ile Lys Arg Gly Glu Phe Ser Tyr Glu Glu Gln Ile Ile Ile Met
 65                  70                  75                  80

Leu His Ala Ser Arg Gly Asn Lys Trp Ser Val Ile Ala Arg His Leu
                 85                  90                  95

Pro Lys Arg Thr Asp Asn Glu Ile Lys Asn Tyr Trp Asn Thr His Leu
            100                 105                 110

Lys Lys Leu Leu Ile Asp Lys Gly Ile Asp Pro Val Thr His Lys Pro
            115                 120                 125

Leu Ala Tyr Asp Ser Asn Pro Asp Glu Gln Ser Gln Ser Gly Ser Ile
        130                 135                 140

Ser Pro Lys Ser Leu Pro Pro Ser Ser Lys Asn Val Pro Glu Ile
145                 150                 155                 160

Thr Ser Ser Asp Glu Thr Pro Lys Tyr Asp Ala Ser Leu Ser Ser Lys
                165                 170                 175

Lys Arg Cys Phe Lys Arg Ser Ser Thr Ser Lys Leu Leu Asn Lys
            180                 185                 190

Val Ala Ala Arg Ala Ser Ser Met Gly Thr Ile Leu Gly Ala Ser Ile
        195                 200                 205

Glu Gly Thr Leu Ile Ser Ser Thr Pro Leu Ser Ser Cys Leu Asn Asp
    210                 215                 220

Asp Phe Ser Glu Thr Ser Gln Phe Gln Met Glu Glu Phe Asp Pro Phe
225                 230                 235                 240

Tyr Gln Ser Ser Glu His Ile Ile Asp His Met Lys Glu Asp Ile Ser
                245                 250                 255

Ile Asn Asn Ser Glu Tyr Asn Phe Ser Gln Phe Leu Glu Gln Phe Ser
            260                 265                 270

Asn Asn Glu Gly Glu Glu Ala Asp Asn Thr Gly Gly Gly Tyr Asn Gln
        275                 280                 285

Asp Leu Leu Met Ser Asp Val Ser Ser Thr Ser Val Asp Glu Asp Glu
    290                 295                 300

Met Met Gln Asn Ile Thr Gly Trp Ser Asn Tyr Leu Leu Asp His Ser
305                 310                 315                 320

Asp Phe Asn Tyr Asp Thr Ser Gln Asp Tyr Asp Lys Asn Phe Ile
                325                 330                 335
```

<210> SEQ ID NO 59
<211> LENGTH: 1651
<212> TYPE: DNA
<213> ORGANISM: Arabidopsis thaliana
<220> FEATURE:
<223> OTHER INFORMATION: G1417

<400> SEQUENCE: 59

```
tctatctcta tctatctctc tttgtctgca aatggaagaa catattcaag atcgccgtga      60
aattgcgttc ttacactcag gagaatttct ccacggagat tctgactcaa aggatcatca     120
```

-continued

```
accgaacgag tctccggtgg aacgtcatca cgagtcgtct atcaaagaag ttgatttctt      180
cgctgctaaa agtcagccgt ttgatcttgg tcatgtgaga acaacgacga tcgttggatc      240
atctggtttt aatgatggat taggtttggt aaattcatgt catggaacat caagcaatga      300
tggcgatgac aaaaccaaaa ctcaaattag tagactgaag ttggagctag agaggcttca      360
cgaggagaat cacaaactga agcatttatt agatgaggtc agtgagagtt acaacgacct      420
ccaaagaaga gttttgttag caagacaaac acaagtggaa ggtcttcatc ataaacaaca      480
tgaggatgta cctcaagctg gttcctcaca agctctagaa acagaagac caaggatat       540 gaaccatgaa actccggcca ccaccttgaa acgacggtct ccagacgacg tggatggtcg      600
tgatatgcac cgaggatcac caaaaactcc tcgaatagac aaaacaaga gtactaatca      660 tgaagaacaa caaaaccctc atgatcaatt accctataga aaagctaggg tttccgttag      720
agctagatct gatgccacta cggtaaatga cggatgtcaa tggagaaaat acggtcagaa      780
aatggcgaaa gggaatccat gtcctcgcgc ttattatcgt tgcaccatgg ccgttggatg      840
tcctgtccgt aaacaggtcc aacgatgcgc ggaggataca actatcttga caacaacgta      900
cgaaggaaac cataaccatc ctcttccccc gtcagccaca gccatggctg caaccacctc      960
cgccgcagca gccatgctct tatcaggctc ctcctccagc aacctccacc aaacactctc     1020
tagcccctcc gccacgtcat catcatcctt ctaccataac ttcccataca cctccacaat     1080
cgcaacactc tctgcctcag ctcctttccc caccataacc ttagacctca ccaacccacc     1140
tcgaccgcta caaccgccac cgcagtttct aagccagtat ggtcccgccg cgttttacc      1200 aaacgctaat caaattaggt ctatgaataa taataaccag cagttattaa tacctaatttt    1260 gtttggccca caagccccac cacgtgaaat ggtcgattca gttagggctg cgattgcgat     1320
ggatccgaac ttcacggcgg cacttgcggc cgcgatctca aacattatcg gaggaggtaa     1380
taacgacaac aataataata ctgatattaa tgataacaag gttgatgcaa aaagtggagg     1440
gagtagtaac ggagattcgc cacagcttcc tcagtcttgc accactttct ctacaaacta     1500
attttactac cattattata tgttatctta ttatatatta cacacacata ttatacatta     1560
tgcgtatctt aagttttttt ttgggggcca ttatatatga atgatatgga gatcactgag     1620
agagagagag agctattatg ggtttttttt t                                    1651
```

<210> SEQ ID NO 60
<211> LENGTH: 489
<212> TYPE: PRT
<213> ORGANISM: Arabidopsis thaliana
<220> FEATURE:
<223> OTHER INFORMATION: G1417

<400> SEQUENCE: 60

```
Met Glu Glu His Ile Gln Asp Arg Arg Glu Ile Ala Phe Leu His Ser
 1               5                  10                  15

Gly Glu Phe Leu His Gly Asp Ser Asp Ser Lys Asp His Gln Pro Asn
            20                  25                  30

Glu Ser Pro Val Glu Arg His His Glu Ser Ser Ile Lys Glu Val Asp
        35                  40                  45

Phe Phe Ala Ala Lys Ser Gln Pro Phe Asp Leu Gly His Val Arg Thr
    50                  55                  60

Thr Thr Ile Val Gly Ser Ser Phe Asn Asp Gly Leu Gly Leu Val
65                  70                  75                  80

Asn Ser Cys His Gly Thr Ser Ser Asn Asp Gly Asp Asp Lys Thr Lys
```

```
                        85                  90                  95
Thr Gln Ile Ser Arg Leu Lys Leu Glu Leu Glu Arg Leu His Glu Glu
                100                 105                 110

Asn His Lys Leu Lys His Leu Leu Asp Glu Val Ser Glu Ser Tyr Asn
        115                 120                 125

Asp Leu Gln Arg Arg Val Leu Leu Ala Arg Gln Thr Gln Val Glu Gly
    130                 135                 140

Leu His His Lys Gln His Glu Asp Val Pro Gln Ala Gly Ser Ser Gln
145                 150                 155                 160

Ala Leu Glu Asn Arg Arg Pro Lys Asp Met Asn His Glu Thr Pro Ala
                165                 170                 175

Thr Thr Leu Lys Arg Arg Ser Pro Asp Asp Val Asp Gly Arg Asp Met
        180                 185                 190

His Arg Gly Ser Pro Lys Thr Pro Arg Ile Asp Gln Asn Lys Ser Thr
    195                 200                 205

Asn His Glu Glu Gln Gln Asn Pro His Asp Gln Leu Pro Tyr Arg Lys
210                 215                 220

Ala Arg Val Ser Val Arg Ala Arg Ser Asp Ala Thr Thr Val Asn Asp
225                 230                 235                 240

Gly Cys Gln Trp Arg Lys Tyr Gly Gln Lys Met Ala Lys Gly Asn Pro
                245                 250                 255

Cys Pro Arg Ala Tyr Tyr Arg Cys Thr Met Ala Val Gly Cys Pro Val
        260                 265                 270

Arg Lys Gln Val Gln Arg Cys Ala Glu Asp Thr Thr Ile Leu Thr Thr
    275                 280                 285

Thr Tyr Glu Gly Asn His Asn His Pro Leu Pro Pro Ser Ala Thr Ala
290                 295                 300

Met Ala Ala Thr Thr Ser Ala Ala Ala Met Leu Leu Ser Gly Ser
305                 310                 315                 320

Ser Ser Ser Asn Leu His Gln Thr Leu Ser Ser Pro Ser Ala Thr Ser
                325                 330                 335

Ser Ser Ser Phe Tyr His Asn Phe Pro Tyr Thr Ser Thr Ile Ala Thr
        340                 345                 350

Leu Ser Ala Ser Ala Pro Phe Pro Thr Ile Thr Leu Asp Leu Thr Asn
    355                 360                 365

Pro Pro Arg Pro Leu Gln Pro Pro Gln Phe Leu Ser Gln Tyr Gly
370                 375                 380

Pro Ala Ala Phe Leu Pro Asn Ala Asn Gln Ile Arg Ser Met Asn Asn
385                 390                 395                 400

Asn Asn Gln Gln Leu Leu Ile Pro Asn Leu Phe Gly Pro Gln Ala Pro
                405                 410                 415

Pro Arg Glu Met Val Asp Ser Val Arg Ala Ala Ile Ala Met Asp Pro
        420                 425                 430

Asn Phe Thr Ala Ala Leu Ala Ala Ile Ser Asn Ile Ile Gly Gly
    435                 440                 445

Gly Asn Asn Asp Asn Asn Asn Thr Asp Ile Asn Asp Asn Lys Val
        450                 455                 460

Asp Ala Lys Ser Gly Gly Ser Ser Asn Gly Asp Ser Pro Gln Leu Pro
465                 470                 475                 480

Gln Ser Cys Thr Thr Phe Ser Thr Asn
                485
```

<210> SEQ ID NO 61

<211> LENGTH: 1046
<212> TYPE: DNA
<213> ORGANISM: Arabidopsis thaliana
<220> FEATURE:
<223> OTHER INFORMATION: G233

<400> SEQUENCE: 61

| | | | | | |
|---|---|---|---|---|---:|
| gaaaaacatt | tcaacttctt | ttatcagcaa | tcacaaatca | aagagatggg | aagagctcca | 60 |
| tgctgtgaga | agatggggtt | gaagagagga | ccatggacac | ctgaagaaga | tcaaatcttg | 120 |
| gtctctttta | tcctcaacca | tggacatagt | aactggcgag | ccctccctaa | gcaagctggt | 180 |
| cttttgagat | gtggaaaaag | ctgtagactt | aggtggatga | actatttaaa | gcctgatatt | 240 |
| aaacgtggca | atttcaccaa | agaagaggaa | gatgctatca | tcagcttaca | ccaaatactt | 300 |
| ggcaatagat | ggtcagcgat | tgcagcaaaa | ctgcctggaa | gaaccgataa | cgagatcaag | 360 |
| aacgtatggc | acactcactt | gaagaagaga | ctcgaagatt | atcaaccagc | taaacctaag | 420 |
| accagcaaca | aaagaaggg | tactaaacca | aaatctgaat | ccgtaataac | gagctcgaac | 480 |
| agtactagaa | gcgaatcgga | gctagcagat | tcatcaaacc | cttctggaga | aagcttattt | 540 |
| tcgacatcgc | cttcgacaag | tgaggtttct | tcgatgacac | tcataagcca | cgacggctat | 600 |
| agcaacgaga | ttaatatgga | taacaaaccg | ggagatatca | gtactatcga | tcaagaatgt | 660 |
| gtttctttcg | aaacttttgg | tgcggatatc | gatgaaagct | tctggaaaga | gacactgtat | 720 |
| agccaagatg | aacacaacta | cgtatcgaat | gacctagaag | tcgctggttt | agttgagata | 780 |
| caacaagagt | ttcaaaactt | gggctccgct | aataatgaga | tgattttga | cagtgagatg | 840 |
| gaacttctgg | ttcgatgtat | tggctagaac | cggcggggaa | caagatctct | tagccgggct | 900 |
| ctagttaaca | tgtttgagga | gtaaagtgaa | atggtgcaaa | ttagttaagg | ctaagaaatt | 960 |
| caaaagcttt | tgtttaccga | gaaaaaaaca | cactctaact | cttgatgtga | tgtagttagt | 1020 |
| gtattaatta | gaggctgcgt | tttcaa | | | | 1046 |

<210> SEQ ID NO 62
<211> LENGTH: 273
<212> TYPE: PRT
<213> ORGANISM: Arabidopsis thaliana
<220> FEATURE:
<223> OTHER INFORMATION: G233

<400> SEQUENCE: 62

```
Met Gly Arg Ala Pro Cys Cys Glu Lys Met Gly Leu Lys Arg Gly Pro
 1               5                  10                  15

Trp Thr Pro Glu Glu Asp Gln Ile Leu Val Ser Phe Ile Leu Asn His
            20                  25                  30

Gly His Ser Asn Trp Arg Ala Leu Pro Lys Gln Ala Gly Leu Leu Arg
        35                  40                  45

Cys Gly Lys Ser Cys Arg Leu Arg Trp Met Asn Tyr Leu Lys Pro Asp
    50                  55                  60

Ile Lys Arg Gly Asn Phe Thr Lys Glu Glu Asp Ala Ile Ile Ser
 65                  70                  75                  80

Leu His Gln Ile Leu Gly Asn Arg Trp Ser Ala Ile Ala Ala Lys Leu
                85                  90                  95

Pro Gly Arg Thr Asp Asn Glu Ile Lys Asn Val Trp His Thr His Leu
            100                 105                 110

Lys Lys Arg Leu Glu Asp Tyr Gln Pro Ala Lys Pro Lys Thr Ser Asn
        115                 120                 125

Lys Lys Lys Gly Thr Lys Pro Lys Ser Glu Ser Val Ile Thr Ser Ser
```

```
                130              135              140
Asn Ser Thr Arg Ser Glu Ser Glu Leu Ala Asp Ser Ser Asn Pro Ser
145                 150                 155                 160

Gly Glu Ser Leu Phe Ser Thr Ser Pro Ser Thr Ser Glu Val Ser Ser
                165                 170                 175

Met Thr Leu Ile Ser His Asp Gly Tyr Ser Asn Glu Ile Asn Met Asp
                180                 185                 190

Asn Lys Pro Gly Asp Ile Ser Thr Ile Asp Gln Glu Cys Val Ser Phe
            195                 200                 205

Glu Thr Phe Gly Ala Asp Ile Asp Glu Ser Phe Trp Lys Glu Thr Leu
    210                 215                 220

Tyr Ser Gln Asp Glu His Asn Tyr Val Ser Asn Asp Leu Glu Val Ala
225                 230                 235                 240

Gly Leu Val Glu Ile Gln Gln Glu Phe Gln Asn Leu Gly Ser Ala Asn
                245                 250                 255

Asn Glu Met Ile Phe Asp Ser Glu Met Glu Leu Leu Val Arg Cys Ile
            260                 265                 270

Gly

<210> SEQ ID NO 63
<211> LENGTH: 1296
<212> TYPE: DNA
<213> ORGANISM: Arabidopsis thaliana
<220> FEATURE:
<223> OTHER INFORMATION: G920

<400> SEQUENCE: 63
aaaaaatcta tttcttctc tttccactat attacaacat tcttcattc tcaaatcatc      60 atactaaaaa cctaaaaaaa gttacatatt cattgtatct ttgtgagaaa aaatggatt    120 cgaatagtaa caacacgaaa tccataaaga gaaagttgt cgaccaactt gtcgaaggct    180
atgaattcgc tactcagctt cagcttctcc tttctcatca acactctaac cagtaccaca   240
tcgatgagac ccgtcttgtt tccgggtcgg gttcagtttc cggtggtcca gatcccgttg   300
atgagctcat gtctaagatc ttgggatctt ccataaaac tatatcggtt cttgattctt    360
ttgatcccgt cgccgtctct gtccccatcg ccgtcgaggg ttcatggaat gcttcatgtg   420
gggatgattc ggcgactccg gtgagttgca acggtggaga ttccggtgag agtaagaaga   480
agagattagg ggttggtaag ggtaaaagag atgctacac tagaaagacg agatcacata    540
caaggatcgt ggaagctaaa agttctgaag acagatatgc ttggaggaaa tatggacaaa   600
aggagattct taataccaca ttcccaagaa gttactttag atgcacacac aagccaacgc   660
aaggatgcaa agcaacaaag caagttcaga acaggatca agattctgag atgttccaaa    720
tcacatacat tggctaccac acatgcactg ccaatgacca aacgcacgcg aagaccgagc   780
cttttgatca agaaatcatt atggattcgg aaaagacatt ggctgctagc actgctcaga   840
accatgtcaa tgctatggtg caagagcaag agaacaacac cagcagtgtg acagcaatag   900
acgcaggcat ggttaaggag gaacaaaata caatggtga tcagagtaaa gattattatg    960
agggctcttc gacaggtgag gacttgtcat tggtttggca agagacgatg atgtttgatg   1020
atcatcaaaa tcactactat tgtggtgaaa ccagtactac ttctcatcaa tttggtttca   1080
tcgacaacga tgatcagttt tcctccttct tcgactcata ttgtgctgat tatgaaagaa   1140
caagtgctat gtgaacatcc aaatctggaa tgatgaatca gcactaggtc ttctctttga   1200
gtatgtctag tttaatgtaa tatttttgtt gtatgtttga taaaaacacc atatatactt   1260
``` ctcttttttac accaaaaaaa aaaaaaaaaa aaaaaa    1296

<210> SEQ ID NO 64
<211> LENGTH: 346
<212> TYPE: PRT
<213> ORGANISM: Arabidopsis thaliana
<220> FEATURE:
<223> OTHER INFORMATION: G920

<400> SEQUENCE: 64

Met Asp Ser Asn Ser Asn Asn Thr Lys Ser Ile Lys Arg Lys Val Val
1               5                   10                  15

Asp Gln Leu Val Glu Gly Tyr Glu Phe Ala Thr Gln Leu Gln Leu Leu
            20                  25                  30

Leu Ser His Gln His Ser Asn Gln Tyr His Ile Asp Glu Thr Arg Leu
        35                  40                  45

Val Ser Gly Ser Gly Ser Ser Gly Gly Pro Asp Pro Val Asp Glu
    50                  55                  60

Leu Met Ser Lys Ile Leu Gly Ser Phe His Lys Thr Ile Ser Val Leu
65                  70                  75                  80

Asp Ser Phe Asp Pro Val Ala Val Ser Val Pro Ile Ala Val Glu Gly
                85                  90                  95

Ser Trp Asn Ala Ser Cys Gly Asp Asp Ser Ala Thr Pro Val Ser Cys
            100                 105                 110

Asn Gly Gly Asp Ser Gly Glu Ser Lys Lys Lys Arg Leu Gly Val Gly
        115                 120                 125

Lys Gly Lys Arg Gly Cys Tyr Thr Arg Lys Thr Arg Ser His Thr Arg
    130                 135                 140

Ile Val Glu Ala Lys Ser Ser Glu Asp Arg Tyr Ala Trp Arg Lys Tyr
145                 150                 155                 160

Gly Gln Lys Glu Ile Leu Asn Thr Thr Phe Pro Arg Ser Tyr Phe Arg
                165                 170                 175

Cys Thr His Lys Pro Thr Gln Gly Cys Lys Ala Thr Lys Gln Val Gln
            180                 185                 190

Lys Gln Asp Gln Asp Ser Glu Met Phe Gln Ile Thr Tyr Ile Gly Tyr
        195                 200                 205

His Thr Cys Thr Ala Asn Asp Gln Thr His Ala Lys Thr Glu Pro Phe
210                 215                 220

Asp Gln Glu Ile Ile Met Asp Ser Glu Lys Thr Leu Ala Ala Ser Thr
225                 230                 235                 240

Ala Gln Asn His Val Asn Ala Met Val Gln Glu Gln Glu Asn Asn Thr
                245                 250                 255

Ser Ser Val Thr Ala Ile Asp Ala Gly Met Val Lys Glu Glu Gln Asn
            260                 265                 270

Asn Asn Gly Asp Gln Ser Lys Asp Tyr Tyr Glu Gly Ser Ser Thr Gly
        275                 280                 285

Glu Asp Leu Ser Leu Val Trp Gln Glu Thr Met Met Phe Asp Asp His
    290                 295                 300

Gln Asn His Tyr Tyr Cys Gly Glu Thr Ser Thr Ser His Gln Phe
305                 310                 315                 320

Gly Phe Ile Asp Asn Asp Asp Gln Phe Ser Phe Phe Asp Ser Tyr
                325                 330                 335

Cys Ala Asp Tyr Glu Arg Thr Ser Ala Met
            340                 345

<210> SEQ ID NO 65
<211> LENGTH: 1281
<212> TYPE: DNA
<213> ORGANISM: Arabidopsis thaliana
<220> FEATURE:
<223> OTHER INFORMATION: G867

<400> SEQUENCE: 65

| | | | | | |
|---|---|---|---|---|---|
| cacaacacaa | acacatttct | gttttctcca | ttgtttcaaa | ccataaaaaa | aaacacagat | 60 |
| taaatggaat | cgagtagcgt | tgatgagagt | actacaagta | caggttccat | ctgtgaaacc | 120 |
| ccggcgataa | ctccggcgaa | aaagtcgtcg | gtaggtaact | tatacaggat | gggaagcgga | 180 |
| tcaagcgttg | tgttagattc | agagaacggc | gtagaagctg | aatctaggaa | gcttccgtcg | 240 |
| tcaaaataca | aggtgtggt | gccacaacca | aacggaagat | ggggagctca | gatttacgag | 300 |
| aaacaccagc | gcgtgtggct | cgggacattc | aacgaagaag | acgaagccgc | tcgtgcctac | 360 |
| gacgtcgcgg | ttcacaggtt | ccgtcgccgt | gacgccgtca | caaatttcaa | agacgtgaag | 420 |
| atggacgaag | acgaggtcga | tttcttgaat | tctcattcga | aatctgagat | cgttgatatg | 480 |
| ttgaggaaac | atacttataa | cgaagagtta | gagcagagta | acggcgtcg | taatggtaac | 540 |
| ggaaacatga | ctaggacgtt | gttaacgtcg | gggttgagta | atgatggtgt | ttctacgacg | 600 |
| gggtttagat | cggcggaggc | actgtttgag | aaagcggtaa | cgccaagcga | cgttgggaag | 660 |
| ctaaaccgtt | tggttatacc | gaaacatcac | gcagagaaac | attttccgtt | accgtcaagt | 720 |
| aacgtttccg | tgaaaggagt | gttgttgaac | tttgaggacg | ttaacgggaa | agtgtggagg | 780 |
| ttccgttact | cgtattggaa | cagtagtcag | agttatgttt | tgactaaagg | ttggagcagg | 840 |
| ttcgttaagg | agaagaatct | acgtgctggt | gacgtggtta | gtttcagtag | atctaacggt | 900 |
| caggatcaac | agttgtacat | tgggtggaag | tcgagatccg | ggtcagattt | agatgcgggt | 960 |
| cgggttttga | gattgttcgg | agttaacatt | tcaccggaga | gttcaagaaa | cgacgtcgta | 1020 |
| ggaaacaaaa | gagtgaacga | tactgagatg | ttatcgttgg | tgtgtagcaa | gaagcaacgc | 1080 |
| atctttcacg | cctcgtaaca | actcttcttc | ttttttttc | ttttgttgtt | ttaataattt | 1140 |
| ttaaaaactc | cattttcgtt | ttctttattt | gcatcggttt | cttcttcttt | gtttaccaaa | 1200 |
| ggttcatgag | ttgttttttgt | tgtattgatg | aactgtaaat | tttatttata | ggataaattt | 1260 |
| taaaaaaaaa | aaaaaaaaa | a | | | | 1281 |

<210> SEQ ID NO 66
<211> LENGTH: 344
<212> TYPE: PRT
<213> ORGANISM: Arabidopsis thaliana
<220> FEATURE:
<223> OTHER INFORMATION: G867

<400> SEQUENCE: 66

Met Glu Ser Ser Ser Val Asp Glu Ser Thr Thr Ser Thr Gly Ser Ile
1               5                   10                  15

Cys Glu Thr Pro Ala Ile Thr Pro Ala Lys Lys Ser Ser Val Gly Asn
            20                  25                  30

Leu Tyr Arg Met Gly Ser Gly Ser Ser Val Val Leu Asp Ser Glu Asn
        35                  40                  45

Gly Val Glu Ala Glu Ser Arg Lys Leu Pro Ser Ser Lys Tyr Lys Gly
    50                  55                  60

Val Val Pro Gln Pro Asn Gly Arg Trp Gly Ala Gln Ile Tyr Glu Lys
65                  70                  75                  80

| | | | | | | | | | | | |
|---|---|---|---|---|---|---|---|---|---|---|---|
|His|Gln|Arg|Val|Trp|Leu|Gly|Thr|Phe|Asn|Glu|Glu|Asp|Ala|Ala|
| | | |85| | | |90| | | |95| | | |

Arg Ala Tyr Asp Val Ala Val His Arg Phe Arg Arg Asp Ala Val
                100                 105                 110

Thr Asn Phe Lys Asp Val Lys Met Asp Glu Asp Glu Val Asp Phe Leu
            115                 120                 125

Asn Ser His Ser Lys Ser Glu Ile Val Asp Met Leu Arg Lys His Thr
    130                 135                 140

Tyr Asn Glu Glu Leu Glu Gln Ser Lys Arg Arg Asn Gly Asn Gly
145                 150                 155                 160

Asn Met Thr Arg Thr Leu Leu Thr Ser Gly Leu Ser Asn Asp Gly Val
                165                 170                 175

Ser Thr Thr Gly Phe Arg Ser Ala Glu Ala Leu Phe Glu Lys Ala Val
                180                 185                 190

Thr Pro Ser Asp Val Gly Lys Leu Asn Arg Leu Val Ile Pro Lys His
            195                 200                 205

His Ala Glu Lys His Phe Pro Leu Pro Ser Ser Asn Val Ser Val Lys
    210                 215                 220

Gly Val Leu Leu Asn Phe Glu Asp Val Asn Gly Lys Val Trp Arg Phe
225                 230                 235                 240

Arg Tyr Ser Tyr Trp Asn Ser Ser Gln Ser Tyr Val Leu Thr Lys Gly
                245                 250                 255

Trp Ser Arg Phe Val Lys Glu Lys Asn Leu Arg Ala Gly Asp Val Val
            260                 265                 270

Ser Phe Ser Arg Ser Asn Gly Gln Asp Gln Gln Leu Tyr Ile Gly Trp
    275                 280                 285

Lys Ser Arg Ser Gly Ser Asp Leu Asp Ala Gly Arg Val Leu Arg Leu
    290                 295                 300

Phe Gly Val Asn Ile Ser Pro Glu Ser Ser Arg Asn Asp Val Val Gly
305                 310                 315                 320

Asn Lys Arg Val Asn Asp Thr Glu Met Leu Ser Leu Val Cys Ser Lys
                325                 330                 335

Lys Gln Arg Ile Phe His Ala Ser
                340

<210> SEQ ID NO 67
<211> LENGTH: 984
<212> TYPE: DNA
<213> ORGANISM: Arabidopsis thaliana
<220> FEATURE:
<223> OTHER INFORMATION: G659

<400> SEQUENCE: 67

| | | |
|---|---|---|
|atggggaagg gaagagcacc ttgttgtgac aagaccaaag tgaagagagg tccatggagc|60|
|ccagaagaag acattaaact catctctttc attcaaaagt ttggtcatga aactggaga|120|
|tctctcccca acaatctgg tatgtcattg cttttgtcat cacaatcaaa gcaaaagcct|180|
|cttcaattgt tttttctttt ctttatgatt ctgaatgtat atatatgcaa aaatgaaggg|240|
|ctattgaggt gtgggaagag ttgtcgtcta aggtggatta actatcttag gccagatctg|300|
|aagcgtggca acttcacttc agaggaggaa gaaacaatca ttaagcttca ccacaactat|360|
|gggaacaagt ggtcgaaaat cgcttctcaa cttccaggta gaacagataa cgagatcaag|420|
|aatgtgtggc acactcatct aaagaaaaga ctggctcaga gctcaggaac tgcagatgaa|480|
|ccggcctcgc cttgttcgag tgattctgtt tctcgtggga aagatgataa gtcatctcac|540|

```
gtagaagatt ctttgaacag agagactaat cataggaatg agttgtctac atctatgtct    600
tctgggggtt ccaaccaaca agatgatcca aagatagacg aactcaggtt tgagtatata    660
gaagaagctt atagcgagtt taacgacatt attattcaag aggtagacaa acccgatctg    720
ctggagatac catttgattc agatcctgac atttggagtt tcttagatac ttcaaactca    780
tttcaacaat ccactgcaaa tgagaacagc tcaggctcaa gagcaacaac agaagaagag    840
tctgatgagg atgaggttaa gaaatggttc aagcacctag aaagcgaact cgggttagaa    900
gaagacgata atcaacaaca atacaaagaa gaagaatcat catcatcatc actcttgaag    960
aactacgagc tcatgataca ttga                                          984
```

<210> SEQ ID NO 68
<211> LENGTH: 327
<212> TYPE: PRT
<213> ORGANISM: Arabidopsis thaliana
<220> FEATURE:
<223> OTHER INFORMATION: G659

<400> SEQUENCE: 68

```
Met Gly Lys Gly Arg Ala Pro Cys Cys Asp Lys Thr Lys Val Lys Arg
  1               5                  10                  15

Gly Pro Trp Ser Pro Glu Glu Asp Ile Lys Leu Ile Ser Phe Ile Gln
             20                  25                  30

Lys Phe Gly His Glu Asn Trp Arg Ser Leu Pro Lys Gln Ser Gly Met
         35                  40                  45

Ser Leu Leu Ser Ser Gln Ser Lys Gln Lys Pro Leu Gln Leu Phe
     50                  55                  60

Phe Leu Phe Phe Met Ile Leu Asn Val Tyr Ile Cys Lys Asn Glu Gly
 65                  70                  75                  80

Leu Leu Arg Cys Gly Lys Ser Cys Arg Leu Arg Trp Ile Asn Tyr Leu
                 85                  90                  95

Arg Pro Asp Leu Lys Arg Gly Asn Phe Thr Ser Glu Glu Glu Thr
            100                 105                 110

Ile Ile Lys Leu His His Asn Tyr Gly Asn Lys Trp Ser Lys Ile Ala
        115                 120                 125

Ser Gln Leu Pro Gly Arg Thr Asp Asn Glu Ile Lys Asn Val Trp His
    130                 135                 140

Thr His Leu Lys Lys Arg Leu Ala Gln Ser Ser Gly Thr Ala Asp Glu
145                 150                 155                 160

Pro Ala Ser Pro Cys Ser Ser Asp Ser Val Ser Arg Gly Lys Asp Asp
                165                 170                 175

Lys Ser Ser His Val Glu Asp Ser Leu Asn Arg Glu Thr Asn His Arg
            180                 185                 190

Asn Glu Leu Ser Thr Ser Met Ser Ser Gly Gly Ser Asn Gln Gln Asp
        195                 200                 205

Asp Pro Lys Ile Asp Glu Leu Arg Phe Glu Tyr Ile Glu Glu Ala Tyr
    210                 215                 220

Ser Glu Phe Asn Asp Ile Ile Ile Gln Glu Val Asp Lys Pro Asp Leu
225                 230                 235                 240

Leu Glu Ile Pro Phe Asp Ser Asp Pro Asp Ile Trp Ser Phe Leu Asp
                245                 250                 255

Thr Ser Asn Ser Phe Gln Gln Ser Thr Ala Asn Glu Asn Ser Ser Gly
            260                 265                 270

Ser Arg Ala Thr Thr Glu Glu Glu Ser Asp Glu Asp Glu Val Lys Lys
        275                 280                 285
```

```
Trp Phe Lys His Leu Glu Ser Glu Leu Gly Leu Glu Glu Asp Asp Asn
    290                 295                 300
Gln Gln Gln Tyr Lys Glu Glu Ser Ser Ser Ser Leu Leu Lys
305                 310                 315                 320
Asn Tyr Glu Leu Met Ile His
                325

<210> SEQ ID NO 69
<211> LENGTH: 826
<212> TYPE: DNA
<213> ORGANISM: Arabidopsis thaliana
<220> FEATURE:
<223> OTHER INFORMATION: G620

<400> SEQUENCE: 69
gaattgaact tggaccagca cagcaacaac ccaaccccaa tgaccagctc agtcatagta      60
gccggcgccg gtgacaagaa caatggtatc gtggtccagc agcaaccacc atgtgtggct    120
cgtgagcaag accaatacat gccaatcgca acgtcataa gaatcatgcg taaaaccttta    180 ccgtctcacg ccaaaatctc tgacgacgcc aaagaaacga ttcaagaatg tgtctccgag    240
tacatcagct tcgtgaccgg tgaagccaac gagcgttgcc aacgtgagca acgtaagacc    300
ataactgctg aagatatcct ttgggctatg agcaagcttg gttcgataa ctacgtggac     360 cccctcaccg tgttcattaa ccggtaccgt gagatagaga ccgatcgtgg ttctgcactt    420
agaggtgagc caccgtcgtt gagacaaacc tatggaggaa atggtattgg gtttcacggc    480
ccatctcatg gcctacctcc tccgggtcct tatggttatg gtatgttgga ccaatccatg    540
gttatgggag gtggtcggta ctaccaaaac gggtcgtcgg gtcaagatga atccagtgtt    600
ggtggtggct cttcgtcttc cattaacgga atgccggctt ttgaccatta tggtcagtat    660
aagtgaagaa ggagttattc ttcatttta tatctattca aaacatgtgt ttcgatagat     720 atttttatttt tatgtcttat caataacatt tctatataat gttgcttctt taaggaaaag    780
tgttgtatgt caatacttta tgagaaactg atttatatat gcaaat                  826

<210> SEQ ID NO 70
<211> LENGTH: 208
<212> TYPE: PRT
<213> ORGANISM: Arabidopsis thaliana
<220> FEATURE:
<223> OTHER INFORMATION: G620

<400> SEQUENCE: 70

Met Thr Ser Ser Val Ile Val Ala Gly Ala Gly Asp Lys Asn Asn Gly
  1               5                  10                  15

Ile Val Val Gln Gln Gln Pro Pro Cys Val Ala Arg Glu Gln Asp Gln
                 20                  25                  30

Tyr Met Pro Ile Ala Asn Val Ile Arg Ile Met Arg Lys Thr Leu Pro
            35                  40                  45

Ser His Ala Lys Ile Ser Asp Asp Ala Lys Glu Thr Ile Gln Glu Cys
        50                  55                  60

Val Ser Glu Tyr Ile Ser Phe Val Thr Gly Glu Ala Asn Glu Arg Cys
 65                  70                  75                  80

Gln Arg Glu Gln Arg Lys Thr Ile Thr Ala Glu Asp Ile Leu Trp Ala
                85                  90                  95

Met Ser Lys Leu Gly Phe Asp Asn Tyr Val Asp Pro Leu Thr Val Phe
            100                 105                 110
```

-continued

```
Ile Asn Arg Tyr Arg Glu Ile Glu Thr Asp Arg Gly Ser Ala Leu Arg
            115                 120                 125
Gly Glu Pro Pro Ser Leu Arg Gln Thr Tyr Gly Gly Asn Gly Ile Gly
        130                 135                 140
Phe His Gly Pro Ser His Gly Leu Pro Pro Pro Gly Pro Tyr Gly Tyr
145                 150                 155                 160
Gly Met Leu Asp Gln Ser Met Val Met Gly Gly Arg Tyr Tyr Gln
                165                 170                 175
Asn Gly Ser Ser Gly Gln Asp Glu Ser Ser Val Gly Gly Ser Ser
            180                 185                 190
Ser Ser Ile Asn Gly Met Pro Ala Phe Asp His Tyr Gly Gln Tyr Lys
        195                 200                 205
```

<210> SEQ ID NO 71
<211> LENGTH: 1394
<212> TYPE: DNA
<213> ORGANISM: Arabidopsis thaliana
<220> FEATURE:
<223> OTHER INFORMATION: G596

<400> SEQUENCE: 71

| | | | | | |
|---|---|---|---|---|---|
| taatttctct | acttcagatt | tttttctcct | tagattaatt | taattgagtt | attgtacatc | 60 |
| cctcaagcta | agattctggt | tttgtgagtt | gagtggatga | gaagaggaga | gattaactaa | 120 |
| attagggttt | caattgttta | cttttgttt | gctttttata | tcaagtaatg | gatcaggtct | 180 |
| ctcgctctct | tcctccacct | tttctctcaa | gagatctcca | tcttcaccca | caccatcaat | 240 |
| tccagcatca | gcagcagcag | cagcaacaga | atcacggcca | cgatatagac | cagcaccgaa | 300 |
| tcggtgggct | aaaacgtgac | cgagatgctg | atatcgatcc | caacgagcac | tcttcagccg | 360 |
| gaaaagatca | aagtactcct | ggctccggtg | gagaaagcgg | cggcggagga | ggaggagata | 420 |
| atcacatcac | gagaaggcca | cgtggcagac | cagcgggatc | taagaacaaa | ccaaaaccgc | 480 |
| caatcatcat | cactcgagac | agcgcaaacg | ctctcaaatc | tcatgtcatg | aagtagcaa | 540 |
| acggatgtga | cgtcatggaa | agtgtcaccg | tcttcgctcg | ccgtcgccaa | cgtggcatct | 600 |
| gcgttttgag | cggaaacggc | gccgttacca | acgttaccat | aagacaacca | gcttcagtac | 660 |
| ctggtggtgg | ctcatctgtc | gttaacttac | acggacgttt | cgagattctt | tctctctcgg | 720 |
| gatcattcct | tcctcctccg | gctccaccag | ctgcgtcagg | tctaacgatt | tacttagccg | 780 |
| gtggtcaggg | acaggttgtt | ggaggaagcg | tggttggtcc | actcatggct | tcaggacctg | 840 |
| tagtgattat | ggcagcttcg | tttggaaacg | ctgcgtatga | gagactgccg | ttggaggaag | 900 |
| acgatcaaga | agagcaaaca | gctggagcgg | ttgctaataa | tatcgatgga | aacgcaacaa | 960 |
| tgggtggtgg | aacgcaaacg | caaactcaga | cgcagcagca | acagcaacaa | cagttgatgc | 1020 |
| aagatccgac | gtcgtttata | caagggttgc | ctccgaatct | tatgaattct | gttcaattgc | 1080 |
| cagctgaagc | ttattgggga | actccgagac | catctttcta | aatcgcgaag | aaaaaacaag | 1140 |
| ttagatacgt | tcgttgtttt | taatttataa | tctctcttct | gtcaagtttt | aatttttcttt | 1200 |
| ttcttcttct | ttgttttcta | aagataattg | tagtctttga | cgaagattcg | tggtacgtat | 1260 |
| gaatcgaaga | gaatcgtttt | ggtcatggga | ttgctcgatc | tattaggttt | gagagggggt | 1320 |
| ttgtgttttg | cgttgactag | cagattataa | aattgttgat | tttcgagttt | ttatttcat | 1380 |
| gtgttggtga | taaa | | | | | 1394 |

<210> SEQ ID NO 72
<211> LENGTH: 317

<212> TYPE: PRT
<213> ORGANISM: Arabidopsis thaliana
<220> FEATURE:
<223> OTHER INFORMATION: G596

<400> SEQUENCE: 72

Met Asp Gln Val Ser Arg Ser Leu Pro Pro Phe Leu Ser Arg Asp
1               5                   10                  15

Leu His Leu His Pro His His Gln Phe Gln His Gln Gln Gln Gln
            20                  25                  30

Gln Gln Asn His Gly His Asp Ile Asp Gln His Arg Ile Gly Gly Leu
        35                  40                  45

Lys Arg Asp Arg Asp Ala Asp Ile Asp Pro Asn Glu His Ser Ser Ala
    50                  55                  60

Gly Lys Asp Gln Ser Thr Pro Gly Ser Gly Gly Ser Gly Ser Gly Gly
65                  70                  75                  80

Gly Gly Gly Asp Asn His Ile Thr Arg Arg Pro Arg Gly Arg Pro Ala
                85                  90                  95

Gly Ser Lys Asn Lys Pro Lys Pro Pro Ile Ile Ile Thr Arg Asp Ser
            100                 105                 110

Ala Asn Ala Leu Lys Ser His Val Met Glu Val Ala Asn Gly Cys Asp
        115                 120                 125

Val Met Glu Ser Val Thr Val Phe Ala Arg Arg Arg Gln Arg Gly Ile
    130                 135                 140

Cys Val Leu Ser Gly Asn Gly Ala Val Thr Asn Val Thr Ile Arg Gln
145                 150                 155                 160

Pro Ala Ser Val Pro Gly Gly Ser Ser Val Val Asn Leu His Gly
                165                 170                 175

Arg Phe Glu Ile Leu Ser Leu Ser Gly Ser Phe Leu Pro Pro Ala
            180                 185                 190

Pro Pro Ala Ala Ser Gly Leu Thr Ile Tyr Leu Ala Gly Gly Gln Gly
        195                 200                 205

Gln Val Val Gly Gly Ser Val Val Gly Pro Leu Met Ala Ser Gly Pro
    210                 215                 220

Val Val Ile Met Ala Ala Ser Phe Gly Asn Ala Ala Tyr Glu Arg Leu
225                 230                 235                 240

Pro Leu Glu Glu Asp Asp Gln Glu Glu Gln Thr Ala Gly Ala Val Ala
                245                 250                 255

Asn Asn Ile Asp Gly Asn Ala Thr Met Gly Gly Gly Thr Gln Thr Gln
            260                 265                 270

Thr Gln Thr Gln Gln Gln Gln Gln Gln Gln Leu Met Gln Asp Pro Thr
        275                 280                 285

Ser Phe Ile Gln Gly Leu Pro Pro Asn Leu Met Asn Ser Val Gln Leu
    290                 295                 300

Pro Ala Glu Ala Tyr Trp Gly Thr Pro Arg Pro Ser Phe
305                 310                 315

<210> SEQ ID NO 73
<211> LENGTH: 913
<212> TYPE: DNA
<213> ORGANISM: Arabidopsis thaliana
<220> FEATURE:
<223> OTHER INFORMATION: G511

<400> SEQUENCE: 73
gtttcttgtt gttaaaaata tcgtacaaaa atggccgatg aggtcacaat cgggtttcgc      60

-continued

```
ttctatccca cggaagaaga actggtttcg ttctacctac gaaaccagct cgaaggaagg    120
agtgatgact caatgcatcg tgtcattccc gtacttgacg tctttgaggt cgagcctagt    180
catcttccaa atgttgctgg agtgagatgt cgaggagacg ctgagcaatg gttcttcttc    240
gtgccacgac aagaacgcga agcaagagga ggcagaccga gtagaactac tggttcagga    300
tactggaaag caactggatc acctggtcca gtcttttcca aagacaacaa aatgattgga    360
gcaaagaaaa ctatggtttt ctacactgga aaagcaccca caggaagaaa aactaaatgg    420
aaaatgaatg agtaccacgc cgttgacgaa acagtcaacg cttccacaat ccctaagctg    480
agacgtgagt tcagtttatg tcgagtctac ataacaacag gaagctccag agcttttgat    540
agacgtcctg agggagtttt gcagacagag agaatgctaa caagtgatgt tgcagtagct    600
gagacatcgt tccgtgtgga aagctcactg gaaacttcga tttcaggagg agaacatatt    660
gatgtctcta tgaacacaga gtttgttgat ggactatcag aaccgatgtg ggactgggaa    720
cagctgactt ggccttgaag ctatatagat tttataatca agcaaattta aacttgtttc    780
aattgcttat tgttagtttg aattttatga cccgaaagat tcttttcttt tctttacctt    840
gtaacgtgag aatttgagaa ataataaatg acctagacag tgacatttga aaaaaaaaa    900 aaaaaaaaaa aaa                                                        913
```

<210> SEQ ID NO 74
<211> LENGTH: 235
<212> TYPE: PRT
<213> ORGANISM: Arabidopsis thaliana
<220> FEATURE:
<223> OTHER INFORMATION: G511

<400> SEQUENCE: 74

```
Met Ala Asp Glu Val Thr Ile Gly Phe Arg Phe Tyr Pro Thr Glu Glu
 1               5                  10                  15

Glu Leu Val Ser Phe Tyr Leu Arg Asn Gln Leu Glu Gly Arg Ser Asp
                20                  25                  30

Asp Ser Met His Arg Val Ile Pro Val Leu Asp Val Phe Glu Val Glu
            35                  40                  45

Pro Ser His Leu Pro Asn Val Ala Gly Val Arg Cys Arg Gly Asp Ala
        50                  55                  60

Glu Gln Trp Phe Phe Val Pro Arg Gln Glu Arg Glu Ala Arg Gly
 65                  70                  75                  80

Gly Arg Pro Ser Arg Thr Thr Gly Ser Gly Tyr Trp Lys Ala Thr Gly
                85                  90                  95

Ser Pro Gly Pro Val Phe Ser Lys Asp Asn Lys Met Ile Gly Ala Lys
               100                 105                 110

Lys Thr Met Val Phe Tyr Thr Gly Lys Ala Pro Thr Gly Arg Lys Thr
           115                 120                 125

Lys Trp Lys Met Asn Glu Tyr His Ala Val Asp Glu Thr Val Asn Ala
       130                 135                 140

Ser Thr Ile Pro Lys Leu Arg Arg Glu Phe Ser Leu Cys Arg Val Tyr
145                 150                 155                 160

Ile Thr Thr Gly Ser Ser Arg Ala Phe Asp Arg Arg Pro Glu Gly Val
                165                 170                 175

Leu Gln Thr Glu Arg Met Leu Thr Ser Asp Val Ala Val Ala Glu Thr
            180                 185                 190

Ser Phe Arg Val Glu Ser Ser Leu Glu Thr Ser Ile Ser Gly Gly Glu
        195                 200                 205
```

| His | Ile | Asp | Val | Ser | Met | Asn | Thr | Glu | Phe | Val | Asp | Gly | Leu | Ser | Glu |
| | | | | 210 | | | | | 215 | | | | | 220 | |

| Pro | Met | Trp | Asp | Trp | Glu | Gln | Leu | Thr | Trp | Pro |
| 225 | | | | | 230 | | | | | 235 |

<210> SEQ ID NO 75
<211> LENGTH: 2332
<212> TYPE: DNA
<213> ORGANISM: Arabidopsis thaliana
<220> FEATURE:
<223> OTHER INFORMATION: G471

<400> SEQUENCE: 75

```
gcaattctta gtttctcttc tatccccttt ctgggttttg tttgaaccct agctcgcttt     60
ggatccagtg gttttaagtt aaaggtaaat ttatcgaaag taagtagatt cctaatggca    120
gcttccaatc attcatctgg taaacctgga ggagttttaa gtgatgcttt atgtagggag    180
ctctggcatg cctgtgctgg acctcttgta accctacctc gtgaagggga acgagtttat    240
tatttccctg aaggccacat ggagcagctc gaggcatcaa tgcaccaagg tttggagcaa    300
cagatgcctt ccttcaacct cccatctaag atcctctgta aagttatcaa catccagcgc    360
agggcagagc ccgagactga cgaagtatat gcgcaaataa ccttattgcc agaactggat    420
caaagcgaac ccactagccc agatgcccct gttcaagaac ctgaaaagtg caccgtacat    480
tcattttgca agacactaac tgcttcagac acaagcacac atggtggctt ctcggtgcta    540
cggagacatg cagatgattg tctcccaccc ttggatatgt cccaacaacc accgtggcaa    600
gaattggttg caactgattt gcacaatagt gaatggcatt ttaggcacat tttccgaggc    660
caaccaaggc gtcatttgct aacaactgga tggagtgttt tgttagctc gaagaaacta    720
gtggctggtg atgctttcat attcttaagg ggtgagaatg aagagctccg agtaggtgtt    780
aggcggcaca tgagacaaca gactaatatc ccgtcatctg tcatttcaag tcatagcatg    840
catattgggg tccttgcaac agcagctcat gccattacaa caggaacaat cttttctgtc    900
ttctacaagc caaggacaag taggtcgag tttattgtga gcgtcaatag gtatctcgaa    960
gctaagaccc agaagctgtc tgtaggcatg cgtttcaaga tgagattcga ggggaagaa   1020
gctcccgaga aaaggttcag tggcacaata gttggtgttc aggaaaataa gtcttcggtc   1080
tggcatgatt ctgaatggag atcgctaaag gttcaatggg acgaaccctc atctgtatt    1140
cgtcctgaaa gagtttcacc ttgggaactt gagcccctag ttgcaaatag tactccgtct   1200
tcacaacctc agcctccgca aggaacaaa cgaccaagac ctcctggttt accttcacca    1260
gccactggtc catctggtcc tgttactcca gatggtgtgt ggaaatcccc ggcagacact   1320
ccttcctcag tgccattatt ctctcctcct gccaaagctg ctacgtttgg tcatggtggg   1380
aacaaatcat ttggagtatc tattggatca gccttttggc ccaccaatgc agatagtgca   1440
gctgaatcct ttgcttcagc gtttaacaat gaatctactg aaaagaaaca actaatgga    1500
aatgtctgta ggcttttgg gtttgagcta gttgaaaatg ttaatgtgga tgaatgtttc   1560
tctgctgcct ctgtgtctgg tgctgtcgct gtagatcaac ctgtcccatc caacgagttt   1620
gactctggcc agcaatctga gccattaaac atcaaccaat ctgatattcc ttcggggagt   1680
ggtgaccctg agaaatcctc tttgaggtct cctcaagaat cacaaagtag acagatacgt   1740
agctgcacaa aggtgcacat gcaaggcagt gcagtaggca gagctattga tttgacaagg   1800
tcagagtgtt atgaagatct gttcaagaag ctggaagaga tgtttgatat caaggctgaa   1860
ctcttagaat ctaccaaaaa atggcaagtc gtttacaccg atgatgaaga tgacatgatg   1920
```

```
atggttggtg atgatccatg gaatgagttc tgtggaatgg tgaggaagat attcatctac    1980
acacctgagg aagtgaagaa actttcaccg aagaacaaac tcgcagtcaa tgcaaggatg    2040
cagctcaaag ctgatgcaga ggaaaatggg aatacagagg cagatcatc atctatggcg     2100 ggatcaagat gagtatatca ctgtgttatg ttttaaatgt acttgccacg taggaaatat    2160
gaaagcagaa gcaagagatc gttagacaat atgaaagttg agatgtctgt gtatagcaat    2220
gaagttttat gtcttcaagt cttatgaatt cacttagatg caatgtgttt tgaggagttg    2280
tgtagctttt gtacgggaaa tatggaaatt aagtttcacg tcttgttcta cc            2332
```

<210> SEQ ID NO 76
<211> LENGTH: 665
<212> TYPE: PRT
<213> ORGANISM: Arabidopsis thaliana
<220> FEATURE:
<223> OTHER INFORMATION: G471

<400> SEQUENCE: 76

```
Met Ala Ala Ser Asn His Ser Ser Gly Lys Pro Gly Gly Val Leu Ser
  1               5                  10                  15

Asp Ala Leu Cys Arg Glu Leu Trp His Ala Cys Ala Gly Pro Leu Val
                 20                  25                  30

Thr Leu Pro Arg Glu Gly Glu Arg Val Tyr Tyr Phe Pro Glu Gly His
             35                  40                  45

Met Glu Gln Leu Glu Ala Ser Met His Gln Gly Leu Glu Gln Gln Met
         50                  55                  60

Pro Ser Phe Asn Leu Pro Ser Lys Ile Leu Cys Lys Val Ile Asn Ile
 65                  70                  75                  80

Gln Arg Arg Ala Glu Pro Glu Thr Asp Glu Val Tyr Ala Gln Ile Thr
                 85                  90                  95

Leu Leu Pro Glu Leu Asp Gln Ser Glu Pro Thr Ser Pro Asp Ala Pro
            100                 105                 110

Val Gln Glu Pro Glu Lys Cys Thr Val His Ser Phe Cys Lys Thr Leu
        115                 120                 125

Thr Ala Ser Asp Thr Ser Thr His Gly Gly Phe Ser Val Leu Arg Arg
    130                 135                 140

His Ala Asp Asp Cys Leu Pro Pro Leu Asp Met Ser Gln Gln Pro Pro
145                 150                 155                 160

Trp Gln Glu Leu Val Ala Thr Asp Leu His Asn Ser Glu Trp His Phe
                165                 170                 175

Arg His Ile Phe Arg Gly Gln Pro Arg Arg His Leu Leu Thr Thr Gly
            180                 185                 190

Trp Ser Val Phe Val Ser Ser Lys Lys Leu Val Ala Gly Asp Ala Phe
        195                 200                 205

Ile Phe Leu Arg Gly Glu Asn Glu Glu Leu Arg Val Gly Val Arg Arg
    210                 215                 220

His Met Arg Gln Gln Thr Asn Ile Pro Ser Ser Val Ile Ser His
225                 230                 235                 240

Ser Met His Ile Gly Val Leu Ala Thr Ala His Ala Ile Thr Thr
                245                 250                 255

Gly Thr Ile Phe Ser Val Phe Tyr Lys Pro Arg Thr Ser Arg Ser Glu
            260                 265                 270

Phe Ile Val Ser Val Asn Arg Tyr Leu Glu Ala Lys Thr Gln Lys Leu
        275                 280                 285
```

Ser Val Gly Met Arg Phe Lys Met Arg Phe Glu Gly Glu Ala Pro
290                 295                 300

Glu Lys Arg Phe Ser Gly Thr Ile Val Gly Val Gln Glu Asn Lys Ser
305                 310                 315                 320

Ser Val Trp His Asp Ser Glu Trp Arg Ser Leu Lys Val Gln Trp Asp
            325                 330                 335

Glu Pro Ser Ser Val Phe Arg Pro Glu Arg Val Ser Pro Trp Glu Leu
            340                 345                 350

Glu Pro Leu Val Ala Asn Ser Thr Pro Ser Ser Gln Pro Gln Pro Pro
            355                 360                 365

Gln Arg Asn Lys Arg Pro Arg Pro Gly Leu Pro Ser Pro Ala Thr
370                 375                 380

Gly Pro Ser Gly Pro Val Thr Pro Asp Gly Val Trp Lys Ser Pro Ala
385                 390                 395                 400

Asp Thr Pro Ser Ser Val Pro Leu Phe Ser Pro Pro Ala Lys Ala Ala
            405                 410                 415

Thr Phe Gly His Gly Gly Asn Lys Ser Phe Gly Val Ser Ile Gly Ser
            420                 425                 430

Ala Phe Trp Pro Thr Asn Ala Asp Ser Ala Ala Glu Ser Phe Ala Ser
            435                 440                 445

Ala Phe Asn Asn Glu Ser Thr Glu Lys Lys Gln Thr Asn Gly Asn Val
            450                 455                 460

Cys Arg Leu Phe Gly Phe Glu Leu Val Glu Asn Val Asn Val Asp Glu
465                 470                 475                 480

Cys Phe Ser Ala Ala Ser Val Ser Gly Ala Val Ala Val Asp Gln Pro
            485                 490                 495

Val Pro Ser Asn Glu Phe Asp Ser Gly Gln Ser Glu Pro Leu Asn
            500                 505                 510

Ile Asn Gln Ser Asp Ile Pro Ser Gly Ser Gly Asp Pro Glu Lys Ser
            515                 520                 525

Ser Leu Arg Ser Pro Gln Glu Ser Gln Ser Arg Gln Ile Arg Ser Cys
            530                 535                 540

Thr Lys Val His Met Gln Gly Ser Ala Val Gly Arg Ala Ile Asp Leu
545                 550                 555                 560

Thr Arg Ser Glu Cys Tyr Glu Asp Leu Phe Lys Lys Leu Glu Glu Met
            565                 570                 575

Phe Asp Ile Lys Gly Glu Leu Leu Glu Ser Thr Lys Lys Trp Gln Val
            580                 585                 590

Val Tyr Thr Asp Asp Glu Asp Met Met Met Val Gly Asp Asp Pro
            595                 600                 605

Trp Asn Glu Phe Cys Gly Met Val Arg Lys Ile Phe Ile Tyr Thr Pro
            610                 615                 620

Glu Glu Val Lys Lys Leu Ser Pro Lys Asn Lys Leu Ala Val Asn Ala
625                 630                 635                 640

Arg Met Gln Leu Lys Ala Asp Ala Glu Glu Asn Gly Asn Thr Glu Gly
            645                 650                 655

Arg Ser Ser Ser Met Ala Gly Ser Arg
            660                 665

<210> SEQ ID NO 77
<211> LENGTH: 2217
<212> TYPE: DNA
<213> ORGANISM: Arabidopsis thaliana
<220> FEATURE:
<223> OTHER INFORMATION: G385

<400> SEQUENCE: 77

```
tagggtttgc tttcagtttc cggagtataa gaaaagatgt tcgagccaaa tatgctgctt      60
gcggctatga acaacgcaga cagcaataac cacaactaca accacgaaga caacaataat     120
gaaggatttc ttcgggacga tgaattcgac agtccgaata ctaaatcggg aagtgagaat     180
caagaaggag gatcaggaaa cgaccaagat cctcttcatc ctaacaagaa gaaacgatat     240
catcgacaca cccaacttca gatccaggag atggaagcgt tcttcaaaga gtgtcctcac     300
ccagatgaca agcaaaggaa acagctaagc cgtgaattga atttggaacc tcttcaggtc     360
aaattctggt tccaaaacaa acgtacccaa atgaagaatc atcacgagcg gcatgagaac     420
tcacatcttc gggcggagaa cgaaaagctt cgaaacgaca acctaagata tcgagaggct     480
cttgcaaatg cttcgtgtcc taattgtggt ggtccaacag ctatcggaga aatgtcattc     540
gacgaacacc aactccgtct cgaaaatgct cgattaaggg aagagatcga ccgtatatcc     600
gcaatcgcag ctaaatacgt aggcaagcca gtctcaaact atccacttat gtctcctcct     660
cctcttcctc cacgtccact agaactcgcc atgggaaata ttggaggaga agcttatgga     720
aacaatccaa acgatctcct taagtccatc actgcaccaa cagaatctga caaacctgtc     780
atcatcgact tatccgtggc tgcaatggaa gagctcatga ggatggttca agtagacgag     840
cctctgtgga agagtttggc tttagacgaa gaagaatatg caaggacctt tcctagaggg     900
atcggaccta gaccggctgg atatagatca gaagcttcgc gagaaagcgc ggttgtgatc     960
atgaatcatg ttaacatcgt tgagattctc atggatgtga atcaatggtc gacgattttc    1020
gcggggatgg tttctagagc aatgacatta gcggttttat cgacaggagt tgcaggaaac    1080
tataatggag ctcttcaagt gatgagcgca gagtttcaag ttccatctcc attagtccca    1140
acacgtgaaa cctatttcgc acgttactgt aaacaacaag gagatggttc gtgggcggtt    1200
gtcgatattt cgttggatag tctccaacca aatccccgg ctagatgcag gcggcgagct    1260
tcaggatgtt tgattcaaga attgccaaat ggatattcta aggtgacttg ggtggagcat    1320
gtggaagttg atgacagagg agttcataac ttatacaaac acatggttag tactggtcat    1380
gccttcggtg ctaaacgctg ggtagccatt cttgaccgcc aatgcgagcg gttagctagt    1440
gtcatggcta caaacatttc ctctggagaa gttggcgtga taaccaacca agaagggagg    1500
aggagtatgc tgaaattggc agagcggatg gttataagct tttgtgcagg agtgagtgct    1560
tcaaccgctc acacgtggac tacattgtcc ggtacaggag ctgaagatgt tagagtgatg    1620
actaggaaga gtgtggatga tccaggaagg tctcctggta ttgttcttag tgcagccact    1680
tctttttgga tccctgttcc tccaaagcga gtctttgact tcctcagaga cgagaattca    1740
agaaatgagt gggatattct gtctaatgga ggagttgtgc aagaaatggc acatattgct    1800
aacgggaggg ataccggaaa ctgtgtttct cttcttcggg taaatagtgc aaactctagc    1860
cagagcaata tgctgatcct acaagagagc tgcattgatc ctacagcttc ctttgtgatc    1920
tatgctccag tcgatattgt agctatgaac atagtgctta atgaggtgaa tccagactat    1980
gtggctctgc ttccatcagg ttttgctatt cttcctgatg gtaatgccaa tagtggagcc    2040
cctggaggag atggagggtc gctcttgact gttgcttttc agattctggt tgactcagtt    2100
cctacggcta agctgtctct tggctctgtt gcaactgtca ataatctaat agcttgcact    2160
gttgagagaa tcaaagcttc aatgtcttgt gagactgctt gaaaaccatc cattagc      2217
```

<210> SEQ ID NO 78

```
<211> LENGTH: 721
<212> TYPE: PRT
<213> ORGANISM: Arabidopsis thaliana
<220> FEATURE:
<223> OTHER INFORMATION: G385

<400> SEQUENCE: 78

Met Phe Glu Pro Asn Met Leu Ala Ala Met Asn Asn Ala Asp Ser
 1               5                  10                  15

Asn Asn His Asn Tyr Asn His Glu Asp Asn Asn Glu Gly Phe Leu
                 20                  25                  30

Arg Asp Glu Phe Asp Ser Pro Asn Thr Lys Ser Gly Ser Glu Asn
             35                  40                  45

Gln Glu Gly Gly Ser Gly Asn Asp Gln Asp Pro Leu His Pro Asn Lys
 50                  55                  60

Lys Lys Arg Tyr His Arg His Thr Gln Leu Gln Ile Gln Glu Met Glu
 65                  70                  75                  80

Ala Phe Phe Lys Glu Cys Pro His Pro Asp Asp Lys Gln Arg Lys Gln
                 85                  90                  95

Leu Ser Arg Glu Leu Asn Leu Glu Pro Leu Gln Val Lys Phe Trp Phe
                100                 105                 110

Gln Asn Lys Arg Thr Gln Met Lys Asn His His Glu Arg His Glu Asn
                115                 120                 125

Ser His Leu Arg Ala Glu Asn Glu Lys Leu Arg Asn Asp Asn Leu Arg
130                 135                 140

Tyr Arg Glu Ala Leu Ala Asn Ala Ser Cys Pro Asn Cys Gly Gly Pro
145                 150                 155                 160

Thr Ala Ile Gly Glu Met Ser Phe Asp Glu His Gln Leu Arg Leu Glu
                165                 170                 175

Asn Ala Arg Leu Arg Glu Glu Ile Asp Arg Ile Ser Ala Ile Ala Ala
                180                 185                 190

Lys Tyr Val Gly Lys Pro Val Ser Asn Tyr Pro Leu Met Ser Pro Pro
                195                 200                 205

Pro Leu Pro Pro Arg Pro Leu Glu Leu Ala Met Gly Asn Ile Gly Gly
210                 215                 220

Glu Ala Tyr Gly Asn Asn Pro Asn Asp Leu Leu Lys Ser Ile Thr Ala
225                 230                 235                 240

Pro Thr Glu Ser Asp Lys Pro Val Ile Ile Asp Leu Ser Val Ala Ala
                245                 250                 255

Met Glu Glu Leu Met Arg Met Val Gln Val Asp Glu Pro Leu Trp Lys
                260                 265                 270

Ser Leu Ala Leu Asp Glu Glu Glu Tyr Ala Arg Thr Phe Pro Arg Gly
                275                 280                 285

Ile Gly Pro Arg Pro Ala Gly Tyr Arg Ser Glu Ala Ser Arg Glu Ser
290                 295                 300

Ala Val Val Ile Met Asn His Val Asn Ile Val Glu Ile Leu Met Asp
305                 310                 315                 320

Val Asn Gln Trp Ser Thr Ile Phe Ala Gly Met Val Ser Arg Ala Met
                325                 330                 335

Thr Leu Ala Val Leu Ser Thr Gly Val Ala Gly Asn Tyr Asn Gly Ala
                340                 345                 350

Leu Gln Val Met Ser Ala Glu Phe Gln Val Pro Ser Pro Leu Val Pro
                355                 360                 365

Thr Arg Glu Thr Tyr Phe Ala Arg Tyr Cys Lys Gln Gln Gly Asp Gly
                370                 375                 380
```

```
Ser Trp Ala Val Val Asp Ile Ser Leu Asp Ser Leu Gln Pro Asn Pro
385                 390                 395                 400

Pro Ala Arg Cys Arg Arg Arg Ala Ser Gly Cys Leu Ile Gln Glu Leu
            405                 410                 415

Pro Asn Gly Tyr Ser Lys Val Thr Trp Val Glu His Val Glu Val Asp
            420                 425                 430

Asp Arg Gly Val His Asn Leu Tyr Lys His Met Val Ser Thr Gly His
            435                 440                 445

Ala Phe Gly Ala Lys Arg Trp Val Ala Ile Leu Asp Arg Gln Cys Glu
    450                 455                 460

Arg Leu Ala Ser Val Met Ala Thr Asn Ile Ser Ser Gly Glu Val Gly
465                 470                 475                 480

Val Ile Thr Asn Gln Glu Gly Arg Arg Ser Met Leu Lys Leu Ala Glu
                485                 490                 495

Arg Met Val Ile Ser Phe Cys Ala Gly Val Ser Ala Ser Thr Ala His
                500                 505                 510

Thr Trp Thr Thr Leu Ser Gly Thr Gly Ala Glu Asp Val Arg Val Met
        515                 520                 525

Thr Arg Lys Ser Val Asp Asp Pro Gly Arg Ser Pro Gly Ile Val Leu
530                 535                 540

Ser Ala Ala Thr Ser Phe Trp Ile Pro Val Pro Pro Lys Arg Val Phe
545                 550                 555                 560

Asp Phe Leu Arg Asp Glu Asn Ser Arg Asn Glu Trp Asp Ile Leu Ser
                565                 570                 575

Asn Gly Gly Val Val Gln Glu Met Ala His Ile Ala Asn Gly Arg Asp
                580                 585                 590

Thr Gly Asn Cys Val Ser Leu Leu Arg Val Asn Ser Ala Asn Ser Ser
            595                 600                 605

Gln Ser Asn Met Leu Ile Leu Gln Glu Ser Cys Ile Asp Pro Thr Ala
        610                 615                 620

Ser Phe Val Ile Tyr Ala Pro Val Asp Ile Val Ala Met Asn Ile Val
625                 630                 635                 640

Leu Asn Gly Gly Asp Pro Asp Tyr Val Ala Leu Leu Pro Ser Gly Phe
                645                 650                 655

Ala Ile Leu Pro Asp Gly Asn Ala Asn Ser Gly Ala Pro Gly Gly Asp
                660                 665                 670

Gly Gly Ser Leu Leu Thr Val Ala Phe Gln Ile Leu Val Asp Ser Val
            675                 680                 685

Pro Thr Ala Lys Leu Ser Leu Gly Ser Val Ala Thr Val Asn Asn Leu
        690                 695                 700

Ile Ala Cys Thr Val Glu Arg Ile Lys Ala Ser Met Ser Cys Glu Thr
705                 710                 715                 720

Ala

<210> SEQ ID NO 79
<211> LENGTH: 1857
<212> TYPE: DNA
<213> ORGANISM: Arabidopsis thaliana
<220> FEATURE:
<223> OTHER INFORMATION: G261

<400> SEQUENCE: 79
gtttaggttc gagaagcaga gagggttcga gaagctaata agggtttctt cttttttgatt      60 ttaatgctaa aagggttcta gattcgttga attttacaag ggttttaggg gttcttagaa     120
```

-continued

```
gcttttgctt gattgtcttt tatttagaaa cagtggtgag ttttagtct ttcactttgt      180
tcaagttcga agcttttttt ggagggaatt ttgggcttct gattttgatc gaaacttact    240
gatagtaagt tctttgagtc ctccttaact gtagtttctg tgtactgaag ttattgaatt    300
gaaagttttt atctttttg gttattgaaa ctttcatagt ttgatcaaaa gagtctcttg     360
ctctgttttt ggctctgttt ttgtgagtgt gattgtaagc tttgttgtga gtagattgaa    420
tcaaggagtg tgagagttgt taaaagtgtt ttcagagatg gatgagaata atcatggagt    480
ttcatcaagc tcacttccac ctttcctcac caaaacatat gagatggttg atgattcttc    540
atccgattct atcgtctctt ggagtcagag caataagagt ttcatcgttt ggaatccgcc    600
ggagttttct agagatcttc ttccgagatt cttcaagcac aataacttct ctagctttat    660
ccgccagctt aacacatatg gttttagaaa agctgatcct gagcaatggg aatttgcgaa    720
tgatgatttt gtgagaggtc aacctcatct tatgaagaac attcatagac gcaaaccagt    780
tcatagccac tctttaccga atcttcaagc tcagttaaac ccgttgacgg attcagaacg    840
agtgagaatg aataatcaga ttgagagatt gacaaaagag aaagaaggat tgcttgaaga    900
gttacataaa caagacgagg aacgagaagt gtttgagatg caagtgaaag aacttaaaga    960
acgattacaa cacatggaga agcgtcagaa acaatggttt cgtttgtttt ctcaagtatt   1020
ggaaaagcca gggcttgctt tgaacctatc gccgtgtgtt cccgaaacaa acgagaggaa   1080
aagaaggttc cctaggatcg agttctttcc cgatgaaccg atgttggaag agaacaaaac   1140
ttgtgttgtt gtgagagagg aaggttctac aagcccttct tcacacacaa gagagcatca   1200
agtggaacag ttagagtcat cgatagcgat ttgggagaat cttgtatcgg attcttgtga   1260
gagtatgtta caatcaagaa gtatgatgac acttgatgtg gatgaatcat ctactttcc    1320
agagagccct cctctttctt gcatacagtt aagtgtcgat tcacgtctca aatctcctcc   1380
ttctccaagg atcatcgata tgaactgtga gcccgatggt tcgaaagaac agaacactgt   1440
tgctgctcct cctcctcctc cagtagcagg agcgaatgat ggcttctggc agcagttttt   1500
ctcagagaat cctggctcaa ccgagcaacg ggaagttcaa ttagagagga agacgataa    1560
agataaagcc ggagtacgta ctgagaaatg ttggtggaat tcgagaaatg ttaatgcaat   1620
tacagaacag cttggacatc tgacttcttc agagagaagt tgatatgtca aagattaaat   1680
ttctagtctg ttttagttac ttgtaaaata gggtttctca gttttattgt tttcgattcc   1740
agtacttagg tatggttcag ctgtttattt atcacttgta tgatctttcc cagttcattg   1800
tagcagactt caatggtaat gataagctag agcttatgga tagtattcat aaaaaaa      1857
```

<210> SEQ ID NO 80
<211> LENGTH: 401
<212> TYPE: PRT
<213> ORGANISM: Arabidopsis thaliana
<220> FEATURE:
<223> OTHER INFORMATION: G261

<400> SEQUENCE: 80

Met Asp Glu Asn Asn His Gly Val Ser Ser Ser Leu Pro Pro Phe
 1               5                  10                  15

Leu Thr Lys Thr Tyr Glu Met Val Asp Asp Ser Ser Asp Ser Ile
            20                  25                  30

Val Ser Trp Ser Gln Ser Asn Lys Ser Phe Ile Val Trp Asn Pro Pro
        35                  40                  45

Glu Phe Ser Arg Asp Leu Leu Pro Arg Phe Phe Lys His Asn Asn Phe

```
                50              55              60
Ser Ser Phe Ile Arg Gln Leu Asn Thr Tyr Gly Phe Arg Lys Ala Asp
65              70              75              80
Pro Glu Gln Trp Glu Phe Ala Asn Asp Asp Phe Val Arg Gly Gln Pro
                85              90              95
His Leu Met Lys Asn Ile His Arg Arg Lys Pro Val His Ser His Ser
                100             105             110
Leu Pro Asn Leu Gln Ala Gln Leu Asn Pro Leu Thr Asp Ser Glu Arg
                115             120             125
Val Arg Met Asn Asn Gln Ile Glu Arg Leu Thr Lys Glu Lys Glu Gly
                130             135             140
Leu Leu Glu Glu Leu His Lys Gln Asp Glu Glu Arg Glu Val Phe Glu
145             150             155             160
Met Gln Val Lys Glu Leu Lys Glu Arg Leu Gln His Met Glu Lys Arg
                165             170             175
Gln Lys Thr Met Val Ser Phe Val Ser Gln Val Leu Glu Lys Pro Gly
                180             185             190
Leu Ala Leu Asn Leu Ser Pro Cys Val Pro Glu Thr Asn Glu Arg Lys
                195             200             205
Arg Arg Phe Pro Arg Ile Glu Phe Phe Pro Asp Glu Pro Met Leu Glu
                210             215             220
Glu Asn Lys Thr Cys Val Val Arg Glu Glu Gly Ser Thr Ser Pro
225             230             235             240
Ser Ser His Thr Arg Glu His Gln Val Glu Gln Leu Glu Ser Ser Ile
                245             250             255
Ala Ile Trp Glu Asn Leu Val Ser Asp Ser Cys Glu Ser Met Leu Gln
                260             265             270
Ser Arg Ser Met Met Thr Leu Asp Val Asp Glu Ser Ser Thr Phe Pro
                275             280             285
Glu Ser Pro Pro Leu Ser Cys Ile Gln Leu Ser Val Asp Ser Arg Leu
                290             295             300
Lys Ser Pro Pro Ser Pro Arg Ile Ile Asp Met Asn Cys Glu Pro Asp
305             310             315             320
Gly Ser Lys Glu Gln Asn Thr Val Ala Ala Pro Pro Pro Pro Val
                325             330             335
Ala Gly Ala Asn Asp Gly Phe Trp Gln Gln Phe Phe Ser Glu Asn Pro
                340             345             350
Gly Ser Thr Glu Gln Arg Glu Val Gln Leu Glu Arg Lys Asp Asp Lys
                355             360             365
Asp Lys Ala Gly Val Arg Thr Glu Lys Cys Trp Trp Asn Ser Arg Asn
                370             375             380
Val Asn Ala Ile Thr Glu Gln Leu Gly His Leu Thr Ser Ser Glu Arg
385             390             395             400
Ser

<210> SEQ ID NO 81
<211> LENGTH: 751
<212> TYPE: DNA
<213> ORGANISM: Arabidopsis thaliana
<220> FEATURE:
<223> OTHER INFORMATION: G25

<400> SEQUENCE: 81
aggactcggt tcaaaaacga aaacgcaaat acgtcttgtt ctagtttgga gttggaagcg    60
```

```
taaaaaacaa aaaacaaaaa tgtgtggggg agctatcatt tctgatttca tctggtcgaa      120
atctgagtca gaaccgagtc aactcggctc tgttagcagc aggaagaagc gtaaacccgt      180
ctcagtgagt gaagaaagag atgggaaacg agagaggaag aatctgtaca gagggataag      240
gcagaggcca tggggcaaat gggcagcgga gattcgtgac ccgagcaaag gtgtacgtgt      300
ctggcttggc acattcaaaa ccgccgacga agctgctcga gcctacgacg ttgctgccat      360
caaaatccgt ggccggaaag ccaaactgaa tttcccaaac actcaagtag aagaagaagc      420
cgatactaaa ccaggggga atcaaaatga gctgatttcg gaaaaccaag tagagagctt      480
atcggaggac ctgatggcat tggaggatta catgagattc tatcagattc cggttgccga      540
cgaccaatcg gcgaccgata ttggaaattt atggagctat caagactcca attaaatctc      600
ttatttcccg gccggtttgc tcactcatta atatgctgct aatttacttg ttttttactt      660
aacaatcaag tctaatttgt ttccatcaat atttcagata agagtaaagc ttcaattgtc      720
tttaaaaaaa aaaaaaaaaa aaaaaaaaaa a                                    751
```

<210> SEQ ID NO 82
<211> LENGTH: 171
<212> TYPE: PRT
<213> ORGANISM: Arabidopsis thaliana
<220> FEATURE:
<223> OTHER INFORMATION: G25

<400> SEQUENCE: 82

```
Met Cys Gly Gly Ala Ile Ile Ser Asp Phe Ile Trp Ser Lys Ser Glu
  1               5                  10                  15

Ser Glu Pro Ser Gln Leu Gly Ser Val Ser Ser Arg Lys Lys Arg Lys
             20                  25                  30

Pro Val Ser Val Ser Glu Glu Arg Asp Gly Lys Arg Glu Arg Lys Asn
         35                  40                  45

Leu Tyr Arg Gly Ile Arg Gln Arg Pro Trp Gly Lys Trp Ala Ala Glu
     50                  55                  60

Ile Arg Asp Pro Ser Lys Gly Val Arg Val Trp Leu Gly Thr Phe Lys
 65                  70                  75                  80

Thr Ala Asp Glu Ala Ala Arg Ala Tyr Asp Val Ala Ala Ile Lys Ile
                 85                  90                  95

Arg Gly Arg Lys Ala Lys Leu Asn Phe Pro Asn Thr Gln Val Glu Glu
            100                 105                 110

Glu Ala Asp Thr Lys Pro Gly Gly Asn Gln Asn Glu Leu Ile Ser Glu
        115                 120                 125

Asn Gln Val Glu Ser Leu Ser Glu Asp Leu Met Ala Leu Glu Asp Tyr
    130                 135                 140

Met Arg Phe Tyr Gln Ile Pro Val Ala Asp Gln Ser Ala Thr Asp
145                 150                 155                 160

Ile Gly Asn Leu Trp Ser Tyr Gln Asp Ser Asn
                165                 170
```

<210> SEQ ID NO 83
<211> LENGTH: 2311
<212> TYPE: DNA
<213> ORGANISM: Arabidopsis thaliana
<220> FEATURE:
<223> OTHER INFORMATION: G610

<400> SEQUENCE: 83

```
tcttaatcag agattcgtga gaggtaaagg tagcgtaatt attcagtttg cgtgatctat       60
```

```
aatttaactg gcgccagatt gtgatccagg aatcgttggc ttgttaggtt gttgttttgt      120
tatgcataat tgagagatgg tggtcaaaag gaagttaaat tgtggtggct ctgatggttt      180
tgatttcccc aatattccca aggctcctcg ttcaagcagg aggaaggtct caggtaagag      240
atctgatgat gaaagtgaga tctgtgcaat tgatttgcta gcttctcttg ctggaaagtt      300
gttggaagaa agtgaaagtt cctcaacgtc tacctatgca tctgaagctg ataatcttga      360
tcatttgggt ggactgatta agcaagaact tgaagatggc tatactacta agccttgtaa      420
atccgagttt ttcgatccag gaaaccctgc ttcaaagtcc actagtgaaa atactagcgt      480
gacttgtttg ccattttcgt ctttcgaaaa tgattgcatt ttggagcaaa caccagtttc      540
tgattgtaag agggcatctg gtttgaagtc cctggtaggg agcatcactg aggagacatg      600
tgttgttaat gaggatgccg gatctgaaca aggtgctaat actttcagct aaaggatcc       660 aagtcaatta cattcgcagt ctccagaatc ggtccttctg gatggcgatg tgaaattagc      720
accatgcacg gatcaagtcc ctaatgattc ttttaaagga tataggaatc attctaagtt      780
agtttgcaga gatgatgacg aaaactattg taagtattat aaatttagtg acaaatgtaa      840
gtcatatagg cctctctccc gggttggcaa tagaagaata atgcagtcgg tgagagcaat      900
ctccaagttg aagtgttttg aagacactag aacagatggt cgtttgaagg ctctctaccg      960
caagagaaaa ttatgttatg gttacaaccc atggaagcgt gagaccattc ataggaagag     1020
aagattgtct gacaaaggtt tggtcgtaaa ttatgatggt gggctcagta gtgaaagtgt     1080
ttccaattca cctgaaaagg gagaatcaga aaatggtgat ttctctgctg caaaaatagg     1140
tcttctttcg aaagactccc gtgtaaagtt cagcatcaag tcccttagga ttccggagct     1200
tgtaattgaa gttccagaaa cagcaacagt aggcttactg aagaggacgg tgaaggaggc     1260
ggttactgct ttactcggtg gtggaatacg tattggggtg ttagtccaag ggaaaaaagt     1320
tagagatgac aacaacactc tatcacagac tggtctttcg tgtagagaaa atcttggcaa     1380
ccttggcttc accttagagc ctggtttgga aacactgcct gtacctcttt gttctgaaac     1440
tcctgtcctt tctctgccaa ctgactctac aaagttgtca gaaaggtccg cagcttctcc     1500
agcgttagag actggaattc ctctccctcc ccaagatgaa gattacttga ttaatttggg     1560
aaatagtgtg gagaacaatg atgaattagt cccacatctg agtgacatac cagctgatga     1620
acaaccttca tcagattcaa gagcgctggt tccagttttg gccttggagt ccgacgctct     1680
tgcacttgtt ccagttaacg agaaacctaa gcgtacagag ctttcacaac gcagaaccag     1740
gagactattc tctgttacag aggtagaagc tctagtaagc gcagttgaag aagttgggac     1800
tggaagatgg cgtgatgtga agttcgcttc ttttgagaat gcaagtcatc gaacctatgt     1860
ggacttgaag gacaaatgga aaacgttggt tcacacagca agtatatcac cacagcaacg     1920
aagaggagaa ccagtgcctc aagaactgct agacagagtc ttaggagcac ataggtactg     1980
gacacagcac caaatgaaac agaacgggaa acatcaggtg gctacaacaa tggtggttga     2040
agcaggttcg tccatgtaaa gaaggagaat ggtagtaaca ataactttca cttgacgact     2100
aaggaaccaa agtgggcaac tgtacaaagg gaaacaacaa aatacagaaa catacttaat     2160
ttctgaaaag aagagtctat attttattt ttttaaatc atagccggta gaaacaagac      2220
gttccttgac acttttggtt acttttatgg taggtctgtt cattccaaat ttctaattga     2280
tttgattatg taatttggtg gtaggaccat g                                    2311
```

<210> SEQ ID NO 84
<211> LENGTH: 640

```
<212> TYPE: PRT
<213> ORGANISM: Arabidopsis thaliana
<220> FEATURE:
<223> OTHER INFORMATION: G610

<400> SEQUENCE: 84
```

| | | | | | | | | | | | | | | | |
|---|---|---|---|---|---|---|---|---|---|---|---|---|---|---|---|
| Met | Val | Val | Lys | Arg | Lys | Leu | Asn | Cys | Gly | Gly | Ser | Asp | Gly | Phe | Asp |
| 1 | | | | 5 | | | | | 10 | | | | | 15 | |
| Phe | Pro | Asn | Ile | Pro | Lys | Ala | Pro | Arg | Ser | Ser | Arg | Arg | Lys | Val | Ser |
| | | | 20 | | | | | 25 | | | | | 30 | | |
| Gly | Lys | Arg | Ser | Asp | Asp | Glu | Ser | Glu | Ile | Cys | Ala | Ile | Asp | Leu | Leu |
| | | 35 | | | | | 40 | | | | | 45 | | | |
| Ala | Ser | Leu | Ala | Gly | Lys | Leu | Leu | Glu | Glu | Ser | Glu | Ser | Ser | Ser | Thr |
| | 50 | | | | | 55 | | | | | 60 | | | | |
| Ser | Thr | Tyr | Ala | Ser | Glu | Ala | Asp | Asn | Leu | Asp | His | Leu | Gly | Gly | Leu |
| 65 | | | | | 70 | | | | | 75 | | | | | 80 |
| Ile | Lys | Gln | Glu | Leu | Glu | Asp | Gly | Tyr | Thr | Thr | Lys | Pro | Cys | Lys | Ser |
| | | | | 85 | | | | | 90 | | | | | 95 | |
| Glu | Phe | Phe | Asp | Pro | Gly | Asn | Pro | Ala | Ser | Lys | Ser | Thr | Ser | Glu | Asn |
| | | | 100 | | | | | 105 | | | | | 110 | | |
| Thr | Ser | Val | Thr | Cys | Leu | Pro | Phe | Ser | Ser | Phe | Glu | Asn | Asp | Cys | Ile |
| | | 115 | | | | | 120 | | | | | 125 | | | |
| Leu | Glu | Gln | Thr | Pro | Val | Ser | Asp | Cys | Lys | Arg | Ala | Ser | Gly | Leu | Lys |
| | 130 | | | | | 135 | | | | | 140 | | | | |
| Ser | Leu | Val | Gly | Ser | Ile | Thr | Glu | Glu | Thr | Cys | Val | Val | Asn | Glu | Asp |
| 145 | | | | | 150 | | | | | 155 | | | | | 160 |
| Ala | Gly | Ser | Glu | Gln | Gly | Ala | Asn | Thr | Phe | Ser | Leu | Lys | Asp | Pro | Ser |
| | | | | 165 | | | | | 170 | | | | | 175 | |
| Gln | Leu | His | Ser | Gln | Ser | Pro | Glu | Ser | Val | Leu | Leu | Asp | Gly | Asp | Val |
| | | | 180 | | | | | 185 | | | | | 190 | | |
| Lys | Leu | Ala | Pro | Cys | Thr | Asp | Gln | Val | Pro | Asn | Asp | Ser | Phe | Lys | Gly |
| | | 195 | | | | | 200 | | | | | 205 | | | |
| Tyr | Arg | Asn | His | Ser | Lys | Leu | Val | Cys | Arg | Asp | Asp | Glu | Asn | Tyr | |
| | 210 | | | | | 215 | | | | | 220 | | | | |
| Cys | Lys | Tyr | Tyr | Lys | Phe | Ser | Asp | Lys | Cys | Lys | Ser | Tyr | Arg | Pro | Leu |
| 225 | | | | | 230 | | | | | 235 | | | | | 240 |
| Ser | Arg | Val | Gly | Asn | Arg | Arg | Ile | Met | Gln | Ser | Val | Arg | Ala | Ile | Ser |
| | | | | 245 | | | | | 250 | | | | | 255 | |
| Lys | Leu | Lys | Cys | Phe | Glu | Asp | Thr | Arg | Thr | Asp | Gly | Arg | Leu | Lys | Ala |
| | | | 260 | | | | | 265 | | | | | 270 | | |
| Leu | Tyr | Arg | Lys | Arg | Lys | Leu | Cys | Tyr | Gly | Tyr | Asn | Pro | Trp | Lys | Arg |
| | | 275 | | | | | 280 | | | | | 285 | | | |
| Glu | Thr | Ile | His | Arg | Lys | Arg | Leu | Ser | Asp | Lys | Gly | Leu | Val | Val | |
| | 290 | | | | | 295 | | | | | 300 | | | | |
| Asn | Tyr | Asp | Gly | Gly | Leu | Ser | Ser | Glu | Ser | Val | Ser | Asn | Ser | Pro | Glu |
| 305 | | | | | 310 | | | | | 315 | | | | | 320 |
| Lys | Gly | Glu | Ser | Glu | Asn | Gly | Asp | Phe | Ser | Ala | Ala | Lys | Ile | Gly | Leu |
| | | | | 325 | | | | | 330 | | | | | 335 | |
| Leu | Ser | Lys | Asp | Ser | Arg | Val | Lys | Phe | Ser | Ile | Lys | Ser | Leu | Arg | Ile |
| | | | 340 | | | | | 345 | | | | | 350 | | |
| Pro | Glu | Leu | Val | Ile | Glu | Val | Pro | Glu | Thr | Ala | Thr | Val | Gly | Leu | Leu |
| | | 355 | | | | | 360 | | | | | 365 | | | |
| Lys | Arg | Thr | Val | Lys | Glu | Ala | Val | Thr | Ala | Leu | Leu | Gly | Gly | Gly | Ile |
| | 370 | | | | | 375 | | | | | 380 | | | | |

```
Arg Ile Gly Val Leu Val Gln Gly Lys Lys Val Arg Asp Asp Asn Asn
385                 390                 395                 400

Thr Leu Ser Gln Thr Gly Leu Ser Cys Arg Glu Asn Leu Gly Asn Leu
            405                 410                 415

Gly Phe Thr Leu Glu Pro Gly Leu Glu Thr Leu Pro Val Pro Leu Cys
            420                 425                 430

Ser Glu Thr Pro Val Leu Ser Leu Pro Thr Asp Ser Thr Lys Leu Ser
            435                 440                 445

Glu Arg Ser Ala Ala Ser Pro Ala Leu Glu Thr Gly Ile Pro Leu Pro
450                 455                 460

Pro Gln Asp Glu Asp Tyr Leu Ile Asn Leu Gly Asn Ser Val Glu Asn
465                 470                 475                 480

Asn Asp Glu Leu Val Pro His Leu Ser Asp Ile Pro Ala Asp Glu Gln
            485                 490                 495

Pro Ser Ser Asp Ser Arg Ala Leu Val Pro Val Leu Ala Leu Glu Ser
            500                 505                 510

Asp Ala Leu Ala Leu Val Pro Val Asn Glu Lys Pro Lys Arg Thr Glu
            515                 520                 525

Leu Ser Gln Arg Arg Thr Arg Arg Leu Phe Ser Val Thr Glu Val Glu
530                 535                 540

Ala Leu Val Ser Ala Val Glu Glu Val Gly Thr Gly Arg Trp Arg Asp
545                 550                 555                 560

Val Lys Leu Arg Ser Phe Glu Asn Ala Ser His Arg Thr Tyr Val Asp
            565                 570                 575

Leu Lys Asp Lys Trp Lys Thr Leu Val His Thr Ala Ser Ile Ser Pro
            580                 585                 590

Gln Gln Arg Arg Gly Glu Pro Val Pro Gln Glu Leu Leu Asp Arg Val
            595                 600                 605

Leu Gly Ala His Arg Tyr Trp Thr Gln His Gln Met Lys Gln Asn Gly
            610                 615                 620

Lys His Gln Val Ala Thr Thr Met Val Val Glu Ala Gly Ser Ser Met
625                 630                 635                 640

<210> SEQ ID NO 85
<211> LENGTH: 1209
<212> TYPE: DNA
<213> ORGANISM: Arabidopsis thaliana
<220> FEATURE:
<223> OTHER INFORMATION: G229

<400> SEQUENCE: 85
ttgtggtcag tggaataaac acatataacc gccggagaaa atgggaagag cgccatgttg     60
cgagaaggtc ggtatcaaga gagggcggtg gacggcggag gaggaccaga ttctctccaa    120
ctacattcaa tccaatggtg aaggttcttg gagatctctc cccaaaaatg ccggattaaa    180 aggtgtgga aagagctgta gattgagatg gataaactat ctaagatcag acctcaagcg    240
tggaaacata actccagaag aagaagaact cgttgttaaa ttgcattcca ctttgggaaa    300
caggtggtca ctaatcgcgg gtcatctacc agggagaaca gacaacgaaa taaaaaatta    360
ttggaactct catctcagcc gtaaactcca caacttcatt aggaagccat ccatctctca    420
agacgtctcc gccgtaatca tggcgaacgc ttcttcagcg ccaccgccgc cgcaggcaaa    480
acgcagactt gggagaacga gtaggtccgc tatgaaacca aaaatccgca gaacaaaaac    540
tcgtaaaacg aagaaaacgt ctgcaccacc ggagcctaac gccgatgtag ctggggctga    600
taaagaagca ttaatggtgg agtcaagtgg agccgaggct gagctaggac gaccatgtga    660
```

```
ctactatgga gatgattgta acaaaaatct catgagcatt aatggcgata atggagtttt     720
aacgtttgat gatgatatca tcgatctttt gttggacgag tcagatcctg gccacttgta     780
cacaaacaca acgtgcggtg gtggtgggga gttgcataac ataagagact ctgaaggagc     840
cagagggttc tcggatactt ggaaccaagg gaatctcgac tgtcttcttc agtcttgtcc     900
atctgtggag tcgtttctca actacgacca ccaagttaac gacgcgtcga cggatgagtt     960
tatcgattgg gattgtgttt ggcaagaagg tagtgataat aatctttggc atgagaaaga    1020
gaatcccgac tcaatggtct cgtggctttt agacggtgat gatgaggcca cgatcgggaa    1080
tagtaattgt gagaactttg gagaaccgtt agatcatgac gacgaaagcg ctttggtcgc    1140
ttggcttctg tcatgatgat attgattgat ccgttatgta atctttttg tgcattcaca    1200
gtttgaatc                                                              1209
```

<210> SEQ ID NO 86
<211> LENGTH: 371
<212> TYPE: PRT
<213> ORGANISM: Arabidopsis thaliana
<220> FEATURE:
<223> OTHER INFORMATION: G229

<400> SEQUENCE: 86

```
Met Gly Arg Ala Pro Cys Cys Glu Lys Val Gly Ile Lys Arg Gly Arg
 1               5                  10                  15
Trp Thr Ala Glu Glu Asp Gln Ile Leu Ser Asn Tyr Ile Gln Ser Asn
            20                  25                  30
Gly Glu Gly Ser Trp Arg Ser Leu Pro Lys Asn Ala Gly Leu Lys Arg
        35                  40                  45
Cys Gly Lys Ser Cys Arg Leu Arg Trp Ile Asn Tyr Leu Arg Ser Asp
    50                  55                  60
Leu Lys Arg Gly Asn Ile Thr Pro Glu Glu Glu Leu Val Val Lys
 65                  70                  75                  80
Leu His Ser Thr Leu Gly Asn Arg Trp Ser Leu Ile Ala Gly His Leu
                85                  90                  95
Pro Gly Arg Thr Asp Asn Glu Ile Lys Asn Tyr Trp Asn Ser His Leu
            100                 105                 110
Ser Arg Lys Leu His Asn Phe Ile Arg Lys Pro Ser Ile Ser Gln Asp
        115                 120                 125
Val Ser Ala Val Ile Met Ala Asn Ala Ser Ser Ala Pro Pro Pro
    130                 135                 140
Gln Ala Lys Arg Arg Leu Gly Arg Thr Ser Arg Ser Ala Met Lys Pro
145                 150                 155                 160
Lys Ile Arg Arg Thr Lys Thr Arg Lys Thr Lys Thr Ser Ala Pro
                165                 170                 175
Pro Glu Pro Asn Ala Asp Val Ala Gly Ala Asp Lys Glu Ala Leu Met
            180                 185                 190
Val Glu Ser Ser Gly Ala Glu Ala Glu Leu Gly Arg Pro Cys Asp Tyr
        195                 200                 205
Tyr Gly Asp Asp Cys Asn Lys Asn Leu Met Ser Ile Asn Gly Asp Asn
    210                 215                 220
Gly Val Leu Thr Phe Asp Asp Ile Ile Asp Leu Leu Leu Asp Glu
225                 230                 235                 240
Ser Asp Pro Gly His Leu Tyr Thr Asn Thr Thr Cys Gly Gly Gly Gly
                245                 250                 255
```

| | | | | | | | | | | | |
|---|---|---|---|---|---|---|---|---|---|---|---|
|Glu|Leu|His|Asn|Ile|Arg|Asp|Ser|Glu|Gly|Ala|Arg|Gly|Phe|Ser|Asp|
| | | |260| | | |265| | | |270| | | | |

Thr Trp Asn Gln Gly Asn Leu Asp Cys Leu Leu Gln Ser Cys Pro Ser
        275             280             285

Val Glu Ser Phe Leu Asn Tyr Asp His Gln Val Asn Asp Ala Ser Thr
    290             295             300

Asp Glu Phe Ile Asp Trp Asp Cys Val Trp Gln Glu Gly Ser Asp Asn
305             310             315             320

Asn Leu Trp His Glu Lys Glu Asn Pro Asp Ser Met Val Ser Trp Leu
            325             330             335

Leu Asp Gly Asp Asp Glu Ala Thr Ile Gly Asn Ser Asn Cys Glu Asn
                340             345             350

Phe Gly Glu Pro Leu Asp His Asp Glu Ser Ala Leu Val Ala Trp
            355             360             365

Leu Leu Ser
    370

<210> SEQ ID NO 87
<211> LENGTH: 1033
<212> TYPE: DNA
<213> ORGANISM: Arabidopsis thaliana
<220> FEATURE:
<223> OTHER INFORMATION: G221

<400> SEQUENCE: 87

```
ctctcttatt ctctcactct ttttttttta tattcctctc tctctaaatc tataaaatat      60
atttaaaaac ttgatcgtat ataataaagt aaataaagaa taataacaaa aaaaatggag     120
aaaagaggag gaggaagtag tggaggttcg ggatcatcag cagaagcaga agtgagaaaa     180
ggaccatgga cgatggaaga agatcttatt cttatcaact atatcgccaa ccacggcgat     240
ggtgtttgga attctctcgc caaatctgca ggtctaaaac gaaccgggaa aagttgccgg     300
ctccggtggc tgaactatct ccgccccgac gtacgacggg gaaacatcac tccagaagag     360
caacttatca tcatggaact tcatgctaag tggggaaaca ggtggtcgaa atcgccaaa     420
catcttccag gaagaacgga caacgagatc aaaaatttct gtaggacaag aattcaaaaa     480
tacatcaagc aatcggatgt aacaacaaca tcgtccgttg gatctcatca tagctcagag     540
atcaacgatc aagctgcaag cacgtcgagc cataatgtct tttgtacaca agatcaagcg     600
atggagactt attctcctac accgacatca tatcaacata ccaatatgga attcaactat     660
ggtaactatt cggccgcggc agtgacggca accgtggatt atccagtacc gatgaccgtt     720
gatgatcaaa ccggtgaaaa ctattggggc atggatgata tttggtcatc aatgcattta     780
ttgaatggta attgattgat cggtggacaa acatggaat attaattgag tattatatat     840
gatttttagg agtactatta ttagtacgtg acatgtatat gtttttgcct cgttgtagag     900
gtttggggtt ataattaata tataatgtta tctaatatgc aaccttgata catatttgga     960
tctttattga acccatgtta tacataaata aaattgttga agggtcata aaaaaaaaa    1020
aaaaaaaaa aaa                                                       1033
```

<210> SEQ ID NO 88
<211> LENGTH: 226
<212> TYPE: PRT
<213> ORGANISM: Arabidopsis thaliana
<220> FEATURE:
<223> OTHER INFORMATION: G221

<400> SEQUENCE: 88

```
Met Glu Lys Arg Gly Gly Ser Ser Gly Ser Gly Ser Ser Ala
 1               5                  10                  15

Glu Ala Glu Val Arg Lys Gly Pro Trp Thr Met Glu Glu Asp Leu Ile
            20                  25                  30

Leu Ile Asn Tyr Ile Ala Asn His Gly Asp Gly Val Trp Asn Ser Leu
         35                  40                  45

Ala Lys Ser Ala Gly Leu Lys Arg Thr Gly Lys Ser Cys Arg Leu Arg
 50                  55                  60

Trp Leu Asn Tyr Leu Arg Pro Asp Val Arg Arg Gly Asn Ile Thr Pro
 65                  70                  75                  80

Glu Glu Gln Leu Ile Ile Met Glu Leu His Ala Lys Trp Gly Asn Arg
                 85                  90                  95

Trp Ser Lys Ile Ala Lys His Leu Pro Gly Arg Thr Asp Asn Glu Ile
                100                 105                 110

Lys Asn Phe Cys Arg Thr Arg Ile Gln Lys Tyr Ile Lys Gln Ser Asp
            115                 120                 125

Val Thr Thr Thr Ser Ser Val Gly Ser His His Ser Ser Glu Ile Asn
130                 135                 140

Asp Gln Ala Ala Ser Thr Ser Ser His Asn Val Phe Cys Thr Gln Asp
145                 150                 155                 160

Gln Ala Met Glu Thr Tyr Ser Pro Thr Pro Thr Ser Tyr Gln His Thr
                165                 170                 175

Asn Met Glu Phe Asn Tyr Gly Asn Tyr Ser Ala Ala Val Thr Ala
            180                 185                 190

Thr Val Asp Tyr Pro Val Pro Met Thr Val Asp Gln Thr Gly Glu
            195                 200                 205

Asn Tyr Trp Gly Met Asp Asp Ile Trp Ser Ser Met His Leu Leu Asn
210                 215                 220

Gly Asn
225

<210> SEQ ID NO 89
<211> LENGTH: 1952
<212> TYPE: DNA
<213> ORGANISM: Arabidopsis thaliana
<220> FEATURE:
<223> OTHER INFORMATION: G186
<220> FEATURE:
<223> OTHER INFORMATION: "n" bases at various positions throughout the
      sequence may be A, T, C, G, other or unknown

<400> SEQUENCE: 89
ctttcaacca aaccoctaaa caaaaaaaaa atacattttc tgatctctct aaaaatcttt      60
ctccttcgtt aatctcgtga tctctttctt tttctatata tggacagagg atggtctggt    120
ctcactcttg attcatcttc tcttgatctt ttaaaccctaa atcgtatttc tcataagaat    180
caccgacgtt tctcaaatcc tttggcgatg tctagaattg acgaagaaga tgatcagaag    240
acgagaatat caaccaacgg tagtgaattt aggtttccgg tgagtctctc aggtattcgt    300
gatcgtgaag atgaagattt tcatctggc gttgctggag ataatgaccg tgaagttccc    360
ggcgaagtgg atttcttctc cgacaagaaa tctagggttt gtcgtgaaga cgacgaagga    420
tttcgtgtga agaaggaaga acaagatgat cgaacggacg taaataccgg tttgaatctt    480
cgaacaactg gtaatacaaa gagtgatgag tcaatgatcg atgatggaga atcttccgaa    540
atggaagata agcgtgcgaa aaatgagttg gtgaaattac aagatgagtt gaagaaaatg    600
```

-continued

```
acaatggata atcaaaagct tagagaattg cttacacaag ttagcaacag ttacacttca    660
cttcagatgc atcttgtttc actaatgcag caacagcaac aacagaacaa taaggtaata    720
gaagctgctg agaagcctga ggagacgata gtaccaaggc aatttattga tttaggccct    780
acgagagcag taggtgaggc cgaggatgtg tcaaattctt catccgaaga tagaactcgt    840 tcgggggggtt cttctgcagc cgagaggcgt agtaacggga agagacttgg gcgtgaagaa    900
agccccgaaa ctgagtccaa caaaattcag aaggtgaatt ctactacccc gacgacattt    960
gatcaaaccg ctgaagctac gatgaggaaa gcccgtgtct ccgttcgtgc ccgatcggaa   1020
gctccgatga taagcgatgg atgtcaatgg agaaaatatg ccagaagat ggccaaaggg    1080 aatccttgtc cgcgggcata ttaccgctgc acgatggcca cgggctgtcc cgttcgcaaa   1140
caagttcaac gttgcgcgga agacagatca attctgatta caacctacga gggaaaccat   1200
aaccatccgt tgccgccagc cgcggtagcc atggcttcta ccaccacggc ggcggctaac   1260
atgttgctat ccgggtcaat gtctagtcac gacgggatga tgaaccctac aaatttacta   1320
gctagggctg ttcttccttg ctccacaagc atggcaacaa tctcagcctc cgcgccgttt   1380
ccaaccgtca cattagacct cacccactca cctccgcctc ctaatggttc caatccttcc   1440
tcttccgcgg ctaccaacaa caaccacaac tcactgatgc agcggccgca acaacaacaa   1500
cagcaaatga cgaacttacc tccgggaatg ctacctcatg taataggcca ggcattgtat   1560
aaccaatcca agttctcggg gctgcagttc tctggtggct ctccctcgac ggcagcgttt   1620
tctcagtcac acgcggtggc tgatacaata acggcactca cagctgaccc gaatttcacg   1680
gcggctcttg cagccgttat ttcttctatg atcaatggta cgaaccacca cgacggcgaa   1740
ggaaacaaca aaaatcaata gaaaaatatt acatttttt tttgggtatc tacattttt   1800 ttccaactgg gttataggaa acagagagtt tatttcattg attcacattt gttctgtttc   1860
gtaccaaaat cccagtaaat atacaaaagc aaactatact caagttcata ttcgtaaaca   1920
ctataaatag tncgttnctt antaaaaaaa aa                                 1952
```

<210> SEQ ID NO 90
<211> LENGTH: 553
<212> TYPE: PRT
<213> ORGANISM: Arabidopsis thaliana
<220> FEATURE:
<223> OTHER INFORMATION: G186

<400> SEQUENCE: 90

```
Met Asp Arg Gly Trp Ser Gly Leu Thr Leu Asp Ser Ser Ser Leu Asp
 1               5                  10                  15

Leu Leu Asn Pro Asn Arg Ile Ser His Lys Asn His Arg Arg Phe Ser
            20                  25                  30

Asn Pro Leu Ala Met Ser Arg Ile Asp Glu Glu Asp Asp Gln Lys Thr
        35                  40                  45

Arg Ile Ser Thr Asn Gly Ser Glu Phe Arg Phe Pro Val Ser Leu Ser
    50                  55                  60

Gly Ile Arg Asp Arg Glu Asp Glu Asp Phe Ser Gly Val Ala Gly
 65                  70                  75                  80

Asp Asn Asp Arg Glu Val Pro Gly Glu Val Asp Phe Phe Ser Asp Lys
                85                  90                  95

Lys Ser Arg Val Cys Arg Glu Asp Glu Gly Phe Arg Val Lys Lys
            100                 105                 110

Glu Glu Gln Asp Asp Arg Thr Asp Val Asn Thr Gly Leu Asn Leu Arg
        115                 120                 125
```

-continued

```
Thr Thr Gly Asn Thr Lys Ser Asp Glu Ser Met Ile Asp Asp Gly Glu
    130                 135                 140
Ser Ser Glu Met Glu Asp Lys Arg Ala Lys Asn Glu Leu Val Lys Leu
145                 150                 155                 160
Gln Asp Glu Leu Lys Lys Met Thr Met Asp Asn Gln Lys Leu Arg Glu
                165                 170                 175
Leu Leu Thr Gln Val Ser Asn Ser Tyr Thr Ser Leu Gln Met His Leu
            180                 185                 190
Val Ser Leu Met Gln Gln Gln Gln Asn Lys Val Ile Glu
            195                 200                 205
Ala Ala Glu Lys Pro Glu Glu Thr Ile Val Pro Arg Gln Phe Ile Asp
210                 215                 220
Leu Gly Pro Thr Arg Ala Val Gly Glu Ala Glu Asp Val Ser Asn Ser
225                 230                 235                 240
Ser Ser Glu Asp Arg Thr Arg Ser Gly Gly Ser Ser Ala Ala Glu Arg
                245                 250                 255
Arg Ser Asn Gly Lys Arg Leu Gly Arg Glu Glu Ser Pro Glu Thr Glu
            260                 265                 270
Ser Asn Lys Ile Gln Lys Val Asn Ser Thr Thr Pro Thr Thr Phe Asp
        275                 280                 285
Gln Thr Ala Glu Ala Thr Met Arg Lys Ala Arg Val Ser Val Arg Ala
    290                 295                 300
Arg Ser Glu Ala Pro Met Ile Ser Asp Gly Cys Gln Trp Arg Lys Tyr
305                 310                 315                 320
Gly Gln Lys Met Ala Lys Gly Asn Pro Cys Pro Arg Ala Tyr Tyr Arg
                325                 330                 335
Cys Thr Met Ala Thr Gly Cys Pro Val Arg Lys Gln Val Gln Arg Cys
            340                 345                 350
Ala Glu Asp Arg Ser Ile Leu Ile Thr Thr Tyr Glu Gly Asn His Asn
        355                 360                 365
His Pro Leu Pro Pro Ala Ala Val Ala Met Ala Ser Thr Thr Thr Ala
    370                 375                 380
Ala Ala Asn Met Leu Leu Ser Gly Ser Met Ser Ser His Asp Gly Met
385                 390                 395                 400
Met Asn Pro Thr Asn Leu Leu Ala Arg Ala Val Leu Pro Cys Ser Thr
                405                 410                 415
Ser Met Ala Thr Ile Ser Ala Ser Ala Pro Phe Pro Thr Val Thr Leu
            420                 425                 430
Asp Leu Thr His Ser Pro Pro Pro Asn Gly Ser Asn Pro Ser Ser
        435                 440                 445
Ser Ala Ala Thr Asn Asn Asn His Asn Ser Leu Met Gln Arg Pro Gln
    450                 455                 460
Gln Gln Gln Gln Gln Met Thr Asn Leu Pro Pro Gly Met Leu Pro His
465                 470                 475                 480
Val Ile Gly Gln Ala Leu Tyr Asn Gln Ser Lys Phe Ser Gly Leu Gln
                485                 490                 495
Phe Ser Gly Gly Ser Pro Ser Thr Ala Ala Phe Ser Gln Ser His Ala
            500                 505                 510
Val Ala Asp Thr Ile Thr Ala Leu Thr Ala Asp Pro Asn Phe Thr Ala
        515                 520                 525
Ala Leu Ala Ala Val Ile Ser Ser Met Ile Asn Gly Thr Asn His His
    530                 535                 540
```

Asp Gly Glu Gly Asn Asn Lys Asn Gln
545             550

<210> SEQ ID NO 91
<211> LENGTH: 1554
<212> TYPE: DNA
<213> ORGANISM: Arabidopsis thaliana
<220> FEATURE:
<223> OTHER INFORMATION: G562

<400> SEQUENCE: 91

```
atttgaattt ctgggtttct ctctgtttaa gcttcttctt cttcatcttc tgcttacgtt      60
tcttcttcaa ggagctttcg gattcttgta gaaagagtca ttgttctctt gagtgggaaa     120
ccttgaaacc attcctatgg gaaatagcag cgaggaacca aagcctccta ccaaatcaga     180
taaaccatct tcaccccggg tggatcaaac aaatgttcat gtctaccctg attgggcagc     240
tatgcaggca tattatggtc caagagtagc aatgcctcct tattacaatt cagctatggc     300
tgcatctggt catcctcctc ctccttacat gtggaatcct cagcatatga tgtcaccatc     360
tggagcaccc tatgctgctg tttatcctca tggaggagga gtttacgctc atcccggtat     420
tcccatggga tcactgcctc aaggtcaaaa ggatccacct ttaacaactc cggggacgct     480
tttgagcatc gacactccta ctaaatctac agggaacaca gacaatggat tgatgaagaa     540
gctgaaagag tttgatgggc ttgctatgtc tctaggaaat gggaatcctg aaaatggtgc     600
agatgaacat aaacgatcac ggaacagctc agaaactgat ggttctactg atggaagtga     660
tgggaataca actggggcag atgaaccgaa acttaaaaga agtcgagagg gaactccaac     720
aaaagatggg aaacaattgg ttcaagctag ctcatttcat tctgtttctc cgtcaagtgg     780
tgataccggc gtaaaactca ttcaaggatc tggagctata ctctctcctg gtgtaagtgc     840
aaattccaac cccttcatgt cacaatcttt agccatggtt cctcctgaaa cttggcttca     900
gaacgagaga gaactgaaac gggagcgaag gaaacagtct aatagagaat ctgctagaag     960
gtcaagatta aggaaacagg ccgagacaga agaacttgct aggaaagtgg aagccttgac    1020
agccgaaaac atggcattaa gatctgaact aaaccaactt aatgagaaat ctgataaact    1080
aagaggagca aatgcaacct tgttggacaa actgaaatgc tcggaacccg aaaagagagt    1140
ccccgcaaat atgttgtcta gagttaagaa ctcaggagct ggagataaga acaagaacca    1200
aggagacaat gattctaact ctacaagcaa attccatcaa ctgctcgata cgaagcctcg    1260
agctaaagca gtagctgcag gctgaatcga tggtaattca tgtcgatttc tacttaattt    1320
gtcgacataa acaaagaaaa taagtgctac taatttcaga aaaacttgat agatagatag    1380
tatagtagag agagagagag agagagaggt gtgatgatta ttgatctata aattttcgga    1440
gagagagagg gagaaagaga aactttcct ccagatgaaa atttggtgtt atggtttgtt    1500
actgttaata tagagaggct tttctttttt tataaaatgg cttcctttgt tgca          1554
```

<210> SEQ ID NO 92
<211> LENGTH: 382
<212> TYPE: PRT
<213> ORGANISM: Arabidopsis thaliana
<220> FEATURE:
<223> OTHER INFORMATION: G562

<400> SEQUENCE: 92

Met Gly Asn Ser Ser Glu Glu Pro Lys Pro Pro Thr Lys Ser Asp Lys
1               5                   10                  15

Pro Ser Ser Pro Pro Val Asp Gln Thr Asn Val His Val Tyr Pro Asp

```
                    20                  25                  30
          Trp Ala Ala Met Gln Ala Tyr Tyr Gly Pro Arg Val Ala Met Pro Pro
                       35                  40                  45
          Tyr Tyr Asn Ser Ala Met Ala Ser Gly His Pro Pro Pro Tyr
           50                  55                  60
          Met Trp Asn Pro Gln His Met Met Ser Pro Ser Gly Ala Pro Tyr Ala
           65                  70                  75                  80
          Ala Val Tyr Pro His Gly Gly Val Tyr Ala His Pro Gly Ile Pro
                           85                  90                  95
          Met Gly Ser Leu Pro Gln Gly Gln Lys Asp Pro Pro Leu Thr Thr Pro
                          100                 105                 110
          Gly Thr Leu Leu Ser Ile Asp Thr Pro Thr Lys Ser Thr Gly Asn Thr
                          115                 120                 125
          Asp Asn Gly Leu Met Lys Lys Leu Lys Glu Phe Asp Gly Leu Ala Met
          130                 135                 140
          Ser Leu Gly Asn Gly Asn Pro Glu Asn Gly Ala Asp Glu His Lys Arg
          145                 150                 155                 160
          Ser Arg Asn Ser Ser Glu Thr Asp Gly Ser Thr Asp Gly Ser Asp Gly
                          165                 170                 175
          Asn Thr Thr Gly Ala Asp Glu Pro Lys Leu Lys Arg Ser Arg Glu Gly
                          180                 185                 190
          Thr Pro Thr Lys Asp Gly Lys Gln Leu Val Gln Ala Ser Ser Phe His
                          195                 200                 205
          Ser Val Ser Pro Ser Ser Gly Asp Thr Gly Val Lys Leu Ile Gln Gly
                          210                 215                 220
          Ser Gly Ala Ile Leu Ser Pro Gly Val Ser Ala Asn Ser Asn Pro Phe
          225                 230                 235                 240
          Met Ser Gln Ser Leu Ala Met Val Pro Pro Glu Thr Trp Leu Gln Asn
                          245                 250                 255
          Glu Arg Glu Leu Lys Arg Glu Arg Arg Lys Gln Ser Asn Arg Glu Ser
                          260                 265                 270
          Ala Arg Arg Ser Arg Leu Arg Lys Gln Ala Glu Thr Glu Glu Leu Ala
                          275                 280                 285
          Arg Lys Val Glu Ala Leu Thr Ala Glu Asn Met Ala Leu Arg Ser Glu
          290                 295                 300
          Leu Asn Gln Leu Asn Glu Lys Ser Asp Lys Leu Arg Gly Ala Asn Ala
          305                 310                 315                 320
          Thr Leu Leu Asp Lys Leu Lys Cys Ser Glu Pro Glu Lys Arg Val Pro
                          325                 330                 335
          Ala Asn Met Leu Ser Arg Val Lys Asn Ser Gly Ala Gly Asp Lys Asn
                          340                 345                 350
          Lys Asn Gln Gly Asp Asn Asp Ser Asn Ser Thr Ser Lys Phe His Gln
                          355                 360                 365
          Leu Leu Asp Thr Lys Pro Arg Ala Lys Ala Val Ala Ala Gly
                          370                 375                 380

<210> SEQ ID NO 93
<211> LENGTH: 918
<212> TYPE: DNA
<213> ORGANISM: Arabidopsis thaliana
<220> FEATURE:
<223> OTHER INFORMATION: G255

<400> SEQUENCE: 93
agcatcatca tcatcagaag aagagagtca tgggaagatc tccttgctgc gagaaagaac     60
```

-continued

```
acatgaacaa aggtgcttgg actaaagaag aagatgagag actagtctct tacatcaagt      120
ctcacggtga aggttgttgg cgatctcttc ctagagccgc tggtctcctt cgctgcggta      180
aaagctgccg tcttcggtgg attaactatc tccgacctga tctcaaaaga ggaaacttta      240
cacatgatga agatgaactt atcatcaagc ttcatagcct cctaggcaac aagtggtctt      300
tgattgcggc gagattacct ggaagaacag ataacgagat caagaactac tggaacacac      360
atataaagag gaagcttttg agcaaaggga ttgatccagc cactcataga gggatcaacg      420
aggcaaaaat ttctgatttg aagaaaacaa aggaccaaat tgtaaaagat gtttcttttg      480
tgacaaagtt tgaggaaaca gacaagtctg gggaccagaa gcaaataag tatattcgaa       540 atgggttagt ttgcaaagaa gagagagttg ttgttgaaga aaaataggc ccagatttga       600 atcttgagct taggatcagt ccaccatggc aaaaccagag agaaatatct acttgcactg      660
cgtcccgttt ttacatggaa aacgacatgg agtgtagtag tgaaactgtg aaatgtcaaa      720
cagagaatag tagcagcatt agctattctt ctattgatat tagtagtagt aacgttggtt     780
atgacttctt gggtttgaag acaagaattt tggattttcg aagcttggaa atgaaataaa     840
tgaatagtat tagattctta atttgtaggt ctgataatga atgttagatt cgcggccctc     900
tagacaggcc tcgtaccg                                                    918
```

<210> SEQ ID NO 94
<211> LENGTH: 269
<212> TYPE: PRT
<213> ORGANISM: Arabidopsis thaliana
<220> FEATURE:
<223> OTHER INFORMATION: G255

<400> SEQUENCE: 94

```
Met Gly Arg Ser Pro Cys Cys Glu Lys Glu His Met Asn Lys Gly Ala
 1               5                  10                  15

Trp Thr Lys Glu Glu Asp Glu Arg Leu Val Ser Tyr Ile Lys Ser His
                20                  25                  30

Gly Glu Gly Cys Trp Arg Ser Leu Pro Arg Ala Ala Gly Leu Leu Arg
            35                  40                  45

Cys Gly Lys Ser Cys Arg Leu Arg Trp Ile Asn Tyr Leu Arg Pro Asp
        50                  55                  60

Leu Lys Arg Gly Asn Phe Thr His Asp Glu Asp Glu Leu Ile Ile Lys
    65                  70                  75                  80

Leu His Ser Leu Leu Gly Asn Lys Trp Ser Leu Ile Ala Ala Arg Leu
                85                  90                  95

Pro Gly Arg Thr Asp Asn Glu Ile Lys Asn Tyr Trp Asn Thr His Ile
                100                 105                 110

Lys Arg Lys Leu Leu Ser Lys Gly Ile Asp Pro Ala Thr His Arg Gly
            115                 120                 125

Ile Asn Glu Ala Lys Ile Ser Asp Leu Lys Lys Thr Lys Asp Gln Ile
        130                 135                 140

Val Lys Asp Val Ser Phe Val Thr Lys Phe Glu Thr Asp Lys Ser
145                 150                 155                 160

Gly Asp Gln Lys Gln Asn Lys Tyr Ile Arg Asn Gly Leu Val Cys Lys
                165                 170                 175

Glu Glu Arg Val Val Val Glu Glu Lys Ile Gly Pro Asp Leu Asn Leu
            180                 185                 190

Glu Leu Arg Ile Ser Pro Pro Trp Gln Asn Gln Arg Glu Ile Ser Thr
        195                 200                 205
```

```
Cys Thr Ala Ser Arg Phe Tyr Met Glu Asn Asp Met Glu Cys Ser Ser
        210                 215                 220

Glu Thr Val Lys Cys Gln Thr Glu Asn Ser Ser Ile Ser Tyr Ser
225                 230                 235                 240

Ser Ile Asp Ile Ser Ser Asn Val Gly Tyr Asp Phe Leu Gly Leu
                245                 250                 255

Lys Thr Arg Ile Leu Asp Phe Arg Ser Leu Glu Met Lys
                260                 265
```

```
<210> SEQ ID NO 95
<211> LENGTH: 759
<212> TYPE: DNA
<213> ORGANISM: Arabidopsis thaliana
<220> FEATURE:
<223> OTHER INFORMATION: G3

<400> SEQUENCE: 95
gtttgtcttt tatcaatgga aagagaacaa gaagagtcta cgatgagaaa gagaaggcag      60
ccacctcaag aagaagtgcc taaccacgtg gctacaagga agccgtacag agggatacgg     120
aggaggaagt ggggcaagtg ggtggctgag attcgtgagc ctaacaaacg ctcacggctt     180
tggcttggct cttacacaac cgatatcgcc gccgctagag cctacgacgt ggccgtcttc     240
tacctccgtg gccctccgc acgtctcaac ttccctgatc ttctcttgca agaagaggac     300
catctctcag ccgccaccac cgctgacatg cccgcagctc ttataaggga aaaagcggcg     360
gaggtcggcg ccagagtcga cgctcttcta gcttctgccg ctccttcgat ggctcactcc     420
actccgccgg taataaaacc cgacttgaat caaatacccg aatccggaga tatatagtca     480
atttatatac atgtagtttg ttttgtttga ttagaagatt acatttacat acaagataca     540
catagatact ggaaaatata ggtatgtata cattcataaa ttatcttatg tatcaaagaa     600
ttttatagat tctgattagc ttttgttttt tgttttgat aagaactctg attagttgtc     660
cggagacaaa accggctaag agcaatccat gagaagctag cgagtgtttt ttagttcaag     720
ttgtaatata aatgcatatt aattctttag taattttgt                            759
```

```
<210> SEQ ID NO 96
<211> LENGTH: 153
<212> TYPE: PRT
<213> ORGANISM: Arabidopsis thaliana
<220> FEATURE:
<223> OTHER INFORMATION: G3

<400> SEQUENCE: 96

Met Glu Arg Glu Gln Glu Glu Ser Thr Met Arg Lys Arg Arg Gln Pro
1               5                   10                  15

Pro Gln Glu Glu Val Pro Asn His Val Ala Thr Arg Lys Pro Tyr Arg
                20                  25                  30

Gly Ile Arg Arg Arg Lys Trp Gly Lys Trp Val Ala Glu Ile Arg Glu
        35                  40                  45

Pro Asn Lys Arg Ser Arg Leu Trp Leu Gly Ser Tyr Thr Thr Asp Ile
    50                  55                  60

Ala Ala Ala Arg Ala Tyr Asp Val Ala Val Phe Tyr Leu Arg Gly Pro
65                  70                  75                  80

Ser Ala Arg Leu Asn Phe Pro Asp Leu Leu Gln Glu Glu Asp His
                85                  90                  95

Leu Ser Ala Ala Thr Thr Ala Asp Met Pro Ala Ala Leu Ile Arg Glu
                100                 105                 110
```

```
Lys Ala Ala Glu Val Gly Ala Arg Val Asp Ala Leu Leu Ala Ser Ala
        115                 120                 125

Ala Pro Ser Met Ala His Ser Thr Pro Pro Val Ile Lys Pro Asp Leu
    130                 135                 140

Asn Gln Ile Pro Glu Ser Gly Asp Ile
145                 150

<210> SEQ ID NO 97
<211> LENGTH: 965
<212> TYPE: DNA
<213> ORGANISM: Arabidopsis thaliana
<220> FEATURE:
<223> OTHER INFORMATION: G713

<400> SEQUENCE: 97
ggcacgagcc ttctctctta atcaaaatca agaaacttac aagatctggt gaaaaccatg    60
gaagaaggag atttttttcaa ctgctgtttc agcgagatta gtagtggcat gaccatgaat   120
aagaagaaga tgaagaagag caataaccaa aagaggttta cgaggaaca gatcaagtca    180
cttgagctta tatttgagtc tgagacgagg cttgagccga ggaagaaggt tcaggtagct    240
agagagctag gctgcaacc aagacaaatg actatatggt ttcaaaacaa gagggctcga    300
tggaaaacta agcaacttga aaagagtat aacactctta gagccaatta caacaatttg    360
gcttcacaat tgaaatcat gaagaaagaa aagcaatctc tggtctctga gctgcagaga    420
ctaaacgaag agatgcaaag gcctaaagaa gaaaagcatc atgagtgttg tggtgatcaa    480
ggactggctc taagcagcag cacagagtcg cataatggaa agagtgagcc agaagggagg    540
ttagaccaag ggagtgttct atgtaatgat ggtgattaca caacaacat taaacagag     600
tattttaggg tccagggaga gactgatcat gagctgatga acattgtgga gaaagctgat    660
gatagttgct tgacatcttc tgagaattgg ggaggtttca attctgattc tctcttagac    720
caatctagca gcaattaccc taactggtgg gagttttggt cataaaagca tataagaaaa    780
aaacagaaca taagcgaaga gaaagagtgt gaatagtttg taaattatgt gttaagaaaa    840
taaatttagt ttagtttaaa tcttgtttcg atctatgtat ctactatgtt caatactctt    900
tgtagctaat tagtagctta taatgagact agaaaagttt tgaagtcaaa aaaaaaaaa    960
aaaaa                                                               965

<210> SEQ ID NO 98
<211> LENGTH: 235
<212> TYPE: PRT
<213> ORGANISM: Arabidopsis thaliana
<220> FEATURE:
<223> OTHER INFORMATION: G713

<400> SEQUENCE: 98

Met Glu Glu Gly Asp Phe Phe Asn Cys Cys Phe Ser Glu Ile Ser Ser
  1               5                  10                  15

Gly Met Thr Met Asn Lys Lys Met Lys Lys Ser Asn Asn Gln Lys
             20                  25                  30

Arg Phe Asn Glu Glu Gln Ile Lys Ser Leu Glu Leu Ile Phe Glu Ser
         35                  40                  45

Glu Thr Arg Leu Glu Pro Arg Lys Lys Val Gln Val Ala Arg Glu Leu
     50                  55                  60

Gly Leu Gln Pro Arg Gln Met Thr Ile Trp Phe Gln Asn Lys Arg Ala
 65                  70                  75                  80
```

```
Arg Trp Lys Thr Lys Gln Leu Glu Lys Glu Tyr Asn Thr Leu Arg Ala
             85                  90                  95

Asn Tyr Asn Asn Leu Ala Ser Gln Phe Glu Ile Met Lys Lys Glu Lys
            100                 105                 110

Gln Ser Leu Val Ser Glu Leu Gln Arg Leu Asn Glu Glu Met Gln Arg
        115                 120                 125

Pro Lys Glu Glu Lys His His Glu Cys Cys Gly Asp Gln Gly Leu Ala
    130                 135                 140

Leu Ser Ser Ser Thr Glu Ser His Asn Gly Lys Ser Glu Pro Glu Gly
145                 150                 155                 160

Arg Leu Asp Gln Gly Ser Val Leu Cys Asn Asp Gly Asp Tyr Asn Asn
                165                 170                 175

Asn Ile Lys Thr Glu Tyr Phe Arg Val Gln Gly Glu Thr Asp His Glu
            180                 185                 190

Leu Met Asn Ile Val Glu Lys Ala Asp Asp Ser Cys Leu Thr Ser Ser
        195                 200                 205

Glu Asn Trp Gly Gly Phe Asn Ser Asp Ser Leu Leu Asp Gln Ser Ser
    210                 215                 220

Ser Asn Tyr Pro Asn Trp Trp Glu Phe Trp Ser
225                 230                 235

<210> SEQ ID NO 99
<211> LENGTH: 1339
<212> TYPE: DNA
<213> ORGANISM: Arabidopsis thaliana
<220> FEATURE:
<223> OTHER INFORMATION: G515

<400> SEQUENCE: 99
gtcgacaaga agggccgcat aaatacaaaa ccctatacgt ctttcttctc catcatttta      60
agttgcagaa gaacatcaac catggcgaaa gctctccaat gcatattttt ttgatctttt     120
ccttttccct tcttttttga tcgctgcaga gaaatggaaa ctcctgtggg tttaagattc     180
tgtccgaccg acgaggagat cgtcgtcgat tacctttggc cgaaaaattc cgatagagac     240
acgagccatg tcgatcgatt cattaacaca gtccctgtct gtagactcga tccttgggag     300
ttaccttgcc agtcaaggat caaactgaaa gatgtggctt ggtgtttctt cagacctaag     360
gagaacaaat atggcagagg tgatcagcag atgagaaaaa cgaaatctgg gttttggaag     420
agtactggca gaccaaagcc tatcatgcgt aatcgccaac agatcggtga aaaaagatt      480 ttgatgtttt acacgagtaa ggaatccaaa tccgattggg ttatacacga gtaccacggt     540
ttctctcata accagatgat gatgacatac acactctgta agttatgtt taatggtggc     600 atgagagaga agtcttcctc ttctccttct tcttctggtg ttagtggaat tgagcagagt     660
cgtcgtgact ctttaatccc tcagcttgtc aacaattctg agggatcctc acttcacaga     720
gaagatccaa gtcagtttgg tgatgtgctg caagaagctc caatcgagga tgctaaactg     780
accgaggaat tggtaaaatg gctgatgaat gatgaggatg atgctcaaat cgaggatgct     840
ataccgattg aggaatggga acatggttga atgatattg atgatgctaa ggagaagagt     900 atcatgtttta tgcatgataa tcgaagtgat tacagacctc caaactcatt aactggtgtc     960
ttcagtgatg atgttagcag tgatgataat gattctgatt tgctaactcc aaaaacaaac    1020
tctattcaaa cttcgagcac ttgtgatagt tttggtagct caaatcatcg catagaccag    1080
atcaaagacc tgcaagaatc tcctacctca acaatcaact tagtgtcact aactcaagag    1140
gtgagcgcgg ccgctaataa ccagtattga taccgccgag aagaagaaga atccttatga    1200
```

-continued

```
tgatgcacaa gggactgaga ttggtgagca taaattgggt caagagacga tcaagaagaa   1260
aagagctggt ttctttcaca ggatgataca aaaattcgtc aagaaaattc acctatgttc   1320
ttccatctca agaacttga                                                 1339
```

<210> SEQ ID NO 100
<211> LENGTH: 338
<212> TYPE: PRT
<213> ORGANISM: Arabidopsis thaliana
<220> FEATURE:
<223> OTHER INFORMATION: G515

<400> SEQUENCE: 100

```
Met Glu Thr Pro Val Gly Leu Arg Phe Cys Pro Thr Asp Glu Ile
 1               5                  10                  15

Val Val Asp Tyr Leu Trp Pro Lys Asn Ser Asp Arg Asp Thr Ser His
                20                  25                  30

Val Asp Arg Phe Ile Asn Thr Val Pro Val Cys Arg Leu Asp Pro Trp
            35                  40                  45

Glu Leu Pro Cys Gln Ser Arg Ile Lys Leu Lys Asp Val Ala Trp Cys
        50                  55                  60

Phe Phe Arg Pro Lys Glu Asn Lys Tyr Gly Arg Gly Asp Gln Gln Met
65                  70                  75                  80

Arg Lys Thr Lys Ser Gly Phe Trp Lys Ser Thr Gly Arg Pro Lys Pro
                85                  90                  95

Ile Met Arg Asn Arg Gln Gln Ile Gly Glu Lys Lys Ile Leu Met Phe
            100                 105                 110

Tyr Thr Ser Lys Glu Ser Lys Ser Asp Trp Val Ile His Glu Tyr His
        115                 120                 125

Gly Phe Ser His Asn Gln Met Met Met Thr Tyr Thr Leu Cys Lys Val
    130                 135                 140

Met Phe Asn Gly Gly Met Arg Glu Lys Ser Ser Ser Ser Pro Ser Ser
145                 150                 155                 160

Ser Gly Val Ser Gly Ile Glu Gln Ser Arg Arg Asp Ser Leu Ile Pro
                165                 170                 175

Gln Leu Val Asn Asn Ser Glu Gly Ser Ser Leu His Arg Glu Asp Pro
            180                 185                 190

Ser Gln Phe Gly Asp Val Leu Gln Glu Ala Pro Ile Glu Asp Ala Lys
        195                 200                 205

Leu Thr Glu Glu Leu Val Lys Trp Leu Met Asn Asp Glu Asp Ala
    210                 215                 220

Gln Ile Glu Asp Ala Ile Pro Ile Glu Glu Trp Glu Thr Trp Leu Asn
225                 230                 235                 240

Asp Ile Asp Asp Ala Lys Glu Lys Ser Ile Met Phe Met His Asp Asn
                245                 250                 255

Arg Ser Asp Tyr Arg Pro Pro Asn Ser Leu Thr Gly Val Phe Ser Asp
            260                 265                 270

Asp Val Ser Ser Asp Asp Asn Asp Ser Asp Leu Leu Thr Pro Lys Thr
        275                 280                 285

Asn Ser Ile Gln Thr Ser Ser Thr Cys Asp Ser Phe Gly Ser Ser Asn
    290                 295                 300

His Arg Ile Asp Gln Ile Lys Asp Leu Gln Glu Ser Pro Thr Ser Thr
305                 310                 315                 320

Ile Asn Leu Val Ser Leu Thr Gln Glu Val Ser Ala Ala Asn Asn
                325                 330                 335
```

Gln Tyr

<210> SEQ ID NO 101
<211> LENGTH: 2526
<212> TYPE: DNA
<213> ORGANISM: Arabidopsis thaliana
<220> FEATURE:
<223> OTHER INFORMATION: G390

<400> SEQUENCE: 101

| | | | | | |
|---|---|---|---|---|---|
| atgatggctc | atcactccat | ggacgataga | gactctcctg | ataaggatt | tgattccggc | 60 |
| aagtacgtta | gatacacgcc | ggaacaagtt | gaagctcttg | agagagttta | tgctgagtgt | 120 |
| cctaaaccta | gctctctgag | aagacaacag | cttattcgtg | aatgtcccat | tctctgtaac | 180 |
| atcgagcctc | gacagatcaa | agtttggttc | cagaatcgca | gatgtcgaga | gaagcagagg | 240 |
| aaagagtcag | ctcgtcttca | gacagtgaac | aggaagctga | gtgctatgaa | caagctttg | 300 |
| atggaagaga | tgatcgtttt | gcagaagcaa | gtctccaact | tggtttatga | aatggattc | 360 |
| atgaaacatc | gaatccacac | tgcttctggg | acgaccacag | acaacagctg | tgagtctgtg | 420 |
| gtcgtgagtg | gtcagcaacg | tcagcagcaa | acccaacac | atcagcatcc | tcagcgtgat | 480 |
| gttaacaacc | cagctaatct | tctctcgatt | gcggaggaga | ccttggcgga | gttcctttgc | 540 |
| aaggctacag | gaactgctgt | cgactgggtc | cagatgattg | ggatgaagcc | tggtccggat | 600 |
| tctattggta | tcgtagctgt | ttcacgcaac | tgcagtggaa | tagcagcacg | tgcctgtggc | 660 |
| ctcgtgagtt | tagaacccat | gaaggtcgct | gaaatcctca | agatcgtcc | atcttggttc | 720 |
| cgtgactgtc | gatgtgtcga | gactctgaat | gttataccca | ctggaaatgg | tggtactatc | 780 |
| gagcttgtca | acactcagat | ttatgctcct | acaacattag | cagcagctcg | tgacttttgg | 840 |
| acgctgagat | atagtacaag | tctagaagat | ggaagctatg | tggtctgtga | gagatcactc | 900 |
| acttctgcaa | ctggtggccc | caatggtcca | ctttcttcaa | gcttcgtgag | agccaaaatg | 960 |
| ctgtcaagcg | ggtttcttat | ccgtccttgt | gatggtggtg | gttccattat | tcacatcgtt | 1020 |
| gatcatgtgg | acttggatgt | ctcaagtgtt | cctgaagtcc | tcaggcctct | ttatgagtct | 1080 |
| tccaaaatcc | ttgctcaaaa | aatgactgtc | gctgctctga | acatgtgcg | ccaaattgct | 1140 |
| caagagacta | gtggagaagt | ccagtatagt | ggtggacgcc | agcctgcagt | tttaaggact | 1200 |
| ttcagccaga | gactctgccg | gggttttcaat | gatgctgtaa | atggttttgt | cgatgatgga | 1260 |
| tggtctccaa | tgagtagtga | tggaggagag | gatattacga | tcatgattaa | ctcttcctct | 1320 |
| gctaaatttg | ctggctccca | atacggtagc | tcatttcttc | caagttttgg | aagtggtgtc | 1380 |
| ctctgtgcca | agcttctat | gctgttgcag | aatgttccac | cccttgtatt | gattcggttc | 1440 |
| ctgagagaac | accgagctga | atgggcagac | tatggtgtcg | atgcctattc | tgctgcatct | 1500 |
| ctcagagcaa | ctccatatgc | tgttccatgc | gtcagaaccg | tgggttccc | gagtaaccaa | 1560 |
| gtcattcttc | ctctcgcaca | gacactcgaa | catgaagagt | ttctcgaagt | ggttagactt | 1620 |
| ggaggtcatg | cttactcacc | tgaagacatg | ggcttatccc | gggatatgta | tttactgcag | 1680 |
| cttttgtagcg | gcgttgatga | aaatgtggtt | ggaggttgtg | ctcagcttgt | ctttgccccca | 1740 |
| atcgatgaat | catttgctga | tgatgcacct | ttgcttcctt | ctggtttccg | tgtcatacca | 1800 |
| ctcgaccaaa | aaacaaatcc | gaatgatcat | caatctgcaa | gtcgaacacg | ggatctagca | 1860 |
| tcgtccctag | atggttccac | caaaaccgat | tcggaaacaa | actctagatt | ggtcttaaca | 1920 |
| atagccttcc | agttcacgtt | tgataaccat | tccagagaca | atgttgctac | aatggcgaga | 1980 |

-continued

```
cagtatgtga ggaacgttgt tggttcgatt cagagagtgg ctctagccat acgcctcgt     2040 cctggctcaa tgcaacttcc cacttcccct gaagctctca ctcttgtccg ttggatcacc     2100
cgtagttaca gtattcatac aggtgcagat ctgtttggag ctgattctca gtcctgtgga     2160
ggagacacat tgcttaagca actctgggac catagtgatg ccatattgtg ctgctccctg     2220
aaaactaatg cctcaccggt attcacattt gcaaaccaag ctggtttaga catgcttgaa     2280
actacacttg tggcacttca ggatataatg ctcgacaaaa cacttgatga ctctggtcgt     2340
agagctcttt gctccgagtt cgccaagatc atgcagcagg gatatgcgaa tcttccggca     2400
ggaatatgtg tgtcgagcat gggcagaccg gtttcgtatg agcaagcgac ggtgtggaaa     2460
gttgttgatg acaacgaatc aaaccactgc ttggctttta ccctcgttag ttggtcgttt     2520
gtttga                                                                 2526
```

<210> SEQ ID NO 102
<211> LENGTH: 841
<212> TYPE: PRT
<213> ORGANISM: Arabidopsis thaliana
<220> FEATURE:
<223> OTHER INFORMATION: G390

<400> SEQUENCE: 102

```
Met Met Ala His His Ser Met Asp Asp Arg Asp Ser Pro Asp Lys Gly
 1               5                  10                  15

Phe Asp Ser Gly Lys Tyr Val Arg Tyr Thr Pro Glu Gln Val Glu Ala
            20                  25                  30

Leu Glu Arg Val Tyr Ala Glu Cys Pro Lys Pro Ser Ser Leu Arg Arg
        35                  40                  45

Gln Gln Leu Ile Arg Glu Cys Pro Ile Leu Cys Asn Ile Glu Pro Arg
    50                  55                  60

Gln Ile Lys Val Trp Phe Gln Asn Arg Arg Cys Arg Glu Lys Gln Arg
65                  70                  75                  80

Lys Glu Ser Ala Arg Leu Gln Thr Val Asn Arg Lys Leu Ser Ala Met
                85                  90                  95

Asn Lys Leu Leu Met Glu Glu Asn Asp Arg Leu Gln Lys Gln Val Ser
            100                 105                 110

Asn Leu Val Tyr Glu Asn Gly Phe Met Lys His Arg Ile His Thr Ala
        115                 120                 125

Ser Gly Thr Thr Thr Asp Asn Ser Cys Glu Ser Val Val Ser Gly
    130                 135                 140

Gln Gln Arg Gln Gln Gln Asn Pro Thr His Gln His Pro Gln Arg Asp
145                 150                 155                 160

Val Asn Asn Pro Ala Asn Leu Leu Ser Ile Ala Glu Glu Thr Leu Ala
                165                 170                 175

Glu Phe Leu Cys Lys Ala Thr Gly Thr Ala Val Asp Trp Val Gln Met
            180                 185                 190

Ile Gly Met Lys Pro Gly Pro Asp Ser Ile Gly Ile Val Ala Val Ser
        195                 200                 205

Arg Asn Cys Ser Gly Ile Ala Ala Arg Ala Cys Gly Leu Val Ser Leu
    210                 215                 220

Glu Pro Met Lys Val Ala Glu Ile Leu Lys Asp Arg Pro Ser Trp Phe
225                 230                 235                 240

Arg Asp Cys Arg Cys Val Glu Thr Leu Asn Val Ile Pro Thr Gly Asn
                245                 250                 255

Gly Gly Thr Ile Glu Leu Val Asn Thr Gln Ile Tyr Ala Pro Thr Thr
```

-continued

```
                260                 265                 270
Leu Ala Ala Ala Arg Asp Phe Trp Thr Leu Arg Tyr Ser Thr Ser Leu
            275                 280                 285
Glu Asp Gly Ser Tyr Val Val Cys Glu Arg Ser Leu Thr Ser Ala Thr
        290                 295                 300
Gly Gly Pro Asn Gly Pro Leu Ser Ser Ser Phe Val Arg Ala Lys Met
305                 310                 315                 320
Leu Ser Ser Gly Phe Leu Ile Arg Pro Cys Asp Gly Gly Ser Ile
            325                 330                 335
Ile His Ile Val Asp His Val Asp Leu Asp Val Ser Ser Val Pro Glu
                340                 345                 350
Val Leu Arg Pro Leu Tyr Glu Ser Ser Lys Ile Leu Ala Gln Lys Met
            355                 360                 365
Thr Val Ala Ala Leu Arg His Val Arg Gln Ile Ala Gln Glu Thr Ser
        370                 375                 380
Gly Glu Val Gln Tyr Ser Gly Gly Arg Gln Pro Ala Val Leu Arg Thr
385                 390                 395                 400
Phe Ser Gln Arg Leu Cys Arg Gly Phe Asn Asp Ala Val Asn Gly Phe
            405                 410                 415
Val Asp Asp Gly Trp Ser Pro Met Ser Ser Asp Gly Gly Glu Asp Ile
                420                 425                 430
Thr Ile Met Ile Asn Ser Ser Ser Ala Lys Phe Ala Gly Ser Gln Tyr
            435                 440                 445
Gly Ser Ser Phe Leu Pro Ser Phe Gly Ser Gly Val Leu Cys Ala Lys
        450                 455                 460
Ala Ser Met Leu Leu Gln Asn Val Pro Pro Leu Val Leu Ile Arg Phe
465                 470                 475                 480
Leu Arg Glu His Arg Ala Glu Trp Ala Asp Tyr Gly Val Asp Ala Tyr
            485                 490                 495
Ser Ala Ala Ser Leu Arg Ala Thr Pro Tyr Ala Val Pro Cys Val Arg
                500                 505                 510
Thr Gly Gly Phe Pro Ser Asn Gln Val Ile Leu Pro Leu Ala Gln Thr
            515                 520                 525
Leu Glu His Glu Glu Phe Leu Glu Val Val Arg Leu Gly Gly His Ala
        530                 535                 540
Tyr Ser Pro Glu Asp Met Gly Leu Ser Arg Asp Met Tyr Leu Leu Gln
545                 550                 555                 560
Leu Cys Ser Gly Val Asp Glu Asn Val Gly Gly Cys Ala Gln Leu
            565                 570                 575
Val Phe Ala Pro Ile Asp Glu Ser Phe Ala Asp Ala Pro Leu Leu
            580                 585                 590
Pro Ser Gly Phe Arg Val Ile Pro Leu Asp Gln Lys Thr Asn Pro Asn
        595                 600                 605
Asp His Gln Ser Ala Ser Arg Thr Arg Asp Leu Ala Ser Ser Leu Asp
    610                 615                 620
Gly Ser Thr Lys Thr Asp Ser Glu Thr Asn Ser Arg Leu Val Leu Thr
625                 630                 635                 640
Ile Ala Phe Gln Phe Thr Phe Asp Asn His Ser Arg Asp Asn Val Ala
            645                 650                 655
Thr Met Ala Arg Gln Tyr Val Arg Asn Val Val Gly Ser Ile Gln Arg
                660                 665                 670
Val Ala Leu Ala Ile Thr Pro Arg Pro Gly Ser Met Gln Leu Pro Thr
            675                 680                 685
```

```
Ser Pro Glu Ala Leu Thr Leu Val Arg Trp Ile Thr Arg Ser Tyr Ser
        690                 695                 700
Ile His Thr Gly Ala Asp Leu Phe Gly Ala Asp Ser Gln Ser Cys Gly
705                 710                 715                 720
Gly Asp Thr Leu Leu Lys Gln Leu Trp Asp His Ser Asp Ala Ile Leu
                725                 730                 735
Cys Cys Ser Leu Lys Thr Asn Ala Ser Pro Val Phe Thr Phe Ala Asn
                740                 745                 750
Gln Ala Gly Leu Asp Met Leu Glu Thr Thr Leu Val Ala Leu Gln Asp
            755                 760                 765
Ile Met Leu Asp Lys Thr Leu Asp Asp Ser Gly Arg Arg Ala Leu Cys
770                 775                 780
Ser Glu Phe Ala Lys Ile Met Gln Gln Gly Tyr Ala Asn Leu Pro Ala
785                 790                 795                 800
Gly Ile Cys Val Ser Ser Met Gly Arg Pro Val Ser Tyr Glu Gln Ala
                805                 810                 815
Thr Val Trp Lys Val Val Asp Asp Asn Glu Ser Asn His Cys Leu Ala
                820                 825                 830
Phe Thr Leu Val Ser Trp Ser Phe Val
            835                 840
```

<210> SEQ ID NO 103
<211> LENGTH: 1771
<212> TYPE: DNA
<213> ORGANISM: Arabidopsis thaliana
<220> FEATURE:
<223> OTHER INFORMATION: G1034

<400> SEQUENCE: 103

| | | | | |
|---|---|---|---|---|
| ggtgccggtt | taattgggtt | atcggctttt | attccctcta | tcgattattt aatcatcatt | 60 |
| tttcttcgcg | catcttttgt | ttagcgcaac | tgcatgtttt | tggttatccc ttcaacataa | 120 |
| ttgcatatta | atttctttca | ttttaatacc | tgatacaaaa | aagtcgctct aatatataat | 180 |
| ttattctcaa | actttcaata | cactccacac | agcatggaaa | ctgtacgata tccaaagtac | 240 |
| gaaaattcgc | cggccgagac | catggtggaa | agcttcgtgt | cgacaccttc ttcatttcat | 300 |
| aaccctccac | ttttcgacaa | caacttaaac | cctgtagatg | ggttttcccc acaatcattt | 360 |
| gaccgtgact | acaatttcaa | cggtagttta | tcagggctga | accttcccga gaaaaaccc | 420 |
| atcaaaaagc | gcaagtcttg | gggacagcaa | cttcccgaac | ccaaaacaaa ccttcctccg | 480 |
| aggaagcgcg | caaagactca | agatgaaaaa | gagcaacggc | gtgttgagcg cgtcctacgc | 540 |
| aatcgtagag | cggcccaatc | atcacgagaa | cgaaaacgcc | aggaggtcga ggctttggaa | 600 |
| gtcgagaaac | gagctattga | gcgcaaaaac | atggatcttg | agatgcgctt agcagacatg | 660 |
| gaagcaaagt | actaccttct | tcaacaggaa | ctgaaacgag | ccagtggtta caacaagaca | 720 |
| aactttctt | cctactctga | ttcttcaact | ccagacatct | ccgaagattc acaattatca | 780 |
| cctttgactt | tctctaagca | actcttcaac | gctcaagatg | aattgtgtcg accaataagt | 840 |
| cctcagtcaa | tcggtccgct | gacttcaaga | accgttgacc | cttctacact ctcacctaag | 900 |
| tctttatctt | ctcccgattc | atccaattct | aattcttccg | acatgacaca acatcctgcc | 960 |
| gtggtgttgt | gcgacctgca | gtgtcagtcg | gaactgggtc | agccttggat gaattcgaca | 1020 |
| tatctttctt | tgagaacgaa | agctctgaaa | ttatcggtaa | cttaccttat tacaatgtta | 1080 |
| acaactttt | tgattgtcct | cggaaacctg | aatcagaata | tcatgttttt aatgacgaga | 1140 |

-continued

```
tttctcctca caccaacgta ttttattcag aggatgaaaa tattcgggga cagaacgacg    1200
gtgttttcga tgaatttgtc gtatgtgatc ttctcaacga tgaaactcta tcaaacgaga    1260
gtctgcattc ggatcagctt gctgggacga cgacaagcct gcagccgcaa tttggcgcgt    1320
tctctaatga atgcgacgat ggcggcattg cggtttgagt ccaaacagcg acttttcgc     1380 aattttctct ctactgtagc gcttcagatt tctcgaagat cctcccactt tttatggtac    1440
tgaaaatact cgaagacact aaactgaacg agagaaatga gaagcgatgg ttccaatttc    1500
aaatgtcgac cttaacttat tgtgttcgat tgaggattag taaaaatcta atggtatatt    1560
tagaataata ttcataaaga aaatttataa taaatctact caatacattg aaaaattagc    1620
ttttggattt ttactgctta ggatatagaa atggtcacag ttcatagctg gttatagaca    1680
acgatcatga aattttaaat gtatctatcc tccagtaagg tagtaatcaa cgattttgat    1740
cgtctaccac caaaaaaaaa aaaaaaaaa a                                    1771
```

<210> SEQ ID NO 104
<211> LENGTH: 409
<212> TYPE: PRT
<213> ORGANISM: Arabidopsis thaliana
<220> FEATURE:
<223> OTHER INFORMATION: G1034

<400> SEQUENCE: 104

```
Met Glu Thr Val Arg Tyr Pro Lys Tyr Glu Asn Ser Pro Ala Glu Thr
  1               5                  10                  15
Met Val Glu Ser Phe Val Ser Thr Pro Ser Ser Phe His Asn Pro Pro
                 20                  25                  30
Leu Phe Asp Asn Asn Leu Asn Pro Val Asp Gly Phe Ser Pro Gln Ser
             35                  40                  45
Phe Asp Arg Asp Tyr Asn Phe Asn Gly Ser Leu Ser Gly Leu Asn Leu
         50                  55                  60
Pro Glu Lys Lys Pro Ile Lys Lys Arg Lys Ser Trp Gly Gln Gln Leu
 65                  70                  75                  80
Pro Glu Pro Lys Thr Asn Leu Pro Pro Arg Lys Arg Ala Lys Thr Gln
                 85                  90                  95
Asp Glu Lys Glu Gln Arg Arg Val Glu Arg Val Leu Arg Asn Arg Arg
                100                 105                 110
Ala Ala Gln Ser Ser Arg Glu Arg Lys Arg Gln Glu Val Glu Ala Leu
            115                 120                 125
Glu Val Glu Lys Arg Ala Ile Glu Arg Lys Asn Met Asp Leu Glu Met
        130                 135                 140
Arg Leu Ala Asp Met Glu Ala Lys Tyr Tyr Leu Leu Gln Gln Glu Leu
145                 150                 155                 160
Lys Arg Ala Ser Gly Tyr Asn Lys Thr Asn Phe Leu Ser Tyr Ser Asp
                165                 170                 175
Ser Ser Thr Pro Asp Ile Ser Glu Asp Ser Gln Leu Ser Pro Leu Thr
            180                 185                 190
Phe Ser Lys Gln Leu Phe Asn Ala Gln Asp Glu Leu Cys Arg Pro Ile
        195                 200                 205
Ser Pro Gln Ser Ile Gly Pro Leu Thr Ser Arg Thr Val Asp Pro Ser
    210                 215                 220
Thr Leu Ser Pro Lys Ser Leu Ser Ser Pro Asp Ser Ser Asn Ser Asn
225                 230                 235                 240
Ser Ser Asp Met Thr Gln His Pro Ala Val Val Leu Cys Asp Leu Gln
                245                 250                 255
```

```
Cys Gln Ser Glu Leu Gly Gln Pro Trp Met Asn Ser Thr Tyr Leu Ser
            260                 265                 270
Leu Arg Thr Lys Ala Leu Lys Leu Ser Val Thr Tyr Leu Ile Thr Met
        275                 280                 285
Leu Thr Thr Phe Leu Ile Val Leu Gly Asn Leu Asn Gln Asn Ile Met
    290                 295                 300
Phe Leu Met Thr Arg Phe Leu Leu Thr Pro Thr Tyr Phe Ile Gln Arg
305                 310                 315                 320
Met Lys Ile Phe Gly Asp Arg Thr Thr Val Phe Ser Met Asn Leu Ser
                325                 330                 335
Tyr Val Ile Phe Ser Thr Met Lys Leu Tyr Gln Thr Arg Val Cys Ile
            340                 345                 350
Arg Ile Ser Leu Leu Gly Arg Gln Ala Cys Ser Arg Asn Leu Ala
        355                 360                 365
Arg Ser Leu Met Asn Ala Thr Met Ala Ala Leu Arg Phe Glu Ser Lys
    370                 375                 380
Gln Arg Leu Phe Arg Asn Phe Leu Ser Thr Val Ala Leu Gln Ile Ser
385                 390                 395                 400
Arg Arg Ser Ser His Phe Leu Trp Tyr
                405

<210> SEQ ID NO 105
<211> LENGTH: 2910
<212> TYPE: DNA
<213> ORGANISM: Arabidopsis thaliana
<220> FEATURE:
<223> OTHER INFORMATION: G1149

<400> SEQUENCE: 105
atgtcaaatc gtggtggtgg tggtcacggc ggcgctagtc gtggtcgagg aggtggacga      60
aggtctgacc agagacaaga tcagtcttct ggtcaagttg cttggccggg tttacaacaa     120
agctacggtg gtcgtggtgg ttctgttttcc gccggtagag gtcgtggaaa cgtcggaaga    180
ggtgaaaata ctggagatct gacggcgacg caagttccgg ttgcttctgc tgtttctggc    240
gggagaggtc gtggtaacat cggagatccg acgttttctg ttgcgtcttc gtctaagacg    300
gtgtctgttg cttcttcatc taaagaggaa agtaagaata cggaggtttc tgagaccatg    360
tcgaaccttc agattacttc gacggagacg aaacctgaaa tgacgtcact tcctccggcg    420
tcatctaaag cggttacgtt tccggtacgg ccaggacgtg gtactttggg gaagaaagtc    480
atggttcgtg cgaatcattt ccttgttcaa gttgctgatc gtgatctcta ccattacgat    540
gtttcgatca atcctgaggt tatatcaaag acagtgaaca gaaacgtgat gaaacttctg    600
gttaagaatt ataaagactc tcacttggga gggaagtcac cagcgtatga tggaaggaaa    660
agcctctata ctgctggtcc attaccttt gactcgaaag agtttgttgt gaatctggcg    720
gagaaaagag ctgacggttc ctctgggaag gacagaccgt ttaaagttgc tgtaaagaat    780
gtgacaagca ctgatcttta tcagttgcaa cagttccttg atcgtaagca agagaggct    840
ccatatgata ctatccaagt gcttgatgtt gttcttaggg ataagccctc taatgattat    900
gtctctgttg ggaggtcttt tttccacact agtttgggaa aggacgcaag agatggtagg    960
ggtgagcttg gagatggtat tgagtactgg agaggttatt tccaaagtct aaggctgact   1020
cagatggggt tgtctctgaa cattgacgtt tcagcaagat catttatga accgattgtt   1080
gtcactgact ttattagcaa gttctgaat ataagggact taaacaggcc acttagagac   1140
```

-continued

```
tcagatcgac ttaaggtgaa gaaagttttg aggacactga agttaagtt gcttcactgg    1200 aacggcacaa aaagtgccaa aattagtggg atttctagtc tacccatcag ggagctaagg    1260
ttcactctgg aggacaaatc agagaagacg gttgttcaat attttgctga aaaatataat    1320
tatagagtga ataccaggc tctacctgct attcaaacag ggagtgacac aagacccgtc    1380
tacctaccaa tggagctctg ccaaattgac gaagggcaaa gatacaccaa aaggctcaat    1440
gagaagcaag tgactgcatt gctaaaagct acctgccaac gaccccctga tagagagaac    1500
tcgatcaaaa acttggttgt gaaaaataat tacaatgatg atctgagcaa ggagtttggg    1560
atgtcagtga ctacccaact agcctcgatt gaagctcgtg tacttccccc accgatgttg    1620
aagtaccatg acagtggtaa agagaaaatg gtaaatccaa ggctaggaca gtggaacatg    1680
attgacaaga aaatggttaa tggagcaaaa gtcacttctt ggacttgcga atttaagcct    1740
caacctgcta ttccgttcat ctcttgtccc cctgaacata ttgaggaagc tcttctcgat    1800
atccacaaaa gggcacctgg tctccaactg ttgattgtaa tattgcctga tgtgactgga    1860
tcatatggaa aaataaaaag gatctgtgaa acagaattgg ggattgtctc tcagtgttgc    1920
caacctagac aagttaataa actcaacaag cagtacatgg aaaatgttgc cttgaagatc    1980
aatgtcaaga ctgggggaag gaacactgtt cttaatgatg ctattagaag aaacatacct    2040
cttattactg atcgtccaac catcatcatg ggtgctgatg tgactcaccc acagcctgga    2100
gaggactcaa gtccttctat tgctgctgtt gtggcctcta tggactggcc tgagataaac    2160
aaataccgag gattggtttc tgctcaagct catagggaag aaattattca ggacctgtat    2220
aagctggttc aggatccaca acgtgggcta gtccactctg gtttgataag gaacatttc    2280 atagcattca ggagagctac aggccagata cctcaaagga tcatcttcta tcgtgacgga    2340
gtaagcgaag ggcagtttag tcaggttctg ctacatgaga tgactgctat ccgcaaggct    2400
tgtaactctc tccaagagaa ttatgttcct cgtgttactt tcgtgattgt ccagaaacgt    2460
caccacacac gtttgttccc tgagcaacac gggaatcgtg atatgactga taagagtggc    2520
aatattcaac caggtactgt cgtggacact aaaatctgtc accctaatga attcgacttc    2580
tatttgaaca gccatgctgg tattcaggga acaagcaggc cggcacatta ccatgtactt    2640
ctcgatgaga acgtttcac cgctgatcag ttgcaaatgc tcacaaacaa cctctgctac    2700
acgtatgcga ggtgtacaaa atctgtgtca attgtgccac cagcctacta cgctcacttg    2760
gctgcattcc gtgcccgcta ctacatggag agtgagatgt ctgatggagg ttcgagcagg    2820
tccaggagct caacaacagg tgtgggtcaa gtcatttcgc agctcccagc aataaaagat    2880
aacgtcaagg aggttatgtt ttattgctaa                                     2910
```

<210> SEQ ID NO 106
<211> LENGTH: 969
<212> TYPE: PRT
<213> ORGANISM: Arabidopsis thaliana
<220> FEATURE:
<223> OTHER INFORMATION: G1149

<400> SEQUENCE: 106

```
Met Ser Asn Arg Gly Gly Gly His Gly Gly Ala Ser Arg Gly Arg
 1               5                  10                  15

Gly Gly Gly Arg Arg Ser Asp Gln Arg Gln Asp Gln Ser Ser Gly Gln
            20                  25                  30

Val Ala Trp Pro Gly Leu Gln Gln Ser Tyr Gly Gly Arg Gly Gly Ser
        35                  40                  45
```

```
Val Ser Ala Gly Arg Gly Arg Gly Asn Val Gly Arg Gly Glu Asn Thr
 50                  55                  60

Gly Asp Leu Thr Ala Thr Gln Val Pro Val Ala Ser Ala Val Ser Gly
 65                  70                  75                  80

Gly Arg Gly Arg Gly Asn Ile Gly Asp Pro Thr Phe Ser Val Ala Ser
                 85                  90                  95

Ser Ser Lys Thr Val Ser Val Ala Ser Ser Lys Glu Glu Ser Lys
                100                 105                 110

Asn Thr Glu Val Ser Glu Thr Met Ser Asn Leu Gln Ile Thr Ser Thr
            115                 120                 125

Glu Thr Lys Pro Glu Met Thr Ser Leu Pro Ala Ser Ser Lys Ala
        130                 135                 140

Val Thr Phe Pro Val Arg Pro Gly Arg Gly Thr Leu Gly Lys Lys Val
145                 150                 155                 160

Met Val Arg Ala Asn His Phe Leu Val Gln Val Ala Asp Arg Asp Leu
                165                 170                 175

Tyr His Tyr Asp Val Ser Ile Asn Pro Glu Val Ile Ser Lys Thr Val
                180                 185                 190

Asn Arg Asn Val Met Lys Leu Leu Val Lys Asn Tyr Lys Asp Ser His
            195                 200                 205

Leu Gly Gly Lys Ser Pro Ala Tyr Asp Gly Arg Lys Ser Leu Tyr Thr
    210                 215                 220

Ala Gly Pro Leu Pro Phe Asp Ser Lys Glu Phe Val Asn Leu Ala
225                 230                 235                 240

Glu Lys Arg Ala Asp Gly Ser Ser Gly Lys Asp Arg Pro Phe Lys Val
                245                 250                 255

Ala Val Lys Asn Val Thr Ser Thr Asp Leu Tyr Gln Leu Gln Gln Phe
                260                 265                 270

Leu Asp Arg Lys Gln Arg Glu Ala Pro Tyr Asp Thr Ile Gln Val Leu
        275                 280                 285

Asp Val Val Leu Arg Asp Lys Pro Ser Asn Asp Tyr Val Ser Val Gly
290                 295                 300

Arg Ser Phe Phe His Thr Ser Leu Gly Lys Asp Ala Arg Asp Gly Arg
305                 310                 315                 320

Gly Glu Leu Gly Asp Gly Ile Glu Tyr Trp Arg Gly Tyr Phe Gln Ser
                325                 330                 335

Leu Arg Leu Thr Gln Met Gly Leu Ser Leu Asn Ile Asp Val Ser Ala
            340                 345                 350

Arg Ser Phe Tyr Glu Pro Ile Val Val Thr Asp Phe Ile Ser Lys Phe
        355                 360                 365

Leu Asn Ile Arg Asp Leu Asn Arg Pro Leu Arg Asp Ser Asp Arg Leu
    370                 375                 380

Lys Val Lys Lys Val Leu Arg Thr Leu Lys Val Lys Leu Leu His Trp
385                 390                 395                 400

Asn Gly Thr Lys Ser Ala Lys Ile Ser Gly Ile Ser Ser Leu Pro Ile
                405                 410                 415

Arg Glu Leu Arg Phe Thr Leu Glu Asp Lys Ser Glu Lys Thr Val Val
                420                 425                 430

Gln Tyr Phe Ala Glu Lys Tyr Asn Tyr Arg Val Lys Tyr Gln Ala Leu
            435                 440                 445

Pro Ala Ile Gln Thr Gly Ser Asp Thr Arg Pro Val Tyr Leu Pro Met
    450                 455                 460

Glu Leu Cys Gln Ile Asp Glu Gly Gln Arg Tyr Thr Lys Arg Leu Asn
```

-continued

```
465                 470                 475                 480
Glu Lys Gln Val Thr Ala Leu Leu Lys Ala Thr Cys Gln Arg Pro Pro
                    485                 490                 495
Asp Arg Glu Asn Ser Ile Lys Asn Leu Val Lys Asn Asn Tyr Asn
            500                 505                 510
Asp Asp Leu Ser Lys Glu Phe Gly Met Ser Val Thr Thr Gln Leu Ala
            515                 520                 525
Ser Ile Glu Ala Arg Val Leu Pro Pro Met Leu Lys Tyr His Asp
        530                 535                 540
Ser Gly Lys Glu Lys Met Val Asn Pro Arg Leu Gly Gln Trp Asn Met
545                 550                 555                 560
Ile Asp Lys Lys Met Val Asn Gly Ala Lys Val Thr Ser Trp Thr Cys
                565                 570                 575
Glu Phe Lys Pro Gln Pro Ala Ile Pro Phe Ile Ser Cys Pro Pro Glu
                580                 585                 590
His Ile Glu Glu Ala Leu Leu Asp Ile His Lys Arg Ala Pro Gly Leu
                595                 600                 605
Gln Leu Leu Ile Val Ile Leu Pro Asp Val Thr Gly Ser Tyr Gly Lys
        610                 615                 620
Ile Lys Arg Ile Cys Glu Thr Glu Leu Gly Ile Val Ser Gln Cys Cys
625                 630                 635                 640
Gln Pro Arg Gln Val Asn Lys Leu Asn Lys Gln Tyr Met Glu Asn Val
                645                 650                 655
Ala Leu Lys Ile Asn Val Lys Thr Gly Gly Arg Asn Thr Val Leu Asn
                660                 665                 670
Asp Ala Ile Arg Arg Asn Ile Pro Leu Ile Thr Asp Arg Pro Thr Ile
                675                 680                 685
Ile Met Gly Ala Asp Val Thr His Pro Gln Pro Gly Glu Asp Ser Ser
        690                 695                 700
Pro Ser Ile Ala Ala Val Val Ala Ser Met Asp Trp Pro Glu Ile Asn
705                 710                 715                 720
Lys Tyr Arg Gly Leu Val Ser Ala Gln Ala His Arg Glu Glu Ile Ile
                725                 730                 735
Gln Asp Leu Tyr Lys Leu Val Gln Asp Pro Gln Arg Gly Leu Val His
                740                 745                 750
Ser Gly Leu Ile Arg Glu His Phe Ile Ala Phe Arg Arg Ala Thr Gly
                755                 760                 765
Gln Ile Pro Gln Arg Ile Ile Phe Tyr Arg Asp Gly Val Ser Glu Gly
        770                 775                 780
Gln Phe Ser Gln Val Leu Leu His Glu Met Thr Ala Ile Arg Lys Ala
785                 790                 795                 800
Cys Asn Ser Leu Gln Glu Asn Tyr Val Pro Arg Val Thr Phe Val Ile
                805                 810                 815
Val Gln Lys Arg His His Thr Arg Leu Phe Pro Glu Gln His Gly Asn
                820                 825                 830
Arg Asp Met Thr Asp Lys Ser Gly Asn Ile Gln Pro Gly Thr Val Val
                835                 840                 845
Asp Thr Lys Ile Cys His Pro Asn Glu Phe Asp Phe Tyr Leu Asn Ser
        850                 855                 860
His Ala Gly Ile Gln Gly Thr Ser Arg Pro Ala His Tyr His Val Leu
865                 870                 875                 880
Leu Asp Glu Asn Gly Phe Thr Ala Asp Gln Leu Gln Met Leu Thr Asn
                        885                 890                 895
```

```
Asn Leu Cys Tyr Thr Tyr Ala Arg Cys Thr Lys Ser Val Ser Ile Val
            900                 905                 910
Pro Pro Ala Tyr Tyr Ala His Leu Ala Ala Phe Arg Ala Arg Tyr Tyr
        915                 920                 925
Met Glu Ser Glu Met Ser Asp Gly Gly Ser Ser Arg Ser Arg Ser Ser
    930                 935                 940
Thr Thr Gly Val Gly Gln Val Ile Ser Gln Leu Pro Ala Ile Lys Asp
945                 950                 955                 960
Asn Val Lys Glu Val Met Phe Tyr Cys
                965

<210> SEQ ID NO 107
<211> LENGTH: 1274
<212> TYPE: DNA
<213> ORGANISM: Arabidopsis thaliana
<220> FEATURE:
<223> OTHER INFORMATION: G1334

<400> SEQUENCE: 107
atagctccca actaatagga atctcaagct tctcactctc tcttgttttt ccattggact      60
tttggaacat aagctatgca aactgaggag cttttgtcgc caccacagac tccttggtgg     120
aatgctttg gatctcagcc gttgactaca gagagccttt ccggcgaagc ttctgattca     180
ttcaccggag ttaaggcagt tactacggag gcagaacaag gtgtggtgga taaacaaact     240
tctacaactc tcttcacttt ctcacctggt ggtgaaaaga gttcaagaga gtgtgccaaag    300
cctcatgttg ctttcgcgat gcaatcagct tgcttcgagt ttggatttgc tcagccaatg     360
atgtacacaa agcatcctca tgttgaacaa tactatggag ttgtttcagc atacggatct     420
cagaggtctt cgggccgagt aatgattcca ctgaagatgg agacagaaga agatggtacc     480
atctatgtga actcaaagca gtaccatgga attatcaggc gacgccagtc ccgagcaaag     540
gctgaaaaac tgagtagatg ccgtaagcca tatatgcatc actcacgcca tctccatgct     600
atgcgccgtc ctagaggatc tggcgggcgt ttccttgaaca ccaagacagc tgatgcggct    660
aagcagtcta agccgagtaa ttctcagagt tctgaagtct tcatccgga aaatgagacc     720
ataaactcat cgagggaagc aaatgagtca aatctctcgg attctgcagt tacaagtatg     780
gattacttc taagttcgtc ggcttattct cctggtggca tggtcatgcc tatcaagtgg     840
aatgcagcag caatggatat tggctgctgc aaacttaata tatgatcagc agatagggga     900
caagacatga ttggtcacca gtccttttgt cttgtccctt atctttcagc caaacggaaa     960
gagaacttgt gtcttggaaa aaagacattg agtttccttg gtttataaga ttggtccttt    1020
taccatccgt ttggctgtaa acaggcaaat catctttggc tcatgcttca tcaagttctt    1080
atcttcgtct gttttcttct acgcatcttc ataagatctc tgaactagtg aataacattt    1140
cctagcatca tgtttcaact agtgtgtgtt gtaagaaact ctgccttatt tccagatgat    1200
gtattgtgtg taacgtgttt atgaaacaaa cgtaagactt tcaagttaaa aaaaaaaaa     1260
aaaaaaaaa aaaa                                                      1274

<210> SEQ ID NO 108
<211> LENGTH: 269
<212> TYPE: PRT
<213> ORGANISM: Arabidopsis thaliana
<220> FEATURE:
<223> OTHER INFORMATION: G1334

<400> SEQUENCE: 108
```

```
Met Gln Thr Glu Glu Leu Leu Ser Pro Pro Gln Thr Pro Trp Trp Asn
  1               5                  10                  15

Ala Phe Gly Ser Gln Pro Leu Thr Thr Glu Ser Leu Ser Gly Glu Ala
             20                  25                  30

Ser Asp Ser Phe Thr Gly Val Lys Ala Val Thr Thr Glu Ala Glu Gln
         35                  40                  45

Gly Val Val Asp Lys Gln Thr Ser Thr Thr Leu Phe Thr Phe Ser Pro
 50                  55                  60

Gly Gly Glu Lys Ser Ser Arg Asp Val Pro Lys Pro His Val Ala Phe
 65                  70                  75                  80

Ala Met Gln Ser Ala Cys Phe Glu Phe Gly Phe Ala Gln Pro Met Met
                 85                  90                  95

Tyr Thr Lys His Pro His Val Glu Gln Tyr Tyr Gly Val Val Ser Ala
                100                 105                 110

Tyr Gly Ser Gln Arg Ser Ser Gly Arg Val Met Ile Pro Leu Lys Met
             115                 120                 125

Glu Thr Glu Glu Asp Gly Thr Ile Tyr Val Asn Ser Lys Gln Tyr His
        130                 135                 140

Gly Ile Ile Arg Arg Arg Gln Ser Arg Ala Lys Ala Glu Lys Leu Ser
145                 150                 155                 160

Arg Cys Arg Lys Pro Tyr Met His Ser Arg His Leu His Ala Met
                165                 170                 175

Arg Arg Pro Arg Gly Ser Gly Arg Phe Leu Asn Thr Lys Thr Ala
            180                 185                 190

Asp Ala Ala Lys Gln Ser Lys Pro Ser Asn Ser Gln Ser Ser Glu Val
            195                 200                 205

Phe His Pro Glu Asn Glu Thr Ile Asn Ser Ser Arg Glu Ala Asn Glu
        210                 215                 220

Ser Asn Leu Ser Asp Ser Ala Val Thr Ser Met Asp Tyr Phe Leu Ser
225                 230                 235                 240

Ser Ser Ala Tyr Ser Pro Gly Gly Met Val Met Pro Ile Lys Trp Asn
                245                 250                 255

Ala Ala Ala Met Asp Ile Gly Cys Cys Lys Leu Asn Ile
            260                 265
```

<210> SEQ ID NO 109
<211> LENGTH: 1423
<212> TYPE: DNA
<213> ORGANISM: Arabidopsis thaliana
<220> FEATURE:
<223> OTHER INFORMATION: G1650

<400> SEQUENCE: 109

```
tcgacagtca caaatgtcca tatgagtttc tgggcgactt ctatcagaat ttttgttcat      60
aatttttttt attgtatcaa gggatgactt ggaaaccgaa gatgcttata ttatcccatg     120
atctaatctc accagaaaaa tacatcatgg gtgaagatga tatcgtggag ctcttaggga     180
agagcagcca agtagttaca agtagccaga cacaaacacc ctcttgcgat cctcctctca     240
ttctccgggg cagcggaagc ggggacggag aaggaaatgg tcctctaccg cagcctccgc     300
ctcccctgta ccatcagcag agtctcttta tccaagaaga cgaaatggct tcttggcttc     360
accagcctaa tcgccaagat tatctctact cccaacttct ttactccgga gtagcctcga     420
ctcacccgca aagtttggcc tcctagaac caccaccacc acctagggct cagtacattc     480
tggcggcgga tagaccgacc ggtcatattt tggccgagag aagggcggag aatttatga      540
```

```
atatctcgag gcaaagaggg aacatatttc ttggcggtgt tgaagctgta ccgtcgaact    600
cgaccctgtt gtcttcagcc actgaatcaa taccagcgac tcacggcacc gagagtcgag    660
caacagtcac tggcggagta tctcgtactt ttgcagttcc tggtcttggt ccgaggggaa    720
aggcggtggc gattgagacg gcgggaacac aatcttgggg gttgtgcaag gccgaaacag    780
agccggttca gagacaacca gcgacggaga cggatatcac cgatgaacgg aagagaaaaa    840
cgagagagga aacaaatgtc gaaaaccagg gaactgaaga agctcgtgat tcgacgtcta    900
gtaagaggtc acgagctgca ataatgcata aactctccga aggagacgg agacaaaaga    960
ttaacgagat gatgaaggct ttgcaagaac tccttcctcg ctgcacaaag actgatagat   1020
cttccatgct ggatgatgtt atagagtacg tgaaatctct acagagccaa atacaggatg   1080
ttctcaatgg gacatgttat gattccaccg atgatgtatg cggggaatat acaacaacag   1140
tacatgcccc acatggccat gggtatgaat cggcctcctg cattcatacc tttccctagg   1200
caggctcata tggcggaagg tgtaggtcct gttgatttat ttagagagaa tgaagaaaca   1260
gagcaagaga caatgtctct tctccttaga gaagacaaaa gaacaaaaca gaaaatgttt   1320
tcttgaactg aaacttgtta gttctttat taagacaaga cacactctta tatacatgtt   1380
cacataacta ctctacgttg gtaacagttg taacttctcc agc                     1423
```

<210> SEQ ID NO 110
<211> LENGTH: 371
<212> TYPE: PRT
<213> ORGANISM: Arabidopsis thaliana
<220> FEATURE:
<223> OTHER INFORMATION: G1650

<400> SEQUENCE: 110

```
Met Thr Trp Lys Pro Lys Met Leu Ile Leu Ser His Asp Leu Ile Ser
 1               5                  10                  15
Pro Glu Lys Tyr Ile Met Gly Glu Asp Asp Ile Val Glu Leu Leu Gly
                20                  25                  30
Lys Ser Ser Gln Val Val Thr Ser Ser Gln Thr Gln Thr Pro Ser Cys
            35                  40                  45
Asp Pro Pro Leu Ile Leu Arg Gly Ser Gly Ser Gly Asp Gly Glu Gly
        50                  55                  60
Asn Gly Pro Leu Pro Gln Pro Pro Pro Leu Tyr His Gln Gln Ser
 65                  70                  75                  80
Leu Phe Ile Gln Glu Asp Met Ala Ser Trp Leu His Gln Pro Asn
                85                  90                  95
Arg Gln Asp Tyr Leu Tyr Ser Gln Leu Leu Tyr Ser Gly Val Ala Ser
            100                 105                 110
Thr His Pro Gln Ser Leu Ala Ser Leu Glu Pro Pro Pro Pro Arg
        115                 120                 125
Ala Gln Tyr Ile Leu Ala Ala Asp Arg Pro Thr Gly His Ile Leu Ala
    130                 135                 140
Glu Arg Arg Ala Glu Asn Phe Met Asn Ile Ser Arg Gln Arg Gly Asn
145                 150                 155                 160
Ile Phe Leu Gly Gly Val Glu Ala Val Pro Ser Asn Ser Thr Leu Leu
                165                 170                 175
Ser Ser Ala Thr Glu Ser Ile Pro Ala Thr His Gly Thr Glu Ser Arg
            180                 185                 190
Ala Thr Val Thr Gly Gly Val Ser Arg Thr Phe Ala Val Pro Gly Leu
        195                 200                 205
```

```
Gly Pro Arg Gly Lys Ala Val Ala Ile Glu Thr Ala Gly Thr Gln Ser
    210                 215                 220
Trp Gly Leu Cys Lys Ala Glu Thr Pro Val Gln Arg Gln Pro Ala
225                 230                 235                 240
Thr Glu Thr Asp Ile Thr Asp Glu Arg Lys Arg Lys Thr Arg Glu Glu
                245                 250                 255
Thr Asn Val Glu Asn Gln Gly Thr Glu Glu Ala Arg Asp Ser Thr Ser
            260                 265                 270
Ser Lys Arg Ser Arg Ala Ala Ile Met His Lys Leu Ser Glu Arg Arg
        275                 280                 285
Arg Arg Gln Lys Ile Asn Glu Met Met Lys Ala Leu Gln Glu Leu Leu
    290                 295                 300
Pro Arg Cys Thr Lys Thr Asp Arg Ser Ser Met Leu Asp Asp Val Ile
305                 310                 315                 320
Glu Tyr Val Lys Ser Leu Gln Ser Gln Ile Gln Asp Val Leu Asn Gly
                325                 330                 335
Thr Cys Tyr Asp Ser Thr Asp Asp Val Cys Gly Glu Tyr Thr Thr Thr
            340                 345                 350
Val His Ala Pro His Gly His Gly Tyr Glu Ser Ala Ser Cys Ile His
        355                 360                 365
Thr Phe Pro
    370

<210> SEQ ID NO 111
<211> LENGTH: 646
<212> TYPE: DNA
<213> ORGANISM: Arabidopsis thaliana
<220> FEATURE:
<223> OTHER INFORMATION: G241

<400> SEQUENCE: 111
atgggaagag ctccatgctg tgagaagatg gggttgaaga gaggaccatg gacacctgaa      60
gaagatcaaa tcttggtctc ttttatcctc aaccatggac atagtaactg gcagccctc     120
cctaagcaag ctggtatgta aaattataa tatcaaattt cttaattttg atcaaatttc     180
ttacattaat tattggtaat tattatttac aggtcttttg agatgtggaa aaagctgtag     240
acttaggtgg atgaactatt taaagcctga tattaaacgt ggcaatttca ccaaagaaga     300
ggaagatgct atcatcagct acaccaaat acttggcaat aggtatttta cttcaacata     360
taagtatata accgacacac aagttttatt ttgttttctt actatatata aatcaccaaa     420
agaaagtaac tttattacac acgtctaggt cgcactacta ttcttttaac tacacaatga     480
tcggctcttt aattactttt gtattgatgt tcttcgtttt ccttttggta tcatctttag     540
atggtcagcg attgcagcaa aactgcctgg aagaaccgat aacgagatca agaacgtatg     600
gcacactcac ttgaagaaga gactcgaaga tttatcaacc agctaa                   646

<210> SEQ ID NO 112
<211> LENGTH: 122
<212> TYPE: PRT
<213> ORGANISM: Arabidopsis thaliana
<220> FEATURE:
<223> OTHER INFORMATION: G241

<400> SEQUENCE: 112

Met Gly Arg Ala Pro Cys Cys Glu Lys Met Gly Leu Lys Arg Gly Pro
1               5                   10                  15
```

```
Trp Thr Pro Glu Glu Asp Gln Ile Leu Val Ser Phe Ile Leu Asn His
             20                  25                  30

Gly His Ser Asn Trp Arg Ala Leu Pro Lys Gln Ala Gly Leu Leu Arg
         35                  40                  45

Cys Gly Lys Ser Cys Arg Leu Arg Trp Met Asn Tyr Leu Lys Pro Asp
     50                  55                  60

Ile Lys Arg Gly Asn Phe Thr Lys Glu Glu Asp Ala Ile Ile Ser
 65                  70                  75                  80

Leu His Gln Ile Leu Gly Asn Arg Trp Ser Ala Ile Ala Ala Lys Leu
                 85                  90                  95

Pro Gly Arg Thr Asp Asn Glu Ile Lys Asn Val Trp His Thr His Leu
                100                 105                 110

Lys Lys Arg Leu Glu Asp Leu Ser Thr Ser
            115                 120

<210> SEQ ID NO 113
<211> LENGTH: 375
<212> TYPE: DNA
<213> ORGANISM: Arabidopsis thaliana
<220> FEATURE:
<223> OTHER INFORMATION: G348

<400> SEQUENCE: 113
atggatccaa ggaagctact atcttgttca tcctcttacg tgtcagtgag aatgaaagaa        60
gagaagggga caattaggtg ttgcagtgag tgtaagacca ccaagacacc aatgtggaga       120
ggtggaccaa ctggtcctaa ggtctcttct tctacccttta attactatat tcataacttt     180
gtttgatctt aagataattc atcaagtgtt cttaagttgt ttattttgat ttgtggtggg       240
atttgcagtc actttgcaat gcatgtggaa ttagacacag aaaacagaga cgatcagagt       300
tattgggtat tcatattatt cgcagccaca aaagcttagc ctccaagaag ataaacctat       360
tatcatcatc acacg                                                        375

<210> SEQ ID NO 114
<211> LENGTH: 861
<212> TYPE: DNA
<213> ORGANISM: Arabidopsis thaliana
<220> FEATURE:
<223> OTHER INFORMATION: G171

<400> SEQUENCE: 114
tcaaacggaa gaaacaaatg acatttctca catagaaagt ttacttgaat cctccaaatc        60
attaacttgt gcaaacctga agggataatc ttggaactgc ttcacattgt tgaacatact      120
gtttcctaaa ccccaatgta ttggctccat ataagctgtc ctctgtacca tcggaccata      180
tggaccatcc gaacaactcc cgtaaaacaa gctttgcccg ttcgctatca tcggctctgt      240
cacattcgag aaggaagaca cttccgcagt atttgaggtc atctggttat taaagggaa       300 gaaagagagc ccgttgtaat ccatagtagg cagaggaaac aactgatact gctcaaaaca      360
ttgccgattg taaccgcata aaccaagttg gtcattagac caacaactag tgtcaggaaa      420
tgtctgattc ctattcgtag cctcttggat cttgttttct actgccatga aaaccgcata     480
gaggtcattt aaagaacact ggtcgagctt tttgtcccat gtaggatact ttgtcgcaat     540
cgtcggtttc tccaccttag tgttgttttt ctccaagcat tcttgcacgg tgtatgtctt     600
ggtgcagctg cttgacgcag tgtctctgta cttggttaag atttcacgga ctttgctccc     660
atcctttggc cataactcgg gctccatgac catttcgtcc cctgctctgc tcgggccgta     720
```

-continued

| | |
|---|---|
| cacaatgaca caagtgtcca caccgcagag tgttgagaac tcactggctt tcttatacaa | 780 |
| acatgctttc ctcttcttgt aagtcgttat cctcgttttc tcgttcgtta tcctcgtcat | 840 |
| ctttaccatc tttcgaccca t | 861 |

<210> SEQ ID NO 115
<211> LENGTH: 1332
<212> TYPE: DNA
<213> ORGANISM: Arabidopsis thaliana
<220> FEATURE:
<223> OTHER INFORMATION: G521

<400> SEQUENCE: 115

| | |
|---|---|
| atcgtcctta gtctgaccgt tgcttcttga gtcatcagga atactagctt gagctggagg | 60 |
| agaaggagga tgaggagtgg gtgactgtat cagatcctgt agctctacga cttggtcatt | 120 |
| gctcaggtca acattccac tgaaattgcc atctcctaag aacaccggag cttccttgtt | 180 |
| tacaaaacca tcaggatgtc ttacctgtag tttcagaagc aatcaaaaca gtttcttttt | 240 |
| caggaacact gaaatctgat tcatcaaaag catgatgatg cagagacaga cttacctcat | 300 |
| tatggtagtc gaaatcgtcg aaaagtaaac agtcgtcatt gtcaacagaa aagagatcaa | 360 |
| gcatcgaatt taactcgcca ccatcgagag atacttgagg aacctcaaga agaggtgaag | 420 |
| aagaaaaggg attgtaagct ataacatcac ttgttagagg tggaagcact gtggcagtta | 480 |
| gtggcggcac atcagagacg caagattctg agatcactcc tgtcaaacca tccttaggag | 540 |
| cgtacgagtg tgaggcctta gcagctagac tggtttcttt actaggacca gctacaagat | 600 |
| gattctgagt atattcttct tccttatcac tccaatcctc ttccttaaat ggagcaccat | 660 |
| attgagatcc atgtcttggt ccaagtccat ttttcttaaa gagaacgcaa agcacataag | 720 |
| tatcctgcag ggcacaacaa gcatgtttag taaacttgca aggaatcaaa acgttaaaaa | 780 |
| aagacaagaa cgaatcgtca ttacctgagg aacattcttt tgagccagta ctttgtcttc | 840 |
| aagtctatat tcatgtatga cccaatcagt ccgatcaccg cgaggtattt tcccgtagtg | 900 |
| ataaatcaga gttcttatct tcccagtgac ttcgtcatta taagaaacat ctctgtctct | 960 |
| ccctgtggtc ttccagtaac cacattcagt agagcggttt gccttaccgc ctttgggata | 1020 |
| cttctttttct cttggacaga agaagtacca cttaagatct ccagtcccta gacatgattt | 1080 |
| gtctgtacaa tgtaaagaaa cctctgttag taatcaggaa ataaataaga aagcatgaaa | 1140 |
| cagaacaaag atttctgaaa gaatgagtta gttaccgggt aaatcaggag gttcgaactt | 1200 |
| gtaaatgtcg acctcagcaa tggcatcaac ttggaacttt tttcccataa ctttcctctt | 1260 |
| caagtagtat ctcacaagtt caacatcagt cggatgaaac cgaaaccag gtgccaagtt | 1320 |
| agttttcccc at | 1332 |

<210> SEQ ID NO 116
<211> LENGTH: 878
<212> TYPE: DNA
<213> ORGANISM: Arabidopsis thaliana
<220> FEATURE:
<223> OTHER INFORMATION: G1274

<400> SEQUENCE: 116

| | |
|---|---|
| ggtcatcgag ttgcatttag aacgagatcg aagattgatg tgatggatga tggtttaaa | 60 |
| tggaggaagt atggcaagaa atctgtcaaa acaacatta acaagaggta acttattcat | 120 |
| ttacaaatta ctcatttgat ctaattaata tgttttacta gtacttgttt ttaacataac | 180 |
| atatggttgc ttgataattt tctataacca tcttgtaatc ctgttgttat agaatatata | 240 |

-continued

```
gccactagct agctagacca tatagtgatt tgaatactat ttaatggacc cgtattatct      300
accaacccac ttggaataaa atttagcttc tatatacatc atgcatgtgt gttttgttta      360
tacaaatata taaaaggttc ctatagcaaa attgattgat tagtggtata tggatcaatg      420
aatccatggt tgataatcag tcatcgtata gatttatttt gactcatata tcataagaga      480
aacaaatata atgaattcat catctaaaca tatcactttc attcaaagca tggtttgaaa      540
gcaatttaca cactctgtaa ttggttaatg atattcttat atatatacat acatatatat      600
atatatatat atatatatat aacttggtgc gatatattat aaaagtgatt acaatttaac      660
atgtggtgga tgaatttata ataaaagga attactacaa atgctcaagt gaaggttgct      720
cggtgaagaa gagggtagag agagatggtg acgatgcagc ttatgtaatt acaacatatg      780
aaggagtcca taaccatgag agtctctcta atgtctatta caatgaaatg gttttatctt      840
atgatcatga taactggaac caacactctc ttcttcga                              878
```

<210> SEQ ID NO 117
<211> LENGTH: 2352
<212> TYPE: DNA
<213> ORGANISM: Arabidopsis thaliana
<220> FEATURE:
<223> OTHER INFORMATION: G182

<400> SEQUENCE: 117

```
tctctgagct tcttgacatg gaaaacttcc aaggagactt aaccgacgtc gtacgaggaa       60
tcggaggcca cgtgttatca ccggagactc ctccctcgaa catctggcct cttcctctgt      120
cacatccaac accatcaccg tcagatctta acataaaccc cttcggagat cccttttgtga     180 gcatggacga tccactcctc caagaactaa actccatcac aaactccggc tatttctcca     240
ccgtaggaga taacaacaac aacattcaca acaacaatgg tttcttggtt ccaaaggtat      300
ttgaggagga tcatataaag agtcaatgta gtatcttccc aagaatccgg atctcgcata     360
gtaacatcat ccacgattct ctccgtgta attctccggc catgtcggct cacgttgtcg       420
cagccgcagc agccgcctcg ccgagaggca tcatcaacgt agacacaaac agtcctagaa      480
actgtctatt ggttgatggt accacgttct cctcgcagat tcagatatct tcccctcgga     540
atctaggcct taaagaagg tacaaaattt agtttatcaa cttttctcga tcttggatca      600
aatgattcat taattgttag ctttacacac gatatattga attaatcaaa gatggttttg      660
tgttatgata tgtataaaat aattgggatc caatttacat tattttatg ataccatata      720 gagtagagtg aattagggtt ctataggcca cttggtagct aggttatag gaatctatca       780 atcgctatta acattcggaa aaagtcggat gcatgcattg ctaataatag aatgaattat       840
atatggtttg tttgtttgtg tgacacttcc ctttattgag ttttataggg ggttttattt      900 tattttgtt tgtcttttat caggatcaat atcataatca tgaatttgtg tgtatataga      960
cactatatat ataattattt agattcataa gaagaaggag ggttgaggtt gaagacacat     1020
gcaggagaat ctatgaactg tcacaattaa agaacatat aactgcgtta catcatatct     1080
taaacccaac tgataataat gtcccactag tccactacca aacttagctt tcataactta     1140
atgtacacac gtgtcttgta tatagatcaa aaaccacacg tttgtaagta tgtatgtact     1200
tggatgcagg aagagtcagg caaagaaggt ggtgtgtatt ccggcccegg ctgcaatgaa     1260 cagccgatca agcggagaag tggttccatc ggatctatgg gcttggcgta aatacggtca     1320
aaaacctatc aaaggctctc cttttccaag gtattacatt aactcatcat accataatac     1380
```

-continued

| | |
|---|---|
| tcatatgatt cgaaactaaa ctttctttca ccaccacatt tttcatggct caagttttta | 1440 |
| tattcgtatg ttgttacaac tctcctctca aattgtgaca ttttgttggt ctatacaata | 1500 |
| tactcaccca tgaaaataac atttgtttac atatacaaat tatgataagt tactattaca | 1560 |
| gttcagtcat tacgttaact ctaaagtaat gaatgacaaa aggaaagaaa aaatttgcaa | 1620 |
| tgatgtcgtt ttaattaact tcattttgta attttatcct tcattttctc atattttgat | 1680 |
| gataatcttg atgaatatta gtgattcata atggttttt attatatatt tggctaatct | 1740 |
| ctatggttac ttatgattgt tgctttcagg gttattata gatgcagcag ctcaaaaggt | 1800 |
| tgttcagcaa gaaagcaagt cgaaagaagc cgaaccgatc caaacatgtt ggtgattaca | 1860 |
| tatacctccg aacataacca tccttggccc atccaacgca acgctctcgc cggctccaca | 1920 |
| cgctcctcca cctcctcctc atctaaccct aatccttcca aaccctcaac cgcaaacgta | 1980 |
| aactcctcat ccattggctc ccaaaacacc atctacttgc cttcctccac cactcctcct | 2040 |
| cctaccctct catcctccgc catcaaagat gaacgagggg acgatatgga gttggaaaac | 2100 |
| gtagatgatg atgatgataa ccagattgct ccatacagac cggagcttca tgatcatcag | 2160 |
| caccaaccag atgatttctt tgcagatctt gaagagctag aaggagattc tctaagcatg | 2220 |
| ttgctttctc atggctgtgg cggcgacggg aaggataaaa cgaccgcgtc cgatgggatc | 2280 |
| agcaatttct tcgggtggtc gggagataat aattataata attacgacga ccaagactca | 2340 |
| aggtcgttat ag | 2352 |

<210> SEQ ID NO 118
<211> LENGTH: 2043
<212> TYPE: DNA
<213> ORGANISM: Arabidopsis thaliana
<220> FEATURE:
<223> OTHER INFORMATION: G1290

<400> SEQUENCE: 118

| | |
|---|---|
| atgatggcca ccaccaccac caccaccacc gctagattct ctgattcata cgagttcagc | 60 |
| aacacaagcg gcaatagctt cttcgccgcc gagtcatctc ttgattatcc gacggaattt | 120 |
| ctcacgccac cggaggtatc agctcttaaa cttctgtcta actgcctcga gtctgttttc | 180 |
| gactcgccgg agacgttcta cagcgatgct aagctagttc tcgccggcgg ccgggaagtt | 240 |
| tcttttcacc gttgtattct ttccgcgaga attcctgtct tcaaaagcgc tttagccacc | 300 |
| gtgaaggaac aaaaatcctc caccaccgtg aagctccagc tgaaagagat cgccagagat | 360 |
| tacgaagtcg gctttgactc ggttgtggcg gttttggcgt atgtttacag cggcagagtg | 420 |
| aggtccccgc cgaagggagc ttctgcttgc gtagacgacg attgttgcca cgtggcttgc | 480 |
| cggtcaaagg tggatttcat ggtggaggtt ctttatctgt ctttcgtttt ccagattcaa | 540 |
| gaattagtta ctctgtatga ggtaaaacac aatccactaa attctcattg actcataaca | 600 |
| tcatcttaag tctcctctgt tttcatttca gaggcagttc ttggaaattg tagacaaagt | 660 |
| tgtagtcgaa gacatcttgg ttatattcaa gcttgatact ctatgtggta caacatacaa | 720 |
| gaagcttttg gatagatgca tagaaattat cgtgaagtct gatatagaac tagttagtct | 780 |
| tgagaagtct ttacctcaac acattttcaa gcaaatcata gacatccgcg aagcgctctg | 840 |
| tctagagcca cctaaactag aaaggcatgt caagaacata tacaaggcgc tagactcaga | 900 |
| tgatgttgag cttgtcaaga tgcttttgct agaaggacac accaatctcg atgaggcgta | 960 |
| tgctcttcat tttgctatcg ctcactgcgc tgtgaagacc gcgtatgatc tcctcgagct | 1020 |
| tgagcttgcg gatgttaacc ttagaaatcc gagggggatac actgtgcttc atgttgctgc | 1080 |

```
gatgcggaag gagccgaagt tgataatatc tttgttaatg aaagggcaa atattttaga   1140 cacaacattg gatggtagaa ccgctttagt gattgtaaaa cgactcacta aagcggatga   1200
ctacaaaact agtacggagg acggtacgcc ttctctgaaa ggcggattat gcatagaggt   1260
acttgagcat gaacaaaaac tagaatattt gtcgcctata gaggcttcac tttctcttcc   1320
agtaactcca gaggagttga ggatgaggtt gctctattat gaaaaccgag gtatgctttc   1380
ttccttcact tgaatatcga atttcgggta ggaaaatgag tggaactaat gataacgatg   1440
gtctatactt ttcagttgca cttgctcgac ttctcttccc agtggaaact gaaactgtac   1500
agggtattgc caaattggag gaaacatgcg agtttacagc ttctagtctc gagcctgatc   1560
atcacattgg tgaaaagcgg acatcactag acctaaatat ggcgccgttc caaatccatg   1620
agaagcattt gagtagacta agagcacttt gtaaaaccgg tatggattga ttcttatatg   1680
tcatctcttt tctagccaac aaagaaatga tgtttagaac tttatttttgt tgtatcttca   1740 gtggaactgg ggaaacgcta cttcaaacga tgttcgcttg atcactttat ggatactgag   1800
gacttgaatc atcttgctag cgtagaagaa gatactcctg agaaacggct acaaaagaag   1860
caaaggtaca tggaactaca agagactctg atgaagacct ttagtgagga caaggaggaa   1920
tgtggaaagt cttccacacc gaaaccaacc tctgcggtga ggtctaatag aaaactctct   1980
caccggcgcc taaaagtgga caaacgggat ttttttgaaac gaccttacgg gaacggggat   2040
taa                                                                 2043

<210> SEQ ID NO 119
<211> LENGTH: 5428
<212> TYPE: DNA
<213> ORGANISM: Arabidopsis thaliana
<220> FEATURE:
<223> OTHER INFORMATION: G374

<400> SEQUENCE: 119
aggtaattta gtcgtctctg tggattcata agcagcatca gctgaagaag tatctatgtc     60
gttgagaccc aactcctcgt tttgatccca tgacctctcg tactcttcaa ctgtagttca    120
aacataacaa aacttgttat tcaaaaccca agtcctgtcc taattcacat attgattgag    180
tcctaattta tgtctcagtt tcattataaa attcatcaag aaaggaatgg ataagtctga    240
atatttgttt agttcgtatt catatcccac ttaaggctac ataggcaggg taaacgagta    300
acttacatgt gagctgatgg tcatctttga tatcatctgt tactggtgca ataaaggaat    360
ttgctaattc atcatcaaga atcaatgtcc acggctgttc aaagcttagg agctgcaagc    420
aaacaaaaca catattcatt attgcttttt cttccacatc aagcacacga caaaggctaa    480
taaacagaaa ttcaatcaag ttcctacctt agtgagcctg gctccaaatt ctctccattt    540
gttcaactta ctctcttcca tactatcacc aaaagtgaat ccgtgaactc tcgctaggcc    600
tgtgagaacc aaccatacca cacttgggtc agtaatagct aggagctata atccatcatt    660
ggcaataaca aatatcgaat cgcttccatt atccaaacaa caaagctttg caaggcaga     720 atataagata cttggattac tgagttatgc catggttcaa tatatgtgtt ctagagtact    780
taaatcactt aaaatgatta taacaaggat aaaggataat gttgagattt tgaagggaat    840
gtagagattt tgaagggcac actcactttc tctgatctgt gtaaccaacc cttcaactgt    900
tgttaccatt ccaccaagtg taccaccagc tagctccaga tcaagttctg ggattatcac    960
tcctgcagtg tccgactaat acacacgatc aaaatttacc attaatgaca tagtagaagg   1020
```

-continued

```
tgttgctata aaaatctaaa ggatcataag gttgtctact ataatattgc catcagatgt      1080
gttatatagc cacaccaaag gcctagaaag atcaaacaag cctgttttac atctgatctc      1140
gaagtttcga cacttatctg ccactaccta gatatattat tttctgccag acatgagaa      1200 taccatatat aatttggcag cgagcaagat tccttgtcaa acctttaccc aacttaaact      1260
acatacattc tgtaaactta aactgtgaca atcttagcta cttttaaggt acatagaata      1320
atatgaggaa atatctattg atccgccact gagagaactg gtgcaaaaca aaatgaagcg      1380
aaaactgacc ttgataacat ctcggctaag gtctgtaatg ttcctcacag agagagtaat      1440
cttctttccc ttttcaggaa ttgcaccacc aggcttcaac tgctcacgat aacccaaaaa      1500
aagttagtaa cctaaacacc aggcatatat cagaaattct ctaacaagat caaaccaacg      1560
aaacccaacc tcagaattac gatagccaca actgtcacat gtagatgcca tgacaataac      1620
ttcctgaaag tacgggattt ctattttctg ttaagtggta acaacatct aggaattcac       1680 caacaaacac aaatatggaa acttgttgcg gaaaccaag aaatgaacgg gtccaaactt       1740
tgaaaggata ctagtcacga acatccgtgt ctcacacggc tccgtacatg ctccgcaagt      1800
tgaagggaaa gtcatcacct gttagagaaa ttgtaacggg atatgaaatt atattactat      1860
gatctaagta ttcactctca caaatacaac cttgggcgct gattatttc tcgagcaata      1920 ataaccttga aacagaacat ccaacaaaaa ctatttcaaa agttacagcg tcagaagtta      1980
cctcttcagg cgcagagtat ctgaacaagt tgtcggaaat atcagtgcta ttactctgag      2040
caatcgcgcg atgaccagca gttgctccga ttgttccatt aggtacataa gctgttttag      2100
tagaaggtgc gccaaggctt ccttctgatt gtccagcctg agatgggtta gcaacatatc      2160
caagtgttgc ttgttgctct ggtgttcgct catagaattt gatggttaga gagggatctg      2220
gtgatggagc atgtctgtca tgttgtaaac ttgtcataaa caaataaaag aaacataact      2280
tcttccatat ctttaggtat ttccaaattg aatatactta cgggttctca atgaaactgt      2340
ttccagcagg atcatccaaa atgaaggtga aggatgtctc tgctttagca caagctctca      2400
gtttggacaa gaattggtct attgcttcag cagttttagg atcaactttc tgtgtccagc      2460
aaaatatgca ttactattaa tgacttaaac ccaattaaat gggcataaaa acattaatgt      2520
caagctccag acagaattta ccttgcgttc ttcttgaagg gcactcagtt catcagcagc      2580
ccgtgctaat atcccttcca cctgtaaata aaacaaaaaa acgggagctg ttgacaagga      2640
cgaggtaata ggaaacctaa caatctgaaa cgaagttgca taggactatt atacaccaac      2700
aagatgtttt ccaagctgct aacaccgggt ggaagctaac aaagtaacaa agatagggtt      2760
ctcgctcttc ctaataaatt actacccaag tgacagtttg atgattatat tgtcattaag      2820
tgcaccacca atatgttctc acgagtagac cacacatttt aggttgttct aagaaacgaa      2880
gacacccaaa aatgaactgt gcataacaag atggttaaga tattaaggac ttacagtaga      2940
caaacttcca cgttgggcct ctggtggaat ctcaaaatcc agttcaggaa tctgaagaaa      3000
tttattcgca aactactgtc agtttccagc ttcaaatcag tccagttttc atggtatgat      3060
aagcaaacta attcacagtt ttcaaaaacg ttaggggaag caatttctta taaatgtgca      3120
ggaagcagct taggtttgga aaaccagtat tttgattcca aagaagcaat gacatgccca      3180
gaattaaaaa gaccgctcac cttaatagtg gctgattcag atttcacaac ttgccggtca      3240
aatatctgca tatagacaga tataagaagg taaaaaataa gctgaaggag tgagagacca      3300
ctaaaaacaa atatctttat ttcttaaaat aagcatggag ggctacattc tactacatgg      3360
taagtatatc accaaatgaa ataaaaaaaa tatgtataga caagaacaga aattctacct      3420
```

```
tcacatcacc agctagaacc tctagattgt aacagcatcc acggggttga atctcgcctg   3480
cgaactgaac ttcattattc ctataaaata gatcaaagat aaaataaaag gttacttaaa   3540
atattctagt gattcttttg aacaatgagt acttaaaata atctcaattc attaaaattt   3600
gtacctttcc ccgcaatgcg gacattcaaa tgcagatatt aagacctgta cccacaagta   3660
agttaacaat aagcttgtaa gctcacacaa ggtatggaaa tgtataaata caacaaagaa   3720
aacatgtttc tttaaaccaa ctagaaatct atagcccaag aatgtggtca attcataggg   3780
aattaagtat gaaaaatttg aatctggaaa atgaacagaa ttggttatct tcaaaacaga   3840
gtatgacata cctttctgaa gtgaggaatt aaggtcaata gaaatctggt tgttccctgg   3900
aaaaaaatta ttattagcta tttgtgcata gaagaaggat caggagaaag acaagacaat   3960
ttcatacaac agcttataac taaaagaatt cggtaaaaat acactagtaa ctgaaagttc   4020
acaatataca gatcctccaa ttaattgcca cagaaccata aatatcactt atatcacctc   4080
aaatttctca gcccatcacc aagacatgcc aataagttgt gtttcatcct tactacagtt   4140
catagcagtc taaagaacag aaagaactaa tgataatgct gaagtacaca acagctatgt   4200
gcatgtacac aattggaaac aagctgcaac taaagaccaa aggctacaga gaaactagcc   4260
tgtttcctag accttatatt agttaagaaa ggttgcaaac tctataattc tgcctatgaa   4320
aaaggataag gactacataa ccaccaacat caggaatctc aaagaaacta tataagtatg   4380
tgcgtgagag ggagacatac attttcttgg cagcgcatgc acatgctctc aaccacatag   4440 agggagcac caaaggaaag atcggcggaa acagcttcaa ccactgatct aacatcaata   4500
tcctgatcat ttttgttgtc catcacctcc aaagtttctc caaacaatcc caagaaatcc   4560
gattgaccgc aaagtcagct gattccaaga agatgcacac ctaaatggtt tgtgagcaaa   4620
cacatcagga aacaaaaaag aagctaaaag attgaaactt ttctgcccat caacagctaa   4680
ctctataagg gtctctactg aattcatatt tgaaactaaa gaagaacaaa attttcgaag   4740
acgattagta tttgcaattt cctggaaaag cttatagaag tttaaaccat atagcattat   4800
ctattggttc ccaacctaaa cactaatggc aaggttccaa ggattcgtaa agattaaacc   4860
atataataca aagtagagag agataagaga gtctcgagac agaagagagc taagagcaga   4920
tacgaaacag agagctttgt acctcgagca ggcaaggaac agaacagaga cagagaggtt   4980
acgtcgccgg tagagaaacg agcagaggag caaggaatta aaaatcgaag agagggaatc   5040
aaatctagct ttggctctgc tgctcgagat tttagggttc gttcgtacga cgtcgttttt   5100
gttgaaaacg agggaaaata ggtcaaatta tacacgaact aaaaattgac catatccgat   5160
ttcgacgata tagactatag tctattgtaa aatgatgttc gtagttttta ctatcttttt   5220
aaaaaaaaaa attgttacta tcttttaaaa aaaaaaatt gttactatct ttactacatt    5280
aatagttttc tcaaaatctc catcgacaac ataagcaaat caaagaaaca tggaagacta   5340
tatttggtta tggttgagaa tgatccttag ttccttacca atatcgacat gagtttcgaa   5400
tctcacattt ctcaaagcag attccccat                                      5428
```

<210> SEQ ID NO 120
<211> LENGTH: 434
<212> TYPE: DNA
<213> ORGANISM: Arabidopsis thaliana
<220> FEATURE:
<223> OTHER INFORMATION: G682

<400> SEQUENCE: 120

-continued

```
tcaattttc atgacccaaa acctctcaat ttctccagcg gttcttcctg ggatcctccc      60
agctatcagt tcccacctt catcaaataa taacacacaa aattcagctt ttactatggt     120
gttacaatta aattattttc ctacgaaata gtattcatta ttagttaaaa gatcaaacct    180
gtcaccgaca agcttatgca ttcgagagac caaatcttct tcttcttgac tcatgttcac    240
aacttcccac tcaagactac tcacttctgt tccttgtcat caccaaaatt cagatttctc    300
attatatata gataagtata aaaaaacatg gaaaaatgag aaaacgaagg tgtttaagtt    360
ttcagcttac cttcagaaga agaagtaacg atggagttgg tcttgggttg cttagtcctg    420
cgatggttat ccat                                                      434
```

<210> SEQ ID NO 121
<211> LENGTH: 1216
<212> TYPE: DNA
<213> ORGANISM: Arabidopsis thaliana
<220> FEATURE:
<223> OTHER INFORMATION: G501

<400> SEQUENCE: 121

```
aattgaattt tcaaccaacg aagaagagat ttttccaaga gcaacagaca agaagaagag     60
aatgaagtcg gagctaaatt taccagctgg gttccgattc catccaacgg acgaggagct    120
tgtgaaattc tacttgtgcc ggaaatgtgc ttccgagcag atctcggctc cggttatcgc    180
cgagattgat ctctacaagt tcaatccttg ggagcttcca gagatgtctc tgtacggaga    240
gaaagagtgg tacttcttct cacctagaga tcggaaatac ccaaacggtt cgcgtcctaa    300
ccgggcagca ggaaccggtt attggaaagc taccggagca gataaaccga ttggtaaacc    360
gaagacgttg ggtatcaaga aagcactcgt cttctacgca gggaaagctc caaaagggat    420
taagaccaat tggataatgc atgagtatcg tctcgctaat gttgatagat cagcttctgt    480
taacaaaaag aacaacctac gacttgatga ttgggtttta tgtcgaatat acaacaagaa    540
aggaaccatg gagaagtatt tccccgcgga tgagaagccg aggaccacga caatggctga    600
acagtcatca tcaccttttg atacatcaga ctcgacttac ccgacattgc aagaggatga    660
ttccagcagc tcaggtggtc acggtcacgt ggtgtcaccg gatgttttgg aggttcagag    720
cgagcctaaa tggggagagc ttgaggatgc tttggaagct tttgatactt caatgttggt    780
agttccatgg agttgttgca gcctgacgct tttgtccctc agttcttgta tcagtctgat    840
tatttcactt ccttccagga tccgcctgag cagaaaccat tcttgaattg gagttttgct    900 ccacagggt aaaaacggaa gagaccaaaa aaggtgtttg ctagtagtac tgtgatgtgc    960
cagagagaag agtctcatct caactcatcc ctggctctta gtagtaaaag aagattgtag   1020
aatgttaata gcttttagca tcaatgtctc attagcaggc acattcttgt tctttcatga   1080
gaagtttata tgaaaactaa aaatttatat tcaaattctt caagatgttg cacttatgta   1140
gatactgata ttaaataaca acctaacctt tatgagaaaa aaaaaaaaaa aaaaaaaaa   1200 aaaaaaaaa aaccct                                                   1216
```

US 6,664,446 B2

TRANSGENIC PLANTS COMPRISING POLYNUCLEOTIDES ENCODING TRANSCRIPTION FACTORS THAT CONFER DISEASE TOLERANCE

The present invention claims benefit of U.S. Provisional Application Serial No. 60/125,814 filed Mar. 23, 1999.

FIELD OF THE INVENTION

This invention is in the field of plant molecular biology and relates to compositions and methods for modifying a plant's traits, in particular plant disease tolerance or resistance.

BACKGROUND OF THE INVENTION

Gene expression levels are controlled in part at the level of transcription, and transcription is affected by transcription factors. Transcription factors regulate gene expression throughout the life cycle of an organism and so are responsible for differential levels of gene expression at various developmental stages, in different tissue and cell types, and in response to different stimuli. Transcription factors may interact with other proteins or with specific sites on a target gene sequence to activate, suppress or otherwise regulate transcription. In addition, the transcription of the transcription factors themselves may be regulated.

Because transcription factors are key controlling elements for biological pathways, altering the expression levels of one or more transcription factors may change entire biological pathways in an organism. For example, manipulation of the levels of selected transcription factors may result in increased expression of economically useful proteins or metabolic chemicals in plants or to improve other agriculturally relevant characteristics. Conversely, blocked or reduced expression of a transcription factor may reduce biosynthesis of unwanted compounds or remove an undesirable trait. Therefore, manipulating transcription factor levels in a plant offers tremendous potential in agricultural biotechnology for modifying a plant's traits.

The present invention provides transcription factors for use in modifying a plant's disease tolerance or resistance.

SUMMARY OF THE INVENTION

In one aspect, the present invention relates to a transgenic plant comprising a recombinant polynucleotide. The recombinant polynucleotide comprises a nucleotide sequence encoding a polypeptide comprising at least 6 consecutive amino acids of a sequence selected from the group consisting of protein SEQ ID Nos. 2N, where N=1–56. And the presence of the recombinant polynucleotide alters the disease tolerance or resistance of the transgenic plant when compared with the same trait of another plant lacking the recombinant polynucleotide.

In one embodiment, the nucleotide sequence encodes a polypeptide comprising a conserved domain which may be 1) a localization domain, 2) an activation domain, 3) a repression domain, 4) an oligomerization domain or 5) a DNA binding domain. In a further embodiment, the nucleotide sequence further comprises a promoter operably linked to the nucleotide sequence. The promoter may be a constitutive or inducible or tissue-active.

In a second aspect, the present invention relates to a method for altering a plant's deisease tolerance or resistance. The method comprises (a) transforming a plant with a recombinant polynucleotide comprising a nucleotide sequence encoding a polypeptide comprising at least 6 consecutive amino acids of a sequence selected from the group consisting of protein SEQ ID Nos. 2N, where N=1–56; (b) selecting transformed plants; and (c) identifying a transformed plant with roots having an altered trait.

In one embodiment, the nucleotide sequence encodes a polypeptide comprising a conserved domain which may be 1) a localization domain, 2) an activation domain, 3) a repression domain, 4) an oligomerization domain or 5) a DNA binding domain. In a further embodiment, the nucleotide sequence further comprises a promoter operably linked to the nucleotide sequence. The promoter may be a constitutive or inducible or tissue-active.

In a third aspect, the present invention relates to a method for altering the expression levels of at least one gene in a plant. The method comprises (a) transforming the plant with a recombinant polynucleotide comprising a nucleotide sequence encoding a polypeptide comprising at least 6 consecutive amino acids of a sequence selected from the group consisting of protein SEQ ID Nos. 2N, where N=1–56; and (b) selecting said transformed plant.

In one embodiment, the nucleotide sequence encodes a polypeptide comprising a conserved domain which may be 1) a localization domain, 2) an activation domain, 3) a repression domain, 4) an oligomerization domain or 5) a DNA binding domain. In a further embodiment, the nucleotide sequence further comprises a promoter operably linked to the nucleotide sequence. The promoter may be a constitutive or inducible or tissue-active.

In a fourth aspect, the present invention relates to another method for altering the disease tolerance of a plant. The method comprises (a) transforming the plant with a recombinant polynucleotide comprising a nucleotide sequence comprising at least 18 consecutive nucleotides of a sequence selected from the group consisting of SEQ ID Nos. 2N–1, where N=1–56, and SEQ ID Nos. 113–121; and (b) selecting said transformed plant.

In yet another aspect, the present invention is yet another method for altering a plant's trait. The method comprises (a) providing a database sequence; (b) comparing the database sequence with a polypeptide selected from SEQ ID Nos. 2N, where N=1–56; (c) selecting a database sequence that meets selected sequence criteria; and (d) transforming said database sequence in the plant. Alternatively, the database sequence can be compared with a polynucleotide selected from SEQ ID Nos. 2N–1, where N=1–56 or SEQ ID Nos. 113–121.

In a further aspect, the present invention is method for altering a plant's trait, and the method entails (a) providing a test polynucleotide; (b) hybridizing the test polynucleotide with a polynucleotide selected from SEQ ID Nos. 2N–1, where N=1–56 or SEQ ID Nos. 113–121 at low stringency; and (c) transforming the hybridizing test polynucleotide in a plant to alter a trait of the plant.

BRIEF DESCRIPTION OF THE FIGURES

FIGS. 1a–1e provide a table of exemplary polynucleotide and polypeptide sequences of the invention. The table includes from left to right for each sequence: the SEQ ID No., the internal code reference number, the transcription factor family of the sequence, particular DNA or protein fragments for each sequence, whether the sequence is a polynucleotide or polypeptide sequence, identification of the coding sequence for each full length and identification of any conserved domains for the polypeptide sequences.

DETAILED DESCRIPTION OF THE INVENTION

Definitions

A "recombinant polynucleotide" is a nucleotide sequence comprising a gene coding sequence or a fragment thereof (comprising at least 18 consecutive nucleotides, preferably at least 30 consecutive nucleotides, and more preferably at least 50 consecutive nucleotides). Additionally, the polynucleotide may comprise a promoter, an intron, an enhancer region, a polyadenylation site, a translation initiation site, 5' or 3' untranslated regions, a reporter gene, a selectable marker or the like. The polynucleotide may comprise single stranded or double stranded DNA or RNA. The polynucleotide may comprise modified bases or a modified backbone. The polynucleotide may be genomic, a transcript (such as an mRNA) or a processed nucleotide sequence (such as a cDNA). The polynucleotide may comprise a sequence in either sense or antisense orientations.

A "recombinant polynucleotide" is a polynucleotide that is not in its native state, e.g., the polynucleotide is comprised of a nucleotide sequence not found in nature or the polynucleotide is separated from nucleotide sequences with which it typically is in proximity or is next to nucleotide sequences with which it typically is not in proximity.

An "recombinant polypeptide" is a polypeptide derived from the translation of a recombinant polynucleotide or is more enriched in a cell than the polypeptide in its natural state in a wild type cell, e.g. more than 5% enriched, more than 10% enriched or more than 20% enriched and is not the result of a natural response of a wild type plant or is separated from other components with which it is typically associated with in a cell.

A "transgenic plant" may refer to a plant that contains genetic material not normally found in a wild type plant of the same species, or in a naturally occurring variety or in a cultivar, and which has been introduced into the plant by human manipulation. A transgenic plant is a plant that may contain an expression vector or cassette. The expression cassette comprises a gene coding sequence and allows for the expression of the gene coding sequence. The expression cassette may be introduced into a plant by transformation or by breeding after transformation of a parent plant.

A transgenic plant refers to a whole plant as well as to a plant part, such as seed, fruit, leaf, or root, plant tissue, plant cells or any other plant material, and progeny thereof.

The phrase "altered expression" in reference to polynucleotide or polypeptide expression refers to an expression pattern in the transgenic plant that is different from the expression pattern in the wild type plant or a reference; for example, by expression in a cell type other than a cell type in which the sequence is expressed in the wild type plant, or by expression at a time other than at the time the sequence is expressed in the wild type plant, or by a response to different inducible agents, such as hormones or environmental signals, or at different expression levels (either higher or lower) compared with those found in a wild type plant. The term also refers to lowering the levels of expression to below the detection level or completely abolishing expression. The resulting expression pattern may be transient or stable, constitutive or inducible.

A "transcription factor" (TF) refers to a polynucleotide or polypeptide that controls the expression of a gene or genes either directly by binding to one or more nucleotide sequences associated with a gene coding sequence or indirectly by affecting the level or activity of other polypeptides that do bind directly or indirectly to one or more nucleotide sequences associated with a gene coding sequence. A TF, in this definition, includes any polypeptide that can activate or repress transcription of a single gene or a number of genes. This polypeptide group includes, but is not limited to, DNA binding proteins, protein kinases, protein phosphatases, GTP-binding proteins and receptors.

The transcription factor sequence may comprise a whole coding sequence or a fragment or domain of a coding sequence. A "fragment or domain", as referred to polypeptides, may be a portion of a polypeptide which performs at least one biological function of the intact polypeptide in substantially the same manner or to a similar extent as does the intact polypeptide. A fragment may comprise, for example, a DNA binding domain that binds to a specific DNA promoter region, an activation domain or a domain for protein-protein interactions. Fragments may vary in size from as few as 6 amino acids to the length of the intact polypeptide, but are preferably at least 30 amino acids in length and more preferably at least 60 amino acids in length. In reference to a nucleotide sequence "a fragment" refers to any sequence of at least consecutive 18 nucleotides, preferably at least 30 nucleotides, more preferably at least 50, of any of the sequences provided herein. Exemplary polynucleotides or polypeptides comprise a sequence provided in the Sequence Listing as SEQ ID No.1 (G1043), SEQ ID No.2 (G1043 protein), SEQ ID No.3 (G759), SEQ ID No.4 (G759 protein), SEQ ID No.5 (G185), SEQ ID No.6 (G185 protein), SEQ ID No.7 (G629), SEQ ID No.8 (G629 protein), SEQ ID No.9 (G435), SEQ ID No.10 (G435 protein), SEQ ID No.11 (G4), SEQ ID No.12 (G4 protein), SEQ ID No.13 (G1035), SEQ ID No.14 (G1035 protein), SEQ ID No.15 (G179), SEQ ID No.16 (G179 protein), SEQ ID No.17 (G28), SEQ ID No.18 (G28 protein), SEQ ID No.19 (G1241), SEQ ID No.20 (G1241 protein), SEQ ID No.21 (G19), SEQ ID No.22 (G19 protein), SEQ ID No.23 (G503), SEQ ID No.24 (G503 protein), SEQ ID No.25 (G263), SEQ ID No.26 (G263 protein), SEQ ID No.27 (G921), SEQ ID No.28 (G921 protein), SEQ ID No.29 (G1275), SEQ ID No.30 (G1275 protein), SEQ ID No.31 (G242), SEQ ID No.32 (G242 protein), SEQ ID No.33 (G1006), SEQ ID No.34 (G1006 protein), SEQ ID No.35 (G1049), SEQ ID No.36 (G1049 protein), SEQ ID No.37 (G502), SEQ ID No.38 (G502 protein), SEQ ID No.39 (G239), SEQ ID No.40 (G239 protein), SEQ ID No.41 (G555), SEQ ID No.42 (G555 protein), SEQ ID No.43 (G352), SEQ ID No.44 (G352 protein), SEQ ID No.45 (G1352), SEQ ID No.46 (G1352 protein), SEQ ID No.47 (G1089), SEQ ID No.48 (G1089 protein), SEQ ID No.49 (G553), SEQ ID No.50 (G553 protein), SEQ ID No.51 (G1221), SEQ ID No.52 (G1221 protein), SEQ ID No.53 (G580), SEQ ID No.54 (G580 protein), SEQ ID No.55 (G270), SEQ ID No.56 (G270 protein), SEQ ID No.57 (G201), SEQ ID No.58 (G201 protein), SEQ ID No.59 (G1417), SEQ ID No.60 (G1417 protein), SEQ ID No.61 (G233), SEQ ID No.62 (G233 protein), SEQ ID No.63 (G920), SEQ ID No.64 (G920 protein), SEQ ID No.65 (G867), SEQ ID No.66 (G867 protein), SEQ ID No.67 (G659), SEQ ID No.68 (G659 protein), SEQ ID No.69 (G620), SEQ ID No.70 (G620 protein), SEQ ID No.71 (G596), SEQ ID No.72 (G596 protein), SEQ ID No.73 (G511), SEQ ID No.74 (G511 protein), SEQ ID No.75 (G471), SEQ ID No.76 (G471 protein), SEQ ID No.77 (G385), SEQ ID No.78 (G385 protein), SEQ ID No.79 (G261), SEQ ID No.80 (G261 protein), SEQ ID No.81 (G25), SEQ ID No.82 (G25 protein), SEQ ID No.83 (G610), SEQ ID No.84 (G610 protein), SEQ ID No.85 (G229), SEQ ID No.86 (G229 protein), SEQ ID No.87 (G221), SEQ ID No.88 (G221 protein), SEQ ID No.89 (G186), SEQ ID No.90 (G186 protein), SEQ ID No.91 (G562), SEQ ID No.92 (G562 protein), SEQ ID No.93 (G255), SEQ ID No.94 (G255 protein), SEQ ID No.95 (G3), SEQ ID No.96 (G3 protein), SEQ ID No.97 (G713), SEQ ID No.98 (G713 protein), SEQ ID No.99 (G515), SEQ ID No.100 (G515 protein), SEQ ID No.101 (G390), SEQ ID No.102 (G390 protein), SEQ ID No.103 (G1034), SEQ ID No.104 (G1034 protein), SEQ ID No.105 (G1149), SEQ ID No.106 (G1149 protein), SEQ ID No.107 (G1334), SEQ ID No.108 (G1334 protein), SEQ ID No.109 (G1650), SEQ ID No.110 (G1650 protein), SEQ ID No.111 (G241), SEQ ID No.112 (G241 protein), SEQ ID No.113 (G348), SEQ ID No.114 (G171), SEQ ID No.115 (G521), SEQ ID No.116 (G1274), SEQ ID No.117 (G182), SEQ ID No.118 (G1290), SEQ ID No.119 (G374), SEQ ID No.120 (G682) and SEQ ID No.121 (G501).

A "conserved domain" refers to a polynucleotide or polypeptide fragment that is more conserved at a sequence level than other fragments when the polynucleotide or polypeptide is compared with homologous genes or proteins from other plants. The conserved domain may be 1) a localization domain, 2) an activation domain, 3) a repression domain, 4) an oligomerization domain or 5) a DNA binding domain.

A nucleotide sequence is "operably linked" when it is placed into a functional relationship with another nucleotide sequence. For example, a promoter or enhancer is operably linked to a gene coding sequence if the presence of the promoter or enhancer increases the level of expression of the gene coding sequence.

"Trait" refers to a physiological, morphological, biochemical or physical characteristic of a plant or particular plant material or cell. This characteristic may be visible to the human eye, such as seed or plant size, or be measured by biochemical techniques, such as the protein, starch or oil content of seed or leaves or by the observation of the expression level of genes by employing Northerns, RT PCR, microarray gene expression assays or reporter gene expression systems or be measured by agricultural observations such as stress tolerance, yield or disease resistance.

"Trait modification" refers to a detectable difference in a characteristic in a transgenic plant expressing a polynucleotide or polypeptide of the present invention relative to a plant not doing so, such as a wild type plant. The trait modification may entail at least a 5% increase or decrease in an observed trait (difference), at least a 10% difference, at least a 20% difference, at least a 30%, at least a 50%, at least a 70%, at least a 100% or a greater difference. It is known that there may be a natural variation in the modified trait. Therefore, the trait modification observed entails a change in the normal distribution of the trait in transgenic plants compared with the distribution observed in wild type plant.

Trait modifications of particular interest include those to seed (embryo), fruit, root, flower, leaf, stem, shoot, seedling or the like, including: enhanced tolerance to environmental conditions including freezing, chilling, heat, drought, water saturation, radiation and ozone; enhanced resistance to microbial, fungal or viral diseases; resistance to nematodes, decreased herbicide sensitivity, enhanced tolerance of heavy metals (or enhanced ability to take up heavy metals), enhanced growth under poor photoconditions (e.g., low light and/or short day length), or changes in expression levels of genes of interest. Other phenotypes that may be modified relate to the production of plant metabolites, such as variations in the production of taxol, tocopherol, tocotrienol, sterols, phytosterols, vitamins, wax monomers, antioxidants, amino acids, lignins, cellulose, tannins, prenyllipids (such as chlorophylls and carotenoids), glucosinolates, and terpenoids, enhanced or compositionally altered protein or oil production (especially in seeds), or modified sugar (insoluble or soluble) and/or starch composition. Physical plant characteristics that may be modified include cell development (such as the number of trichomes), fruit and seed size and number, yields of plant parts such as stems, leaves and roots, the stability of the seeds during storage, characteristics of the seed pod (e.g., susceptibility to shattering), root hair length and quantity, internode distances, or the quality of seed coat. Plant growth characteristics that may be modified include growth rate, germination rate of seeds, vigor of plants and seedlings, leaf and flower senescence, male sterility, apomixis, flowering time, flower abscission, rate of nitrogen uptake, biomass or transpiration characteristics, as well as plant architecture characteristics such as apical dominance, branching patterns, number of organs, organ identity, organ shape or size.

Of particular interest are traits relating to increased disease resistance or tolerance of a plant, such as alterations in cell wall composition, trichome number or structure, callose induction, phytoalexin induction, alterations in the cell death response or the like. These transgenic plants may be more resistant to biotrophic or necrotrophic pathogens such as a fungus, bacterium, mollicute, virus, nematode, a parasitic higher plant or the like and associated diseases. Another desirable phenotype is a change in the overall gene expression pattern of the plant in response to disease.

1. The Sequences

We have discovered particular plant transcription factors (TFs) that are induced when plants are exposed to either biotropic or necrotropic pathogens.. These transgenic plants may be more resistant to biotrophic or necrotrophic pathogens such as a fungus, bacterium, mollicute, virus, nematode, a parasitic higher plant or the like and associated diseases, in particular, pathogens such as *Fusarium oxysporum, Erysyphe orontii* and other powdery mildews, Sclerotinia spp., soil-borne oomycetes, foliar oomycetes, Botrytis spp., Rhizoctonia spp, *Verticillium dahliae/alboatrum*, Alternaria spp., rusts, Mycosphaerella spp, *Fusarium solani*, or the like. The diseases include fungal diseases such as rusts, smuts, wilts, yellows, root rot, leaf drop, ergot, leaf blight of potato, brown spot of rice, leaf blight, late blight, powdery mildew, downy mildew, and the like; viral diseases such as sugarcane mosaic, cassava mosaic, sugar beet yellows, plum pox, barley yellow dwarf, tomato yellow leaf curl, tomato spotted wilt virus, and the like; bacterial diseases such as citrus canker, bacterial leaf blight, bacterial will, soft rot of vegetables, and the like; nematode diseases such as root knot, sugar beet cyst nematode or the like.

These transcription factors can be used to modulate a plant's response to disease. The plant transcription factors may belong to one of the following transcription factor families: the AP2 (APETALA2) domain transcription factor family (Riechmann and Meyerowitz (1998) Biol. Chem. 379:633–646); the MYB transcription factor family (Martin and Paz-Ares, (1997) Trends Genet. 13:67–73); the MADS domain transcription factor family (Riechmann and Meyerowitz (1997) Biol. Chem. 378:1079–1101); the WRKY protein family (Ishiguro and Nakamura (1994) Mol. Gen. Genet. 244:563–571); the ankyrin-repeat protein family (Zhang et al. (1992) Plant Cell 4:1575–1588); the zinc finger protein (Z) family (Klug and Schwabe (1995) FASEB J. 9:597–604); the homeobox (HB) protein family (Buerglin, in: Duboule (1994) Guidebook to the Homeobox Genes, Oxford University Press, pp. 27–71); the CAAT-element binding proteins (Forsburg and Guarente (1989) Genes Dev. 3:1166–1178); the squamosa promoter binding proteins (SPB) (Klein et al. (1996) Mol. Gen. Genet. 1996 250:7–16); the NAM protein family (Souer et al. (1996) Cell 85:159–170); the IAA/AUX proteins (Rouse et al. (1998)

Science 279:1371–1373); the HLH/MYC protein family (Littlewood et al. (1994) Prot. Profile 1:639–709); the DNA-binding protein (DBP) family (Tucker et al. (1994) EMBO J. 13:2994–3002); the bZIP family of transcription factors (Foster et al. (1994) FASEB J. 8:192–200); the Box P-binding protein (the BPF-1) family (da Costa e Silva et al. (1993) Plant J. 4:125–135); the high mobility group (HMG) family (Bustin and Reeves (1996) Prog. Nucl. Acids Res. Mol. Biol. 54:35–100); the scarecrow (SCR) family (Di Laurenzio et al. (1996) Cell 86:423–433); the GF14 family (Wu et al. (1997) Plant Physiol. 114:1421–1431); the poly-comb (PCOMB) family (Kennison (1995) Annu. Rev. Genet. 29:289–303); the teosinte branched (TEG) family (Luo et al. (1996) Nature 383:794–799; the ABI3 family (Giraudat et al. (1992) Plant Cell 4:1251–1261); the triple helix (TH) family (Dehesh et al. (1990) Science 250:1397–1399); the EIL family (Chao et al. (1997) Cell 89:1133–44); the AT-HOOK family (Reeves and Nissen (1990) Journal of Biological Chemistry 265:8573–8582); the S1FA family (Zhou et al. (1995) Nucleic Acids Res. 23:1165–1169); the bZIPT2 family (Lu and Ferl (1995) Plant Physiol. 109:723); the YABBY family (Bowman et al. (1999) Development 126:2387–96); the PAZ family (Bohmert et al. (1998) EMBO J. 17:170–80); a family of miscellaneous (MISC) transcription factors including the DPBF family (Kim et al. (1997) Plant J. 11:1237–1251) and the SPF1 family (Ishiguro and Nakamura (1994) Mol. Gen. Genet. 244:563–571); the golden (GLD) family (Hall et al. (1998) Plant Cell 10:925–936).

Producing transgenic plants with modified expression levels of one or more of these transcription factors compared with those levels found in a wild type or reference plant may be used to modify a plant's traits. The effect of modifying the expression levels of a particular transcription factor on the traits of a transgenic plant is described further in the Examples.

The polynucleotides and polypeptides are provided in the Sequence Listing and are tabulated in FIG. 1. FIG. 1 identifies a SEQ ID No., its corresponding GID number, the transcription factor family to which the sequence belongs, fragments derived from the sequences, whether the sequence is a polynucleotide or a polypeptide sequence, the full length coding sequences and conserved domains. We have also identified domains or fragments derived from the sequences. The numbers indicating the fragment location for the DNA sequences may be from either 5' or 3' end of the DNA. For the protein sequences the fragment location is determined from the N-terminus of the protein and may include adjacent amino acid sequences, such as for example for SEQ ID No.2 an additional 10, 20, 40, 60 or 100 amino acids in either N-terminal or C-terminal direction of the described fragments.

The identified polypeptide fragments may be linked to fragments or sequences derived from other transcription factors so as to generate additional novel sequences, such as by employing the methods described in Short, PCT publication WO9827230, entitled "Methods and Compositions for Polypeptide Engineering" or in Patten et al., PCT publication WO9923236, entitled "Method of DNA Shuffling". Alternatively, the identified fragment may be linked to a transcription activation domain. A transcription activation domain assists in initiating transcription from a DNA binding site. A common feature of some activation domains is that they are designed to form amphiphilic alpha helices with excess positive or negative charge (Giniger and Ptashne (1987) Nature 330:670–672, Gill and Ptashne (1987) Cell 51:121–126, Estruch et al (1994) Nucl. Acids Res. 22:3983–3989). Examples include the transcription activation region of VP16 or GAL4 (Moore et al. (1998) Proc. Natl. Acad. Sci. USA 95:376–381; and Aoyama et al. (1995) Plant Cell 7:1773–1785), peptides derived from bacterial sequences (Ma and Ptashne (1987) Cell 51;113–119) and synthetic peptides (Giniger and Ptashne, supra).

The isolated polynucleotides and polypeptides may be used to modify plant development, physiology or biochemistry such that the modified plants have a trait advantage over wild type plants. The identified polynucleotide fragments are also useful as nucleic acid probes and primers. A nucleic acid probe is useful in hybridization protocols, including protocols for microarray experiments. Primers may be annealed to a complementary target DNA strand by nucleic acid hybridization to form a hybrid between the primer and the target DNA strand, and then extended along the target DNA strand by a DNA polymerase enzyme. Primer pairs can be used for amplification of a nucleic acid sequence, e.g., by the polymerase chain reaction (PCR) or other nucleic-acid amplification methods. See Sambrook et al., *Molecular Cloning. A Laboratory Manual*, Ed. 2, Cold Spring Harbor Laboratory Press, New York (1989) and Ausubel et al. (eds) *Current Protocols in Molecular Biology*, John Wiley & Sons (1998).

2. Identification of Homologous Sequences (Homologs)

Homologous sequences to those provided in the Sequence Listing derived from *Arabidopsis thaliana* or from other plants may be used to modify a plant trait. Homologous sequences may be derived from any plant including monocots and dicots and in particular agriculturally important plant species, including but not limited to, crops such as soybean, wheat, corn, potato, cotton, rice, oilseed rape (including canola), sunflower, alfalfa, sugarcane and turf; or fruits and vegetables, such as banana, blackberry, blueberry, strawberry, and raspberry, cantaloupe, carrot, cauliflower, coffee, cucumber, eggplant, grapes, honeydew, lettuce, mango, melon, onion, papaya, peas, peppers, pineapple, spinach, squash, sweet corn, tobacco, tomato, watermelon, rosaceous fruits (such as apple, peach, pear, cherry and plum) and vegetable brassicas (such as broccoli, cabbage, cauliflower, brussel sprouts and kohlrabi). Other crops, fruits and vegetables whose phenotype may be changed include barley, currant, avocado, citrus fruits such as oranges, lemons, grapefruit and tangerines, artichoke, cherries, nuts such as the walnut and peanut, endive, leek, roots, such as arrowroot, beet, cassava, turnip, radish, yam, sweet potato and beans. The homologs may also be derived from woody species, such pine, poplar and eucalyptus.

Substitutions, deletions and insertions introduced into the sequences provided in the Sequence Listing are also envisioned by the invention. Such sequence modifications can be engineered into a sequence by site-directed mutagenesis (Wu (ed.) *Meth. Enzymol.* (1993) vol. 217, Academic Press). Amino acid substitutions are typically of single residues; insertions usually will be on the order of about from 1 to 10 amino acid residues; and deletions will range about from 1 to 30 residues. In preferred embodiments, deletions or insertions are made in adjacent pairs, e.g., a deletion of two residues or insertion of two residues. Substitutions, deletions, insertions or any combination thereof may be combined to arrive at a sequence. The mutations that are made in the polynucleotide encoding the transcription factor should not place the sequence out of reading frame and should not create complementary regions that could produce secondary mRNA structure.

Substitutions are those in which at least one residue in the amino acid sequence has been removed and a different residue inserted in its place. Such substitutions may be conservative with little effect on the function of the gene, for example by substituting alanines for serines, arginines for lysines, glutamate for aspartate and the like. The substitutions which are not conservative are expected to produce the greatest changes in protein properties will be those in which (a) a hydrophilic residue, e.g., seryl or threonyl, is substituted for (or by) a hydrophobic residue, e.g., leucyl, isoleucyl, phenylalanyl, valyl or alanyl; (b) a cysteine or proline is substituted for (or by) any other residue; (c) a residue having an electropositive side chain, e.g., lysyl, arginyl, or histidyl, is substituted for (or by) an electronegative residue, e.g., glutamyl or aspartyl; or (d) a residue having a bulky side chain, e.g., phenylalanine, is substituted for (or by) one not having a side chain, e.g., glycine.

Additionally, the term "homologous sequence" may encompass a polypeptide sequence that is modified by chemical or enzymatic means. The homologous sequence may be a sequence modified by lipids, sugars, peptides, organic or inorganic compounds, by the use of modified amino acids or the like. Protein modification techniques are illustrated in Ausubel et al. (eds) *Current Protocols in Molecular Biology*, John Wiley & Sons (1998).

Homologous sequences also may mean two sequences having a substantial percentage of sequence identity after alignment as determined by using sequence analysis programs for database searching and sequence alignment and comparison available, for example, from the Wisconsin Package Version 10.0, such as BLAST, FASTA, PILEUP, FINDPATTERNS or the like (GCG, Madision, Wis.). Public sequence databases such as GenBank, EMBL, Swiss-Prot and PIR or private sequence databases such as PhytoSeq (Incyte Pharmaceuticals, Palo Alto, Calif.) may be searched. Alignment of sequences for comparison may be conducted by the local homology algorithm of Smith and Waterman (1981) *Adv. Appl. Math.* 2:482, by the homology alignment algorithm of Needleman and Wunsch (1970) *J. Mol. Biol.* 48:443, by the search for similarity method of Pearson and Lipman (1988) *Proc. Natl. Acad. Sci. U.S.A.* 85:2444, by computerized implementations of these algorithms. After alignment, sequence comparisons between two (or more) polynucleotides or polypeptides are typically performed by comparing sequences of the two sequences over a comparison window to identify and compare local regions of sequence similarity. The comparison window may be a segment of at least about 20 contiguous positions, usually about 50 to about 200, more usually about 100 to about 150 contiguous positions. A description of the method is provided in Ausubel et al. (eds) (1999) *Current Protocols in Molecular Biology*, John Wiley & Sons.

Transcription factors that are homologs of the disclosed sequences will typically share at least 40% amino acid sequence identity. More closely related TFs may share at least 50%, 60%, 65%, 70%, 75% or 80% sequence identity with the disclosed sequences. Factors that are most closely related to the disclosed sequences share at least 85%, 90% or 95% sequence identity. At the nucleotide level, the sequences will typically share at least 40% nucleotide sequence identity, preferably at least 50%, 60%, 70% or 80% sequence identity, and more preferably 85%, 90%, 95% or 97% sequence identity. The degeneracy of the genetic code enables major variations in the nucleotide sequence of a polynucleotide while maintaining the amino acid sequence of the encoded protein.

One way to identify whether two nucleic acid molecules are closely related is that the two molecules hybridize to each other under stringent conditions. Generally, stringent conditions are selected to be about 5° C. to 20° C. lower than the thermal melting point (Tm) for the specific sequence at a defined ionic strength and pH. The $T_m$ is the temperature (under defined ionic strength and pH) at which 50% of the target sequence hybridizes to a perfectly matched probe. Conditions for nucleic acid hybridization and calculation of stringencies can be found in Sambrook et al. (1989) *Molecular Cloning. A Laboratory Manual*, Ed. 2, Cold Spring Harbor Laboratory Press, New York and Tijssen (1993) *Laboratory Techniques in Biochemistry and Molecular Biology—Hybridization with Nucleic Acid Probes* Part I, Elsevier, N.Y. Nucleic acid molecules that hybridize under stringent conditions will typically hybridize to a probe based on either the entire cDNA or selected portions of the cDNA under wash conditions of 0.2×SSC to 2.0×SSC, 0.1% SDS at 50–65° C., for example 0.2×SSC, 0.1% SDS at 65° C. For detecting less closely related homologs washes may be performed at 50° C.

For conventional hybridization the hybridization probe is conjugated with a detectable label such as a radioactive label, and the probe is preferably of at least 20 nucleotides in length. As is well known in the art, increasing the length of hybridization probes tends to give enhanced specificity. The labeled probe derived from the Arabidopsis nucleotide sequence may be hybridized to a plant cDNA or genomic library and the hybridization signal detected using means known in the art. The hybridizing colony or plaque (depending on the type of library used) is then purified and the cloned sequence contained in that colony or plaque isolated and characterized. Homologs may also be identified by PCR-based techniques, such as inverse PCR or RACE, using degenerate primers. See Ausubel et al. (eds) (1998) *Current Protocols in Molecular Biology*, John Wiley & Sons.

TF homologs may alternatively be obtained by immunoscreening an expression library. With the provision herein of the disclosed TF nucleic acid sequences, the polypeptide may be expressed and purified in a heterologous expression system (e.g., *E. coli*) and used to raise antibodies (monoclonal or polyclonal) specific for the TF. Antibodies may also be raised against synthetic peptides derived from TF amino acid sequences. Methods of raising antibodies are well known in the art and are described in Harlow and Lane (1988) *Antibodies: A Laboratory Manual*, Cold Spring Harbor Laboratory, New York. Such antibodies can then be used to screen an expression library produced from the plant from which it is desired to clone the TF homolog, using the methods described above. The selected cDNAs may be confirmed by sequencing and enzymatic activity.

3. Altered Expression of Transcription Factors

Any of the identified sequences may be incorporated into a cassette or vector for expression in plants. A number of expression vectors suitable for stable transformation of plant cells or for the establishment of transgenic plants have been described including those described in Weissbach and Weissbach, (1989) *Methods for Plant Molecular Biology*, Academic Press, and Gelvin et al., (1990) *Plant Molecular Biology Manual*, Kluwer Academic Publishers. Specific examples include those derived from a Ti plasmid of *Agrobacterium tumefaciens*, as well as those disclosed by Herrera-Estrella, L., et al., (1983) *Nature* 303:209, Bevan, M., *Nucl. Acids Res.* (1984) 12: 8711–8721, Klee, H. J., (1985) *Bio/Technology* 3:637–642, for dicotyledonous plants. Ti-derived plasmids can be transferred into both monocotonous and docotyledonous species using Agrobacterium-mediated transformation (Ishida et al (1996) *Nat. Biotechnol.* 14:745–50; Barton et al. (1983) *Cell* 32:1033–1043).

Alternatively, non-Ti vectors can be used to transfer the DNA into plants and cells by using free DNA delivery techniques. Such methods may involve, for example, the use of liposomes, electroporation, microprojectile bombardment, silicon carbide wiskers, and viruses. By using these methods transgenic plants such as wheat, rice (Christou, P., (1991) *Bio/Technology* 9:957–962) and corn (Gordon-Kamm, W., (1990) *Plant Cell* 2:603–618) can be produced. An immature embryo can also be a good target tissue for monocots for direct DNA delivery techniques by using the particle gun (Weeks, T. et al., (1993) *Plant Physiol.* 102:1077–1084; Vasil, V., (1993) *Bio/Technology* 10:667–674; Wan, Y. and Lemeaux, P., (1994) *Plant Physiol.* 104:37–48, and for Agrobacterium-mediated DNA transfer (Ishida et al., (1996) *Nature Biotech.* 14:745–750).

Typically, plant transformation vectors include one or more cloned plant coding sequences (genomic or cDNA) under the transcriptional control of 5' and 3' regulatory sequences and a dominant selectable marker. Such plant transformation vectors typically also contain a promoter (e.g., a regulatory region controlling inducible or constitutive, environmentally-or developmentally-regulated, or cell- or tissue-specific expression), a transcription initiation start site, an RNA processing signal (such as intron splice sites), a transcription termination site, and/or a polyadenylation signal.

Examples of constitutive plant promoters which may be useful for expressing the TF sequence include: the cauliflower mosaic virus (CaMV) 35S promoter, which confers constitutive, high-level expression in most plant tissues (see, e.g., Odel et al., (1985) *Nature* 313:810); the nopaline synthase promoter (An et al., (1988) *Plant Physiol.* 88:547); and the octopine synthase promoter (Fromm et al., (1989) *Plant Cell* 1:977).

A variety of plant gene promoters that regulate gene expression in response to environmental, hormonal, chemical, developmental signals, and in a tissue-active manner can be used for expression of the TFs in plants, as illustrated by seed-specific promoters (such as the napin, phaseolin or DC3 promoter described in U.S. Pat. No. 5,773,697), root-specific promoters, such as those disclosed in U.S. Pat. Nos. 5,618,988, 5,837,848 and 5,905,186; fruit-specific promoters that are active during fruit ripening (such as the dru 1 promoter (U.S. Pat. No. 5,783,393), or the 2A11 promoter (U.S. Pat. No. 4,943,674) and the tomato polygalacturonase promoter (Bird et al. (1988) *Plant Mol. Biol.* 11:651), root-specific promoters, such as those disclosed in U.S. Pat. Nos. 5,618,988, 5,837,848 and 5,905,186, pollen-active promoters such as PTA29, PTA26 and PTA13 (U.S. Pat. No. 5,792,929), promoters active in vascular tissue (Ringli and Keller (1998) *Plant Mol Biol.* 37:977–988), flower-specific (Kaiser et al, (1995) *Plant Mol. Biol.* 28:231–243), pollen (Baerson et al. (1994) *Plant Mol. Biol.* 26:1947–1959), carpels (Ohl et al. (1990) *Plant Cell* 2:837–848), pollen and ovules (Baerson et al. (1993) *Plant Mol. Biol.* 22:255–267)auxin-inducible promoters (such as that described in van der Kop et al (1999) *Plant Mol. Biol.* 39:979–990 or Baumann et al. (1999) *Plant Cell* 11:323–334), cytokinin-inducible promoter (Guevara-Garcia (1998) *Plant Mol. Biol.* 38:743–753), promoters responsive to gibberellin (Shi et al. (1998) *Plant Mol. Biol.* 38:1053–1060, Willmott et al. (1998) 38:817–825) and the like. Additional promoters are those that elicit expression in response to heat (Ainley, et al. (1993) *Plant Mol. Biol.* 22:13–23), light (e.g., the pea rbcS-3A promoter, Kuhlemeier et al., (1989) *Plant Cell* 1:471, and the maize rbcS promoter, Schaffner and Sheen, (1991) *Plant Cell* 3:997); wounding (e.g., wunl, Siebertz et al., (1989) *Plant Cell* 1:961); pathogen resistance, and chemicals such as methyl jasmonate or salicylic acid (Gatz et al., (1997) *Plant Mol. Biol.* 48:89–108). In addition, the timing of the expression can be controlled by using promoters such as those acting at late seed development (Odell et al. (1994) *Plant Physiol.* 106:447–458).

Plant expression vectors may also include RNA processing signals that may be positioned within, upstream or downstream of the coding sequence. In addition, the expression vectors may include additional regulatory sequences from the 3'-untranslated region of plant genes, e.g., a 3' terminator region to increase mRNA stability of the mRNA, such as the PI-II terminator region of potato or the octopine or nopaline synthase 3' terminator regions.

Finally, as noted above, plant expression vectors may also include dominant selectable marker genes to allow for the ready selection of transformants. Such genes include those encoding antibiotic resistance genes (e.g., resistance to hygromycin, kanamycin, bleomycin, G418, streptomycin or spectinomycin) and herbicide resistance genes (e.g., phosphinothricin acetyltransferase).

A reduction of TF expression in a transgenic plant to modifiy a plant trait may be obtained by introducing into plants antisense constructs based on the TF cDNA. For antisense suppression, the TF cDNA is arranged in reverse orientation relative to the promoter sequence in the expression vector. The introduced sequence need not be the full length TF cDNA or gene, and need not be identical to the TF cDNA or a gene found in the plant type to be transformed. Generally, however, where the introduced sequence is of shorter length, a higher degree of homology to the native TF sequence will be needed for effective antisense suppression. Preferably, the introduced antisense sequence in the vector will be at least 30 nucleotides in length, and improved antisense suppression will typically be observed as the length of the antisense sequence increases. Preferably, the length of the antisense sequence in the vector will be greater than 100 nucleotides. Transcription of an antisense construct as described results in the production of RNA molecules that are the reverse complement of mRNA molecules transcribed from the endogenous TF gene in the plant cell. Suppression of endogenous TF gene expression can also be achieved using a ribozyme. Ribozymes are synthetic RNA molecules that possess highly specific endoribonuclease activity. The production and use of ribozymes are disclosed in U.S. Pat. No. 4,987,071 to Cech and U.S. Pat. No. 5,543,508 to Haselhoff. The inclusion of ribozyme sequences within antisense RNAs may be used to confer RNA cleaving activity on the antisense RNA, such that endogenous mRNA molecules that bind to the antisense RNA are cleaved, which in turn leads to an enhanced antisense inhibition of endogenous gene expression.

Vectors in which RNA encoded by the TF cDNA (or variants thereof) is over-expressed may also be used to obtain co-suppression of the endogenous TF gene in the manner described in U.S. Pat. No. 5,231,020 to Jorgensen. Such co-suppression (also termed sense suppression) does not require that the entire TF cDNA be introduced into the plant cells, nor does it require that the introduced sequence be exactly identical to the endogenous TF gene. However, as with antisense suppression, the suppressive efficiency will be enhanced as (1) the introduced sequence is lengthened and (2) the sequence similarity between the introduced sequence and the endogenous TF gene is increased.

Vectors expressing an untranslatable form of the TF mRNA may also be used to suppress the expression of endogenous TF activity to modify a trait. Methods for producing such constructs are described in U.S. Pat. No. 5,583,021 to Dougherty et al. Preferably, such constructs are made by introducing a premature stop codon into the TF gene. Alternatively, a plant trait may be modified by gene silencing using double-strand RNA (Sharp (1999) *Genes and Development* 13:139–141).

Another method for abolishing the expression of a gene is by insertion mutagenesis using the T-DNA of *Agrobacterium tumefaciens*. After generating the insertion mutants, the mutants can be screened to identify those containing the insertion in a TF gene. Mutants containing a single mutation event at the desired gene may be crossed to generate homozygous plants for the mutation (Koncz et al. (1992) *Methods in Arabidopsis Research*. World Scientific).

A plant trait may also be modified by using the cre-lox system (for example, as described in U.S. Pat. No. 5,658,772). A plant genome may be modified to include first and second lox sites that are then contacted with a Cre recombinase. If the lox sites are in the same orientation, the intervening DNA sequence between the two sites is excised. If the lox sites are in the opposite orientation, the intervening sequence is inverted.

The polynucleotides and polypeptides of this invention may also be expressed in a plant in the absence of an expression cassette by manipulating the activity or expression level of the endogenous gene by other means. For example, by ectopically expressing a gene by T-DNA activation tagging (Ichikawa et al., (1997) *Nature* 390 698–701, Kakimoto et al., (1996) *Science* 274:982–985). This method entails transforming a plant with a gene tag containing multiple transcriptional enhancers and once the tag has inserted into the genome, expression of a flanking gene coding sequence becomes deregulated. In another example, the transcriptional machinery in a plant may be modified so as to increase transcription levels of a polynucleotide of the invention (See PCT Publications WO9606166 and WO 9853057 which describe the modification of the DNA binding specificity of zinc finger proteins by changing particular amino acids in the DNA binding motif).

The transgenic plant may also comprise the machinery necessary for expressing or altering the activity of a polypeptide encoded by an endogenous gene, for example by altering the phosphorylation state of the polypeptide to maintain it in an activated state.

4. Transgenic Plants with Modified TF Expression

Once an expression cassette comprising a polynucleotide encoding a TF gene of this invention has been constructed, standard techniques may be used to introduce the polynucleotide into a plant in order to modify a trait of the plant. The plant may be any higher plant, including gymnosperms, monocotyledonous and dicotyledenous plants. Suitable protocols are available for Leguminosae (alfalfa, soybean, clover, etc.), Umbelliferae (carrot, celery, parsnip), Cruciferae (cabbage, radish, rapeseed, broccoli, etc.), Curcurbitaceae (melons and cucumber), Gramineae (wheat, corn, rice, barley, millet, etc.), Solanaceae (potato, tomato, tobacco, peppers, etc.), and various other crops. See protocols described in Ammirato et al. (1984) *Handbook of Plant Cell Culture—Crop Species*. Macmillan Publ. Co. Shimamoto et al. (1989) *Nature* 338:274–276; Fromm et al. (1990) *Bio/Technology* 8:833–839; and Vasil et al. (1990) *Bio/Technology* 8:429–434.

Transformation and regeneration of both monocotyledonous and dicotyledonous plant cells is now routine, and the selection of the most appropriate transformation technique will be determined by the practitioner. The choice of method will vary with the type of plant to be transformed; those skilled in the art will recognize the suitability of particular methods for given plant types. Suitable methods may include, but are not limited to: electroporation of plant protoplasts; liposome-mediated transformation; polyethylene glycol (PEG) mediated transformation; transformation using viruses; micro-injection of plant cells; microprojectile bombardment of plant cells; vacuum infiltration; and *Agrobacterium tumeficiens* mediated transformation. Transformation means introducing a nucleotide sequence in a plant in a manner to cause stable or transient expression of the sequence.

Successful examples of the modification of plant characteristics by transformation with cloned sequences which serve to illustrate the current knowledge in this field of technology, and which are herein incorporated by reference, include: U.S. Pat. Nos. 5,571,706; 5,677,175; 5,510,471; 5,750,386; 5,597,945; 5,589,615; 5,750,871; 5,268,526; 5,780,708; 5,538,880; 5,773,269; 5,736,369 and 5,610,042.

Following transformation, plants are preferably selected using a dominant selectable marker incorporated into the transformation vector. Typically, such a marker will confer antibiotic or herbicide resistance on the transformed plants, and selection of transformants can be accomplished by exposing the plants to appropriate concentrations of the antibiotic or herbicide.

After transformed plants are selected and grown to maturity, those plants showing a modified trait are identified. The modifed trait may be any of those traits described above. Additionally, to confirm that the modified trait is due to changes in expression levels or activity of the polypeptide or polynucleotide of the invention may be determined by analyzing mRNA expression using Northern blots, RT-PCR or microarrays, or protein expression using immunoblots or Western blots or gel shift assays.

The plants may have commercial utility for increasing tolerance or resistance to pathogens and pests. These transgenic plants may be more resistant to biotrophic or necrotrophic pathogens or belonging to the following groups such as a fungus, bacterium, mollicute, virus, nematode, a parasitic higher plant or the like and associated diseases. In particular, pathogens such as *Fusarium oxysporum*, *Erysyphe orontii* and other powdery mildews, Sclerotinia spp., soil-borne oomycetes, foliar oomycetes, Botrytis spp., Rhizoctonia spp, *Verticillium dahliae/albo-atrum*, Alternaria spp., rusts, Mycosphaerella spp, *Fusarium solani*, or the like. The diseases include fungal diseases such as rusts, smuts, wilts, yellows, root rot, leaf drop, ergot, leaf blight of potato, brown spot of rice, leaf blight, late blight, powdery mildew, downy mildew, and the like; viral diseases such as sugarcane mosaic, cassava mosaic, sugar beet yellows, plum pox, barley yellow dwarf, tomato yellow leaf curl, tomato spotted wilt virus, and the like; bacterial diseases such as citrus canker, bacterial leaf blight, bacterial will, soft rot of vegetables, and the like; nematode diseases caused by parasitic nematodes such as root-knot nematodes, cyst nematodes or the like.

5. Other Utility of the Polypeptide and Polynucleotide Sequences

A transcription factor provided by the present invention may also be used to identify exogenous or endogenous molecules that may affect expression of the transcription factors and may affect any of the traits described herein. These molecules may include organic or inorganic compounds.

For example, the method may entail first placing the molecule in contact with a plant or plant cell. The molecule may be introduced by topical administration, such as spraying or soaking of a plant, and then the molecule's effect on the expression or activity of the TF polypeptide or the expression of the polynucleotide monitored. Changes in the expression of the TF polypeptide may be monitored by use of polyclonal or monoclonal antibodies, gel electrophoresis or the like. Changes in the expression of the corresponding polynucleotide sequence may be detected by use of microarrays, Northerns or any other technique for monitoring changes in mRNA expression. These techniques are exemplified in Ausubel et al. (eds) *Current Protocols in Molecular Biology*, John Wiley & Sons (1998). Such changes in the expression levels may be correlated with modified plant traits and thus identified molecules may be useful for soaking or spraying on fruit, vegetable and grain crops to modify traits in plants.

The transcription factors may also be employed to identify promoter sequences with which they may interact. After identifying a promoter sequence, interactions between the transcription factor and the promoter sequence may be modified by changing specific nucleotides in the promoter sequence or specific amino acids in the transcription factor that interact with the promoter sequence to alter a plant trait. Typically, transcription factor DNA binding sites are identified by gel shift assays. After identifying the promoter regions, the promoter region sequences may be employed in double-stranded DNA arrays to identify molecules that affect the interactions of the TFs with their promoters (Bulyk et al. (1999) *Nature Biotechnology* 17:573–577).

The identified transcription factors are also useful to identify proteins that modify the activity of the transcription factor. Such modification may occur by covalent modification, such as by phosphorylation, or by protein-protein (homo or-heteropolymer) interactions. Any method suitable for detecting protein-protein interactions may be employed. Among the methods that may be employed are co-immunoprecipitation, cross-linking and co-purification through gradients or chromatographic columns, and the two-hybrid yeast system.

The two-hybrid system detects protein interactions in vivo and is described in Chien, et al., (1991), *Proc. Natl. Acad. Sci. USA*, 88, 9578–9582 and is commercially available from Clontech (Palo Alto, Calif.). In such a system, plasmids are constructed that encode two hybrid proteins: one consists of the DNA-binding domain of a transcription activator protein fused to the TF polypeptide and the other consists of the transcription activator protein's activation domain fused to an unknown protein that is encoded by a cDNA that has been recombined into the plasmid as part of a cDNA library. The DNA-binding domain fusion plasmid and the cDNA library are transformed into a strain of the yeast *Saccharomyces cerevisiae* that contains a reporter gene (e.g., lacZ) whose regulatory region contains the transcription activator's binding site. Either hybrid protein alone cannot activate transcription of the reporter gene. Interaction of the two hybrid proteins reconstitutes the functional activator protein and results in expression of the reporter gene, which is detected by an assay for the reporter gene product. Then, the library plasmids responsible for reporter gene expression are isolated and sequenced to identify the proteins encoded by the library plasmids. After identifying proteins that interact with the transcription factors, assays for compounds that interfere with the TF protein-protein interactions may be preformed.

The following examples are intended to illustrate but not limit the present invention.

EXAMPLE I

Full Length Gene Identification and Cloning

Putative transcription factor sequences (genomic or ESTs) related to known transcription factors were identified in the *Arabidopsis thaliana* GenBank database using the tblastn sequence analysis program using default parameters and a P-value cutoff threshold of −4 or −5 or lower, depending on the length of the query sequence. Putative transcription factor sequence hits were then screened to identify those containing particular sequence strings. If the sequence hits contained such sequence strings, the sequences were confirmed as transcription factors.

Alternatively, *Arabidopsis thaliana* cDNA libraries derived from different tissues or treatments, or genomic libraries were screened to identify novel members of a transcription family using a low stringency hybridization approach. Probes were synthesized using gene specific primers in a standard PCR reaction (annealing temperature 60° C.) and labeled with $^{32}$P dCTP using the High Prime DNA Labeling Kit (Boehringer Mannheim). Purified radiolabelled probes were added to filters immersed in Church hybridization medium (0.5 M $NaPO_4$ pH 7.0, 7% SDS, 1% w/v bovine serum albumin) and hybridized overnight at 60° C. with shaking. Filters were washed two times for 45 to 60 minutes with 1×SCC, 1% SDS at 60° C.

To identify additional sequence 5' or 3' of a partial cDNA sequence in a cDNA library, 5' and 3' rapid amplification of cDNA ends (RACE) was performed using the Marathon™ cDNA amplification kit (Clontech, Palo Alto, Calif.). Generally, the method entailed first isolating poly(A) mRNA, performing first and second strand cDNA synthesis to generate double stranded cDNA, blunting cDNA ends, followed by ligation of the Marathon™ Adaptor to the cDNA to form a library of adaptor-ligated ds cDNA. Gene-specific primers were designed to be used along with adaptor specific primers for both 5' and 3' RACE reactions. Nested primers, rather than single primers, were used to increase PCR specificity. Using 5' and 3+ RACE reactions, 5' and 3' RACE fragments were obtained, sequenced and cloned. The process may be repeated until 5' and 3' ends of the full-length gene were identified. Then the full-length cDNA was generated by PCR using primers specific to 5' and 3' ends of the gene by end-to-end PCR.

EXAMPLE II

Pathogen Resistance Genes

RT-PCR and microarray experiments were performed to identify those genes induced after exposure to biotropic fungal pathogens, such as *Erisyphe orontii*, necrotropic fungal pathogens, such as *Fusarium oxysporum*, and disease associated growth-regulators such as salicylic acid, methyl jasmonate and ethylene (ACC). The gene expression patterns from soil grown as well as tissue culture grown plant tissue were investigated.

*Fusarium oxysporum* isolates cause vascular wilts and damping off of various annual vegetables, perennials and weeds (Mauch-Mani and Slusarenko (1994) Molecular Plant-Microbe Interactions 7:378–383). For *Fusarium oxysporum* experiments, plants grown on petri dishes were sprayed with a fresh spore suspension of *F. oxysporum*. The spore suspension was prepared as follows: A plug of fungal hyphae from a plate culture was placed on a fresh potato dextrose agar plate and allowed to spread for one week. 5 ml sterile water was then added to the plate, swirled, and pipetted into 50 ml Armstrong Fusarium medium. Spores were grown overnight in Fusarium medium and then sprayed onto plants using a Preval paint sprayer. Plant tissue was harvested and frozen in liquid nitrogen 48 hours post infection

*Erysiphe orontii* is a causal agent of powdery mildew. For *Erysiphe orontii* experiments, plants were grown approximately 4 weeks in a greenhouse under 12 hour light (20° C., ~30% relative humidity (rh)). Individual leaves were infected with *E. orontii* spores from infected plants using a camel's hair brush, and the plants were transferred to a Percival growth chamber (20° C., 80% rh.). Plant tissue was harvested and frozen in liquid nitrogen 7 days post infection.

For salicylic acid experiments, 15 day old seedlings grown on petri dishes were transferred to plates containing 0.5 mM salicylic acid (SA). After 72 hours, leaves were harvested and frozen in liquid nitrogen.

Reverse transcriptase PCR was done using gene specific primers within the coding region for each sequence identified. The primers were designed near the 3' region of each coding sequence initially identified.

Total RNA from these tissues were isolated using the CTAB extraction protocol. Once extracted total RNA was normalized in concentration across all the tissue types to ensure that the PCR reaction for each tissue received the same amount of cDNA template using the 28S band as reference. Poly A+ was purified using a modified protocol from the Qiagen Oligotex kit batch protocol. cDNA was synthesized using standard protocols. After the first strand cDNA synthesis, primers for Actin 2 were used to normalize the concentration of cDNA across the tissue types. Actin 2 is found to be constitutively expressed in fairly equal levels across the tissue types we are investigating.

For RT PCR, cDNA template was mixed with corresponding primers and Taq polymerase. Each reaction consisted of 0.2 ul cDNA template, 2 ul 10x Tricine buffer, 2 ul 10x Tricine buffer and 16.8 ul water, 0.05 ul Primer 1, 0.05 ul, Primer 2, 0.3 ul Taq polymerase and 8.6 ul water.

The 96 well plate was covered with microfilm and set in the Thermocycler to start the following reaction cycle. Step1 93° C. for 3 mins, Step 2 93° C. for 30 sec, Step 3 65° C. for 1 min, Step 4 72° C. for 2 mins,. Steps 2, 3 and 4 were repeated for 28 cycles, Step 5 72° C. for 5 mins and Step 6 4° C. The PCR plate was placed back in the thermocycler to amplify more products at 8 more cycles to identify genes that have very low expression. The reaction cycle was as follows: Step 2 93° C. for 30 sec, Step 3 65° C. for 1 min, and Step 4 72° C. for 2 ins, repeated for 8 cycles, and Step 4 4° C.

8 ul of PCR product and 1.5 ul of loading dye were loaded on a 1.2% agarose gel for analysis after 28 cycles and 36 cycles. Expression levels of specific transcripts were considered low if they were only detectable after 36 cycles of PCR. Expression levels were considered medium or high depending on the levels of transcript compared with observed transcript levels for actin2.

In some instances, expression patterns of the transcription factors was monitored by microarray experiments. cDNAs were generated by PCR and resuspended at a final concentration of ~100 ng/ul in 3xSSC or 150 mM Na-phosphate (Eisen and Brown (1999) *Meth. in Enzymol.* 303:179–205). The cDNAs were spotted on microscope glass slides coated with polylysine. The prepared cDNAs were aliquoted into 384 well plates and spotted on the slides using an x-y-z gantry (OmniGrid) purchased from GeneMachines (Menlo Park, Calif.) outfitted with quill type pins purchased from Telechem International (Sunnyvale, Calif.). After spotting, the arrays were cured for a minimum of one week at room temperature, rehydrated and blocked following the protocol recommended by Eisen and Brown (1999).

Sample total RNA (10 ug) samples were labeled using fluorescent Cy3 and Cy5 dyes. Labeled samples were resuspended in 4xSSC/0.03% SDS/4 ug salmon sperm DNA/2 ug tRNA/50 mM Na-pyrophosphate, heated for 95° C. for 2.5 minutes, spun down and placed on the array. The array was then covered with a glass coverslip and placed in a sealed chamber. The chamber was then kept in a water bath at 62° C. overnight. The arrays were washed as described in Eisen and Brown (1999) and scanned on a General Scanning 3000 laser scanner. The resulting files are subsequently quantified using Imagene a software purchased from BioDiscovery (Los Angeles, Calif.).

The transcript levels were observed to be upregulated between 1.5 and 100 fold when compared with control plants not exposed to the pathogens.

EXAMPLE III
Construction of Expression Vectors

The sequence was amplified from a genomic or cDNA library using primers specific to sequences upstream and downstream of the coding region. The expression vector was pMEN20, which is derived from pMON316 (Sanders et al, (1987) *Nucleic Acids Research* 15:1543–58). To clone the sequence into the vector, both pMEN20 and the amplified DNA fragment were digested separately with SalI and NotI restriction enzymes at 37° C. for 2 hours. The digestion products were subject to electrophoresis in a 0.8% agarose gel and visualized by ethidium bromide staining. The DNA fragments containing the sequence and the linearized plasmid were excised and purified by using a Qiaquick gel extraction kit (Qiagen, Calif.). The fragments of interest were ligated at a ratio of 3:1 (vector to insert). Ligation reactions using T4 DNA ligase (New England Biolabs, MA) were carried out at 16° C. for 16 hours. The ligated DNAs were transformed into competent cells of the *E. coli* strain DH5alpha by using the heat shock method. The transformations were plated on LB plates containing 50 mg/l spectinomycin (Sigma).

Individual colonies were grown overnight in five milliliters of LB broth containing 50 mg/l spectinomycin at 37° C. Plasmid DNA was purified by using Qiaquick Mini Prep kits (Qiagen, Calif.).

EXAMPLE IV
Transformation of Agrobacterium with the Expression Vector

After the plasmid vector containing the gene was constructed, the vector was used to transform *Agrobacterium tumefaciens* cells expressing the gene products. The stock of *Agrobacterium tumefaciens* cells for transformation were made as described by Nagel et al. *FEMS Microbiol Letts* 67:325–328 (1990). Agrobacterium strain GV3101 was grown in 250 ml LB medium (Sigma) overnight at 28° C. with shaking until an absorbance ($A_{600}$) of 0.5–1.0 was reached. Cells were harvested by centrifugation at 4,000xg for 15 min at 4° C. Cells were then resuspended in 250 $\mu$l chilled buffer (1 mM HEPES, pH adjusted to 7.0 with KOH). Cells were centrifuged again as described above and resuspended in 125 $\mu$l chilled buffer. Cells were then centrifuged and resuspended two more times in the same HEPES buffer as described above at a volume of 100 $\mu$l and 750 $\mu$l, respectively. Resuspended cells were then distributed into 40 $\mu$l aliquots, quickly frozen in liquid nitrogen, and stored at −80° C.

Agrobacterium cells were transformed with plasmids prepared as described above following the protocol described by Nagel et al. *FEMS Microbiol Letts* 67:325–328 (1990). For each DNA construct to be transformed, 50–100 ng DNA (generally resuspended in 10 mM Tris-HCl, 1 mM EDTA, pH 8.0) was mixed with 40 $\mu$l of Agrobacterium cells. The DNA/cell mixture was then transferred to a chilled cuvette with a 2 mm electrode gap and subject to a 2.5 kV charge dissipated at 25 μF and 200 μF using a Gene Pulser II apparatus (Bio-Rad). After electroporation, cells were immediately resuspended in 1.0 ml LB and allowed to recover without antibiotic selection for 2–4 hours at 28° C. in a shaking incubator. After recovery, cells were plated onto selective medium of LB broth containing 100 μg/ml spectinomycin (Sigma) and incubated for 24–48 hours at 28° C. Single colonies were then picked and inoculated in fresh medium. The presence of the plasmid construct was verified by PCR amplification and sequence analysis.

EXAMPLE V
Transformation of Arabidopsis Plants with *Agrobacterium tumefaciens* with Expression Vector After transformation of *Agrobacterium tumefaciens* with plasmid vectors containing the gene, single Agrobacterium colonies were identified, propagated, and used to transform Arabidopsis plants. Briefly, 500 ml cultures of LB medium containing 50 mg/l spectinomycin were inoculated with the colonies and grown at 28° C. with shaking for 2 days until an absorbance ($A_{600}$) of >2.0 is reached. Cells were then harvested by centrifugation at 4,000×g for 10 min, and resuspended in infiltration medium (½× Murashige and Skoog salts (Sigma), 1× Gamborg's B-5 vitamins (Sigma), 5.0% (w/v) sucrose (Sigma), 0.044 μM benzylamino purine (Sigma), 200 μl/L Silwet L-77 (Lehle Seeds) until an absorbance ($A_{600}$) of 0.8 was reached.

Prior to transformation, *Arabidopsis thaliana* seeds (ecotype Columbia) were sown at a density of ~10 plants per 4" pot onto Pro-Mix BX potting medium (Hummert International) covered with fiberglass mesh (18 mm×16 mm). Plants were grown under continuous illumination (50–75 μE/m$^2$/sec) at 22–23° C. with 65–70% relative humidity. After about 4 weeks, primary inflorescence stems (bolts) are cut off to encourage growth of multiple secondary bolts. After flowering of the mature secondary bolts, plants were prepared for transformation by removal of all siliques and opened flowers.

The pots were then immersed upside down in the mixture of Agrobacterium infiltration medium as described above for 30 sec, and placed on their sides to allow draining into a 1'×2' flat surface covered with plastic wrap. After 24 h, the plastic wrap was removed and pots are turned upright. The immersion procedure was repeated one week later, for a total of two immersions per pot. Seeds were then collected from each transformation pot and analyzed following the protocol described below.

EXAMPLE VI
Identification of Arabidopsis Primary Transformants

Seeds collected from the transformation pots were sterilized essentially as follows. Seeds were dispersed into in a solution containing 0.1% (v/v) Triton X-100 (Sigma) and sterile $H_2O$ and washed by shaking the suspension for 20 min. The wash solution was then drained and replaced with fresh wash solution to wash the seeds for 20 min with shaking. After removal of the second wash solution, a solution containing 0.1% (v/v) Triton X-100 and 70% ethanol (Equistar) was added to the seeds and the suspension was shaken for 5 min. After removal of the ethanol/detergent solution, a solution containing 0.1% (v/v) Triton X-100 and 30% (v/v) bleach (Clorox) was added to the seeds, and the suspension was shaken for 10 min. After removal of the bleach/detergent solution, seeds were then washed five times in sterile distilled $H_2O$. The seeds were stored in the last wash water at 4° C. for 2 days in the dark before being plated onto antibiotic selection medium (1× Murashige and Skoog salts (pH adjusted to 5.7 with 1M KOH), 1× Gamborg's B-5 vitamins, 0.9% phytagar (Life Technologies), and 50 mg/l kanamycin). Seeds were germinated under continuous illumination (50–75 μE/m$^2$/sec) at 22–23° C. After 7–10 days of growth under these conditions, kanamycin resistant primary transformants ($T_1$ generation) were visible and obtained. These seedlings were transferred first to fresh selection plates where the seedlings continued to grow for 3–5 more days, and then to soil (Pro-Mix BX potting medium).

Primary transformants are self-crossed and progeny seeds (T2) collected.

EXAMPLE VII
Analysis of Arabidopsis T2 Progeny Plants for Pathogen Resistance or Pathogen Tolerance T2 or knockout mutant seed were surface sterilized and sown on MS media containing sucrose. Ten days postplanting, seedlings were transferred to MS media without sucrose. At two weeks of age Arabidopsis seedlings were inoculated with Fusarium by spraying with a spore suspension (2×10$^6$ conidia per milliliter) and incubated under high humidity. Plants were then scored macroscopically for disease symptoms or microscopically for fungal growth or using microarrays for the induction of resistance associated genes (such as the defensin genes) to detect resistance or tolerance of the plant tissue. A wild type plant shows the first signs of damage (gradual yellowing of leaves, damping off of seedlings or growth of fungal mycelium) after two to four days after inoculation. Transgenic plants that are pathogen resistant or tolerant showed a delay in disease or symptom development compared to wild-type control plants.

Alternatively, Erysiphe inoculations were done by tapping conidia from 1 to 2 heavily infected leaves onto the mesh cover of a settling tower, brushing the mesh with a camel's hair paint brush to break up the conidial chains, and letting the conidia settle for 10 minutes. Plants were 4 to 4.5 weeks old at the time of inoculation. Spores were obtained from 10 to 14 day old Erysiphe cultures. Typically, within the first twenty-four hours, the spores differentiated into several fungal structures including the haustorium that invaginates a host's epidermal plasma membrane. Formation of aerial mycelium and sporulation represent late differentiation events between 4 and 7 days post inoculation (Freilaldenhoven et al. (1994) *Plant Cell* 6:983–994). Plant resistance was scored based on the relative number and size of mycelial patches bearing conidia compared to wild-type control plants. Events associated with disease resistance to the pathogens and pests include: the induction of pathogen resistance related genes (R genes), the activation of cell death in the attacked epidermal cells (hypersensitive response), the induction of anti-microbial compounds, such as phytoalexins, and the lignification that occurs at attempted penetration sites. Assays are performed to observe these events. Transgenic plants identified that induce R genes, activate cell death, induce anti-microbial compounds or increase lignification sooner or to a greater extent than wild-type plants when exposed to pathogen are potentially more resistant to infection by Erysiphe as well as a number of other pathogens and pests.

We have also observed that when the expression levels of the genes are altered, that the disease phenotype can be varied. For example, G19 was significantly induced upon infection by the fungal pathogen *Erysiphe orontii* as well as the disease associated growth regulator, ethylene. Our data show that G19 overexpressing plants were more tolerant to infection with a moderate dose of *Erysiphe orontii* and in a nematode screen. The transgenic plants overexpressing G19 under the control of the 35S promoter were morphologically similar to control plants.

Additionally, G511 was another example of a gene that when overexpressed showed an increased tolerance to the fungal pathogen *Erysiphe orontii*. In both cases increased tolerance includes a significant reduction in pathogen growth and symptom development compared to wild type plants that were treated with pathogen in an identical manner.

EXAMPLE VIII
Transformation of Cereal Plants with the Expression Vector

A cereal plant, such as corn, wheat, rice, sorghum or barley, can also be transformed with the plasmid vectors containing the sequence and constitutive or inducible promoters to modify a trait. In these cases, a cloning vector, pMEN020, is modified to replace the NptII coding region with the BAR gene of *Streptomyces hygroscopicus* that confers resistance to phosphinothricin. The KpnI and BglII sites of the Bar gene are removed by site-directed mutagenesis with silent codon changes.

Plasmids according to the present invention may be transformed into corn embryogenic cells derived from immature scutellar tissue by using microprojectile bombardment, with the A188XB73 genotype as the preferred genotype (Fromm et al., *Bio/Technology* 8:833–839 (1990); Gordon-Kamm et al., *Plant Cell* 2:603–618 (1990)). After microprojectile bombardment the tissues are selected on phosphinothricin to identify the transgenic embryogenic cells (Gordon-Kamm et al., *Plant Cell* 2:603–618 (1990)). Transgenic plants are regenerated by standard corn regeneration techniques (Fromm, et al., *Bio/Technology* 8:833–839 (1990); Gordon-Kamm et al., *Plant Cell* 2:603–618 (1990)).

EXAMPLE IX
Identification of Homologous Sequences

Homologs from the same plant, different plant species or other organisms were identified using database sequence search tools, such as the Basic Local Alignment Search Tool (BLAST) (Altschul et al. (1990) *J. Mol. Biol.* 215:403–410; and Altschul et al. (1997) *Nucl. Acid Res.* 25:3389–3402). The tblastn or blastn sequence analysis programs were employed using the BLOSUM-62 scoring matrix (Henikoff, S. and Henikoff, J. G. (1992) *Proc. Natl. Acad. Sci. USA* 89:10915–10919). The output of a BLAST report provides a score that takes into account the alignment of similar or identical residues and any gaps needed in order to align the sequences. The scoring matrix assigns a score for aligning any possible pair of sequences. The P values reflect how many times one expects to see a score occur by chance. Higher scores are preferred and a low threshold P value threshold is preferred. These are the sequence identity criteria. The tblastn sequence analysis program was used to query a polypeptide sequence against six-way translations of sequences in a nucleotide database. Hits with a P value less than −25, preferably less than −70, and more preferably less than −100, were identified as homologous sequences (exemplary selected sequence criteria). The blastn sequence analysis program was used to query a nucleotide sequence against a nucleotide sequence database. In this case too, higher scores were preferred and a preferred threshold P value was less than −13, preferably less than −50, and more preferably less than −100.

Alternatively, a fragment of a sequence from FIG. 1 is $^{32}$P-radiolabeled by random priming (Sambrook et al., (1989) *Molecular Cloning. A Laboratory Manual*, 2$^{nd}$ Ed., Cold Spring Harbor Laboratory Press, New York) and used to screen a plant genomic library (the exemplary test polynucleotides). As an example, total plant DNA from *Arabidopsis thaliana, Nicotiana tabacum, Lycopersicon pimpinellifolium*, Prunus avium, Prunus cerasus, Cucumis sativus, or *Oryza sativa* are isolated according to Stockinger al (Stockinger, E. J., et al., (1996), *J. Heredity*, 87:214–218). Approximately 2 to 10 μg of each DNA sample are restriction digested, transferred to nylon membrane (Micron Separations, Westboro, Mass.) and hybridized. Hybridization conditions are: 42° C. in 50% formamide, 5×SSC, 20 mM phosphate buffer 1× Denhardt's, 10% dextran sulfate, and 100 μg/ml herring sperm DNA. Four low stringency washes at RT in 2×SSC, 0.05% sodium sarcosyl and 0.02% sodium pyrophosphate are performed prior to high stringency washes at 55° C. in 0.2×SSC, 0.05% sodium sarcosyl and 0.01% sodium pyrophosphate. High stringency washes are performed until no counts are detected in the washout according to Walling et al. (Walling, L. L., et al., (1988) *Nucl. Acids Res.* 16:10477–10492).

All references (publications and patents) are incorporated herein by reference in their entirety for all purposes.

Although the invention has been described with reference to the embodiments and examples above, it should be understood that various modifications can be made without departing from the spirit of the invention. Accordingly, the invention is limited only by the following claims.

We claim:

1. A transgenic plant comprising a recombinant polynucleotide encoding SEQ ID NO: 18, and said transgenic plant has enhanced tolerance to fungal disease due to expression of SEQ ID NO: 18.

2. The transgenic plant of claim 1, wherein the recombinant polynucleotide comprises SEQ ID NO: 17.

3. The transgenic plant of claim 1, wherein the recombinant polynucleotide further comprises one or more regulatory sequences.

4. The transgenic plant of claim 3, wherein said one or more regulatory sequences are selected from the group consisting of a promoter, a transcription initiation start site, an RNA processing signal, a transcription termination site, and a polyadenylation signal.

5. The transgenic plant of claim 4, wherein the selected promoter is constitutive, inducible, or tissue-specific.

6. The transgenic plant of claim 1, wherein said fungal disease is caused by Fusarium, Erysiphe, Sclerotinia or Botrytis.

7. A method for enhancing the disease tolerance or resistance of a plant comprising transforming a plant with a recombinant polynucleotide encoding SEQ ID NO: 18, and said transgenic plant has enhanced tolerance to fungal disease due to expression of SEQ ID NO: 18.

8. The method of claim 7, wherein the recombinant polynucleotide comprises SEQ ID NO: 17.

9. The method of claim 7, wherein the recombinant polynucleotide further comprises one or more regulatory sequences.

10. The method of claim 9, wherein said one or more regulatory sequences are selected from the group consisting of a promoter, a transcription initiation start site, an RNA processing signal, a transcription termination site, and a polyadenylation signal.

11. The method of claim 10, wherein the selected promoter is constitutive, inducible, or tissue-specific.

12. The transgenic plant of claim 7, wherein said fungal disease is caused by Fusarium, Erysiphe, Sclerotinia or Botrytis.

13. A method for altering the expression levels of at least one gene in a plant comprising transforming the plant with a recombinant polynucleotide encoding SEQ ID NO: 18, and said transgenic plant has enhanced tolerance to fungal disease due to expression of SEQ ID NO: 18.

14. The method of claim 13, wherein the recombinant polynucleotide comprises SEQ ID NO: 17.

15. The method of claim 13, wherein the recombinant polynucleotide further comprises one or more regulatory sequences.

16. The method of claim 15, wherein said one or more regulatory sequences are selected from the group consisting of a promoter, a transcription initiation start site, an RNA processing signal, a transcription termination site, and a polyadenylation signal.

17. The method of claim 16, wherein the selected promoter is constitutive, inducible, or tissue-specific.

18. The transgenic plant of claim 13, wherein said fungal disease is caused by Fusarium, Erysiphe, Sclerotinia or Botrytis.

* * * * *

UNITED STATES PATENT AND TRADEMARK OFFICE
Certificate

Patent No. 6,664,446 B2                                                                                      Patented: December 16, 2003

On petition requesting issuance of a certificate for correction of inventorship pursuant to 35 U.S.C. 256, it has been found that the above identified patent, through error and without any deceptive intent, improperly sets forth the inventorship.
   Accordingly, it is hereby certified that the correct inventorship of this patent is: Jacqueline Heard, Webster Groves, MO (US); Jose Luis Riechmann, Barcelona, (ES); Omaira Pineda, Vero Beach, FL (US); Luc Adam, Hayward, CA (US); Oliver Ratcliff; Oakland, CA (US); and T. Lynne Reuber, San Mateo, CA (US).

Signed and Sealed this Fifth Day of January 2010.

<div style="text-align:right">ANNE MARIE GRUNBERG<br>*Supervisory Patent Examiner*<br>Art Unit 1638</div>